US010246509B2

(12) United States Patent
Macdonald et al.

(10) Patent No.: US 10,246,509 B2
(45) Date of Patent: Apr. 2, 2019

(54) RESTRICTED IMMUNOGLOBULIN HEAVY CHAIN MICE

(71) Applicant: Regeneron Pharmaceuticals, Inc., Tarrytown, NY (US)

(72) Inventors: Lynn Macdonald, Harrison, NY (US); John McWhirter, Hasings-on-Hudson, NY (US); Cagan Gurer, Chappaqua, NY (US); Karolina A. Hosiawa, Yorktown Heights, NY (US); Andrew J. Murphy, Croton-on-Hudson, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 13/653,456

(22) Filed: Oct. 17, 2012

(65) Prior Publication Data

US 2013/0096287 A1 Apr. 18, 2013

Related U.S. Application Data

(60) Provisional application No. 61/658,459, filed on Jun. 12, 2012, provisional application No. 61/597,969, filed on Feb. 13, 2012, provisional application No. 61/547,974, filed on Oct. 17, 2011.

(51) Int. Cl.

| | |
|---|---|
| ***A01K 67/027*** | (2006.01) |
| ***C12N 5/10*** | (2006.01) |
| ***C12N 5/20*** | (2006.01) |
| ***C07K 16/28*** | (2006.01) |
| ***C12N 15/85*** | (2006.01) |
| ***C07K 16/00*** | (2006.01) |

(52) U.S. Cl.

CPC .......... *C07K 16/28* (2013.01); *A01K 67/0278* (2013.01); *C07K 16/00* (2013.01); *C12N 15/8509* (2013.01); *A01K 2217/072* (2013.01); *A01K 2217/15* (2013.01); *A01K 2227/105* (2013.01); *A01K 2267/01* (2013.01); *C07K 2317/21* (2013.01); *C07K 2317/56* (2013.01); *C07K 2317/565* (2013.01); *C12N 2800/204* (2013.01)

(58) Field of Classification Search

CPC ............ A01K 67/0278; A01K 2267/01; A01K 2227/105; A01K 67/0275; A01K 2207/15; A01K 2217/05; A01K 2217/072; A01K 2217/00; A01K 2217/15; C07K 2317/24; C07K 16/00; C07K 16/462; C07K 2317/21; C07K 2317/56; C07K 2317/52

USPC ........................................................... 800/18

See application file for complete search history.

(56) References Cited

U.S. PATENT DOCUMENTS

| | | | | |
|---|---|---|---|---|
| 5,545,807 | A | 8/1996 | Surani et al. | |
| 5,633,425 | A | 5/1997 | Lonberg et al. | |
| 5,770,429 | A | 6/1998 | Lonberg et al. | |
| 5,939,598 | A | 8/1999 | Kucherlapati et al. | |
| 6,075,181 | A | 6/2000 | Kucherlapati et al. | |
| 6,150,584 | A | 11/2000 | Kucherlapati et al. | |
| 6,162,963 | A | 12/2000 | Kucherlapati et al. | |
| 6,586,251 | B2 | 7/2003 | Economides et al. | |
| 6,596,541 | B2 * | 7/2003 | Murphy et al. | 435/463 |
| 6,657,103 | B1 | 12/2003 | Kucherlapati et al. | |
| 6,673,986 | B1 | 1/2004 | Kucherlapati et al. | |
| 7,105,348 | B2 | 9/2006 | Murphy et al. | |
| 7,183,076 | B2 | 2/2007 | Arathoon et al. | |
| 7,501,552 | B2 | 3/2009 | Lonberg et al. | |
| 7,582,298 | B2 | 9/2009 | Stevens et al. | |
| 7,585,668 | B2 | 9/2009 | Buelow et al. | |
| 7,910,798 | B2 | 3/2011 | Tanamachi et al. | |
| 8,158,419 | B2 | 4/2012 | Lonberg et al. | |
| 8,502,018 | B2 | 8/2013 | Murphy et al. | |
| 8,642,835 | B2 | 2/2014 | Macdonald et al. | |
| 8,697,940 | B2 | 4/2014 | Macdonald et al. | |
| 8,754,287 | B2 | 6/2014 | Macdonald et al. | |

(Continued)

FOREIGN PATENT DOCUMENTS

| | | | |
|---|---|---|---|
| CN | 1203922 | A | 1/1999 |
| EP | 2003960 | B1 | 6/2015 |

(Continued)

OTHER PUBLICATIONS

Suarez et al, Molecular Immunology, 2006, 43:1827-1835.*
Tobin et al, Blood, 2004, 104:2879-2885.*
Paul, Fundamental Immunology, 3rd Edition, 1993, pp. 292-295, under the heading "Fv Structure and Diversity in Three Dimensions".*
Bendig, Methods: A Companion to Methods in Enzymology, 1995; 8:83-93.*
Sasso et al, J Clin Invest, 1996, 97:2074-2080.*
Widhopf II et al, Blood, 2004, 104:2499-2504.*
Moran, Nuala, "Mouse platforms jostle for slice of humanized antibody market," Nature Biotechnology, vol. 31(4): 267-268, 2013.

(Continued)

*Primary Examiner* — Valarie E Bertoglio
(74) *Attorney, Agent, or Firm* — Rita S. Wu; Elysa Goldberg; Ilona Gont

(57) ABSTRACT

Mice having a restricted immunoglobulin heavy chain locus are provided, wherein the locus is characterized by a single polymorphic human $V_H$ gene segment, a plurality of human $D_H$ gene segments and a plurality of $J_H$ gene segments. Methods for making antibody sequences that bind an antigen (e.g., a viral antigen) are provided, comprising immunizing a mouse with an antigen of interest, wherein the mouse comprises a single human $V_H$ gene segment, a plurality of human $D_H$ gene segments and a plurality of $J_H$ gene segments, at the endogenous immunoglobulin heavy chain locus.

24 Claims, 24 Drawing Sheets

Specification includes a Sequence Listing.

(56) References Cited

U.S. PATENT DOCUMENTS

| | | | |
|---|---|---|---|
| 2002/0106628 | A1 | 8/2002 | Economides et al. |
| 2002/0106629 | A1 | 8/2002 | Murphy et al. |
| 2003/0108925 | A1 | 6/2003 | Dix et al. |
| 2003/0109021 | A1 | 6/2003 | Wu et al. |
| 2004/0018626 | A1 | 1/2004 | Murphy et al. |
| 2006/0015957 | A1 | 1/2006 | Lonberg et al. |
| 2006/0015958 | A1 | 1/2006 | Kuroiwa et al. |
| 2006/0199204 | A1 | 9/2006 | Dix et al. |
| 2008/0267982 | A1 | 10/2008 | Kiselev et al. |
| 2009/0258392 | A1 | 10/2009 | Gallo et al. |
| 2010/0146647 | A1 | 6/2010 | Logtenberg et al. |
| 2011/0111406 | A1 | 5/2011 | Igawa et al. |
| 2011/0195454 | A1 | 8/2011 | McWhiter et al. |
| 2011/0236378 | A1 | 9/2011 | Green et al. |
| 2011/0314563 | A1 | 12/2011 | Craig et al. |
| 2012/0021409 | A1 | 1/2012 | McWhirter et al. |
| 2012/0047585 | A1 | 2/2012 | Rohrer et al. |
| 2012/0096572 | A1 | 4/2012 | Macdonald et al. |
| 2012/0167237 | A1 | 6/2012 | Bradley et al. |
| 2012/0204278 | A1 | 8/2012 | Bradley et al. |
| 2012/0272344 | A1 | 10/2012 | Tanamachi et al. |
| 2013/0096287 | A1 | 4/2013 | Macdonald et al. |
| 2013/0185821 | A1 | 7/2013 | Babb et al. |
| 2013/0198879 | A1 | 8/2013 | McWhirter et al. |
| 2013/0198880 | A1 | 8/2013 | Babb et al. |
| 2013/0243759 | A1 | 9/2013 | Friedrich et al. |
| 2013/0243773 | A1 | 9/2013 | Van Berkel et al. |
| 2013/0263292 | A1 | 10/2013 | Liang et al. |
| 2013/0323235 | A1 | 12/2013 | Craig et al. |
| 2013/0323791 | A1 | 12/2013 | MacDonald et al. |
| 2013/0333057 | A1 | 12/2013 | Macdonald et al. |
| 2014/0245468 | A1 | 8/2014 | McWhirter et al. |
| 2015/0020224 | A1 | 1/2015 | McWhirter et al. |
| 2015/0201589 | A1 | 7/2015 | Macdonald et al. |
| 2015/0210776 | A1 | 7/2015 | Macdonald et al. |
| 2015/0250152 | A1 | 9/2015 | Jakobovits et al. |
| 2016/0100561 | A1 | 4/2016 | McWhirter et al. |

FOREIGN PATENT DOCUMENTS

| | | | |
|---|---|---|---|
| KR | 1020050042792 | A | 5/2005 |
| WO | WO90/04036 | A1 | 4/1990 |
| WO | 1991/000906 | A1 | 1/1991 |
| WO | 1994/025585 | A1 | 11/1994 |
| WO | 1998/024893 | A2 | 6/1998 |
| WO | 2000/073323 | A2 | 12/2000 |
| WO | 2002/012437 | A2 | 2/2002 |
| WO | 2002/046237 | A2 | 6/2002 |
| WO | 2002/066630 | A1 | 8/2002 |
| WO | 2002/085944 | A2 | 10/2002 |
| WO | 2004/049794 | A2 | 6/2004 |
| WO | 2004/106375 | A1 | 12/2004 |
| WO | 2005/019463 | A1 | 3/2005 |
| WO | 2005/028510 | A2 | 3/2005 |
| WO | 2005/038001 | A2 | 4/2005 |
| WO | 2006/117699 | A2 | 11/2006 |
| WO | 2007/096779 | A2 | 8/2007 |
| WO | 2007/117410 | A2 | 10/2007 |
| WO | 2008/151081 | A1 | 12/2008 |
| WO | 2009/013620 | A2 | 1/2009 |
| WO | 2009/076464 | A2 | 6/2009 |
| WO | WO 2009/097006 | | 8/2009 |
| WO | WO-2009/097006 | A2 | 8/2009 |
| WO | 2009/143472 | A2 | 11/2009 |
| WO | WO-2010/039900 | A2 | 4/2010 |
| WO | WO-2011/004192 | A1 | 1/2011 |
| WO | 2011/072204 | A1 | 6/2011 |
| WO | WO-2011/158009 | A1 | 12/2011 |
| WO | WO-2012/063048 | A1 | 5/2012 |
| WO | WO-2012/141798 | A1 | 10/2012 |
| WO | 2012/148873 | A2 | 11/2012 |
| WO | WO-2013/022782 | A1 | 2/2013 |
| WO | WO-2013/041844 | A2 | 3/2013 |
| WO | WO-2013/041845 | A2 | 3/2013 |
| WO | WO-2013/041846 | A2 | 3/2013 |
| WO | 2013/059230 | A1 | 4/2013 |
| WO | WO-2013/045916 | A1 | 4/2013 |
| WO | 2013/061098 | A2 | 5/2013 |
| WO | WO-2013/061078 | A1 | 5/2013 |
| WO | 2013/079953 | A1 | 6/2013 |
| WO | 2013/138680 | A1 | 9/2013 |
| WO | 2013/144566 | A2 | 10/2013 |
| WO | 2013/144567 | A1 | 10/2013 |
| WO | 2013/171505 | A2 | 11/2013 |
| WO | 2013/187953 | A1 | 12/2013 |
| WO | 2014/130690 | A1 | 8/2014 |
| WO | 2014/160202 | A1 | 10/2014 |

OTHER PUBLICATIONS

Communication Relating to the Results of the Partial International Search for PCT/US2013/029624 (9 pages), dated May 17, 2013.
Featherstone K. et al., The mouse immunoglobulin heavy chain V-D intergenic sequence contains insulators that may regulate ordered V(D)J recombination, The Journal of Biological Chemistry, 285(13):9327-38 (2010).
Han C. et al., Comprehensive analysis of reproductive ADAMs: relationship of ADAM4 and ADAM6; with an ADAM complex required for fertilization in mice, Biology of Reproduction, 80(5):1001-8 (2009).
International Search Report for PCT/US2013/029624 (9 pages), dated Aug. 2, 2013.
Suarez et al., "Rearrangement of only one human IGHV gene is sufficient to generate a wide repertoire of antigen specific antibody responses in transgenic mice," Molecular Immunology, 43(11): 1827-1835, 2006.
Written Opinion for PCT/US2013/029624 (12 pages), dated Aug. 2, 2013.
Bruggemann et al. 1989. PNAS USA 86:6709-6713.
Berberian et al. 1991. Blood 78(1):175-179.
Muller et al. 1993. Scand. Journal of Immunology 38:327-334.
Sasso et al. 1993. Journal of Clinical Investigation 91:2358-2367.
Sasso et al. 1996. Journal of Clinical Investigation 97(9):2074-2080.
Johnson et al. 1997. Journal of Immunology 158:235-246.
Mahmoudi et al. 1997. Lupus 6:578-589.
Sibilia et al. 1997. Journal of Immunology 159:712-719.
Rodriguez et al. 2000. Nature Genetics 25:139-140.
Xu and Davis. 2000. Immunity 13:37-45.
Chan et al. 2001. Blood 91(4):1023-1026.
Mageed et al. 2001. Clin. Exp. Immunol. 123:1-8.
Bando et al. 2004. Immunology Letters 94:99-106.
Kunert et al. 2004. AIDS Research & Human Retroviruses 20(7):755-762.
Carbonari et al. 2005. Journal of Immunology 174:6352-6539.
Pos et al. 2008. Journal of Thrombosis & Haemostasis 7:421-428.
Sui et al. 2009. Nature Structural & Molecular Biology 16(3):265-273.
Wang & Palese. 2009. Nature Structural & Molecular Biology 16 (3):233-234.
Baseggio et al. 2010. Haematologica 95(4):604-612.
Perez et al. 2010. British Journal of Dermatology 162:611-618.
Charles et al. 2011. Journal of Immunol. Methods 363:210-220.
Souroujon et al. 1989. Journal of Immunology 143(2):706-711.
Sasso et al. 1990. Journal of Immunology 145(8):2751-2757.
Adderson et al. 1991. Journal of Immunology 147(5):1667-1674.
Yamada et al. 1991. Journal of Experimental Medicine 173:395-407.
Taylor et al. 1992. Nucleic Acids Research 20(23):6287-6295.
Adderson et al. 1993. Journal of Clinical Investigation 91:2734-2743.
Tuaillon et al. 1993. PNAS 90:3720-3724.
Wagner et al. 1994. Nucleic Acids Research 22(8):1389-1393.
Brezinschek et al. 1995. Journal of Immunology 155:190-202.
Davidkova et al. 1997. Scand. Journal of Immunology 45:62-73.
Miklos et al. 2000. Blood 95(12):3878-3884.
Bruggemann. 2001. Archivum Immunologiae et Therapiae Experimentalis 49:203-208.

(56) References Cited

OTHER PUBLICATIONS

Marasca et al. 2001. American Journal of Pathology 159(1):253-261.
Schelonka et al. 2005. Journal of Immunology 175:6624-6632.
Mahmoud et al. 2011. Journal of Immunology 187:879-886.
Huang and Stollar. 1993. Journal of Immunology 151(10):5290-5300.
Mortari et al. 1993. Journal of Immunology 150(4):1348-1357.
Suzuki et al. 1995. Journal of Immunology 154:3902-3911.
Kantor et al. 1997. Journal of Immunology 158:1175-1186.
De Wildt et al. 1999. Journal of Molecular Biology 285:895-901.
Lefranc, M. 2000. Current Protocols in Immunology. A.1P.1-A.1P.37.
Mageed et al., "Rearrangement of the human heavy chain variable region gene V3-23 in transgenic mice generates antibodies reactive with a range of antigens on the basis of $V_H$CDR3 and residues intrinsic to the heavy chain variable region," Clin Exp Immunol 123: 1-8, 2001.
Nadine Tuaillon, "Repertoire analysis in human immunoglobulin heavy chain minilocus transgenic, µMT/µMT mice," Molecular Immunology 37: 221-231, 2000.
Xu et al., "Diversity in the CDR3 Region of $V_H$ Is Sufficient for Most Antibody Specificities," Immunity, 13: 37-45, 2000.
Wagner et al., "The diversity of antigen-specific monoclonal antibodies from transgenic mice bearing human immunoglobulin gene miniloci," Eur. J. Immunol. 24: 2672-2681, 1994.
International Search Report for PCT/US2012/060487 filed Oct. 17, 2012 dated Feb. 1, 2013, 7 pages.
Written Opinion for PCT/US2012/060487 filed Oct. 17, 2012 dated Feb. 1, 2013, 5 pages.
Third Party Observations for European Patent Application No. 12783456.2 filed on Mar. 12, 2014.
Briney, B. S., et al., "Human Peripheral Blood Antibodies with Long HCDR3s Are Established Primarily at Original Recombination Using a Limited Subset of Germline Genes," *PLoS ONE*, 2012, vol. 7, Issue 5, pp. 1-13.
Chain, C. H., et al., "$V_H$I-69 gene is perferentially used by neptitis C virus-associated B cell lymphomas and by normal B cells responding to the E2 viral antigen," *Blood*, 2001, vol. 97, No. 4, pp. 1023-1026.
Chothia, C., et al., "Structural Repertoire of the Human $V_H$ Segments," *J. Mol. Biol.*, 1992, vol. 227, pp. 799-817.
Lonberg, N., "Human antibodies from transgenic animals," *Nature Biotechnology*, 2005, vol. 23, No. 9, pp. 1117-1125.
Matsuda, F., et al., "The Complete Nucleotide Sequence of the Human Immunoglobulin Heavy Chain Variable Region Locus," *J. Exp. Med.*, 1998, vol. 188, No. 11, pp. 2151-2162.
Romo-González, T. and Vargas-Madrazo, E., "Structural analysis of substitution patterns in alleles of human immunoglobulin VH genes," *Molecular Immunology*, 2005, vol. 42, pp. 1085-1097.
Clark, et al., (2003) "A future for transgenic livestock," Nature Reviews Genetics, 4:825-833.
Munoz et al., (2009) "Constraints to Progress in Embryonic Stem Cells from Domestic Species," Stem Cell Rev. and Rep, 5:6-9.
Niemann, et al., (2005) "Transgenic farm animals: present and future," Rev. sci tech Off. Int. Epiz., 24 (1), 285-298.
Prelle, et al., (2002) "Pluripotent Stem Cells—Model of Embryonic Development, Tools for Gene Targeting, and Basis of Cell Therapy," Anat. Histol. Embryol., 31:169-186.
Wagner, et al., (1996) "Antibody Expression from the Core Region of the Human IgH Locus Reconstructed in Transgenic Mice Using Bacteriophage P1 Clones," GENOMICS, 35:405-414.
Wheeler, et al., (2001) "Transgenic Technology and Applications in Swine," Theriogenology, 56:1345-1369.
International Search Report & Written Opinion with respect to PCT/US2014/17427 dated Aug. 1, 2014.
Choi, et al., "Characterization and comparative genomic analysis of intronless Adams with testicular gene expression," Genomics, 83(4):636-46 (2004) (Abstract Only).

Edwards, et al., (2008) "The ADAM metalloproteinases," Molecular Aspects of Medicine, 29(5):258-89.
Forconi, et al., (2010) "The normal IGHV1-69—derived B-cell repertoire contains stereotypic patterns of characteristic of unmutated CLL," Blood, vol. 115(1):71-77.
Giallourakis, et al., (2010) "Elements between the IgH variable (V) and diversity (D) clusters influence antisense transcription and lineage-specific V(D)J recombination," Proceedings of the National Academy of Sciences of the USA, 107(51):22207-12.
Hendricks, et al., (2010) "Organization of the variable region of the immunoglobulin heavy-chain gene locus of the rat," Immunogenetics, 62(7):479-86.
Kim, et al., "Expression and relationship of male reproductive ADAMs in mouse," Biology of Reproduction, 74(4):744-50 (2006).
Ray, (1991) "Ectopic expression of a c-kitW42 minigene in transgenic mice: recapitulation of W phenotypes and evidence for c-kit function in melanoblast progenitors," Genes Dev., 5(12A):2265-73.
Seals, et al., (2003) "The ADAMs family of metalloproteases: multidomain: proteins with multiple functions," Genes and Development, 17(1):7-30.
International Search Report & Written Opinion with respect to PCT/US2012/026416, dated Jun. 25, 2012.
PCT/US2013/029624 Invitation to Pay Additional Fees and Where Applicable, Protest Fee dated May 17, 2013, 9 pages.
Brüggemann (2004) "Human Monoclonal Antibodies from Translocus Mice," Molecular Biology of B Cells, Eds. Honjo, T. and Neuberger, M.S., New York, NY: Academic Press, pp. 547-561.
Defrancesco (1999) "Transgenic Mice that Produce Fully Humanized Antibodies—Abgenix Granted Patent," Bioprocess Online, 2 pages, Aug. 23, 1999.
Echelard, (2009) "Year of the ox," Nat. Biotechnol., 27(2):146-147.
Gallo et al. (2000) "The human immunoglobulin loci introduced into mice: V (D) and J gene segment usage similar to that of adult humans," Eur. J. Immunol., 30(2):534-540.
Genbank Accession AAA53514.1; GI:553403, 1 page, first referenced Jul. 30, 1993, updated Nov. 23, 1994.
Harding and Lonberg (1995) "Class switching in human immunoglobulin transgenic Mice," Ann. N Y Acad. Sci., 764:536-546.
Kuroiwa et al. (2002) "Cloned transchromosomic calves producing human immunoglobulin," Nat. Biotechnol., 20(9):889-894.
Mendez et al. (1997) "Functional Transplant of Megabase Human Immunoglobulin Loci Recapitulates Human Antibody Response in Mince," Nature 15:146-156.
Murphy (2014) Declaration Under 37 C.F.R. §1.132, 4 pages.
Murphy PowerPoint (2009) BAC-based Modifications of the Mouse Genome: The Big and the Backward, Welcome Trust Advanced Course: Genetic Manipulation of ES Cells, 58 pages.
Ramsden et al. (1994) "Conservation of sequence in recombination signal sequence spacers," Nucleic Acids Res., 22(10):1785-1796.
Taki et al. (1993) "Targeted Insertion of a Variable Region Gene into the Immunoglobuliin Heavy Chain Locus," Science, 262:1268-1271.
Timetable for Mouse ES Cells course at Wellcome Trust Sanger Institute Oct. 26, 2009-Nov. 8, 2009 (black and white).
Timetable for Mouse ES Cells course at Wellcome Trust Sanger Institute Oct. 26, 2009-Nov. 8, 2009 (greyscale).
UniProtKB/Swiss-Prot Accession No. P23083, HV103_Human, 7 pages, integrated into UniProtKB/Swiss-Prot Nov. 1, 1991, last modified Nov. 11, 2015, last accessed Dec. 9, 2015 <http://www.uniprot.org/P23083>.
EP1360287 Appeal Decision Mar. 10, 2016.
Non-Final Office Action dated Oct. 30, 2015 with Respect to U.S. Appl. No. 14/137,902.
*Regeneron v. Merus B.V.* Opinion and Order Nov. 2, 2015.
UK Decision EP1360287 and EP2264163 Feb. 1, 2016.
Statement of Relatedness under MPEP Jun. 2001 dated Jun. 16, 2016 with Respect to U.S. Appl. No. 13/653,456.
Amit and Itskovitz-Eldor (2009) "Embryonic Stem Cells: Isolation, Characterization and Culture," Adv. Biochem. Eng. Biotechnol., 114:173-184.
Astellas Negotiates $295M License Extension to Regeneron's VelocImmune mAb Platform, Genetic Engineering & Biotechnology News, Jul. 28, 2010, 2 pages.

(56) References Cited

OTHER PUBLICATIONS

Brouwers et al. (2015) "Unexpected Phenotypes in Mouse Models Carrying the Human Growth Hormone Minigene to Enhance Transgene Expression," Journal of Steroids & Hormonal Science, 6(2):1-2.
Brüggemann and Neuberger (1996) "Strategies for expressing human antibody repertoires in transgenic mice," Review Immunology Today, 192(17):391-397.
Butler, (1998) "Immunoglobulin diversity, B-cell and antibody repertoire development in large farm animals," Rev. Sco. Tech. Off. Int. Epiz., 17(1):43-70.
Cheval et al. (2012) Of Mice and Men: Divergence of Gene Expression Patterns in Kidney, PLoS One, 7(10): e46876 (12 pages).
Choi et al. (2011) "Expression of the metabotropic glutamate receptor 5 (mGluR5) induces melanoma in transgenic mice," PNAS, 108(37):15219-15224.
Slick and Pasternak (2002) Molekulyarnaya biotekhnologiya. Printsipy i primeneniye, Moscow Mir., 45-47, including English translation.
Hoiruchi and Blobel (2005) Studies from Adam Knockout Mice, in Hooper and Lendeckel, The Adam Family of proteases, Netherlands 2005, Springer (37 pages).
Kong et al. (2009) "Transgene expression is associated with copy number and cytomegalovirus promoter methylation in transgenic pigs," PLoS One 4(8):1-10.
Kuroiwa et al. (2004) "Sequential targeting of the genes encoding immunoglobulin-μ and prion protein in cattle," Nature Genetics, 36:775-780.
Lee et al. (2014) "Complete humanization of the mouse immunoglobulin loci enables efficient therapeutic antibody discovery," Nature Biotechnology, 32(4):356.
Lin et al. (1990) "Research of Immune Globulin in Mice," Guangzhou Medical Journal, 1:49-50, including English Translation.
Liu et al. (2014) "Primary Genetic Investigation of a Hyperlipidemia Model: Molecular Characteristics and Variants of the Apolipoprotein E Gene in Mongolian Gerbil;" Biomed. Research International, (9 pages).
Lovell-Badge (2007) "Many ways to pluripotency," Nature Biotechnology, 25:1114-1116.
MacDonald et al. (2006) "Velocigene Technology Extended to Humanization of Several Megabases of complex Gene Loci," First International MUGEN Conference of Animal Models for Human Immunological Disease, Sep. 10-13, 2006—Athens, Greece, Abstract 21 and Poster, 2 pages original (pp. 3-11 are p. 2 of the original, enlarged).
Manis et al. (2002) "Mechanism and control of class-switch recombination," TRENDS in Immunology, 23(1):31-39.
McGoldrick et al. (2013) "Rodent models of amyotrophic lateral sclerosis," Biochimica et Biophysica Acta, 1832:1421-1436.
Murphy and Silha (2000) "Unexpected and unexplained phenotypes in transgenic models," Growth Hormone & IGF Research, 10:233-235.
Nagle, Regeneron helps make Sanofi Veloclmmune to its "weak pipeline". <http://www.outsourcing-pharma.com> Published Dec. 3, 2007.
Osborn et al. (2013) "High-Affinity IgG Antibodies Develop Naturally in Ig-Knockout Rats Carrying Germline Human IgH/Igκ/Igλ Loci Bearing the Rat CH Region," J. Immunol., 190:1481-1490.
Pasqualini and Arap (2004) "Hybridoma-free generation of monoclonal antibodies," Proceedings of the National Academy of Sciences USA, 101(1):257-259.
Rudikoff et al. (1982) "Single amino acid substitution altering antigen-binding specificity," PNAS 79:1979-1983.
Schulze et al. (2006) "Derivation, Maintenance, and Characterization of Rat Embryonic Stem Cells in Vitro," Methods in Molecular Biology, 329:45-58.
Shmerling et al. (2005) "Strong and ubiquitous expression of transgenes targeted into the β-actin locus by Cre/lox cassette replacement," Genesis, 42(5):229-235.
Sigmund (2000) "Viewpoint: Are Studies in Genetically Altered Mice Out of Control?" Arterioscler. Thomb. Vasc. Biol., 20(6):1425-1429.
Stevens et al. (2006) "Velocimmune: Humanization of Immunoglobulin Loc Using Velocigene Technology," First International MUGEN Conference of Animal Models for Human Immunological Disease, Sep. 10-13, 2016—Athens, Greece, Abstract 4 and Poster, 2 pages original (pp. 3-11 are p. 2 of the original, enlarged).
Tong et al. (2010) "Production of p53 gene knockout rats by homologous recombination in embryonic stem cells," Nature Letters, 467:211-215.
Yantha et al. (2010) "Unexpected Acceleration of Type 1 Diabetes by Transgenic Expression of B7-H1 in NOD Mouse Peri-Islet Glia," Diabetes, 59:2588-2596.
Zou et al. (1994) Cre-IoxP-mediated gene replacement: a mouse strain producing humanized antibodies, Current Biology, 4:1099-1103.
Canadian Office Action for Application No. 2,820,824, 3 pages, dated Aug. 5, 2014.
Gay et al. (1993) "Receptor Editing: An Approach by Autoreactive B Cells to Escape Tolerance," J. Exp. Med., 177:999-1008.
Tiller et al. (2013) "A fully synthetic human Fab antibody library based on fixed VH/VL framework pairings with favorable biophysical properties," mAbs, 5(3):445-470 (http://www.tandfonline.com/loi/kmab20).
Extended European Search Report with respect to EP 14754019.9 dated Aug. 28, 2015.
Third Party Observations with Respect to European Patent Application No. EP12783456.2, EPO Communication submitted on Feb. 25, 2015.
Third Party Observations with Respect to European Patent Application No. EP12783456.2, EPO Communication submitted on Jun. 22, 2016.
Statement of Relatedness under MPEP Jun. 2001 dated Aug. 23, 2017 with Respect to U.S. Appl. No. 13/653,456.
Adkins et al. (2004) "Neonatal Adaptive Immunity Comes of Age," Nature Reviews Immunol., 4:553-564.
Dennis (2002) "Welfare issues of genetically modified animals," ILAR Journal, 43(2):100-109.
Zhou et al., (2009) "Developing tTA transgenic rats for inducible and reversible gene expression," International Journal of Biological Sciences, 5:171-181.
Statement of Relatedness under MPEP Jun. 2001 dated Sep. 25, 2017 with Respect to U.S. Appl. No. 13/653,456.
Austin et al. (2004) "The Knockout Mouse Project," Nature Genetics, 36(9):921-924.
Biao et al. (2013) "Human anitbody expression in transgenic rats: Comparison of chimeric IgH loci with human VH, D and JH but bearing different rat C-gene regions," Journal of Immunological Methods, 400:78-86.
Gorman et al. (1996) "The LGK 3' Enhancer Influences the Ratio of LGK Versus LGL B Lymphocytes," Immunity, 5(3):241-252.
Kenny, et al. (2000) Positive and negative selection of antigen-specific B cells in transgenic mice expressing variant forms of the VH1 (T15) heavy chain, International Immunology, 12(6):873-885.
MacDonald et al. (2014) "Precise and in situ genetic humanization of 6 Mb of mouse immunoglobulin genes," Proceedings of the National Academy of Sciences, 111(14):5147-5152.
Melton (2002) Chapter 8: Gene-Targeting Strategies, Methods in Molecular Biology, Transgenesis Techniques, 2nd Edition, Principles and Protocols, 180:19 pages.
Murphy et al. (2014) "Mice with megabase humanization of their immunoglobulin genes generate antibodies as efficiently as normal mice," Proceedings of the National Academy of Sciences, 111(14):5153-5158.
Popov et al. (1999) "A Human Immunoglobulin lambda locus is Similarly Well Expressed in Mice and Humans," J. Exp. Med., 189(10):1611-1619.
Poueymirou et al (2007) "F0 generation mice fully derived from gene-targeted embryonic stem cells allowing immediate phenotypic analyses," Nat Biotechnol., 25, 91-99.

(56) References Cited

OTHER PUBLICATIONS

Roebroek et al. (2003) "Chapter 10: Knockin Approaches," Methods in Molecular Biology, Transgenic Mouse Methods and Protocols, 209:16 pages.
Schwartz and Cantor (1984) "Separation of Yeast Chromosome-Sized DNAs by Pulsed Field Gradient Gel Electrophoresis," Cell, 37:67-75.
Sorrell and Kolb (2004) "Chapter XI: Targeted Modification of Mammalian Genomes," Focus on Genome Research, 6 pages.
Storb et al. (1986) "Transgenic Mice with μ and κ Genes Encoding Antiphosphorycholine Antibodies," J. Exp. Med., 164:627-664.
Valenzuela et al (2003) "High-throughput engineering of the mouse genome coupled with high-resolution expression analysis," Nat. Biotechnol., 21:652-659.
Vakil et al. (1991) "Antigen-Independent Selection of T15 Idotype During B-Cell Ontogeny in Mice," Developmental Immunology, 1:203-212.
Zhang et al. (1998) "A new logic for DNA engineering using recombination in *Escherichia coli*," Nature Genetics, 20:123-138.
Extended European Search Report with respect to EP 18158956.5 dated Jun. 8, 2018.
Statement of Relatedness under MPEP 2001.06 dated Sep. 21, 2018 with Respect to U.S. Appl. No. 13/653,456.
Office Action issued in U.S. Appl. No. 14/185,679, dated Dec. 1, 2017.

* cited by examiner

```
                    10        20        30        40        50        60        70
VH1-69*01 CAGGTgCAGCTGGTGCAGTCTGGGGCTGAGGTGAAGAAGCCTGGGTCCTCGGTGAAGGTCTCCTGCAAGGCTTCT
VH1-69*02 CAGGTCCAGCTGGTGCAaTCTGGGGCTGAGGTGAAGAAGCCTGGGTCCTCGGTGAAGGTCTCCTGCAAGGCTTCT
VH1-69*03 CAGGTgCAGCTGGTGCAGTCTGGGGCTGAGGTGAAGAAGCCTGGGTCCTCGGTGAAGGTCTCCTGCAAGGCTTCT
VH1-69*04 CAGGTCCAGCTGGTGCAGTCTGGGGCTGAGGTGAAGAAGCCTGGGTCCTCGGTGAAGGTCTCCTGCAAGGCTTCT
VH1-69*05 CAGGTCCAGCTGGTGCAGTCTGGGGCTGAGGTGAAGAAGCCTGGGTCCTCGGTGAAGGTCTCCTGCAAGGCTTCT
VH1-69*06 CAGGTgCAGCTGGTGCAGTCTGGGGCTGAGGTGAAGAAGCCTGGGTCCTCGGTGAAGGTCTCCTGCAAGGCTTCT
VH1-69*07 ----------------------------------AGAAGCCTGGGTCCTCGGTGAAGGTCTCCTGCAAGGCTTCT
VH1-69*08 CAGGTCCAGCTGGTGCAaTCTGGGGCTGAGGTGAAGAAGCCTGGGTCCTCGGTGAAGGTCTCCTGCAAGGCTTCT
VH1-69*09 CAGGTgCAGCTGGTGCAGTCTGGGGCTGAGGTGAAGAAGCCTGGGTCCTCGGTGAAGGTCTCCTGCAAGGCTTCT
VH1-69*10 CAGGTCCAGCTGGTGCAGTCTGGGGCTGAGGTGAAGAAGCCTGGGTCCTCaGTGAAGGTCTCCTGCAAGGCTTCT
VH1-69*11 CAGGTCCAGCTGGTGCAGTCTGGGGCTGAGGTGAAGAAGCCTGGGTCCTCGGTGAAGGTCTCCTGCAAGGCTTCT
VH1-69*12 CAGGTCCAGCTGGTGCAGTCTGGGGCTGAGGTGAAGAAGCCTGGGTCCTCGGTGAAGGTCTCCTGCAAGGCTTCT
VH1-69*13 CAGGTCCAGCTGGTGCAGTCTGGGGCTGAGGTGAAGAAGCCTGGGTCCTCaGTGAAGGTCTCCTGCAAGGCTTCT
          CAGGTCCAGCTGGTGCAGTCTGGGGCTGAGGTGAAGAAGCCTGGGTCCTCGGTGAAGGTCTCCTGCAAGGCTTCT

              80        90       100       110       120       130       140       150
VH1-69*01 GGAGGCACCTTCAGCAGCTATGCTATCAGCTGGGTGCGACAGGCCCCTGGACAAGGGCTTGAGTGGATGGGAGGG
VH1-69*02 GGAGGCACCTTCAGCAGCTATaCTATCAGCTGGGTGCGACAGGCCCCTGGACAAGGGCTTGAGTGGATGGGAaGG
VH1-69*03 GGAGGCACCTTCAGCAGCTATGCTATCAGCTGGGTGCGACAGGCCCCTGGACAAGGGCTTGAGTGGATGGGAGGG
VH1-69*04 GGAGGCACCTTCAGCAGCTATGCTATCAGCTGGGTGCGACAGGCCCCTGGACAAGGGCTTGAGTGGATGGGAaGG
VH1-69*05 GGAGGCACCTTCAGCAGCTATGCTATCAGCTGGGTGCGACAGGCCCCTGGACAAGGGCTTGAGTGGATGGGAGGG
VH1-69*06 GGAGGCACCTTCAGCAGCTATGCTATCAGCTGGGTGCGACAGGCCCCTGGACAAGGGCTTGAGTGGATGGGAGGG
VH1-69*07 GGAGGCACCTTCAGCAGCTATGCTATCAGCTGGGTGCGACAGGCCCCTGGACAAGGGCTTGAGTGGATGGGAaGG
VH1-69*08 GGAGGCACCTTCAGCAGCTATaCTATCAGCTGGGTGCGACAGGCCCCTGGACAAGGGCTTGAGTGGATGGGAaGG
VH1-69*09 GGAGGCACCTTCAGCAGCTATGCTATCAGCTGGGTGCGACAGGCCCCTGGACAAGGGCTTGAGTGGATGGGAaGG
VH1-69*10 GGAGGCACCTTCAGCAGCTATGCTATCAGCTGGGTGCGACAGGCCCCTGGACAAGGGCTTGAGTGGATGGGAGGG
VH1-69*11 GGAGGCACCTTCAGCAGCTATGCTATCAGCTGGGTGCGACAGGCCCCTGGACAAGGGCTTGAGTGGATGGGAaGG
VH1-69*12 GGAGGCACCTTCAGCAGCTATGCTATCAGCTGGGTGCGACAGGCCCCTGGACAAGGGCTTGAGTGGATGGGAGGG
VH1-69*13 GGAGGCACCTTCAGCAGCTATGCTATCAGCTGGGTGCGACAGGCCCCTGGACAAGGGCTTGAGTGGATGGGAGGG
          GGAGGCACCTTCAGCAGCTATGCTATCAGCTGGGTGCGACAGGCCCCTGGACAAGGGCTTGAGTGGATGGGAGGG

                    160       170       180       190       200       210       220
VH1-69*01 ATCATCCCTATCTTTGGTACAGCAAACTACGCACAGAAGTTCCAGGGCAGAGTCACGATTACCGCGGACGAATCC
VH1-69*02 ATCATCCCTATCcTTGGTAtAGCAAACTACGCACAGAAGTTCCAGGGCAGAGTCACGATTACCGCGGACaAATCC
VH1-69*03 ATCATCCCTATCTTTGGTACAGCAAACTACGCACAGAAGTTCCAGGGCAGAGTCACGATTACCGCGGACGAATCC
VH1-69*04 ATCATCCCTATCcTTGGTAtAGCAAACTACGCACAGAAGTTCCAGGGCAGAGTCACGATTACCGCGGACaAATCC
VH1-69*05 ATCATCCCTATCTTTGGTACAGCAAACTACGCACAGAAGTTCCAGGGCAGAGTCACGATTACCaCGGACGAATCC
VH1-69*06 ATCATCCCTATCTTTGGTACAGCAAACTACGCACAGAAGTTCCAGGGCAGAGTCACGATTACCGCGGACaAATCC
VH1-69*07 ATCATCCCTATCTTTGGTACAGCAAACTACGCACAGAAGTTCCAGGGCAGAGTCACGATTACCGCGGACGAATCC
VH1-69*08 ATCATCCCTATCcTTGGTACAGCAAACTACGCACAGAAGTTCCAGGGCAGAGTCACGATTACCGCGGACaAATCC
VH1-69*09 ATCATCCCTATCcTTGGTAtAGCAAACTACGCACAGAAGTTCCAGGGCAGAGTCACGATTACCGCGGACaAATCC
VH1-69*10 ATCATCCCTATCcTTGGTAtAGCAAACTACGCACAGAAGTTCCAGGGCAGAGTCACGATTACCGCGGACaAATCC
VH1-69*11 ATCATCCCTATCcTTGGTACAGCAAACTACGCACAGAAGTTCCAGGGCAGAGTCACGATTACCGCGGACGAATCC
VH1-69*12 ATCATCCCTATCTTTGGTACAGCAAACTACGCACAGAAGTTCCAGGGCAGAGTCACGATTACCGCGGACGAATCC
VH1-69*13 ATCATCCCTATCTTTGGTACAGCAAACTACGCACAGAAGTTCCAGGGCAGAGTCACGATTACCGCGGACGAATCC
          ATCATCCCTATCTTTGGTACAGCAAACTACGCACAGAAGTTCCAGGGCAGAGTCACGATTACCGCGGACGAATCC

            230       240       250       260       270       280       290
VH1-69*01 ACGAGCACAGCCTACATGGAGCTGAGCAGCCTGAGATCTGAGGACACGGCCGTGTATTACTGTGCGAGAGAA
VH1-69*02 ACGAGCACAGCCTACATGGAGCTGAGCAGCCTGAGATCTGAGGACACGGCCGTGTATTACTGTGCGAGA---
VH1-69*03 ACGAGCACAGCCTACATGGAGCTGAGCAGCCTGAGATCTGAtGACACGGC----------------------
VH1-69*04 ACGAGCACAGCCTACATGGAGCTGAGCAGCCTGAGATCTGAGGACACGGCCGTGTATTACTGTGCGAGAGAA
VH1-69*05 ACGAGCACAGCCTACATGGAGCTGAGCAGCCTGAGATCTGAGGACACGGCCGTGTATTACTGTGCGAGA---
VH1-69*06 ACGAGCACAGCCTACATGGAGCTGAGCAGCCTGAGATCTGAGGACACGGCCGTGTATTACTGTGCGAGAGAA
VH1-69*07 ACGAGCACAGCCTACATGGAGCTGAGCAGCCTGAGATCTGAG------------------------------
VH1-69*08 ACGAGCACAGCCTACATGGAGCTGAGCAGCCTGAGATCTGAGGACACGGCCGTGTATTACTGTGCGAGAGAA
VH1-69*09 ACGAGCACAGCCTACATGGAGCTGAGCAGCCTGAGATCTGAGGACACGGCCGTGTATTACTGTGCGAGAGAA
VH1-69*10 ACGAGCACAGCCTACATGGAGCTGAGCAGCCTGAGATCTGAGGACACGGCCGTGTATTACTGTGCGAGAGAA
VH1-69*11 ACGAGCACAGCCTACATGGAGCTGAGCAGCCTGAGATCTGAGGACACGGCCGTGTATTACTGTGCGAGAGAA
VH1-69*12 ACGAGCACAGCCTACATGGAGCTGAGCAGCCTGAGATCTGAGGACACGGCCGTGTATTACTGTGCGAGAGAA
VH1-69*13 ACGAGCACAGCCTACATGGAGCTGAGCAGCCTGAGATCTGAGGACACGGCCGTGTATTACTGTGCGAGAGAA
          ACGAGCACAGCCTACATGGAGCTGAGCAGCCTGAGATCTGAGGACACGGCCGTGTATTACTGTGCGAGAGA
```

FIG. 13

```
                     10         20         30         40         50         60
VH1-69*01 QVQLVQSGAEVKKPGSSVKVSCKASGGTFSSYAISWVRQAPGQGLEWMGGIIPIFGTANY
VH1-69*02 QVQLVQSGAEVKKPGSSVKVSCKASGGTFSSYtISWVRQAPGQGLEWMGrIIPIlGiANY
VH1-69*03 QVQLVQSGAEVKKPGSSVKVSCKASGGTFSSYAISWVRQAPGQGLEWMGGIIPIFGTANY
VH1-69*04 QVQLVQSGAEVKKPGSSVKVSCKASGGTFSSYAISWVRQAPGQGLEWMGrIIPIlGiANY
VH1-69*05 QVQLVQSGAEVKKPGSSVKVSCKASGGTFSSYAISWVRQAPGQGLEWMGGIIPIFGTANY
VH1-69*06 QVQLVQSGAEVKKPGSSVKVSCKASGGTFSSYAISWVRQAPGQGLEWMGGIIPIFGTANY
VH1-69*07 ------------KPGSSVKVSCKASGGTFSSYAISWVRQAPGQGLEWMGrIIPIFGTANY
VH1-69*08 QVQLVQSGAEVKKPGSSVKVSCKASGGTFSSYtISWVRQAPGQGLEWMGrIIPIlGTANY
VH1-69*09 QVQLVQSGAEVKKPGSSVKVSCKASGGTFSSYAISWVRQAPGQGLEWMGrIIPIlGiANY
VH1-69*10 QVQLVQSGAEVKKPGSSVKVSCKASGGTFSSYAISWVRQAPGQGLEWMGGIIPIlGiANY
VH1-69*11 QVQLVQSGAEVKKPGSSVKVSCKASGGTFSSYAISWVRQAPGQGLEWMGrIIPIlGTANY
VH1-69*12 QVQLVQSGAEVKKPGSSVKVSCKASGGTFSSYAISWVRQAPGQGLEWMGGIIPIFGTANY
VH1-69*13 QVQLVQSGAEVKKPGSSVKVSCKASGGTFSSYAISWVRQAPGQGLEWMGGIIPIFGTANY
          QVQLVQSGAEVKKPGSSVKVSCKASGGTFSSYAISWVRQAPGQGLEWMGGIIPIFGTANY

                     70         80         90        100
VH1-69*01 AQKFQGRVTITADESTSTAYMELSSLRSEDTAVYYCARR
VH1-69*02 AQKFQGRVTITADkSTSTAYMELSSLRSEDTAVYYCARR
VH1-69*03 AQKFQGRVTITADESTSTAYMELSSLRSDDT--------
VH1-69*04 AQKFQGRVTITADkSTSTAYMELSSLRSEDTAVYYCARR
VH1-69*05 AQKFQGRVTITtDESTSTAYMELSSLRSEDTAVYYCARR
VH1-69*06 AQKFQGRVTITADkSTSTAYMELSSLRSEDTAVYYCARR
VH1-69*07 AQKFQGRVTITADESTSTAYMELSSLRSE----------
VH1-69*08 AQKFQGRVTITADkSTSTAYMELSSLRSEDTAVYYCARR
VH1-69*09 AQKFQGRVTITADkSTSTAYMELSSLRSEDTAVYYCARR
VH1-69*10 AQKFQGRVTITADkSTSTAYMELSSLRSEDTAVYYCARR
VH1-69*11 AQKFQGRVTITADESTSTAYMELSSLRSEDTAVYYCARR
VH1-69*12 AQKFQGRVTITADESTSTAYMELSSLRSEDTAVYYCARR
VH1-69*13 AQKFQGRVTITADESTSTAYMELSSLRSEDTAVYYCARR
          AQKFQGRVTITADESTSTAYMELSSLRSEDTAVYYCAR
```

FIG. 14

% Identity

| $V_H$1-69 Allele | $V_H$1-69 Allele | | | | | | | | | | | | |
|---|---|---|---|---|---|---|---|---|---|---|---|---|---|
| | 01 | 02 | 03 | 04 | 05 | 06 | 07 | 08 | 09 | 10 | 11 | 12 | 13 |
| 01 | 100 | 94.9 | 91.8 | 95.9 | 99 | 99 | 77.6 | 95.9 | 95.9 | 96.9 | 98 | 100 | 100 |
| 02 | 95.9 | 100 | 86.7 | 99 | 93.9 | 95.9 | 74.5 | 99 | 99 | 98 | 96.9 | 94.9 | 94.9 |
| 03 | 92.9 | 88.8 | 100 | 87.8 | 90.8 | 90.8 | 82.4 | 87.8 | 87.8 | 88.8 | 89.8 | 91.8 | 91.8 |
| 04 | 95.9 | 100 | 88.8 | 100 | 94.9 | 96.9 | 75.5 | 98 | 100 | 99 | 98 | 95.9 | 95.9 |
| 05 | 100 | 95.9 | 92.9 | 95.9 | 100 | 98 | 76.5 | 94.9 | 94.9 | 95.9 | 96.9 | 99 | 99 |
| 06 | 99.0 | 96.9 | 91.8 | 96.9 | 99 | 100 | 76.5 | 96.9 | 96.9 | 98 | 96.9 | 99 | 99 |
| 07 | 77.6 | 75.5 | 83.5 | 75.5 | 77.6 | 76.5 | 100 | 75.5 | 75.5 | 74.5 | 77.6 | 77.6 | 77.6 |
| 08 | 96.9 | 99 | 89.8 | 99 | 96.9 | 98 | 76.5 | 100 | 98 | 96.9 | 98 | 95.9 | 95.9 |
| 09 | 95.9 | 100 | 88.8 | 100 | 95.9 | 96.9 | 75.5 | 99 | 100 | 99 | 98 | 95.9 | 95.9 |
| 10 | 96.9 | 99 | 89.8 | 99 | 96.9 | 98 | 74.5 | 98 | 99 | 100 | 96.9 | 96.9 | 96.9 |
| 11 | 98 | 98 | 90.8 | 98 | 98 | 96.9 | 77.6 | 99 | 98 | 96.9 | 100 | 98 | 98 |
| 12 | 100 | 95.9 | 92.9 | 95.9 | 100 | 99 | 77.6 | 96.9 | 95.9 | 96.9 | 98 | 100 | 100 |
| 13 | 100 | 95.9 | 92.9 | 95.9 | 100 | 99.0 | 77.6 | 96.9 | 95.9 | 96.9 | 98 | 100 | 100 |

% Similarity

FIG. 15

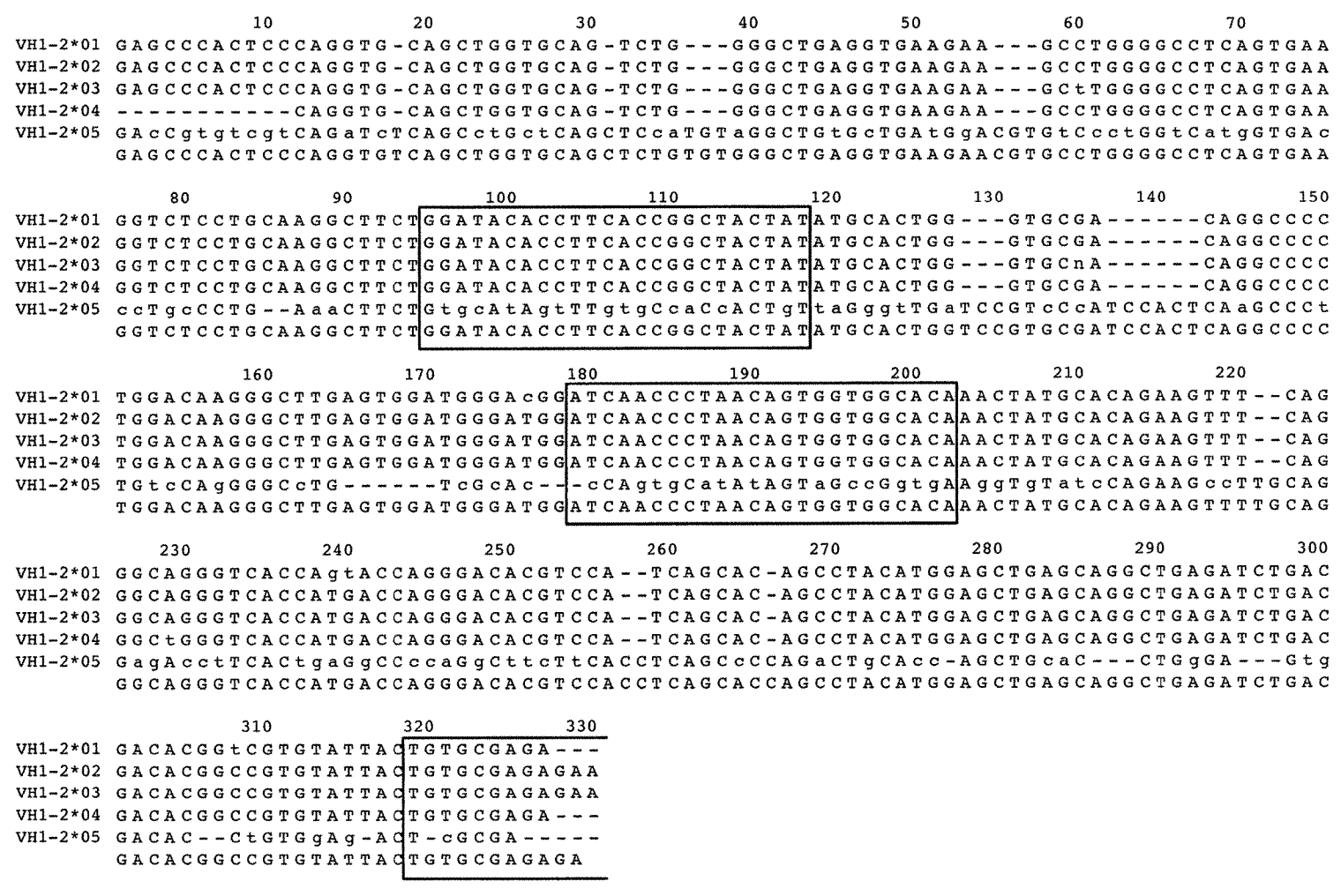

```
                  10        20        30        40        50        60        70
VH1-2*01 GAGCCCACTCCCAGGTG-CAGCTGGTGCAG-TCTG---GGGCTGAGGTGAAGAA---GCCTGGGGCCTCAGTGAA
VH1-2*02 GAGCCCACTCCCAGGTG-CAGCTGGTGCAG-TCTG---GGGCTGAGGTGAAGAA---GCCTGGGGCCTCAGTGAA
VH1-2*03 GAGCCCACTCCCAGGTG-CAGCTGGTGCAG-TCTG---GGGCTGAGGTGAAGAA---GCtTGGGGCCTCAGTGAA
VH1-2*04 -----------CAGGTG-CAGCTGGTGCAG-TCTG---GGGCTGAGGTGAAGAA---GCCTGGGGCCTCAGTGAA
VH1-2*05 GAcCgtgtcgtCAGaTcTCAGCctGctCAGCTCcaTGTaGGCTGtGcTGAtGgACGTGtCcctGGtCatgGTGAc
         GAGCCCACTCCCAGGTGTCAGCTGGTGCAGCTCTGTGTGGGCTGAGGTGAAGAACGTGCCTGGGGCCTCAGTGAA

              80        90       100       110       120       130       140       150
VH1-2*01 GGTCTCCTGCAAGGCTTCTGGATACACCTTCACCGGCTACTATATGCACTGG---GTGCGA------CAGGCCCC
VH1-2*02 GGTCTCCTGCAAGGCTTCTGGATACACCTTCACCGGCTACTATATGCACTGG---GTGCGA------CAGGCCCC
VH1-2*03 GGTCTCCTGCAAGGCTTCTGGATACACCTTCACCGGCTACTATATGCACTGG---GTGCnA------CAGGCCCC
VH1-2*04 GGTCTCCTGCAAGGCTTCTGGATACACCTTCACCGGCTACTATATGCACTGG---GTGCGA------CAGGCCCC
VH1-2*05 ccTgcCCTG--AaaCTTCTGtgcAtAgtTTgtgCcaCcACTgTtaGggtTGaTCCGTcCcATCCACTCAaGCCCt
         GGTCTCCTGCAAGGCTTCTGGATACACCTTCACCGGCTACTATATGCACTGGTCCGTGCGATCCACTCAGGCCCC

                  160       170       180       190       200       210       220
VH1-2*01 TGGACAAGGGCTTGAGTGGATGGGAcGGATCAACCCTAACAGTGGTGGCACAAACTATGCACAGAAGTTT--CAG
VH1-2*02 TGGACAAGGGCTTGAGTGGATGGGATGGATCAACCCTAACAGTGGTGGCACAAACTATGCACAGAAGTTT--CAG
VH1-2*03 TGGACAAGGGCTTGAGTGGATGGGATGGATCAACCCTAACAGTGGTGGCACAAACTATGCACAGAAGTTT--CAG
VH1-2*04 TGGACAAGGGCTTGAGTGGATGGGATGGATCAACCCTAACAGTGGTGGCACAAACTATGCACAGAAGTTT--CAG
VH1-2*05 TGtcCAgGGGCcTG------TcGcAc---cCAgtgCatAtAGTaGccGgtgAAggTgTatcCAGAAGccTTGCAG
         TGGACAAGGGCTTGAGTGGATGGGATGGATCAACCCTAACAGTGGTGGCACAAACTATGCACAGAAGTTTTGCAG

           230       240       250       260       270       280       290       300
VH1-2*01 GGCAGGGTCACCAgtACCAGGGACACGTCCA--TCAGCAC-AGCCTACATGGAGCTGAGCAGGCTGAGATCTGAC
VH1-2*02 GGCAGGGTCACCATGACCAGGGACACGTCCA--TCAGCAC-AGCCTACATGGAGCTGAGCAGGCTGAGATCTGAC
VH1-2*03 GGCAGGGTCACCATGACCAGGGACACGTCCA--TCAGCAC-AGCCTACATGGAGCTGAGCAGGCTGAGATCTGAC
VH1-2*04 GGCtGGGTCACCATGACCAGGGACACGTCCA--TCAGCAC-AGCCTACATGGAGCTGAGCAGGCTGAGATCTGAC
VH1-2*05 GagAcctTCACtgaGgCCcaGgCttcTtCACCTCAGCcCCAGaCTgCAcc-AGCTGcaC---CTGgGA---Gtg
         GGCAGGGTCACCATGACCAGGGACACGTCCACCTCAGCACCAGCCTACATGGAGCTGAGCAGGCTGAGATCTGAC

                  310       320       330
VH1-2*01 GACACGGtCGTGTATTACTGTGCGAGA---
VH1-2*02 GACACGGCCGTGTATTACTGTGCGAGAGAA
VH1-2*03 GACACGGCCGTGTATTACTGTGCGAGAGAA
VH1-2*04 GACACGGCCGTGTATTACTGTGCGAGA---
VH1-2*05 GACAC--CtGTGgAg-ACT-cGCGA-----
         GACACGGCCGTGTATTACTGTGCGAGAGA
```

FIG. 16

```
                                 10        20        30        40        50
VH1-2*01 QVQLVQSGAEVKKPGASVKVSCKASGYTFTGYYMHWVRQAPGQGLEWMGr
VH1-2*02 QVQLVQSGAEVKKPGASVKVSCKASGYTFTGYYMHWVRQAPGQGLEWMGW
VH1-2*03 QVQLVQSGAEVKKlGASVKVSCKASGYTFTGYYMHWVxQAPGQGLEWMGW
VH1-2*04 QVQLVQSGAEVKKPGASVKVSCKASGYTFTGYYMHWVRQAPGQGLEWMGW
VH1-2*05 QVQLVQSGAEVKKPGASVKVSCKASGYTFTGYYMHWVRQAPGQGLEWMGr
         QVQLVQSGAEVKKPGASVKVSCKASGYTFTGYYMHWVRQAPGQGLEWMGW

                 60        70        80        90
VH1-2*01 INPNSGGTNYAQKFQGRVTsTRDTSISTAYMELSRLRSDDTVVYYCAR
VH1-2*02 INPNSGGTNYAQKFQGRVTMTRDTSISTAYMELSRLRSDDTAVYYCAR
VH1-2*03 INPNSGGTNYAQKFQGRVTMTRDTSISTAYMELSRLRSDDTAVYYCAR
VH1-2*04 INPNSGGTNYAQKFQGwVTMTRDTSISTAYMELSRLRSDDTAVYYCAR
VH1-2*05 INPNSGGTNYAQKFQGRVTMTRDTSISTAYMELSRLRSDDTVVYYCAR
         INPNSGGTNYAQKFQGRVTMTRDTSISTAYMELSRLRSDDTAVYYCAR
```

FIG. 17

% Identity

| $V_H1$-2 Allele | $V_H1$-2 Allele 01 | 02 | 03 | 04 | 05 |
|---|---|---|---|---|---|
| 01 | 100 | 96.9 | 94.9 | 95.9 | 99.0 |
| 02 | 96.9 | 100 | 98.0 | 99.0 | 98.0 |
| 03 | 94.9 | 98.0 | 100 | 96.9 | 95.9 |
| 04 | 95.9 | 99.0 | 96.9 | 100 | 96.9 |
| 05 | 99.0 | 98.0 | 95.9 | 96.9 | 100 |

% Similarity

FIG. 18

SEQUENCE LISTING

```
<160> NUMBER OF SEQ ID NOS: 81

<210> SEQ ID NO 1
<211> LENGTH: 872
<212> TYPE: DNA
<213> ORGANISM: Homo sapiens
<220> FEATURE:
<223> OTHER INFORMATION: synthetic

<400> SEQUENCE: 1

gcaggattta gggcttggtc tctcagcatc ccacacttgt acagctgatg tggcatctgt      60

gttttctttc tcatcgtaga tcaggctttg agctgtgaaa taccctgcct catgcatatg     120

caaataacct gaggtcttct gagataaata tagatatatt ggtgccctga gagcatcaca     180

taacaaccac attcctcctc taaagaagcc cctgggagca cagctcatca ccatggactg     240

gacctggagg ttcctctttg tggtggcagc agctacaggt aaggggcttc ctagtcctaa     300

ggctgaggaa gggatcctgg tttagttaaa gaggatttta ttcacccctg tgtcctctcc     360

acaggtgtcc agtcccaggt gcagctggtg cagtctgggg ctgaggtgaa gaagcctggg     420
```

-continued

```
tcctcggtga aggtctcctg caaggcttct ggaggcacct tcagcagcta tgctatcagc    480

tgggtgcgac aggcccctgg acaagggctt gagtggatgg gagggatcat ccctatcttt    540

ggtacagcaa actacgcaca gaagttccag ggcagagtca cgattaccgc ggacgaatcc    600

acgagcacag cctacatgga gctgagcagc ctgagatctg aggacacggc cgtgtattac    660

tgtgcgagag acacagtgtg aaaacccaca tcctgagagt gtcagaaacc ctgagggaga    720

aggcagctgt gccgggctga ggagatgaca gggtttatta ggtttaaggc tgtttacaaa    780

atgggttata tatttgagaa aaaaagaaca gtagaaacaa gtacatactc ctctaatttt    840

aagataatta ttccattcaa gagtcgtaat at                                  872


<210> SEQ ID NO 2
<211> LENGTH: 118
<212> TYPE: PRT
<213> ORGANISM: Homo sapiens
<220> FEATURE:
<223> OTHER INFORMATION: synthetic

<400> SEQUENCE: 2

Met Asp Trp Thr Trp Arg Phe Leu Phe Val Val Ala Ala Ala Thr Gly
1               5                   10                  15

Gly Val Gln Ser Gln Val Gln Leu Val Gln Ser Gly Ala Glu Val Lys
            20                  25                  30

Lys Pro Gly Ser Ser Val Lys Val Ser Cys Lys Ala Ser Gly Gly Thr
        35                  40                  45

Phe Ser Ser Tyr Ala Ile Ser Trp Val Arg Gln Ala Pro Gly Gln Gly
    50                  55                  60

Leu Glu Trp Met Gly Gly Ile Ile Pro Ile Phe Gly Thr Ala Asn Tyr
65                  70                  75                  80

Ala Gln Lys Phe Gln Gly Arg Val Thr Ile Thr Ala Asp Glu Ser Thr
                85                  90                  95

Ser Thr Ala Tyr Met Glu Leu Ser Ser Leu Arg Ser Glu Asp Thr Ala
            100                 105                 110

Val Tyr Tyr Cys Ala Arg
        115


<210> SEQ ID NO 3
<211> LENGTH: 99294
<212> TYPE: DNA
<213> ORGANISM: Artificial Sequence
<220> FEATURE:
<223> OTHER INFORMATION: synthetic

<400> SEQUENCE: 3

aagcttatct ctctgttgct cagactcatc taggaatttc agaaatttct gttctagcat     60

ctcttccagc ttttgtctcc aaccctcatt ctcttctttc ttttttttt taaattatat    120

gttctctgtc tttttaaaaa actttttaaa attaggtatt tatgtcattt acatttccaa    180

tgctatccca aaagtcccac ccacgctccc caacccacta tcccacccac ccactcccac    240

ttcttggccc tggcattcac agtgtactga gacatataaa gtttgcacaa ccaatgggcc    300

tctctttcca ctgatggccg actaggccat cttctgatac atatgcagct agagacacga    360

gattctgggg gtactggtta gttcatattg ttgttccacc tatagggttg cagatccttt    420

tagctccttg ggtactttct ctagctcctc cattgggggc cctgtgatcc atccaatagc    480

tgactgtgag catccacttc tgtgtttgct aggccccaga tagtctcaca agagacagct    540
```

-continued

```
atatctgggt cctttcagca aaatcttgct agtgtatgca acggtgtcag agtttggaag    600

ctgattatgg gatggatccc cggatatggc attctctagt tggttcatcc ttttgtctca    660

gctccaaact ttgtctctgt aactccttcc atgggtgttt tgttcccagt tctaaggagg    720

ggcaaagtat ccacactttg gtcttcattc ttcttgagtt tcatgtgttt tgcaaattgt    780

atcttatatc ttgggtattc taagtttctg ggctaatatc cacttatcag tgagtacaca    840

ttgtgtgagt tcttttgtga ttgggttacc tcactcagta tgatgccctc caggtccatc    900

catttgccta ggaatttcat aaattcattc tttttaatag ctcagtagta ctccattgtg    960

tagatgtacc acattttctg tattcattcc tctgttgagg ggcatctggg ttctttccag   1020

cttctggcta ttataaataa ggctgctatg aacatagtgg agcatgtgac cttcttaccg   1080

gttgggacat cttctggata tatgcccagg agaggtattg ctggatcttc cggtagtact   1140

atgtccaatt ttctgaggaa ctgacaaact gatttccaga gtggttagta ccagcttgca   1200

atcccaccaa caatgagagg agtgttcgtc tttctccaca tcctcaccag catgctgctg   1260

tcacctgaat ttttgatgct tagccattct gactggtgtg aggtggaatc tcagggttgt   1320

tttgatttgt atttccctga tgattaagga tgctgaacat tttctcaggt gcttctcagc   1380

cattcagtat tctttaggtg agaattcttt gtttagctct aagccccatt tttttaatgg   1440

ggttatttga ttttctggag tccaccttct tgagtttttt tttccatttt ttattacata   1500

atttcctcaa ttacatttcc aatgctatcc caaaagtccc ccatacctc ccccccccaa   1560

ttccctaccc accccttccc atttttttgg ccctggcgtt cccctgtact ggggcatata   1620

aagtttgtgt gtccaatggg cttctctttc cagtgatggc tgactaggcc atcttttgat   1680

acatatgcag ctagagtcaa gagctcccgg gtactggtta gttcataatg ttgttccacc   1740

tatagggttg cagatccctt tagcttcttg ggtactttct ctagctcctc cattgggagc   1800

cctgtgatcc atccaatagc tgactgtgag catccacttc tgtgtttgct aggccccggc   1860

atagtctcac aagagacagc tacatctggg tccttttgat aaaatcttgc tagtgtatgc   1920

aagggtgtca gcatttggaa gctgattatg gggtggatcc ctggatatgg cagtctctac   1980

atggtccatc cttttgtctc agctccaaac tttgtctctg taacttcttc catgagtgtt   2040

ttgttcccaa ttctaaggag gggcatagtg tccacacttc attcttcatt cttcttgagt   2100

ttcatgtgtt tagcaaattg tatcttatat cttgggtatc ctaggttttg ggctaatatc   2160

cacttatcag tgagtacata ttgtgtgagt tcctttgtaa atgtgttacc tcactcagga   2220

tgacgccctc caggtccatc catttggcta ggaatttcat aaattcattc tttttaatag   2280

ctgagtagta ctccattgtg taaatgtacc acattttctg tactcattcc tctgttgagg   2340

ggcatctggg ttctttatag gttctggcta ttataaataa ggttgctatg aacatagtgg   2400

agcatgtgtc cttcttaccg gttgagacat cttctggata tatgcccagg cgaggtattg   2460

ctggatcctc cggtagtact atgtccaatt ttctgaggaa ctgccagact gatttccaga   2520

gtggttgtac aagcctgcac tctcaccaac aatggaggag tgttcctctt tctccacatc   2580

cacgccagca tctgctgtca cctgaatttt tgatcttagc cattctgact ggtgtgaggt   2640

ggaatctcag ggttgttttg atttgcattt ccctgatgat taaggatgtt gaacattttt   2700

ttcaggtgct tctctgccat tcggtattcc tcaggtgaga attctttgtt cagttctgag   2760

ccccattttt taatggggtt atttgatttt ctgaagtcca ccttcttgag ttctttatat   2820

atgttggata ttagtcccct atctgattta cgataggtaa agatcctttc ccaatctgtt   2880

ggtggtcttt ttctcttatt gacggtgtct tttgccttgc agaaactttg gagtgagttc   2940
```

```
tttatatata ttggatatta gtcccctatc tgatttagga taggtaaaga tcctttccca   3000
atctgttggt gacctttttg tcttattgac ggtgtctttt gccttgcaga atctttgcaa   3060
ttttatgagg tcgcatttgt caattctcga tcttacagca caagtcattg ctgttctgtt   3120
caggaatttt tcctctgtgc ccatatcttc gaggctttta cctgctttct cctctatatg   3180
tttgagtgtc tctggtttaa tgtggagttc cttaatccac ttagatttga ccttagtaca   3240
aggagatagg aatggatcaa ttcgcattct tctacatgat aaccgctagt tgtgccagca   3300
ccatttgttg ataatgctgt ctttttttcca ctggatggtt tttgctccct tgtctaagat   3360
caagtgacca taggtgtgtg ggttcatttc tgggtcttca attctatttc attggtctac   3420
ttgtctgttg ttataccagt accatgcaga ttttatcaca attgctctgt agtagagttt   3480
taggtcaggc atggtgatta caccagaggt ttttttatc cttgagcaga gtttttgcta   3540
tcctaggttt tgtgttattt cagatgaatt tgcagattgc cctttccagt tcgttgaaga   3600
attgagttgg aattttgatg gggattgcat tgaatctgta gattgctttg gcaatatagc   3660
catttttact atattgatcc tgccaatcca tgagcatggg agatctttcc atcttctcaa   3720
atcttcttta atttctttct tcagagactt gaagttcttg tcatacagat ctttcacttc   3780
cttagttaga gtcacgctaa ggtattttat attatttgtg actattgaga agggtgttgt   3840
ttccctaatt tctttctcag cctgtttatc ctttgtgtac agaaaagcca ttgacttgtg   3900
ttagttaatc tcatatccag ctacttcact gaagcggttt atcaggttta ggagttctct   3960
ggtgtaattt ttagggtcac tcatatatac tatcatatca tctgcaaaaa gtgacatttt   4020
gacttcttcc tttccaattt gtatcccctt gatctccttt tgttgtcgaa ttgctctggc   4080
aaggacatca agtactatat tgaataggta gggagaaaat cggcaccctt gtctagtccc   4140
tgattttagt aggattgctt caagtttctc accatttact ttgatgttgg ctactggttt   4200
gctgttgaat gctttttatc atgtttaggt atgggccttg aattcctgat ctttccaaga   4260
cttttatcat gaaagggtgt tggattttgt caaatgcttt ctccagcctt tcattctgag   4320
gttgtgtctg tctttttccc tgagatgggt ttcctgtaag cagcaaaatg ttgggtcctg   4380
tttgtgtagc ccgtctgtta ttctatgtct ttttattggg gagttgagtc cattgatatt   4440
aagatatatt aaggaaaagt aattgttgct tcctattatt tttgttttta aagttggcat   4500
tctgttcttg tggctgtctt cttttaggtt tgttgaagga ttcctttctt gctttttcta   4560
ggtcgtggtt tccatccttg tattcatttt ttttctgtta ttatcctttg aaggactgga   4620
ttcatggata gataatgtgt gaatttggtt ttgtcttgga atacttttgt ttctccatct   4680
acggtaattg agagtttggc tgggtatagt agcctgggct ggcaattgtg ttgtcttagt   4740
gtctatataa tgtctgtcca ggatcttctg gctttcatag tctgtggtga aaaatctggt   4800
gtaattctga taggcttgcc tttatatgtt acttgaattt ttcacttact gcttttaata   4860
ttctttcttt atttagtgca tttgttgttc tgattattat gtgtcgggag gaatttcttt   4920
tctggtccag tctatttgga gttctgtagg cttcttgtat gttcacgggc atctctttct   4980
ttaggtttgg gaagttttct tctataattt tgttgaagat atttgctggc ccttcaagtt   5040
gaaaatgttc attctcatct actcctatta ttcgtatggt tggtcttctc attgtgtcct   5100
ggatttcctg gatgttttga gttaggatct ttttgcattt tccattttct ttgattgttg   5160
tgcagatgtt ctctatggaa tcttctgcac ctgatattct ctcttccatc tcttgtagtc   5220
tgttgctgat gctcgcatct atggttccag atttctttcc tagggtttct atctccagtg   5280
```

-continued

```
ttgccccact ttgggttttc tgtatagtgt ctacttccct ttttagatct agtatggttt   5340
tgttcatttc catcacctgt ttgggtgtgt tttcctgttt ttctttaaag acttgcaact   5400
ctttagcaga gttctcctgt atttaagtga gttattaaag tccttcttga tgtccagtac   5460
cataattgtg agatatgcct ttaaatccaa gtctaggttt ttgggtgtgt tggggtgccc   5520
tggactggct gagttgggag tgctgcattc tgatgatggt gagtggtctt ggtttctgct   5580
agtaagattc ttacatctgc ctttcgccat ctggtaatct ctggagtcag ttgttaaagt   5640
tgtctctggt taaagcttgt tcctctcgtg attctgttat tctcttccag cagacctggg   5700
agactagctc tttcctgagt ttcagtggtc agagcactct ctgcaggcag gatttcctct   5760
ttcagggaag gtgcacagat atctggtgtt cagatttgcc tcctggcaga agatgatggc   5820
ctgaaacagg acctgtccca gaagctgtta gcttctgtag tcaacactgt cacctgtgca   5880
gactagtctc ggtggagtcc gggaaccaag atgtctcctg cagatgctct ggcattccct   5940
tctgggccgg gtgatcacct ctcctctggc agggaaggtg ccctggtgtc tggaacccga   6000
aaagggggct gcctcagaag ctctgtggct actgcctgtc ccagaagctg ttagcttctg   6060
tagtccacac tctcacctgt gcagactagt cttggtggag tctgggaacc aagatgtctc   6120
ccgcagatgc tccagccatt ctcctctttc tgttgcttat tttgacctat gaaatcctgg   6180
acatatagtt ctagtgttgc ttgtaatctc ttttctaagc caaggaattt tttttatcta   6240
gggcacaatc ttttgagaag acatattaaa tcaagagaat aaatattgca agaccaataa   6300
atgataaggt atctattttc tttaaatcca tcgctgtcaa accattcaaa atatcctcac   6360
ataaagccaa aaagatattt attgtgtttc ccatcttagt tgagttcaag tcaatatttt   6420
ggtgccattt tgttgcagta aatctctaac acaaatatgc ctgggcaatg aaaacacaac   6480
tcagttaata tgaatacaga ttgttcagat ctaccactac actaccatct tcttcatcta   6540
agagacccct tagaacttgc agtttctcca ggccttgtgc ttctgcgctg cttttcttct   6600
tcttcctctt ctacattgct tctctcataa acctacttct ttttttccct ccttctgttc   6660
catcttccct tttatctgcc caatcattag ctctccttta ttttacaaat taaggtgtga   6720
agccggtttc taggaaatca cctgagtgct gacttgttcc ttgttcagag ccacgcacag   6780
gagaacagaa ttaacatcaa atataattat ccccagggct atccacaaca cgtgcatcct   6840
ataagatcac cacggactaa tgctggtctt caattacaac ataaacaaca aaaaccccac   6900
atatatgtgg aaacaaatcg aactatacaa agaatcaatg aaaccaggag cttgttcttt   6960
gagaaaaatc aacaagatag ataaaccctt agccagacta accagagggc acagagacag   7020
tatccaaatt aataaagtca gaaatgaaag gaagacataa caatgaaata tatcttaaaa   7080
taattaatct gtttgtagac tattagcagt tgaaaatatt aaaatcatgt tctacaaacg   7140
tggaattatt attgataatt ttctcactgt gcttgaaatt agcattttct taatgtttaa   7200
cttcaaagag tttttgctat tttgaaatat taaacatata cttactgata aaataatttc   7260
cctcctaaca acactgataa tctttttttta agtaaactga ttattagaca atgtacacag   7320
atatataatg tgttttaaat actctcccac tgtcaggtgg tatcatatag ggcctttgaa   7380
tatattttta aatgtattat ttgtaatatt ttatggtctc tcctatgctt atttctgaaa   7440
gaatattttg tatgttttga aacaatttag tatttaacat tagatatagg atcctcagtt   7500
atggatagta ttaaatattc attaatgata tttttaaggt ataaaaggat atgaatataa   7560
aagtttaaca aattttatgt attatttgat tctaaaaata ctcaatatta ttaatatgtt   7620
tgatgtttaa aatgcattta aataataaaa acatttaaaa aaataaaatc aagaaatgag   7680
```

gttctaagca gaggtcaagg aaaatgagga atagaaaaat agtaaaaatc aatatgtcca 7740
tttattcaag gaaagctcct acatagacat tgcaccagat tagcaaatat tatggtcctc 7800
atattagttt aagttaggag actatgctta tgttatctat ttacattcta aggagcctag 7860
acatttgtga atggattaca ttataagagg aggatgtcta cttaagtagg catgaacgcc 7920
tgtgcattgc accctatgag ttccatcagc attccatgat tggagtatga agaacagcat 7980
tatagacatt acccagaacc ttagtggttc tagaatgcca agataaaaca atctaacctt 8040
ctggatagta gggataaatg ttcctatatc atcagaattc actggtgccc tgaggatgtt 8100
accctgctaa ctgacaattc acaggacatc acatggattc tgataagttg cagaaaagag 8160
gagatgcatt caattggtcc tcctccttct aagctgcaat attaggtgca tccaatttgt 8220
gaacttcaat ttagattaca atagacatga ataatctgaa ttcatgtagt acatattttt 8280
gttttaatat gagttaccat tgttcagaaa attaaataca catgatcaca tattcctaca 8340
tagtgctgtt agtttttcac atctctggga caatattcca aatatctcct tcattagtga 8400
aaatatcaac tactgtaaag cttagctaac atgcctttgc aggaataaga acatcctgga 8460
ttgaaagcta cacagggaga tgtaaaactt tctaagcaca cacattctcc atccattagg 8520
atcatggtcc atgagatttt tctctctctc ttcttcccat taaatgcatg tacatgcagg 8580
ttgggaaaca gattgtgttg cagaatacat ttgcttgatt tccacttcct tctcaatgca 8640
aatatttttg aagtgttaat tttgctgtga gtaccacagt ggttcttgct ctttctgttg 8700
actcctgtct gtgaatgttc caggaattca cacatggaca cacgtggggc tgcatctgag 8760
ctccagactc actgttgtcc ttctgtcctc agctgctctg gcccaggcac agcctcgtga 8820
attcaacaaa gaccctgatc tctcttgttt acacctcatt acaaatggga actgttagag 8880
gtggacccaa ctgcatttcc atgaggaaag cacatgagtt tgagagggtc gttgatgata 8940
aggtagaaac aactttaatt cataggctga gatatcagtc atcacctcca gataaacaag 9000
agccatttct tcctgcatct gagccctgta agcacactag ctttaggaat atgttactgc 9060
tgaagtcaga ttgggcaact tcatagtata caatagaaaa tctacctgca gatgagttca 9120
gaaccagcag ggggcacaat ggggccaaga atccctagca gagagatgtg gtgtgtgtgc 9180
aggggactct gcatcctctg tggtttcctt tcttaactta catgtacctg tagtgattga 9240
catgtaacgt ttccacgctc aaacactgtg aagatacttt gctaaacact tcaaagattt 9300
atgttttctt gatgtgtgca tgtgtgtatt cttttttgtt tttagacaca gggtttctct 9360
gtgtagtcct ggctgccctg gaactcactc tgtagaccag gctggcctcg aactcagaaa 9420
tctgcctgct tctgcctccc aagtgctgaa gttaaagaca tgtgccacca ttgcctggcc 9480
atgtgtgtat tcttgatgca ctcttctgtt gacagataca cagtttattt ccataattta 9540
tttattgtga tggtgctgca ataatcactt atgtacaaat gtttctgaag tatatttagt 9600
tttggtcatt tgggtgatta ttttttttctt tctagtatat agcattttgg aaaggtagat 9660
attaattgta tgtatgggaa ggaggctgta aattctaata acttagctgc ttttgaaatt 9720
tgtcctcaat tctatcatcc ttgtaaccac cttaaatcca tctattagcc ttgtcacaag 9780
tgagccactg tctcaggctg caaatctttt tatagattag gtcgtgatgt tacatccaca 9840
gcctctgcac aatgctcagg ggtgggatat gggatgaatt ccctcagaca gcattaggac 9900
ttggatctca gcagactgat tcttgaccca aatgtctctt cttctctagc aggagtaagt 9960
ccttatctaa gatgtactct gctcatgaat atgcaaatca attgagtcta tggtggtaaa 10020

-continued

```
tatagggatg tctacacccc tcaaaaactt aagatcactg tcgtcttcac agtcacagga  10080
gtacacagga catcaccatg tgttggagct gtatcatcct cttcctgtta gcaacagctg  10140
cacgtaaggg gcttacagta gcaggcttga ggtctggcca tacactcatg tgacaatgac  10200
atccactctg tccttccctt cacaggtgtg cactcccagg tccagctgca gcagtctggg  10260
gctgagctgg tgaggcctgg ggcctcagtg aagatttcct gcaaggcttt tggctacacc  10320
ttcacaaacc atcatataaa ctgggtgaag cagaggcctg gacagggcct ggactggatt  10380
ggatatatta atccttataa tgattatact agctacagaa ccagaagttc aagggcaagg  10440
ccacattgac tgtagacaaa tcctccagca cagcctatat ggagcttagc agcctgacat  10500
ctgaggactc tgcagtctat tactgtgcaa gacacagtgc tacaaacaca tcctgagtgt  10560
gtcagaaacc ctggaggaga agcaagcaga gctggaatgg agatgacaga aagattatca  10620
tttagacttg ctcagaaaga gaaattttga atgcccattt attgcctctt ccttacagta  10680
ctatagtgcc tgtttttgtt gacattttca aactaatttc caaagtcact accacaattt  10740
acaatcacat aaaaagcaag caaggataac attattttct gtgcttactt gccatttata  10800
ttcttgctta ttctcatctc actgaggtca tattgggaca ttaaatttct ggggttactt  10860
tttattaaaa atttttcatt attcattcac tttacatcct tctagtcttc ctctcacaca  10920
tgccctatcc ctttctcctc tgagaggatg gagccctccc taccctcgta tccccttacc  10980
caggcacatc aagtgtctgc agtactagga atattctctg tcaatgctgc cagacaaggc  11040
agacaagtta ggggatcagg attcacagga aggcaacagc ttgagggaca gcccccactg  11100
aagttattgg tggattcaca tgaagactga gttgcacatc tgctacatat attcaggggt  11160
cctatttaca gctcaagtag actcttgttg gtggtttagt ctcttagaac cccaagtgtc  11220
caggttagtt gactctgtgg gtcttccttt ggagttccta tcccctccag atccctcagt  11280
tcttctccca actcttccat aagacacccg taggtccatc caatgtttgg ttttgggttt  11340
ttctgcatct gcttcagtca gctgctgggt ggagcatctc tgaggataat tatgagaagc  11400
tcttatgtgc aagcataaca ggatatcatt attagtgtca gggactggtg cttggccatg  11460
ggatgggtct caagtttggt cagttatttg gccattccca cagtctctga taatctttgt  11520
ccctgcattt cttgtagaca ggaaaaatat tgggttgaaa gttttgtggg tgggttggcg  11580
tctctattgc tccactgggc ttctttctgg atataggagt ttgcctcttc aggttccata  11640
ttcccaaagt agtgtgtcac actaaggtca ctcccataca gagggacact cattctcttg  11700
ccacgtctct gtccaccttc attggacctg aggttcctga atcatacaga actgcatgtg  11760
tgcaaccaca cagaacaagg ctatctatca gaggcctacc ataccaggac catcaaggtt  11820
caccttactc ccaatactga ctacaaaaag aacatcaagg accaatgcag tctatatgga  11880
taaacacact tgaaagaaca caaacaagat tgagggcaac atgacacctc caaagcatac  11940
ctaaccgagt acagcatgcc ctggatatcc taacacaatc aaaacacaag aaagttacct  12000
taaatccagt cttataaagg tgatgaaggc ctttaaatag gaaatgaatt aatccttagg  12060
ataatacagg acaatacatt cgaacagata gaggtcttta ggaggaaaga aataaatccc  12120
tcaaagacat acatgaaaat acaattaaac aggtgaaagt aataactaca atggtgtaag  12180
acctaaaaat ggaaatagaa gcaataaagt aacacaaact tagaatcttg aaggtggaaa  12240
acctagagaa caggaatact agatgcaagg atgatatctt ctaggtccat ccatttgctt  12300
gcacaattta tcatgtcctt gcttttaata gttgaacagt atttcattgt ttaaatgaac  12360
cacatgttct gtctccattc tctggatgag gggtgagca agtttttcca cattctggct  12420
```

-continued

```
attacaaata gagctgctat gaacctagta gaaaacatat cctgtgtatg gtggagagtt  12480
ttggagtata tcaccaagag tgttatagct gggtcttcat gtagaactat tcctaatttt  12540
ctgagaaatc ccaagtcaga tttctagaat ggttgttcaa gtgttcactc caaccatcaa  12600
tggaggactg ttttccttgc cagcatgtgc tgtattttga gtttttgatc ctagccagtt  12660
ttatcctgca tttcacactt agatatggac tatggtacag gacagagaga aaccaacctt  12720
ctactcacca ggatattcta cctgctacca atttatttat ttatttattt atttatttat  12780
ttatttattt atttatttat attagagaac aacaccatgc agtttagaag aagtactaag  12840
acgtcagtga tgttatactg tgcctaacct tgcattgtac aatctcagct ttcaggtaag  12900
acagtgcatg actcttatgc agtgccaact gttttctgat tgtatttatg gtctattgcc  12960
taggaatgac ctcctctcaa ataaacatgg tcaaaagccc atggcctgag atgacagagc  13020
ccctagtaga ccctagttgt atttctgaag tttagatatc ataatgactt ataaatactt  13080
atgtttatac aatagattag agctgctctc agccatgacc aaggagcttc tgtgttcaat  13140
gaataatgat tgatgcagac attcgtgagt ggtcaaagtg gtgagaatga ttagagagtc  13200
ctcagccaca caagcgttaa tgatatgaac tttccaatat attaactgta ttaatgaata  13260
aatgcagaca tcatatgaga tctcattagt agttcttagg tattgcattt ttatatacaa  13320
ttatgcatat cagtacatta tagtgtataa aggaaattgt ctagcataat agagaaaaat  13380
aggacagtca agaaacaaaa gagtagaaat tatgggtgaa atatgcagtg tgaaatattt  13440
acatgaaaat tttaaccata tgtaaaattg ttatttttgt ttttcagaat gagtttgctc  13500
attctttgac atttttattc ctgtgtgaaa tatatcagga tcatatgtat cccattctga  13560
tggtctgact tccactggga atttccaata tatctcttcc aactaactga ccagtttctt  13620
tttttcttat tttctctctt tctcgttttg ttttgctttg ttttgttttt caagacaggg  13680
tttctctgtg tagctctggc tgtcctggaa ctcactttgt agatcaggct ggcttcgagc  13740
tcataaatcc acttgcctct gcctcctgag tgctgggatt aaaggagtgg ctaccacgcc  13800
cggctagttt tttttttct tataagaaca acatttactg gatggtcact tacatattca  13860
gaggttcagt caattattat caaggcagaa gcatggcagt ggtccagtag tcatggcact  13920
ggggaaggag ctgagagatc tacatcttgc tccaaaggga aagaggaata gtctgacttc  13980
catgtgtttc agaggagggt ttcatttccc acccccacag tgacacactt cctccaacac  14040
ggccacacct cctaatattg ccactcttgg atcaagcata ttcacaccac aaaggaaagt  14100
ttagagataa acattaagaa aattaatgaa gtcattttat cttatatgct caacatgact  14160
agtacttaaa accataattt tacatgtaca atatttcatg gcataacata ttttttatat  14220
ttttattaga tattttcttt atttatattt caaatgtgat accctttccc aattcccctc  14280
caaaaatccc ctatgccttc ccctcatagc cagctcccaa acccacccac tcctgctttc  14340
tggtcctggc attcccctat actggggcat aaaaccttca caggaccaag tgcctcttct  14400
ccattgatgg ccaattaggc catcctctgc tacatatgca gctagagcca tgagttccac  14460
catgtgtttt ctttgattgg tggtttagtt ccagggagct ctgggggtat tggttagttc  14520
atattgttcc tcctatgggg ctgcaaaccc tttcagcccc ttgggtattt tttctagctc  14580
cttcattggg gaccctgtgc tccatccaat ggatgagtga gcctccactt ttgtatttgt  14640
caggaactgg cagagtctct caggagacaa ttatatcagg ctcctgtcag caaaatctcg  14700
ttggcatctg caatagtgtc tgggtttggt ggttgtttat gggatggatt tctgggtggg  14760
```

-continued gcagtctctg gattgtcatt cctttagtct ctgcttccac ctttgtcttt gtaactccat 14820
ccatgggtat tttgttcccc cttcaaagaa ggatcaaaat atccacactt tagtcttcct 14880
tcttcttgag tctcatgtgt ttttcaaatt gtatcttggg tattctgagc ttctaggcta 14940
atatccactt atcagtgagt gattatcatg tctgttcttt tgtgattgag ttacctcact 15000
tagcatgata tcctccaggt ctatccattt gtctaagaat ttcataaagt cattgtcttt 15060
aatagctgca tcgtactcaa ttgtgtaaat gcaccacatt ttctttatcc attcctctgt 15120
tgagggacac ttggtttttc ccagcttctg gttattataa ataaggctgc tatgaacata 15180
gtggaacatg tgtccttagt acatgttgga acatcttctg ggtatatgcc caggagtggt 15240
attgctggat cttctggtgg tactatgtcc aaatttttgg ggaaccatca aactgatttc 15300
ctgagtggtt gtacaagctt gcaatcccac accagcaata gtggaatgtt catctttgtc 15360
caagtccttg ccagcatctg ctgtcacctg agtttttgat cttagccatt cttactggtg 15420
tgaggtggaa tcttggggtt gttttgattt gcatttccct gatgtttaag ggttttgaac 15480
atttttaggt gcttattaga catttggtat tcctcagttt agaaatcttt gtttagctct 15540
gtaccacatt tttgaatagg gttatttggt tttctggagt ctaacttctt gagttctttg 15600
tacatattgg atattagccc tctatcagat ttagaattag taaggatctt tccccaaact 15660
gttggtggtt cttttgtctt attgacagtg tactttgcct tagagaagct ttgcaatttt 15720
atgaggtccc atttgtcaat tcttgatctt atagtacaag ccattggtct tttgttcagg 15780
aatttttccc atgtgtccat atgttcaagg catttcccca ctttctccac tacaagtttt 15840
agtgtctctg gttttatgtg gaggtccttg atccacttag atttgagctt tgtacaagga 15900
gataagaatg gatagattca cattcttcta catgctctct gccagttgag ctagcaccat 15960
ttgttgaaaa tgctgtcttt tttttccccc actggatggt ttttagctct tttggccaag 16020
atcaagtgac cattggtgtg tgggttcatt tcttggtctt caattctagt tcactgactt 16080
acctgtttgt cactgtacaa ggaccatgca gctttttttca caattgctct gtagtacagc 16140
ttgaggtctg ggatggtgat tctaccagag agattctttt actgttgtga ataatttttg 16200
ctatcatagg atattttttt atttcagatg aatttacaaa ttgctctttc taactctgtg 16260
aacaattgag ttggaatttt gattgtgatt gctttgaata ctcaagatat aatttacaaa 16320
acacatgaaa cttaacaagg actactaaag tgcagatact tcgatccttc ttagaagggg 16380
gaacaaaata cccatagatg gagttacaga gacaaagttc ggagcagaga ctataggaac 16440
gaccatccag aggtccacct ggggatccat catgtaaaca accacccaaa acagacacta 16500
ttgtggatgc caagaagaac ttgctgacag gagtctgata tagctgtctc ttgagaggct 16560
ctgccagggc ctcagaaagt ggaggctcac agccatccat tggatggagc acagggtccc 16620
caatgaagga gctagagaaa gtactcaagg agctgaaggg gtttgcagcc ccataggagg 16680
aacaacaata tgaactaacc agtacccccca gagctccctg ggactaaacc accaatcaaa 16740
gaaaacacat ggagggactt gaagctcttg ctgcatttat agcagaggat ggcctagatg 16800
gtcatcaatg ggaggagagg tcaatggtcc tgggaaggtt ccatgcccca gtatagggga 16860
atgccagggc caggaagcag gagtgggtgg gctggggatc agggaggggg agatgatagg 16920
gcattttcag tggggaaact aggaaagagg ataacattta aaatataaat aaagaaaata 16980
tctaattaaa aaggattacc tatgtgcatg ggagctcatg agcagcaggg gtcactctaa 17040
ggccaataat ccacatagag cgatgagctg tgtgtgaaca ggactctgta tcctctgtgg 17100
tttcctttct taagtgtatt aactgatctg tccagctgtg attgacatgt gatgtctcca 17160

```
tgctcaagcc cagtaaagat tctctgttaa ataccttaca gacttatgtt tacttgtttt  17220
tatttgcttt tcatattttt ttaaaaagtc atacaatgta ttctaataac tcattctccc  17280
atctccaatt tattctaagt ttttcttaac tcatccaacc acacactttt taattctgat  17340
aaagcacccc cccccccaaa aaaaaaccca accaaccaaa aaaaaaaaaa gccaaggaat  17400
ttaaaagggg attgaaagca aataaaaact aaacaaaaaa gtaaaaacta cacacacaca  17460
cacacacaca cacacacaca cacacacaca cacacactca cacacacaca cacacaccac  17520
acacacacac acccatgcac gaacacacac acacacacac acacacacac acacacacac  17580
acacacacac acacatggaa tccagtaaaa ccacaactct ttacccatga tacacaggaa  17640
aatataagtc aaacaaacag aatggaagaa ggtggtatta taaaaatgtc tgcacaaata  17700
ccattaagtt cattttcttg ttggctacca actgctaagc ctgtctccct tgattaattg  17760
tgcttatcat cccctatgaa ctccattgga ggacactaat tttccttct gtctccagga  17820
attgaagtgt tgcagaactc tcagtagctt tatttacctg cacaatacag cctctaatcc  17880
aaccagtgaa aattaccaca tgagagactt ccaaatgaaa gaacaggtaa agttgtctac  17940
tggcaagctt agtaatatca tgtaaatgcc ttagaattta atgacatatg tcatcctctg  18000
aggttaataa atccattttg gtgcatatat accctgaact caccactaac ataatacaac  18060
aattaaaaaa ttccaacatg gatgcagagg aatccctgag ggacatttgt tgatttgtga  18120
gcacaatata attatttttt ggggggggaaa tgtctgaatg ttaactcttt accagtgata  18180
atctattcta ttaatgtgta cataggtagc actaattaaa atcactgtgt tatcaggtaa  18240
tgaaacagag gaagtaggat gctgggaaac agacttttgg aaggtcccaa gggaaaccac  18300
agggacctag tggtgataga ttatggtgag agtcctgaga gtggtcatag attatagcat  18360
atttcatatg caattgaaaa tttcaaagaa tgaaaatcct tatgaaatat agaaataaca  18420
actttactta tgtacatata cttcatagta caatttttac actgtgcata tttctcctgt  18480
aacatctggt tcctcctatt ttcctttatt ctcctagaca atttcactga tacaatctca  18540
tgtttttgta taaatagttg tatataacta ttaaatacat aagctgttaa tgagtcttca  18600
ttaatgtctg tgattttttt attgtcttaa ttaatactat tatctctaat tgcatccaca  18660
ttttcaaaag caatgtaaat ttcttactca tttctgttca aaaacttctg ttgttgtatc  18720
attaccatgc cttagtgata aaatcctttc ttgacacatc tatagctatt gctataattt  18780
agttattgat gatcctcctg caataatcat tgataggtaa atattttaag cacttttact  18840
tttagtcatt ttagtgagat ttgaagtagt atataacctg ttggaaaggc aaatattaat  18900
tccatatatg tgaaagaaga cgctaaaact aaaaacatta gccactttta gatatcttct  18960
ccttcttctt cttcttcttc ttcttcttct tcttcttctt cttcttcttc ttcttcttct  19020
tcttcttctt cttcttttct tcttcttctt ctccttctcc ttctccttct ccttctcctt  19080
ctcctcttcc tcctccttcc ttccttcctt ccttccttcc ttccttcctt ccttccttcc  19140
ttccttcctt ccttccttcc ttccttcctt ccttccttcc ttccttcctt ccttccttcc  19200
ttcctttctt tctttctttc tttctttctt tctttctttc tttctttctt tctttctttc  19260
tttctttctt tctttctttc tttctttctt ctcctcctcc ttctttttcc ttctccttcc  19320
ccttcacctt ccccttcctt cctctttccc ttccccttct ccttctcctc aatctacaat  19380
ctgttaacat attaacatgt cccagagtag agcaacagac tcaggtcaaa catctactga  19440
gaaatttgcc catgtagtta acatctacag catctgtcta ggggttacaa aaagtctatg  19500
```

-continued

```
ggatacaatt cctcagaaag gaataggatt tggacctgag catactgctg cctaacacat  19560
gaaatggcag ttcttctcca gctggactag gtccttaact aagaaatgca ctgctcatga  19620
atatgcaaat tacccaagtc tatggcagta aatacagaga tgtccacacc ctgaagacaa  19680
cctatgaaca atgttctctc cacagtccct gaagacactg attctaggac cgaagttcct  19740
attccgaagt tcctattctc tagaaagtat aggaacttct cgcgcgtctg gcctccgagg  19800
cctccgcgcc gggttttggc gcctcccgcg ggcgcccccc tcctcacggc gagcgctgcc  19860
acgtcagacg aagggcgcag cgagcgtcct gatccttccg cccggacgct caggacagcg  19920
gcccgctgct cataagactc ggccttagaa ccccagtatc agcagaagga cattttagga  19980
cgggacttgg gtgactctag ggcactggtt ttctttccag agagcggaac aggcgaggaa  20040
aagtagtccc ttctcggcga ttctgcggag ggatctccgt ggggcggtga acgccgatga  20100
ttatataagg acgcgccggg tgtggcacag ctagttccgt cgcagccggg atttgggtcg  20160
cggttcttgt ttgtggatcg ctgtgatcgt cacttggtga gtagcgggct gctgggctgg  20220
ccggggcttt cgtggccgcc gggccgctcg gtgggacgga agcgtgtgga gagaccgcca  20280
agggctgtag tctgggtccg cgagcaaggt tgccctgaac tgggggttgg ggggagcgca  20340
gcaaaatggc ggctgttccc gagtcttgaa tggaagacgc ttgtgaggcg ggctgtgagg  20400
tcgttgaaac aaggtggggg gcatggtggg cggcaagaac ccaaggtctt gaggccttcg  20460
ctaatgcggg aaagctctta ttcgggtgag atgggctggg gcaccatctg gggaccctga  20520
cgtgaagttt gtcactgact ggagaactcg gtttgtcgtc tgttgcgggg gcggcagtta  20580
tggcggtgcc gttgggcagt gcacccgtac ctttgggagc gcgcgccctc gtcgtgtcgt  20640
gacgtcaccc gttctgttgg cttataatgc agggtggggc cacctgccgg taggtgtgcg  20700
gtaggctttt ctccgtcgca ggacgcaggg ttcgggccta gggtaggctc tcctgaatcg  20760
acaggcgccg gacctctggt gaggggaggg ataagtgagg cgtcagtttc tttggtcggt  20820
tttatgtacc tatcttctta agtagctgaa gctccggttt tgaactatgc gctcggggtt  20880
ggcgagtgtg ttttgtgaag ttttttaggc accttttgaa atgtaatcat ttgggtcaat  20940
atgtaatttt cagtgttaga ctagtaaatt gtccgctaaa ttctggccgt ttttggcttt  21000
tttgttagac gtgttgacaa ttaatcatcg gcatagtata tcggcatagt ataatacgac  21060
aaggtgagga actaaaccat gggatcggcc attgaacaag atggattgca cgcaggttct  21120
ccggccgctt gggtggagag gctattcggc tatgactggg cacaacagac aatcggctgc  21180
tctgatgccg ccgtgttccg gctgtcagcg caggggcgcc cggttctttt tgtcaagacc  21240
gacctgtccg gtgccctgaa tgaactgcag gacgaggcag cgcggctatc gtggctggcc  21300
acgacgggcg ttccttgcgc agctgtgctc gacgttgtca ctgaagcggg aagggactgg  21360
ctgctattgg gcgaagtgcc ggggcaggat ctcctgtcat ctcaccttgc tcctgccgag  21420
aaagtatcca tcatggctga tgcaatgcgg cggctgcata cgcttgatcc ggctacctgc  21480
ccattcgacc accaagcgaa acatcgcatc gagcgagcac gtactcggat ggaagccggt  21540
cttgtcgatc aggatgatct ggacgaagag catcaggggc tcgcgccagc cgaactgttc  21600
gccaggctca aggcgcgcat gcccgacggc gatgatctcg tcgtgaccca tggcgatgcc  21660
tgcttgccga atatcatggt ggaaaatggc cgcttttctg gattcatcga ctgtggccgg  21720
ctgggtgtgg cggaccgcta tcaggacata gcgttggcta cccgtgatat tgctgaagag  21780
cttggcggcg aatgggctga ccgcttcctc gtgctttacg gtatcgccgc tcccgattcg  21840
cagcgcatcg ccttctatcg ccttcttgac gagttcttct gaggggatcc gctgtaagtc  21900
```

-continued tgcagaaatt gatgatctat taaacaataa agatgtccac taaaatggaa gtttttcctg 21960
tcatactttg ttaagaaggg tgagaacaga gtacctacat tttgaatgga aggattggag 22020
ctacgggggt gggggtgggg tgggattaga taaatgcctg ctctttactg aaggctcttt 22080
actattgctt tatgataatg tttcatagtt ggatatcata atttaaacaa gcaaaaccaa 22140
attaagggcc agctcattcc tcccactcat gatctataga tctatagatc tctcgtggga 22200
tcattgtttt tctcttgatt cccactttgt ggttctaagt actgtggttt ccaaatgtgt 22260
cagtttcata gcctgaagaa cgagatcagc agcctctgtt ccacatacac ttcattctca 22320
gtattgtttt gccaagttct aattccatca gacctcgacc tgcagcccct agagaagttc 22380
ctattccgaa gttcctattc tctagaaagt ataggaactt cctagggttt caccggttaa 22440
atggcatgtc ccctgttagt ggttcatgca agcagaagct gtatcctgtt tgacaaagat 22500
tcagcatgaa aggtcctgct acctaaaaaa aaatagacag atgagattta attaacctaa 22560
ataatttttt tcacaacaac agagtgaata cgcaatttac agaatgacag aaaacttttg 22620
cacactttgc ctgtgacagg gaactaatat gaagaatttg caaggaactc aaacaactct 22680
acaacaacaa cagcaacaag aaccaaataa ctccgttaaa atgagcaaag gacatgagta 22740
gacattttca aaagaacaca tagaaatgga taataaatat ataaacaata ctcaacatca 22800
ctaaccatca gggaaatgca aattaaaacc acaataagat atcatcttcc accagtcaca 22860
atgactatta ctaaaaactc aaataatatc agatgttgct gaggatggga aatgaaggca 22920
actcttagac attgttgatg aggatgtaga tgagtacaac ctctgtggaa aatggtatgg 22980
agatttccca gaaaactaga aatagaactg tcatttggtc cagcaatccc actactgggt 23040
aactacccaa aggaaaataa actattattt caaaaagata cccaccttct atgcttacca 23100
taaaactact ctcaatagca catatgtcaa actgagtgtc tgccaaccga tgattttata 23160
aaagaatata gcatgtatgc acaattcaat actagtcagc cacaataagg aatgaaactg 23220
tgtcttttgc agcaagatgc atagaagtgg gggacaatat aattagtgaa ctaactcaca 23280
aacagaatgt cacatgtcac acattattac ttgtaagtgg gaggtaaaca gcgtgtacac 23340
aaggatttgt agagagaaat tacacacatt ggagacttac aaggatgggc gggcagaagg 23400
tgggagcatg atgagtcatt acataacagg cacaatataa aataattaag aattgaccaa 23460
tgatcttaaa attaaaatgt agaatatgat caataaatga acttgatatt agttgacctc 23520
attaaattta aaaacttttt ctactcaaat gactgtaaga aaatgaatgc ccggttacag 23580
atgagaaact gtttgcgagt caaataacca ccaatgtaac tataataaga aacttcagaa 23640
ctcaactgtg aataaaaaag aaacaactga tggataaatt aggcaagggt ttctacagac 23700
atttcgtcaa agaagatgtg cagatgacac tgaagcatat aaacaggatc tcaacaggat 23760
tttccgttag agaaattcaa atcaagcccg caaagagaca ccactgtaca ctttttaaaa 23820
tggctgaaat taagaagaaa tacagataac atcaatgctg gtgagcatac caggttgcta 23880
gaggctaaaa cattgctaac aggaatgcaa aatgaaacag atactcagga aaataatttt 23940
tagttttctc taaaatcaaa cataccctta acacctgaat atttgcatca gagaaaaaca 24000
atcttacatt cacgcataac ttctattcaa atattcaaga tatcgtgtgt atgtgtgtta 24060
gaaagtaaaa ataacataaa tgtctcaaaa tttgaatagg tgaagaacta ggaagcatct 24120
ataaattgaa taccaccagc aataaaaaaa taacaagtga ccgatacata aactattaca 24180
ggtgaactcc agacattgtg ctaagtgaga gaagccagtc tcaaagatca aagggacaca 24240

-continued

```
gctgtaagca ccacggtcat cctcaggtgt cagtggtttg ggctggactt tctgtgtctc  24300
tttcctgacc agacccagat attgagctcc accacttgca gatggaaaat cctattttca  24360
accatgcagt gaggtttgaa ctgcttcaca gactgaacga aacaaacacg ggctcctttg  24420
aacagcgtcc ggcatttgtt ccaaccacaa gagaacgtcc ctcagctctc ccacctcctc  24480
ggttctctcc tgcaagccag cagccctgca gtttagcctg catctcccgt gcatccaccc  24540
atctccctcc aagcaccttc ccccacaccc tccactgttt ctgagagcac aggcaggctt  24600
tgaacttttc cgcattctgt tgttattgaa gttaggatgt ttaggaccaa cttaaggatc  24660
atattttatg actgaattcc agtgcccctt ctctcctggg acagagtgca taaccaagtt  24720
tctgcaggtg gagacgaagt tgagcttttt tcttcctcag cctaggagat gagcgctaat  24780
tggagggttg gcagaagctt cccaccatcc cagcactttg gttctggtgg ggcggaatcg  24840
gtgccatagg gcagagctag aaaccgcgga ctgaatgttc ccagtggcac tggacccagg  24900
gcagagcctc catccacgag tggggctcta tggaagaagt gagtctctgg ctctcagtag  24960
ctctcgtcca gcactgaacc tcagcatcat gtgctgtgtg cagggtcaga gggccaacgt  25020
actggcccct gggaaagcgt ttcctctggt gggagttggt agaaggtgtc ctgtcttctt  25080
ggctgcatct gtccgcagtg gagtttacat catgctgagc tgggatgtgg aaggaaggaa  25140
gagcatctta gatcaaatat gatgactggc cttactgagt tttctagatt ttcctgaata  25200
aatgtttctt cactcactgt gtgctgttag agtctttcca aacctgtaat ttcccaaaat  25260
aattttcact ggtctcatga gggcatggat tcattgagcc cctcatgctg tcaaagagaa  25320
atagaactgt ttttttttt cacttcatag cgaacatcca tgggttatca aataatgggc  25380
tggcttttct tccaacactt tacagacacc atcaattttc ttcttgctta taaggtttta  25440
accagaagaa tgctgtcatg gtcttttctg ttcttttgga aggaatgccc cctctactca  25500
cctccacttg tctgcctgta tttctatttg tctttggttt tcaacaattt taataagatt  25560
tacctaaatg tgtgtggggg gagcatgggg tgttattctg ctgttctgtg ttctctgaga  25620
tgcatggatt caccatttac tctgtctcca tttttgtgaa aacaattaga aaaaaagtca  25680
gtatgagccc agaaacaagc ctccctgaag tgggcacagg accacctggg ggcgctcagg  25740
acccactgaa cacaagagcc agccccaggg caggtgcaga tgcgggttaa gttctggttt  25800
cctgtcaacc ctgtggcttc ctctccataa aacagtttcc tttgtggcat atctctggat  25860
tccttatcct gttcttcctg tgaagtctct gaagaagaaa catttgtcgt aacaagagaa  25920
aaactttctc acatgcacca aaggcagagt cacctacagt cacttactcc tgtttctcaa  25980
tgtcaataag ttaccaatgc ttctgaagtt aatcagctaa atctataaaa ggtgcggtgt  26040
ttaactcagc attacagccc agctcaacag aactccaaag gtcagccagc agcagccagg  26100
aaaaagtgca tgctgggcat tggggcagag ggagttacca tccagtgcaa gagaagaaag  26160
cccccgtggt ggtcattgtc aggactccaa tcccacagtt ccaattgtag gtgatgccag  26220
gcaaaggaag agagacccca ccaatggtta gtgtggatgt cgagtttgat gtttccacac  26280
tcacactcca ggtgaatatg aaaagattta ttagctctat ttctgaggtg tctgctgaga  26340
gcagcacagt cctctcaaga aattacagat tggaatttcc tcagtagagc aggaaaggag  26400
gctggctcag ggctttataa tgatttggtg gtggggtcgg cggggggggg ggggcgtttc  26460
tactcaggag aaggagcttg tgtgatttaa acctcacact gacatcacat gagggagctt  26520
ccatgatttc ttactagatt tcccatgtgt gggggacaag gatgagggag aataaacctt  26580
aattcatcag catcaaggca ccaaaaatag gacctgacac tttattctcc ctagcagctt  26640
```

aagaaaatga gtgaaaaaga gagataagag tccacccatg tgctgaaaag catagctctt 26700
ggtaaagacg agaaaaaggc actcctacga agaaggggtt gggcagaagc tttatgctga 26760
agggtttggc taaagagaca taatcaacag gttacaggag gggctactga tgttcatgga 26820
ggtggtcctc acacatgcat actgaacaaa catgtctgta acgtatgacc cctgttcact 26880
taccagtgga gacttagcat ttaaattcat tccagtcagg ccctatgtgc aaacagcaga 26940
agcagagaca caaaggtact cagggtgcag cctctgtgaa cggccagagc caggccatgg 27000
tcagcggtct cggattagga gaaagttcct gatatcactg tagtgttcaa tcaaagctgg 27060
ggttatggtt tgtggaacag gggtcagttc atcagggggt gggctgcaat tgtcttcata 27120
gtgcttgtct cagtgccggt gcttactgag ccactagaga aaaaggttta attgagcttc 27180
tttaaaatca acattttgaa ttatttatca gacgtttcaa atatgtcatg ttgtttagat 27240
tctattgctg gagagttaag gtgatatttg gggttttgta actctgtttt ttcatacttc 27300
ctgaattgct tatctgtttg cttttcatta gctaaactat cgcttcttct tattttttaa 27360
ttcattctga ttttgatgaa tatttaattc cctttagaat gtgaatataa tgtacattgt 27420
gtgggtattt tgattttggt tcttggttta cttagtggca aagactctgt aagagttcct 27480
tgtctataga tagccattat ttagtggctt tctgaaatgg tggttttagt accaaagtac 27540
tggacttgtg agtaggctca ctgccccctg caggtcctag atagtggagg cctcaggaac 27600
tgtttctcat ttggaatgcc tttgtttcag cagattttgt gttgggttgt taagttcacc 27660
ctccacatta gtagatgtcc ttacagatta gagctgactc tggtagaagc agttgagtgc 27720
atgcttgata tctgtgcaca gggagaagct ctctgttgcc tcaggcgatg gactggtcta 27780
tgaaatgcac agtgacctga gttccctgct cagcccctga gaggtggacc aagctggaca 27840
cacatgagcc accgagcctg gcaagcaaaa gcgccagcct tgatggaaat ggcgagctga 27900
gcggcatcta ctcagtgtgg tttcttttgt tattaagagc tttagtgtgg tggctgtttc 27960
aaattcccgt tgtagtagta atatactggg tatgtgagca ggcccgtggt cttttgcggg 28020
gttggaatca ccgaagtaat gagaagctaa tctcattttc aactgctgta cactggtggt 28080
attgagtttg tatgaggtca tgcagtttga acgtcaggcc agtaggtggt gctcgcaggt 28140
aagagccggc tatggtggca gcagaagggt ttatgcttta ctggtgatta aagtgggaaa 28200
cttggcgtgt tccagatctt agagaaaaga tttttagtta tttctcattc aacctgatac 28260
tacctgaaag tctctcgaat gtaactttta ttttgtcgag atgggttctt tctataccca 28320
ttttttatgt tttttttgtg aaaggatgtt gtttcatcaa atgcgttttc agcatcaatt 28380
gaaaaaagtt atatgtggat taaagatcaa aatgtaaaac ctaacactat aaaacctctg 28440
gataataaca taggaaacag aatttaggag gtaagaactg acaaaggttt tataatgaaa 28500
atgctagaag tagttgcaac aaaattgaaa attgacaaat gggacctaag taaattaaag 28560
aacttctgta cagcaaaaga cactatcgac agagtaaaca ggcaacctac agaatgggaa 28620
ataaaatatt tgcagcctat acatctgaca aaggtccgac acttagtata tacatggaaa 28680
tttaacaaac atacaagaaa taaaaagtga ccaaaggaca tgaaaagaca cttcaaaaaa 28740
gacctacatg tggccaacaa gcataggaaa aaatgctgaa tatcactatc attagagaaa 28800
tacatatcaa aacctcaatg aggtaccgtc tcacatcagt caggatggct aatcttaaaa 28860
aaaaaataac agatttttaa ggttacagaa aaaaggggaa atttatacac ttttggcggg 28920
aatataaatg agttcaacca ttgtggaaag cagtgtggtg atccctccaa taacctaaaa 28980
cagaagtttc atttgaccca acaatcctac aactggacat atacctaaag gaatataaac 29040
atgtaggttc actgcagcac tatccacaat agcatagaca tggaatttac ctaaatcccc 29100
atcactggca gaatgataga gaaaaatgtg gtacatacaa ccatggaata ctatgcagct 29160
aaggaaagaa tgaaactatg tcctttgtag gaacatgatg gaactggcag tcaatactct 29220
tagaaaacta attcaggaac agaaaaccag atattatata ttctccctta tttgttggag 29280
ataaataaaa gcaaatattc ttccagggcc tgagtcttcc ttattcaaca agtcattcta 29340
aattaagtgt tcagcaagtt gctgatactc atctaaatat tctatttcat ctgggccact 29400
tacatcactc aaaaagcaat gagagctata tttctaaggg gggttctagg ataataaata 29460
cctgaatagt gagaatatga aggatatgga aactgggcca cttatatcac tcaaaaagga 29520
atgagagcta tatttataag gggggttcta ggataataaa tacctgaata gtgagaatat 29580
gaaggatatg gaaactgggc cacttatatc actcaaaaag caatgaaagc tatatttaca 29640
agggggggttc taggataata aatatctgaa tagtgagaat atgaaggata tggatggttt 29700
ttttttaact caatgggcac ataactgtgg gagatactat attcctatga agaaggtatt 29760
cagacttcag agataagtaa tgtttcctac attgtgcttg tgacttggaa gcagtggatt 29820
gaagagtgtg ataagtgccc agaccaagca gaacagaaat cagcatgtaa agatgatgat 29880
ctatggatat gatctaaaac catgtaaata cttcaaataa ttctatttaa tgcagtttga 29940
aataaaacac aaacttattc aaaatacaaa ttacttggta attattttgg gagctatgag 30000
ttcaccaaga aactcaaatt cctatttcta tttcaacccc tgattcctac tgtcaatggg 30060
agggaagtct cagaaccaat cacacatcag acggcaaatc tgtcaaccaa gagtctttcc 30120
actgaaggac ctgggaggtc aggaccctca ggaaagtgct ggggaccctg tcttgggagt 30180
gcccagcaga tctcagaact ctccatgggt cctgctggac actcatgtag ggtaacgagt 30240
ggccaccttt tcagtgttac cagtgagctc tgagtgttcc taatgggacc aggatgggtc 30300
taggtgcctg ctcaatgtca gagacagcaa tggtcccaca aaaaacccag gtaatcttta 30360
ggccaataaa atgtgggttc acagtgagga gtgcatcctg gggttggggt ttgttctgca 30420
gcgggaagag cgctgtgcac agaaagctta gaaatggggc aagagatgct tttcctcagg 30480
caggatttag ggcttggtct ctcagcatcc cacacttgta cagctgatgt ggcatctgtg 30540
ttttctttct catcctagat caggctttga gctgtgaaat accctgcctc atgcatatgc 30600
aaataacctg aggtcttctg agataaatat agatatattg gtgccctgag agcatcacat 30660
aacaaccaca ttcctcctct gaagaagccc ctgggagcac agctcatcac catggactgg 30720
acctggaggt tcctctttgt ggtggcagca gctacaggta aggggcttcc tagtcctaag 30780
gctgaggaag ggatcctggt ttagttaaag aggattttat tcacccctgt gtcctctcca 30840
caggtgtcca gtcccaggtg cagctggtgc agtctggggc tgaggtgaag aagcctgggt 30900
cctcggtgaa ggtctcctgc aaggcttctg gaggcacctt cagcagctat gctatcagct 30960
gggtgcgaca ggcccctgga caagggcttg agtggatggg agggatcatc cctatctttg 31020
gtacagcaaa ctacgcacag aagttccagg gcagagtcac gattaccgcg gacaaatcca 31080
cgagcacagc ctacatggag ctgagcagcc tgagatctga ggacacggcc gtgtattact 31140
gtgcgagaga cacagtgtga aacccacat cctgagagtg acaaaaaccc tgagggagaa 31200
ggcagctgtg ccgggctgag gagatgacag gggttattag gtttaaggct gtttacaaaa 31260
tgggttatat atttgagaaa aaaagaacag tagaaacaag tacatactct aattttaaga 31320
taaatattcc attcaagagt cgtaatataa gccaaattca cagagtggaa aaggcgcgat 31380

```
cgcggagcag gggatcctta gatattggtt ggggttatct caccttaggt ctgaatatgg  31440
ggttgtctta gactgttttg tgctgttaga atagaatacc caagactggg aaatttatac  31500
tgaacggaaa tttatttctc acagttctag aggctgtgaa gtccaagagc acaggtgcca  31560
gagcaagtcc aagagcaagg gaaagtccaa agcaagtcca ggagcatctg gcgaggacct  31620
tcttgctgtg tcatcacatg gcggaaggca agaaagagag caagaggggg ccgaactcac  31680
ccttttataa cagcaccaat cccacccatg aggtggggac cttatgacct aatcactctt  31740
catactgtta caatggcaat gaaatttcaa catgagtttt ggaggagaga agcattcaaa  31800
ccacagcaag ggtgctccta cctcctctct cagggcatct gcagaaagag ctgcaactgc  31860
acgtccttcc tccgtccatc ctccatccct tcccaatgtc cgtgcatatc ctgtgaccca  31920
ggaggtctgg catagggggt gctcctgcct taggtctgag gccctgtctg aagaggggta  31980
ggtgaggagg ccatctgatg gtctgggcca agacagtcac aggacgcatc atttatcatc  32040
aaggaggctg agggttgagt ctccaggtcc agggaactcc ccacaaagtg ggaaccctgc  32100
ccagctccac acagcctctg ctgggggacc ctgctctggt gcagagcctg gggacaggtc  32160
ttgagctcag ccagagtctg cctccctgtc atttaggaac taaaccaagc ggcaggatgc  32220
tggagcccag cccccatctg accttacagg gccaaggctg gggccctggg ttcccctcaa  32280
ggcgcagcag gactggagcc ccaggcagtg caggagtggc caaagctggg gcttcctcca  32340
gagcccccaa gcatcacggc accaagaagg gtaggaccct ggcctgagga attggcacca  32400
aagccccaga aactaccctg gacaccatgg agagaggcct ggaggggaag caccaggcac  32460
tgcctcccct tctgatccca cctgaggtgg ctgccaagcc cagagagccg ctctgatgtc  32520
ccccagccct gcagcccagg gatacctgta ctgtgcccct gggggacccc tggccagtct  32580
gtgcaaagaa gtcaccaccc tacactcaga gacagtgggg gtcctcgtcc cacatcctca  32640
gagcatggcc cggctgctgc agggatggtc tcctggtcct cagagcatgg cccggctgct  32700
gcagggatgg tctcctggtc ctcagagcat ggcccagctg ctgcagggat ggtctcctgg  32760
aggcccccca gtgctctatt gtcagggctc cctccacccc cccgcaccaa gagagagcca  32820
gaccccagca aggcttccag tggcttcagg tcacacccct aggctgaccc cagccccatt  32880
aacacctgcc tgagaaagct ccacgcacca gaactgaccg tctgctccaa ctcttgacct  32940
cccgttctca gggcgtctgc tgaaaaggct gcaactgcac atccttcctc cgtccgttcc  33000
cgatgtccgt gtgtctcctg tggccaggaa ggtctttctc gggacctgag agccgctccc  33060
tgaagtgtcc ccattgggaa ggatggggcc tgtgtctcca ggctctggga ggacagaatc  33120
ctgacctcaa cagtggccgg cacggacaca actggcccca tcccggggac gctgaccagc  33180
gctgggcaac ttttcccttc cccgacgact gagccccgag caccctccct gctcccctac  33240
cacctccctt tacaaggctg tggcctctgc acagatgata atggagcttg gctcattccc  33300
ctagagtcgg tagggagtta aggacaaaac tcagtttcct ccacctgaac tcaagtctgc  33360
ctatgtttac ctaatcacac ctggtggaca gtttggacaa acttgcacac tcagagacac  33420
agacacttct agaaatcatt atctccctgc cccggggacc ccactccagc agaagtctgc  33480
taggcactgg cctgggccct cctgctgtcc taggaggctg ctgacctcct gcctggctcc  33540
tgtccccagg tccagagtca gagcagactc cagggacgct gcaggctagg aagccgcccc  33600
ctccaggcca gggtctagtg caggtgccca ggacaagaaa gattgtgaat gcaggaatga  33660
ctgggccaca cccctcccgt gcacgccccc tcttgccctg caccccacag cccagccccc  33720
```

-continued

```
cgtgctggat gcccccccac agcagaggtg ctgttctgtg atcccctggg aaagacgccc  33780
tcaacctcca ccctgtccca cggcccaagg aagacaagac acaggccctc tcctcacagt  33840
ctccccacct ggctcctgct gggaccctca aggtgtgaac agggaggatg gttgtctggg  33900
tggcccctag gagcccagat cttcactcta cagaccccaa cccaagcacc cccttctgca  33960
gggcccagct catccccctc ctcctccctc tgctctcctc tcgtcgcctc tacgggaaat  34020
ccgggactca gcagtaaccc tcaggaagca gggcccaggc gccgtttaat aggaggcttc  34080
ctcacaatga aacttttaga aagccttgac tacaatgatg accttggtgt ggctgtgaac  34140
actgtcagct cccacagctg ctgcagcaaa aaatgtccat agacagggtg ggggcccggg  34200
gtcgtctgct gtcctgctca gcccacagca cgcatggagg atctgaggtg ccacacctga  34260
cgcccaggcc agaacatgcc tccctccagg gtgacctgcc atgtcctgca ttgctggagg  34320
gacaggggca gcctatgagg atctggggcc aggagatgaa tcctattaac ccagaggaaa  34380
actaacagga cccaagcacc ctccccgttg aagctgacct gcccagaggg gcctgggccc  34440
accccacaca ccggggcgga atgtgtacag gccccggtct ctgtgggtgt tccgctaact  34500
ggggctccca gtgctcaccc cacaactaaa gcgagcccca gcctccagag cccccgaagg  34560
agatgccgcc cacaagccca gcccccatcc aggaggcccc agagctcagg gcgccggggc  34620
agattctgaa cagccccgag tcacggtggg tacaactgga acgaccaccg tgagaaaaac  34680
tgtgtccaaa actgtctcct ggcccctgct ggaggccgcg ccagagaggg gagcagccgc  34740
cccgaaccta ggtcctgctc agctcacacg acccccagca cccagagcac aacggagtcc  34800
ccattgaatg gtgaggacgg ggaccagggc tccagggggt catggaaggg gctggacccc  34860
atcctactgc tatggtccca gtgctcctgg ccagaactga ccctaccacc gacaagagtc  34920
cctcagggaa acgggggtca ctggcacctc ccagcatcaa ccccaggcag cacaggcata  34980
aaccccacat ccagagccga ctccaggagc agagacaccc cagtaccctg ggggacaccg  35040
accctgatga ctccccactg gaatccaccc cagagtccac caggaccaaa gaccccgccc  35100
ctgtctctgt ccctcactca ggacctgctg cggggcgggc catgagacca gactcgggct  35160
tagggaacac cactgtggcc ccaacctcga ccaggccaca ggcccttcct tcctgccctg  35220
cggcagcaca gactttgggg tctgtgcaga gaggaatcac agaggcccca ggctgaggtg  35280
gtgggggtgg aagaccccca ggaggtggcc cacttccctt cctcccagct ggaacccacc  35340
atgaccttct taagataggg gtgtcatccg aggcaggtcc tccatggagc tcccttcagg  35400
ctcctccccg gtcctcacta ggcctcagtc ccggctgcgg gaatgcagcc accacaggca  35460
caccaggcag cccagaccca gccagcctgc agtgcccaag cccacattct ggagcagagc  35520
aggctgtgtc tgggagagtc tgggctcccc accgcccccc cgcacacccc acccacccct  35580
gtccaggccc tatgcaggag ggtcagagcc ccccatgggg tatggactta gggtctcact  35640
cacgtggctc ccctcctggg tgaaggggtc tcatgcccag atccccacag cagagctggt  35700
caaaggtgga ggcagtggcc ccagggccac cctgacctgg accctcaggc tcctctagcc  35760
ctggctgccc tgctgtccct gggaggcctg gactccacca gaccacaggt ccagggcacc  35820
gcccataggt gctgcccaca ctcagttcac aggaagaaga taagctccag acccccaaga  35880
ctgggacctg ccttcctgcc accgcttgta gctccagacc tccgtgcctc ccccgaccac  35940
ttacacacgg gccagggagc tgttccacaa agatcaaccc caaaccggga ccgcctggca  36000
ctcgggccgc tgccacttcc ctctccattt gttcccagca cctctgtgct ccctccctcc  36060
tccctccttc aggggaacag cctgtgcagc ccctccctgc accccacacc ctggggaggc  36120
```

ccaaccctgc ctccagccct ttctcccccg ctgctcttcc tgcccatcca gacaaccctg 36180
gggtcccatc cctgcagcct acaccctggt ctccacccag acccctgtct ctccctccag 36240
acacccctcc caggccaacc ctgcacatgc aggccctccc cttttctgct gccagagcct 36300
cagtttctac cctctgtgcc taccccctgc ctcctcctgc ccacaactcg agctcttcct 36360
ctcctggggc ccctgagcca tggcactgac cgtgcactcc cacccccaca ctgcccatgc 36420
cctcaccttc ctcctggaca ctctgacccc gctcccctct tggacccagc cctggtattt 36480
ccaggacaaa ggctcaccca agtcttcccc atgcaggccc ttgccctcac tgcccggtta 36540
cacggcagcc tcctgtgcac agaagcaggg agctcagccc ttccacaggc agaaggcact 36600
gaaagaaatc ggcctccagc accctgatgc acgtccgcct gtgtctctca ctgcccgcac 36660
ctgcagggag gctcggcact ccctgtaaag acgagggatc caggcagcaa catcatggga 36720
gaatgcaggg ctcccagaca gcccagccct ctcgcaggcc tctcctggga agagacctgc 36780
agccaccact gaacagccac ggagcccgct ggatagtaac tgagtcagtg accgacctgg 36840
agggcagggg agcagtgaac cggagcccag accataggga cagagaccag ccgctgacat 36900
cccgagcccc tcactggcgg ccccagaaca ccgcgtggaa acagaacaga cccacattcc 36960
cacctggaac agggcagaca ctgctgagcc cccagcacca gccctgagaa acaccaggca 37020
acggcatcag agggggctcc tgagaaagaa aggaggggag gtctccttca ccagcaagta 37080
cttcccttga ccaaaaacag ggtccacgca actcccccag gacaaaggag gagccccctg 37140
tacagcactg ggctcagagt cctctcccac acaccctgag tttcagacaa aaaccccctg 37200
gaaatcatag tatcagcagg agaactagcc agagacagca agaggggact cagtgactcc 37260
cgcggggaca ggaggatttt gtgggggctc gtgtcactgt gaggatattg tagtagtacc 37320
agctgctata cccacagtga cacagcccca ttcccaaagc cctgctgtaa acgcttccac 37380
ttctggagct gaggggctgg ggggagcgtc tgggaagtag ggcctagggg tggccatcaa 37440
tgcccaaaac gcaccagact ccccccccaga catcacccca ctggccagtg agcagagtaa 37500
acagaaaatg agaagcagct gggaagcttg cacaggcccc aaggaaagag ctttggcggg 37560
tgtgcaagag gggatgcggg cagagcctga gcagggcctt ttgctgtttc tgctttcctg 37620
tgcagatagt tccataaact ggtgttcaag atcgatggct gggagtgagc ccaggaggac 37680
agtgtgggaa gggcacaggg aaggagaagc agccgctatc ctacactgtc atctttcaag 37740
agtttgccct gtgcccacaa tgctgcatca tgggatgctt aacagctgat gtagacacag 37800
ctaaagagag aatcagtgaa atggatttgc agcacagatc tgaataaatt ctccagaatg 37860
tggagccaca cagaagcaag cacaaggaaa gtgcctgatg caagggcaaa gtacagtgtg 37920
taccttcagg ctgggcacag acactctgaa aagccttggc aggaactccc tgcaacaaag 37980
cagagccctg caggcaatgc cagctccaga gccctccctg agagcctcat gggcaaagat 38040
gtgcacaaca ggtgtttctc atagccccaa actgagaatg aagcaaacag ccatctgaag 38100
gaaaacaggc aaataaacga tggcaggttc atgaaatgca aacccagaca gccagaagga 38160
caacagtgag ggttacaggt gactctgtgg ttgagttcat gacaatgctg agtaattgga 38220
gtaacaaagg aaagtccaaa aaatactttc aatgtgattt cttctaaata aaatttacag 38280
ccggcaaaat gaactatctt cttaagggat aaactttcca ctaggaaaac tataaggaaa 38340
atcaagaaaa ggatgatcac ataaacacag tggtcgttac ttctactggg gaaggaagag 38400
ggtatgaact gagacacaca gggttggcaa gtctcctaac aagaacagaa caaatacatt 38460
acagtacctt gaaaacagca gttaaaattc taaattgcaa gaagaggaaa atgcacacag 38520
ctgtgtttag aaaattctca gtccagcact gttcataata gcaaagacat taacccaggt 38580
tggataaata aacgatgaca caggcaattg cacaatgata cagacataca ttcagtatat 38640
gagacattga tgatgtatcc ccaaagaaat gactttaaag agaaaaggcc tgatatgtgg 38700
tggcactcac ctccctgggc atccccggac aggctgcagg cacactgtgt ggcagggcag 38760
gctggtacct gctggcagct cctggggcct gatgtggagc aggcacagag ccgtatcccc 38820
ccgaggacat ataccccaa ggacggcaca gttggtacat tccggagaca agcaactcag 38880
ccacactccc aggccagagc ccgagaggga cgcccatgca cagggaggca gagcccagct 38940
cctccacagc cagcagcacc cgtgcagggg ccgccatctg gcaggcacag agcatgggct 39000
gggaggaggg gcagggacac caggcagggt tggcaccaac tgaaaattac agaagtctca 39060
tacatctacc tcagccttgc ctgacctggg cctcacctga cctggacctc acctggcctg 39120
gacctcacct ggcctagacc tcacctctgg gcttcacctg agctcggcct cacctgactt 39180
ggaccttgcc tgtcctgagc tcacatgatc tgggcctcac ctgacctggg tttcacctga 39240
cctgggcttc acctgacctg ggcctcatct gacctgggcc tcactggcct ggacctcacc 39300
tggcctgggc ttcacctggc ctcaggcctc atctgcacct gctccaggtc ttgctggaac 39360
ctcagtagca ctgaggctgc aggggctcat ccagggttgc agaatgactc tagaacctcc 39420
cacatctcag ctttctgggt ggaggcacct ggtggcccag ggaatataaa aagcctgaat 39480
gatgcctgcg tgatttgggg gcaatttata aacccaaaag gacatggcca tgcagcgggt 39540
agggacaata cagacagata tcagcctgaa atggagcctc agggcacagg tgggcacgga 39600
cactgtccac ctaagccagg ggcagacccg agtgtccccg cagtagacct gagagcgctg 39660
ggcccacagc ctcccctcgg tgccctgcta cctcctcagg tcagccctgg acatcccggg 39720
tttccccagg cctggcggta ggtttggggt gaggtctgtg tcactgtggt attacgattt 39780
ttggagtggt tattataccc acagtgtcac agagtccatc aaaaacccat ccctgggaac 39840
cttctgccac agccctccct gtggggcacc gccgcgtgcc atgttaggat tttgactgag 39900
gacacagcac catgggtatg gtggctaccg cagcagtgca gcccgtgacc caaacacaca 39960
gggcagcagg cacaacagac aagcccacaa gtgaccaccc tgagctcctg cctgccagcc 40020
ctggagacca tgaaacagat ggccaggatt atcccatagg tcagccagac ctcagtccaa 40080
caggtctgca tcgctgctgc cctccaatac cagtccggat ggggacaggg ctggcccaca 40140
ttaccatttg ctgccatccg gccaacagtc ccagaagccc ctccctcaag gctgggccac 40200
atgtgtggac cctgagagcc ccccatgtct gagtaggggc accaggaagg tggggctggc 40260
cctgtgcact gtccctgccc ctgtggtccc tggcctgcct ggccctgaca cctgggcctc 40320
tcctgggtca tttccaagac agaagacatt cccaggacag ctggagctgg gagtccatca 40380
tcctgcctgg ccgtcctgag tcctgcgcct ttccaaacct cacccgggaa gccaacagag 40440
gaatcacctc ccacaggcag agacaaagac cttccagaaa tctctgtctc tctccccagt 40500
gggcaccctc ttccagggca gtcctcagtg atatcacagt gggaacccac atctggatcg 40560
ggactgcccc cagaacacaa gatggcccac agggacagcc ccacagccca gcccttccca 40620
gacccctaaa aggcgtccca ccccctgcat ctgccccagg gctcaaactc caggaggact 40680
gactcctgca caccctcctg ccagacatca cctcagcccc tcctggaagg gacaggagcg 40740
cgcaagggtg agtcagaccc tcctgccctc gatggcaggc ggagaagatt cagaaaggtc 40800
tgagatcccc aggacgcagc accactgtca atgggggccc cagacgcctg gaccagggcc 40860

```
tgcgtgggaa aggcctctgg gcacactcag gggctttttg tgaagggtcc tcctactgtg  40920
tgactacagt aactaccaca gtgatgaacc cagcagcaaa aactgaccgg actcccaagg  40980
tttatgcaca cttctccgct cagagctctc caggatcaga agagccgggc ccaagggttt  41040
ctgcccagac cctcggcctc tagggacatc ttggccatga cagcccatgg gctggtgccc  41100
cacacatcgt ctgccttcaa acaagggctt cagagggctc tgaggtgacc tcactgatga  41160
ccacaggtgc cctggcccct tccccaccag ctgcaccaga ccccgtcatg acagatgccc  41220
cgattccaac agccaattcc tggggccagg aatcgctgta gacaccagcc tccttccaac  41280
acctcctgcc aattgcctgg attcccatcc cggttggaat caagaggaca gcatccccca  41340
ggctcccaac aggcaggact cccacaccct cctctgagag gccgctgtgt tccgtagggc  41400
caggctgcag acagtccccc tcacctgcca ctagacaaat gcctgctgta gatgtcccca  41460
cctggaaaat accactcatg gagcccccag ccccaggtac agctgtagag agagtctctg  41520
aggcccctaa gaagtagcca tgcccagttc tgccgggacc ctcggccagg ctgacaggag  41580
tggacgctgg agctgggccc atactgggcc acataggagc tcaccagtga gggcaggaga  41640
gcacatgccg gggagcaccc agcctcctgc tgaccagagg cccgtcccag agcccaggag  41700
gctgcagagg cctctccagg gggacactgt gcatgtctgg tccctgagca gccccccacg  41760
tccccagtcc tgggggcccc tggcacagct gtctggaccc tctctattcc ctgggaagct  41820
cctcctgaca gccccgcctc cagttccagg tgtggttatt gtcagggggt gtcagactgt  41880
ggtggataca gctatggtta ccacagtggt gctgcccata gcagcaacca ggccaagtag  41940
acaggcccct gctgtgcagc cccaggcctc cagctcacct gcttctcctg ggctctcaa   42000
ggctgctgtt ttctgcactc tcccctctgt ggggagggtt ccctcagtgg gagatctgtt  42060
ctcaacatcc cacggcctca ttcctgcaag gaaggccaat ggatgggcaa cctcacatgc  42120
cgcggctaag atagggtggg cagcctggcg gggacaggac atcctgctgg ggtatctgtc  42180
actgtgccta gtggggcact ggctcccaaa caacgcagtc cttgccaaaa tccccacggc  42240
ctcccccgct aggggctggc ctgatctcct gcagtcctag gaggctgctg acctccagaa  42300
tggctccgtc cccagttcca gggcgagagc agatcccagg ccggctgcag actgggaggc  42360
caccccctcc ttcccagggt tcactgcagg tgaccagggc aggaaatggc ctgaacacag  42420
ggataaccgg gccatccccc aacagagtcc acccccctcct gctctgtacc ccgcaccccc  42480
caggccagcc catgacatcc gacaacccca caccagagtc actgcccggt gctgccctag  42540
ggaggacccc tcagccccca ccctgtctag aggactgggg aggacaggac acgccctctc  42600
cttatggttc ccccacctgg ctctggctgg gacccttggg gtgtggacag aaaggacgct  42660
tgcctgattg gcccccagga gcccagaact tctctccagg gaccccagcc cgagcacccc  42720
cttacccagg acccagccct gcccctcctc ccctctgctc tcctctcatc accccatggg  42780
aatccagaat ccccaggaag ccatcaggaa gggctgaggg aggaagtggg gccactgcac  42840
caccaggcag gaggctctgt ctttgtgaac ccagggaggt gccagcctcc tagagggtat  42900
ggtccaccct gcctatggct cccacagtgg caggctgcag ggaaggacca gggacggtgt  42960
gggggagggc tcagggcccc gcgggtgctc catcttggat gagcctatct ctctcaccca  43020
cggactcgcc cacctcctct tcaccctggc cacacgtcgt ccacaccatc ctaagtccca  43080
cctacaccag agccggcaca gccagtgcag acagaggctg gggtgcaggg gggccgactg  43140
ggcagcttcg gggagggagg aatggaggaa ggggagttca gtgaagaggc ccccctcccc  43200
```

```
tgggtccagg atcctcctct gggacccccg gatcccatcc cctccaggct ctgggaggag  43260
aagcaggatg ggagaatctg tgcgggaccc tctcacagtg gaatacctcc acagcggctc  43320
aggccagata caaaagcccc tcagtgagcc ctccactgca gtgctgggcc tgggggcagc  43380
cgctcccaca caggatgaac ccagcacccc gaggatgtcc tgccaggggg agctcagagc  43440
catgaaggag caggatatgg gacccccgat acaggcacag acctcagctc cattcaggac  43500
tgccacgtcc tgccctggga ggaacccctt tctctagtcc ctgcaggcca ggaggcagct  43560
gactcctgac ttggacgcct attccagaca ccagacagag gggcaggccc cccagaacca  43620
gggatgagga cgccccgtca aggccagaaa agaccaagtt gcgctgagcc cagcaaggga  43680
aggtccccaa acaaaccagg aagtttctga aggtgtctgt gtcacagtgg agtatagcag  43740
ctcgtcccac agtgacactc gccaggccag aaaccccatc ccaagtcagc ggaatgcaga  43800
gagagcaggg aggacatgtt taggatctga ggccgcacct gacacccagg ccagcagacg  43860
tctcctgtcc acggcaccct gccatgtcct gcatttctgg aagaacaagg gcaggctgaa  43920
gggggtccag gaccaggaga tgggtccgct ctacccagag aaggagccag gcaggacaca  43980
agccccctcc ccattgaggc tgacctgccc agagggtcct gggcccaccc aacacaccgg  44040
ggcggaatgt gtgcaggcct cggtctctgt gggtgttccg ctagctgggg ctcacagtgc  44100
tcaccccaca cctaaaacga gccacagcct ccggagcccc tgaaggagac cccgcccaca  44160
agcccagccc ccacccagga ggccccagag cacagggcgc cccgtcggat tctgaacagc  44220
cccgagtcac agtgggtata actggaacta ccactgtgag aaaagcttcg tccaaaacgg  44280
tctcctggcc acagtcggag gccccgccag agaggggagc agccacccca aacccatgtt  44340
ctgccggctc ccatgacccc gtgcacctgg agccccacgg tgtccccact ggatgggagg  44400
acaagggccg ggggctccgg cgggtcgggg caggggcttg atggcttcct tctgccgtgg  44460
ccccattgcc cctggctgga gttgaccctt ctgacaagtg tcctcagaga gtcagggatc  44520
agtggcacct cccaacatca accccacgca gcccaggcac aaaccccaca tccagggcca  44580
actccaggaa cagagacacc ccaataccct gggggacccc gaccctgatg actcccgtcc  44640
catctctgtc cctcacttgg ggcctgctgc ggggcgagca cttgggagca aactcaggct  44700
taggggacac cactgtgggc ctgacctcga gcaggccaca gacccttccc tcctgccctg  44760
gtgcagcaca gactttgggg tctgggcagg gaggaacttc tggcaggtca ccaagcacag  44820
agcccccagg ctgaggtggc cccaggggga accccagcag gtggcccact acccttcctc  44880
ccagctggac cccatgtctt ccccaagata ggggtgccat ccaaggcagg tcctccatgg  44940
agcccccttc aggctcctct ccagacccca ctgggcctca gtccccactc taggaatgca  45000
gccaccacgg gcacaccagg cagcccaggc ccagccaccc tgcagtgccc aagcccacac  45060
cctggaggag agcagggtgc gtctgggagg ggctgggctc cccaccccca cccccacctg  45120
cacaccccac ccacccttgc ccgggccccc tgcaggaggg tcagagcccc catgggatat  45180
ggacttaggg tctcactcac gcacctcccc tcctgggaga aggggtctca tgcccagatc  45240
cccccagcag cgctggtcac aggtagaggc agtggcccca gggccaccct gacctggccc  45300
ctcaggctcc tctagccctg gctgccctgc tgtccctggg aggcctgggc tccaccagac  45360
cacaggtcta gggcaccgcc cacactgggg ccgcccacac acagctcaca ggaagaagat  45420
aagctccaga cccccaggcc cgggacctgc cttgctgcta cgacttcctg ccccagacct  45480
cgttgccctc ccccgtccac ttacacacag gccaggaagc tgttcccaca cagaccaacc  45540
ccagacgggg accacctggc actcaggtca ctgccatttc cttctccatt cacttccaat  45600
```

-continued

```
gcctctgtgc ttcctccctc ctccttcctt cgggggagca ccctgtgcag ctcctccctg  45660
cagtccacac cctggggaga cccgaccctg cagcccacac cctggggaga cctgaccctc  45720
ctccagccct ttctccccg ctgctcttgc cacccaccaa gacagccctg gggtcctgtc  45780
cctacagccc ccacccagtt ctctacctag acccgtcttc ctccctctaa acacctctcc  45840
caggccaacc ctacacctgc aggccctccc ctccactgcc aaagaccctc agtttctcct  45900
gcctgtgccc acccccgtgc tcctcctgcc cacagctcga gctcttcctc tcctagggcc  45960
cctgagggat ggcattgacc gtgccctcgc acccacacac tgcccatgcc ctcacattcc  46020
tcctggccac tccagcccca ctcccctctc aggcctggct ctggtatttc tgggacaaag  46080
ccttacccaa gtctttccca tgcaggcctg ggcccttacc ctcactgccc ggttacaggg  46140
cagcctcctg tgcacagaag cagggagctc agcccttcca caggcagaag gcactgaaag  46200
aaatcggcct ccagcgcctt gacacacgtc tgcctgtgtc tctcactgcc cgcacctgca  46260
gggaggctcg gcactccctc taaagacgag ggatccaggc agcagcatca caggagaatg  46320
cagggctacc agacatccca gtcctctcac aggcctctcc tgggaagaga cctgaagacg  46380
cccagtcaac ggagtctaac accaaacctc cctggaggcc gatgggtagt aacggagtca  46440
ttgccagacc tggaggcagg ggagcagtga gcccgagccc acaccatagg gccagaggac  46500
agccactgac atcccaagcc actcactggt ggtcccacaa caccccatgg aaagaggaca  46560
gacccacagt cccacctgga ccagggcaga gactgctgag acccagcacc agaaccaacc  46620
aagaaacacc aggcaacagc atcagagggg gctctggcag aacagaggag gggaggtctc  46680
cttcaccagc aggcgcttcc cttgaccgaa gacaggatcc atgcaactcc cccaggacaa  46740
aggaggagcc ccttgttcag cactgggctc agagtcctct ccaagacacc cagagtttca  46800
gacaaaaacc ccctggaatg cacagtctca gcaggagagc cagccagagc cagcaagatg  46860
gggctcagtg acacccgcag ggacaggagg attttgtggg ggctcgtgtc actgtgagga  46920
tattgtacta atggtgtatg ctatacccac agtgacacag ccccattccc aaagccctac  46980
tgcaaacgca ttccacttct ggggctgagg ggctggggga gcgtctggga aatagggctc  47040
aggggtgtcc atcaatgccc aaaacgcacc agactcccct ccatacatca cacccaccag  47100
ccagcgagca gagtaaacag aaaatgagaa gcaagctggg gaagcttgca caggccccaa  47160
ggaaagagct ttggcgggtg tgtaagaggg gatgcgggca gagcctgagc agggcctttt  47220
gctgtttctg ctttcctgtg cagagagttc cataaactgg tgttcgagat caatggctgg  47280
gagtgagccc aggaggacag cgtgggaaga gcacagggaa ggaggagcag ccgctatcct  47340
acactgtcat ctttcgaaag tttgccttgt gcccacactg ctgcatcatg ggatgcttaa  47400
cagctgatgt agacacagct aaagagagaa tcagtgagat ggatttgcag cacagatctg  47460
aataaattct ccagaatgtg gagcagcaca gaagcaagca cacagaaagt gcctgatgca  47520
aggacaaagt tcagtgggca ccttcaggca ttgctgctgg gcacagacac tctgaaaagc  47580
cctggcagga actccctgtg acaaagcaga accctcaggc aatgccagcc ccagagccct  47640
ccctgagagc ctcatgggca aagatgtgca caacaggtgt ttctcatagc cccaaactga  47700
gagcaaagca aacgtccatc tgaaggagaa caggcaaata aacgatggca ggttcatgaa  47760
atgcaaaccc agacagccac aagcacaaaa gtacagggtt ataagcgact ctggttgagt  47820
tcatgacaat gctgagtaat tggagtaaca aagtaaactc caaaaaatac tttcaatgtg  47880
atttcttcta aataaaattt acaccctgca aaatgaactg tcttcttaag ggatacattt  47940
```

-continued

```
cccagttaga aaaccataaa gaaaaccaag aaaaggatga tcacataaac acagtggtgg  48000
ttacttctgc tggggaagga agagggtatg aactgagata cacagggtgg gcaagtctcc  48060
taacaagaac agaacgaata cattacagta ccttgaaaac agcagttaaa cttctaaatt  48120
gcaagaagag gaaaatgcac acagttgtgt ttagaaaatt ctcagtccag cactgttcat  48180
aatagcaaag acattaaccc aggtcggata aataagcgat gacacaggca attgcacaat  48240
gatacagaca tatatttagt atatgagaca tcgatgatgt atccccaaat aaacgacttt  48300
aaagagataa agggctgatg tgtggtggca ttcacctccc tgggatcccc ggacaggttg  48360
caggctcact gtgcagcagg gcaggcgggt acctgctggc agttcctggg gcctgatgtg  48420
gagcaagcgc agggccatat atcccggagg acggcacagt cagtgaattc cagagagaag  48480
caactcagcc acactcccca ggcagagccc gagagggacg cccacgcaca gggaggcaga  48540
gcccagcacc tccgcagcca gcaccacctg cgcacgggcc accaccttgc aggcacagag  48600
tgggtgctga gaggaggggc agggacacca ggcagggtga gcacccagag aaaactgcag  48660
acgcctcaca catccacctc agcctcccct gacctggacc tcactggcct gggcctcact  48720
taacctgggc ttcacctgac cttggcctca cctgacttgg acctcgcctg tcccaagctt  48780
tacctgacct gggcctcaac tcacctgaac gtctcctgac ctgggtttaa cctgtcctgg  48840
aactcacctg gccttggctt cccctgacct ggacctcatc tggcctgggc ttcacctggc  48900
ctgggcctca cctgacctgg acctcatctg gcctggacct cacctggcct ggacttcacc  48960
tggcctgggc ttcacctgac ctggacctca cctggcctcg ggcctcacct gcacctgctc  49020
caggtcttgc tggagcctga gtagcactga gggtgcagaa gctcatccag ggttggggaa  49080
tgactctaga agtctcccac atctgacctt tctgggtgga ggcagctggt ggccctggga  49140
atataaaaat ctccagaatg atgactctgt gatttgtggg caacttatga acccgaaagg  49200
acatggccat ggggtgggta gggacatagg gacagatgcc agcctgaggt ggagcctcag  49260
gacacaggtg ggcacggaca ctatccacat aagcgaggga tagacccgag tgtccccaca  49320
gcagacctga gagcgctggg cccacagcct cccctcagag ccctgctgcc tcctccggtc  49380
agccctggac atcccaggtt tccccaggcc tggcggtagg tttagaatga ggtctgtgtc  49440
actgtggtat tacgatattt tgactggtta ttataaccac agtgtcacag agtccatcaa  49500
aaacccatgc ctggaagctt cccgccacag ccctccccat ggggccctgc tgcctcctca  49560
ggtcagcccc ggacatcccg ggtttcccca ggctgggcgg taggtttggg gtgaggtctg  49620
tgtcactgtg gtattactat ggttcgggga gttattataa ccacagtgtc acagagtcca  49680
tcaaaaaccc atccctggga gcctcccgcc acagccctcc ctgcagggga ccggtacgtg  49740
ccatgttagg attttgatcg aggagacagc accatgggta tggtggctac cacagcagtg  49800
cagcctgtga cccaaacccg cagggcagca ggcacgatgg acaggcccgt gactgaccac  49860
gctgggctcc agcctgccag ccctggagat catgaaacag atggccaagg tcaccctaca  49920
ggtcatccag atctggctcc gaggggtctg catcgctgct gccctcccaa cgccagtcca  49980
aatgggacag ggacggcctc acagcaccat ctgctgccat caggccagcg atcccagaag  50040
cccctccctc aaggctgggc acatgtgtgg acactgagag ccctcatatc tgagtagggg  50100
caccaggagg gaggggctgg ccctgtgcac tgtccctgcc cctgtggtcc ctggcctgcc  50160
tggccctgac acctgagcct ctcctgggtc atttccaaga cagaagacat tcctggggac  50220
agccggagct gggcgtcgct catcctgccc ggccgtcctg agtcctgctc atttccagac  50280
ctcaccgggg aagccaacag aggactcgcc tcccacattc agagacaaag aaccttccag  50340
```

-continued

```
aaatccctgc ctctctcccc agtggacacc ctcttccagg acagtcctca gtggcatcac  50400
agcggcctga gatccccagg acgcagcacc gctgtcaata ggggccccaa atgcctggac  50460
cagggcctgc gtgggaaagg cctctggcca cactcgggct ttttgtgaag ggccctcctg  50520
ctgtgtgact acagtaacta ccatagtgat gaacccagtg gcaaaaactg gctggaaacc  50580
caggggctgt gtgcacgcct cagcttggag ctctccagga gcacaagagc cgggcccaag  50640
gatttgtgcc cagaccctca gcctctaggg acacctgggt catctcagcc tgggctggtg  50700
ccctgcacac catcttcctc caaatagggg cttcagaggg ctctgaggtg acctcactca  50760
tgaccacagg tgacctggcc cttccctgcc agctatacca gaccctgtct tgacagatgc  50820
cccgattcca acagccaatt cctgggaccc tgaatagctg tagacaccag cctcattcca  50880
gtacctcctg ccaattgcct ggattcccat cctggctgga atcaagaagg cagcatccgc  50940
caggctccca acaggcagga ctcccgcaca ccctcctctg agaggccgct gtgttccgca  51000
gggccaggcc ctggacagtt cccctcacct gccactagag aaacacctgc cattgtcgtc  51060
cccacctgga aaagaccact cgtggagccc ccagccccag gtacagctgt agagacagtc  51120
ctcgaggccc ctaagaagga gccatgccca gttctgccgg gaccctcggc caggccgaca  51180
ggagtggacg ctggagctgg gcccacactg ggccacatag gagctcacca gtgagggcag  51240
gagagcacat gccggggagc acccagcctc ctgctgacca gaggcccgtc ccagagccca  51300
ggaggctgca gaggcctctc cagggagaca ctgtgcatgt ctggtaccta agcagccccc  51360
cacgtcccca gtcctggggg cccctggctc agctgtctgg gccctccctg ctccctggga  51420
agctcctcct gacagccccg cctccagttc caggtgtggt tattgtcagg cgatgtcaga  51480
ctgtggtgga tatagtggct acgattacca cagtggtgcc gcccatagca gcaaccaggc  51540
caagtagaca ggcccctgct gcgcagcccc aggcatccac ttcacctgct tctcctgggg  51600
ctctcaaggc tgctgtctgt cctctggccc tctgtgggga gggttccctc agtgggaggt  51660
ctgtgctcca gggcagggat gattgagata gaaatcaaag gctggcaggg aaaggcagct  51720
tcccgccctg agaggtgcag gcagcaccac ggagccacgg agtcacagag ccacggagcc  51780
cccattgtgg gcatttgaga gtgctgtgcc cccggcaggc ccagccctga tggggaagcc  51840
tgtcccatcc cacagcccgg gtcccacggg cagcgggcac agaagctgcc aggttgtcct  51900
ctatgatcct catccctcca gcagcatccc ctccacagtg gggaaactga ggcttggagc  51960
accacccggc cccctggaaa tgaggctgtg agcccagaca gtgggcccag agcactgtga  52020
gtaccccggc agtacctggc tgcagggatc agccagagat gccaaaccct gagtgaccag  52080
cctacaggag gatccggccc cacccaggcc actcgattaa tgctcaaccc cctgccctgg  52140
agacctcttc cagtaccacc agcagctcag cttctcaggg cctcatccct gcaaggaagg  52200
tcaagggctg ggcctgccag aaacacagca ccctccctag ccctggctaa gacagggtgg  52260
gcagacggct gtggacggga catattgctg gggcatttct cactgtcact tctgggtggt  52320
agctctgaca aaaacgcaga ccctgccaaa atccccactg cctcccgcta ggggctggcc  52380
tggaatcctg ctgtcctagg aggctgctga cctccaggat ggctccgtcc ccagttccag  52440
ggcgagagca gatcccaggc aggctgtagg ctgggaggcc acccctgccc ttgccggggt  52500
tgaatgcagg tgcccaaggc aggaaatggc atgagcacag ggatgaccgg gacatgcccc  52560
accagagtgc gccccttcct gctctgcacc ctgcaccccc caggccagcc cacgacgtcc  52620
aacaactggg cctgggtggc agccccaccc agacaggaca gacccagcac cctgaggagg  52680
```

-continued tcctgccagg gggagctaag agccatgaag gagcaagata tggggccccc gatacaggca 52740
cagatgtcag ctccatccag gaccacccag cccacaccct gagaggaacg tctgtctcca 52800
gcctctgcag gtcgggaggc agctgacccc tgacttggac ccctattcca gacaccagac 52860
agaggcgcag gccccccaga accagggttg agggacgccc cgtcaaagcc agacaaaacc 52920
aaggggtgtt gagcccagca agggaaggcc cccaaacaga ccaggaggtt tctgaaggtg 52980
tctgtgtcac agtggggtat agcagcagct ggtaccacag tgacactcac ccagccagaa 53040
accccattcc aagtcagcgg aagcagagag agcagggagg acacgtttag gatctgagac 53100
tgcacctgac acccaggcca gcagacgtct cccctccagg gcaccccacc ctgtcctgca 53160
tttctgcaag atcaggggcg gcctgagggg gggtctaggg tgaggagatg ggtcccctgt 53220
acaccaagga ggagttaggc aggtcccgag cactctcccc attgaggctg acctgcccag 53280
agagtcctgg gcccacccca cacaccgggg cggaatgtgt gcaggcctcg gtctctgtgg 53340
gtgttccgct agctggggct cacagtgctc accccacacc taaaatgagc cacagcctcc 53400
ggagcccccg caggagaccc cgcccacaag cccagccccc acccaggagg ccccagagct 53460
cagggcgccc cgtcggattc cgaacagccc cgagtcacag cgggtataac cggaaccacc 53520
actgtcagaa tagctacgtc aaaaactgtc cagtggccac tgccggaggc cccgccagag 53580
agggcagcag ccactctgat cccatgtcct gccggctccc atgaccccca gcacgcggag 53640
ccccacagtg tccccactgg atgggaggac aagagctggg gattccggcg ggtcggggca 53700
ggggcttgat cgcatccttc tgccgtggct ccagtgcccc tggctggagt tgacccttct 53760
gacaagtgtc ctcagagaga caggcatcac cggcgcctcc caacatcaac cccaggcagc 53820
acaggcacaa accccacatc cagagccaac tccaggagca gagacacccc aatacccctgg 53880 gggaccccga ccctgatgac ttcccactgg aattcgccgt agagtccacc aggaccaaag 53940
accctgcctc tgcctctgtc cctcactcag gacctgctgc cgggcgaggc cttgggagca 54000
gacttgggct taggggacac cagtgtgacc ccgaccttga ccaggacgca gacctttcct 54060
tcctttcctg gggcagcaca gactttgggg tctgggccag gaggaacttc tggcaggtcg 54120
ccaagcacag aggccacagg ctgaggtggc cctggaaaga cctccaggag gtggccactc 54180
cccttcctcc cagctggacc ccatgtcctc cccaagataa gggtgccatc caaggcaggt 54240
gctccttgga gccccattca gactcctccc tggaccccac tgggcctcag tcccagctct 54300
ggggatgaag ccaccacaag cacaccaggc agcccaggcc cagccaccct gcagtgccca 54360
agcacacact ctggagcaga gcagggtgcc tctgggaggg gctgagctcc cccaccccacc 54420 cccacctgca caccccaccc acccctgccc agcggctctg caggagggtc agagccccac 54480
atggggtatg gacttagggt ctcactcacg tggctcccat catgagtgaa ggggcctcaa 54540
gcccaggttc ccacagcagc gcctgtcgca agtggaggca gaggcccgag ggccaccctg 54600
acctggtccc tgaggttcct gcagcccagg ctgccctgct gtccctggga ggcctgggct 54660
ccaccagacc acaggtccag ggcaccgggt gcaggagcca cccacacaca gctcacagga 54720
agaagataag ctccagaccc ccagggccag aacctgcctt cctgctactg cttcctgccc 54780
cagacctggg cgccctcccc cgtccactta cacacaggcc aggaagctgt tcccacacag 54840
aacaacccca aaccaggacc gcctggcact caggtggctg ccatttcctt ctccatttgc 54900
tcccagcgcc tctgtcctcc ctggttcctc cttcggggga acagcctgtg cagccagtcc 54960
ctgcagccca caccctgggg agacccaacc ctgcctgggg cccttccaac cctgctgctc 55020
ttactgccca cccagaaaac tctggggtcc tgtccctgca gtccctaccc tggtctccac 55080

-continued ccagacccct gtgtatcact ccagacaccc ctcccaggca aaccctgcac ctgcaggccc 55140
tgtcctcttc tgtcgctaga gcctcagttt ctccccccctg tgcccacacc ctacctcctc 55200
ctgcccacaa ctctaactct tcttctcctg gagcccctga gccatggcat tgaccctgcc 55260
ctcccaccac ccacagccca tgccctcacc ttcctcctgg ccactccgac cccgccccct 55320
ctcaggccaa gccctggtat ttccaggaca aaggctcacc caagtctttc ccaggcaggc 55380
ctgggctctt gccctcactt cccggttaca cgggagcctc ctgtgcacag aagcagggag 55440
ctcagccctt ccacaggcag aaggcactga aagaaatcgg cctccagcac cttgacacac 55500
gtccgcccgt gtctctcact gcccgcacct gcagggaggc tccgcactcc ctctaaagac 55560
aagggatcca ggcagcagca tcacgggaga atgcagggct cccagacatc ccagtcctct 55620
cacaggcctc tcctgggaag agacctgcag ccaccaccaa acagccacag aggctgctgg 55680
atagtaactg agtcaatgac cgacctggag ggcaggggag cagtgagccg gagcccatac 55740
catagggaca gagaccagcc gctgacatcc cgagctcctc aatggtggcc ccataacaca 55800
cctaggaaac ataacacacc cacagcccca cctggaacag ggcagagact gctgagcccc 55860
cagcaccagc cccaagaaac accaggcaac agtatcagag gggctcccg agaaagagag 55920 gaggggagat ctccttcacc atcaaatgct tcccttgacc aaaaacaggg tccacgcaac 55980
tcccccagga caaaggagga gccccctata cagcactggg ctcagagtcc tctctgagac 56040
accctgagtt tcagacaaca acccgctgga atgcacagtc tcagcaggag aacagaccaa 56100
agccagcaaa agggacctcg gtgacaccag tagggacagg aggattttgt gggggctcgt 56160
gtcactgtga ggatattgta gtggtggtag ctgctactcc cacagtgaca cagacccatt 56220
cccaaagccc tactgcaaac acacccactc ctggggctga ggggctgggg gagcgtctgg 56280
gaagtagggt ccaggggtgt ctatcaatgt ccaaaatgca ccagactccc cgccaaacac 56340
caccccacca gccagcgagc agggtaaaca gaaaatgaga ggctctggga agcttgcaca 56400
ggccccaagg aaagagcttt ggcgggtgtg caagagggga tgcaggcaga gcctgagcag 56460 ggcctttgc tgtttctgct ttcctgtgca gagagttcca taaactggtg ttcaagatca 56520
gtggctggga atgagcccag gagggcagtc tgtgggaaga gcacagggaa ggaggagcag 56580
ccgctatcct acactgtcat ctttcaaaag tttgccttgt gaccacacta ttgcatcatg 56640
ggatgcttaa gagctgatgt agacacagct aaagagagaa tcagtgagat gaatttgcag 56700
catagatctg aataaactct ccagaatgtg gagcagtaca gaagcaaaca cacagaaagt 56760
gcctgatgca aggacaaagt tcagtgggca ccttcaggca ttgctgctgg gcacagacac 56820
tctgaaaagc cttggcagga tctccctgcg acaaagcaga accctcaggc aatgccagcc 56880
ccagagccct ccctgagagc gtcatgggga aagatgtgca gaacagctga ttatcataga 56940
ctcaaactga gaacagagca aacgtccatc tgaagaacag tcaaataagc aatggtaggt 57000
tcatgcaatg caaacccaga cagccagggg acaacagtag agggctacag gcggctttgc 57060
ggttgagttc atgacaatgc tgagtaattg gagtaacaga ggaaagccca aaaaatactt 57120
ttaatgtgat ttcttctaaa taaaatttac accaggcaaa atgaactgtc ttcttaaggg 57180
ataaactttc ccctggaaaa actacaagga aaattaagaa aacgatgatc acataaacac 57240
agttgtggtt acttctactg gggaaggaag agggtatgag ctgagacaca cagagtcggc 57300
aagtctccaa gcaagcacag aacgaataca ttacagtacc ttgaatacag cagttaaact 57360
tctaaatcgc aagaacagga aaatgcacac agctgtgttt agaaaattct cagtccagca 57420

-continued

```
ctattcataa tagcaaagac attaacccag gttggataaa taaatgatga cacaggcaat  57480
tgcacaatga tacagacata catttagtac atgagacatc gatgatgtat ccccaaagaa  57540
atgactttaa agagaaaagg cctgatgtgt ggtggcactc acctccctgg gatccccgga  57600
caggttgcag gcacactgtg tggcagggca ggctggtaca tgctggcagc tcctggggcc  57660
tgatgtggag caagcgcagg gctgtatacc cccaaggatg gcacagtcag tgaattccag  57720
agagaagcag ctcagccaca ctgcccaggc agagcccgag agggacgccc acgtacaggg  57780
aggcagagcc cagctcctcc acagccacca ccacctgtgc acgggccacc accttgcagg  57840
cacagagtgg gtgctgagag gaggggcagg gacaccaggc agggtgagca cccagagaaa  57900
actgcagaag cctcacacat ccacctcagc ctcccctgac ctggacctca cctggtctgg  57960
acctcacctg gcctgggcct cacctgacct ggacctcacc tggcctgggc ttcacctgac  58020
ctggacctca cctggcctcc ggcctcacct gcacctgctc caggtcttgc tggaacctga  58080
gtagcactga ggctgcagaa gctcatccag ggttggggaa tgactctgga actctcccac  58140
atctgacctt tctgggtgga ggcatctggt ggccctggga atataaaaag ccccagaatg  58200
gtgcctgcgt gatttggggg caatttatga acccgaaagg acatggccat ggggtgggta  58260
gggacatagg gacagatgcc agcctgaggt ggagcctcag gacacagttg gacgcggaca  58320
ctatccacat aagcgaggga cagacccgag tgttcctgca gtagacctga gagcgctggg  58380
cccacagcct cccctcggtg ccctgctgcc tcctcaggtc agccctggac atcccgggtt  58440
tccccaggcc agatggtagg tttgaagtga ggtctgtgtc actgtggtat tatgattacg  58500
tttgggggag ttatcgttat acccacagca tcacacggtc catcagaaac ccatgccaca  58560
gccctccccg caggggaccg ccgcgtgcca tgttacgatt ttgatcgagg acacagcgcc  58620
atgggtatgg tggctaccac agcagtgcag cccatgaccc aaacacacag ggcagcaggc  58680
acaatggaca ggcctgtgag tgaccatgct gggctccagc ccgccagccc cggagaccat  58740
gaaacagatg gccaaggtca ccccacagtt cagccagaca tggctccgtg gggtctgcat  58800
cgctgctgcc ctctaacacc agcccagatg gggacaaggc caaccccaca ttaccatctc  58860
ctgctgtcca cccagtggtc ccagaagccc ctccctcatg gctgagccac atgtgtgaac  58920
cctgagagca ccccatgtca gagtaggggc agcagaaggg cggggctggc cctgtgcact  58980
gtccctgcac ccatggtccc tcgcctgcct ggccctgaca cctgagcctc ttctgagtca  59040
tttctaagat agaagacatt cccggggaca gccggagctg ggcgtcgctc atcccgcccg  59100
gccgtcctga gtcctgcttg tttccagacc tcaccaggga agccaacaga ggactcacct  59160
cacacagtca gagacaaaga accttccaga aatccctgtc tcactcccca gtgggcacct  59220
tcttccagga cattcctcgg tcgcatcaca gcaggcaccc acatctggat caggacggcc  59280
cccagaacac aagatggccc atggggacag ccccacaacc caggccttcc cagaccccta  59340
aaaggcgtcc cacccccctgc acctgcccca gggctaaaaa tccaggaggc ttgactcccg  59400
catacccctcc agccagacat cacctcagcc ccctcctgga ggggacagga gcccgggagg  59460
gtgagtcaga cccacctgcc ctcgatggca ggcggggaag attcagaaag gcctgagatc  59520
cccaggacgc agcaccactg tcaatggggg ccccagacgc ctggaccagg gcctgcgtgg  59580
gaaaggccgc tgggcacact caggggcttt ttgtgaaggc ccctcctact gtgtgactac  59640
ggtgactacc acagtgatga aactagcagc aaaaactggc cggacaccca gggaccatgc  59700
acacttctca gcttggagct ctccaggacc agaagagtca ggtctgaggg tttgtagcca  59760
gaccctcggc ctctagggac accctggcca tcacagcgga tgggctggtg ccccacatgc  59820
```

catctgctcc aaacaggggc ttcagagggc tctgaggtga cttcactcat gaccacaggt 59880
gccctggccc cttccccgcc agctacaccg aaccctgtcc caacagctgc cccagttcca 59940
acagccaatt cctggggccc agaattgctg tagacaccag cctcgttcca gcacctcctg 60000
ccaattgcct ggattcacat cctggctgga atcaagaggg cagcatccgc caggctccca 60060
acaggcagga ctcccgcaca ccctcctctg agaggccgct gtgttccgca gggccaggcc 60120
ctggacagtt cccctcacct gccactagag aaacacctgc cattgtcgtc cccacctgga 60180
aaagaccact cgtggagccc ccagccccag gtacagctgt agagagactc cccgagggat 60240
ctaagaagga gccatgcgca gttctgccgg gaccctcggc caggccgaca ggagtggaca 60300
ctggagctgg gcccacactg ggccacatag gagctcacca gtgagggcag gagagcacat 60360
gccggggagc acccagcctc ctgctgacca gaggcccgtc ccagagccca ggaggctgca 60420
gaggcctctc caggggacca ctgtgcatgt ctggtccctg agcagccccc cacgtcccca 60480
gtcctggggg cccctggcac agctgtctgg accctccctg ttccctggga agctcctcct 60540
gacagccccg cctccagttc caggtgtggt tattgtcagg gggtgtcaga ctgtggtgga 60600
tacagctatg gttaccacag tggtgctgcc catagcagca accaggccaa gtagacaggc 60660
ccctgctgtg cagccccagg cctccacttc acctgcttct cctggggctc tcaaggtcac 60720
tgttgtctgt actctgccct ctgtggggag ggttccctca gtgggaggtc tgttctcaac 60780
atcccagggc ctcatgtctg cacggaaggc caatggatgg gcaacctcac atgccgcggc 60840
taagataggg tgggcagcct ggcgggggac agtacatact gctggggtgt ctgtcactgt 60900
gcctagtggg gcactggctc ccaaacaacg cagtcctcgc caaaatcccc acagcctccc 60960
ctgctagggg ctggcctgat ctcctgcagt cctaggaggc tgctgacctc cagaatgtct 61020
ccgtccccag ttccagggcg agagcagatc ccaggccggc tgcagactgg gaggccaccc 61080
cctccttccc agggttcact ggaggtgacc aaggtaggaa atggccttaa cacagggatg 61140
actgcgccat cccccaacag agtcagcccc ctcctgctct gtaccccgca ccccccaggc 61200
cagtccacga aaaccagggc cccacatcag agtcactgcc tggcccggcc ctggggcgga 61260
cccctcagcc cccaccctgt ctagaggact tggggggaca ggacacaggc cctctcctta 61320
tggttccccc acctgcctcc ggccgggacc cttggggtgt ggacagaaag gacacctgcc 61380
taattggccc ccaggaaccc agaacttctc tccagggacc ccagcccgag cacccccctta 61440
cccaggaccc agccctgccc ctcctcccct ctgctctcct ctcatcaccc catgggaatc 61500
cggtatcccc aggaagccat caggaagggc tgaaggagga agcggggccg tgcaccaccg 61560
ggcaggaggc tccgtcttcg tgaacccagg gaagtgccag cctcctagag ggtatggtcc 61620
accctgcctg gggctcccac cgtggcaggc tgcggggaag gaccagggac ggtgtggggg 61680
agggctcagg gccctgcggg tgctcctcca tcttcggtga gcctcccccct tcacccaccg 61740
tcccgcccac ctcctctcca ccctggctgc acgtcttcca caccatcctg agtcctacct 61800
acaccagagc cagcaaagcc agtgcagaca aaggctgggg tgcagggggg ctgccagggc 61860
agcttcgggg agggaaggat ggagggaggg gaggtcagtg aagaggcccc cttcccctgg 61920
gtccaggatc ctcctctggg acccccggat cccatcccct cctggctctg ggaggagaag 61980
caggatggga gaatctgtgc gggaccctct cacagtggaa tatccccaca gcggctcagg 62040
ccagacccaa aagcccctca gtgagccctc cactgcagtc ctgggcctgg gtagcagccc 62100
ctcccacaga ggacagaccc agcaccccga agaagtcctg ccagggggag ctcagagcca 62160

-continued tgaaagagca ggatatgggg tccccgatac aggcacagac ctcagctcca tccaggccca 62220
ccgggaccca ccatgggagg aacacctgtc tccgggttgt gaggtagctg gcctctgtct 62280
cggaccccac tccagacacc agacagaggg gcaggccccc caaaaccagg gttgagggat 62340
gatccgtcaa ggcagacaag accaaggggc actgacccca gcaagggaag gctcccaaac 62400
agacgaggag gtttctgaag ctgtctgtat cacagtgggg tatagcagtg gctggtacca 62460
cagtgacact cgccaggcca gaaaccccgt cccaagtcag cggaagcaga gagagcaggg 62520
aggacacgtt taggatctga ggccgcacct gacacccagg gcagcagacg tctcccctcc 62580
agggcaccct ccaccgtcct gcgtttcttc aagaataggg gcggcctgag ggggtccagg 62640
gccaggcgat aggtcccctc taccccaagg aggagccagg caggacccga gcaccgtccc 62700
cattgaggct gacctgccca gacgggcctg ggcccacccc acacaccggg gcggaatgtg 62760
tgcaggcccc agtctctgtg ggtgttccgc tagctggggc ccccagtgct caccccacac 62820
ctaaagcgag ccccagcctc cagagccccc taagcattcc ccgcccagca gcccagcccc 62880
tgcccccacc caggaggccc cagagctcag ggcgcctggt cggattctga acagccccga 62940
gtcacagtgg gtataactgg aacgaccacc gtgagaaaaa ctgtgtccaa aactgactcc 63000
tggcagcagt cggaggcccc gccagagagg ggagcagccg gcctgaaccc atgtcctgcc 63060
ggttcccatg acccccagca cccagagccc cacggtgtcc ccgttggata atgaggacaa 63120
gggctggggg ctccggtggt ttgcggcagg gacttgatca catccttctg ctgtggcccc 63180
attgcctctg gctggagttg acccttctga caagtgtcct cagaaagaca gggatcaccg 63240
gcacctccca atatcaaccc caggcagcac agacacaaac cccacatcca gagccaactc 63300
caggagcaga gacaccccaa cactctgggg gaccccaacc gtgataactc cccactggaa 63360
tccgccccag agtctaccag gaccaaaggc cctgccctgt ctctgtccct cactcagggc 63420
ctcctgcagg gcgagcgctt gggagcagac tcggtcttag gggacaccac tgtgggcccc 63480
aactttgatg aggccactga cccttccttc ctttcctggg gcagcacaga ctttggggtc 63540
tgggcaggga agaactactg gctggtggcc aatcacagag cccccaggcc gaggtggccc 63600
caagaaggcc ctcaggaggt ggccactcca cttcctccca gctggacccc aggtcctccc 63660
caagataggg gtgccatcca aggcaggtcc tccatggagc ccccttcaga ctcctcccgg 63720
gaccccactg gacctcagtc cctgctctgg gaatgcagcc accacaagca caccaggaag 63780
cccaggccca gccaccctgc agtgggcaag cccacactct ggagcagagc agggtgcgtc 63840
tgggaggggc taacctcccc accccccacc ccccatctgc acacagccac ctaccactgc 63900
ccagaccctc tgcaggaggg ccaagccacc atggggtatg gacttagggt ctcactcacg 63960
tgcctcccct cctgggagaa ggggcctcat gcccagatcc ctgcagcact agacacagct 64020
ggaggcagtg gccccagggc caccctgacc tggcatctaa ggctgctcca gcccagacag 64080
cactgccgtt cctgggaagc ctgggctcca ccagaccaca ggtccagggc acagcccaca 64140
ggagccaccc acacacagct cacaggaaga agataagctc cagaccccag ggcgggacct 64200
gccttcctgc caccacttac acacaggcca gggagctgtt cccacacaga tcaaccccaa 64260
accgggactg cctggcacta gggtcactgc catttccctc tccattccct cccagtgcct 64320
ctgtgctccc tccttctggg gaacaccctg tgcagcccct ccctgcagcc cacacgctgg 64380
ggagacccca ccctgcctcg ggccttttct acctgctgca cttgccgccc acccaaacaa 64440
ccctgggtac gtgaccctgc agtcctcacc ctgatctgca accagacccc tgtccctccc 64500
tctaaacacc cctcccaggc caactctgca cctgcaggcc ctccgctctt ctgccacaag 64560

-continued

```
agcctcaggt tttcctacct gtgcccaccc cctaacccct cctgcccaca acttgagttc  64620
ttcctctcct ggagcccttg agccatggca ctgaccctac actcccaccc acacactgcc  64680
catgccatca ccttcctcct ggacactctg accccgctcc cctccctctc agacccggcc  64740
ctggtatttc caggacaaag gctcacccaa gtcttcccca tgcaggccct tgccctcact  64800
gcctggttac acgggagcct cctgtgcgca gaagcaggga gctcagctct tccacaggca  64860
gaaggcactg aaagaaatca gcctccagtg ccttgacaca cgtccgcctg tgtctctcac  64920
tgcctgcacc tgcagggagg ctccgcactc cctctaaaga tgagggatcc aggcagcaac  64980
atcacgggag aatgcagggc tcccagacag cccagccctc tcgcaggcct ctcctgggaa  65040
gagacctgca gccaccactg aacagccacg gaggtcgctg gatagtaacc gagtcagtga  65100
ccgacctgga gggcagggga gcagtgaacc ggagcccata ccatagggac agagaccagc  65160
cgctaacatc ccgagcccct cactggcggc cccagaacac cccgtggaaa gagaacagac  65220
ccacagtccc acctggaaca gggcagacac tgctgagccc ccagcaccag ccccaagaaa  65280
cactaggcaa cagcatcaga gggggctcct gagaaagaga ggaggggagg tctccttcac  65340
catcaaatgc ttcccttgac caaaaacagg gtccacgcaa ctcccccagg acaaaggagg  65400
agccccctgt acagcactgg gctcagagtc ctctctgaga caggctcagt ttcagacaac  65460
aacccgctgg aatgcacagt ctcagcagga gagccaggcc agagccagca agaggagact  65520
cggtgacacc agtctcctgt agggacagga ggattttgtg ggggttcgtg tcactgtgag  65580
catattgtgg tggtgactgc tattcccaca gtgacacaac cccattccta aagccctact  65640
gcaaacgcac ccactcctgg gactgagggg ctgggggagc gtctgggaag tatggcctag  65700
gggtgtccat caatgcccaa aatgcaccag actctcccca agacatcacc ccaccagcca  65760
gtgagcagag taaacagaaa atgagaagca gctgggaagc ttgcacaggc cccaaggaaa  65820
gagctttggc aggtgtgcaa gaggggatgt gggcagagcc tcagcagggc cttttgctgt  65880
ttctgctttc ctgtgcagag agttccataa actggtattc aagatcaatg gctgggagtg  65940
agcccaggag gacagtgtgg gaagagcaca gggaaggagg agcagccgct atcctacact  66000
gtcatctttt gaaagtttgc cctgtgccca caatgctgca tcatgggatg cttaacagct  66060
gatgtagaca cagctaaaga gagaatcagt gaaatgcatt tgcagcacag atctgaataa  66120
atcctccaga atgtggagca gcacagaagc aagcacacag aaagtgcctg atgccaaggc  66180
aaagttcagt gggcaccttc aggcattgct gctgggcaca gacactctga aaagcactgg  66240
caggaactgc ctgtgacaaa gcagaaccct caggcaatgc cagccctaga gcccttcctg  66300
agaacctcat gggcaaagat gtgcagaaca gctgtttgtc atagccccaa actatggggc  66360
tggacaaagc aaacgtccat ctgaaggaga acagacaaat aaacgatggc aggttcatga  66420
aatgcaaact aggacagcca gaggacaaca gtagagagct acaggcggct ttgcggttga  66480
gttcatgaca atgctgagta attggagtaa cagaggaaag cccaaaaaat acttttaatg  66540
tgatttcttc taaataaaat ttacacccgg caaaatgaac tatcttctta agggataaac  66600
tttcccctgg aaaaactata aggaaaatca agaaaacgat gatcacataa acacagtggt  66660
ggttacttct actggggaag gaagagggta tgagctgaga cacacagagt cggcaagtct  66720
cctaacaaga acagaacaaa tacattacag taccttgaaa acagcagtta aacttctaaa  66780
tcgcaagaag aggaaaatgc acacacctgt gtttagaaaa ttctcagtcc agcactgttc  66840
ataatagcaa agacattaac ccaggttgga taaataagcg atgacacagg caattgcaca  66900
```

-continued atgatacaga catacattca gtatatgaga catcgatgat gtatccccaa agaaatgact 66960
ttaaagagaa aaggcctgat gtgtggtggc aatcacctcc ctgggcatcc ccggacaggc 67020
tgcaggctca ctgtgtggca gggcaggcag gcacctgctg gcagctcctg gggcctgatg 67080
tggagcaggc acagagctgt atatccccaa ggaaggtaca gtcagtgcat tccagagaga 67140
agcaactcag ccacactccc tggccagaac ccaagatgca cacccatgca cagggaggca 67200
gagcccagca cctccgcagc caccaccacc tgcgcacggg ccaccacctt gcaggcacag 67260
agtgggtgct gagaggaggg gcagggacac caggcagggt gagcacccag agaaaactgc 67320
agaagcctca cacatccacc tcagcctccc ctgacctgga cctcacctgg cctgggcctc 67380
acctgacctg gacctcacct ggcctgggct tcacctggcc tgggcttcac ctgacctgga 67440
cctcacctgg cctcgggcct cacctggcct gggcttcacc tggcctgggc ttcacctgac 67500
ctggacctca cctggcctgg gcctcacctg acctggacct cacctggcct gggcttcacc 67560
tggcctgggc ttcacctggc ctgggcttca cctgacctgg acctcacctg gcctgggctt 67620
cacctgacct ggacctcacc tggcctcggg cctcacctgc acctgctcca ggtcttgctg 67680
gagcctgagt agcactgagg ctgtagggac tcatccaggg ttggggaatg actctgcaac 67740
tctcccacat ctgacctttc tgggtggagg cacctggtgg cccagggaat ataaaaagcc 67800
ccagaatgat gcctgtgtga tttgggggca atttatgaac ccgaaaggac atggccatgg 67860
ggtgggtagg gacagtaggg acagatgtca gcctgaggtg aagcctcagg acacaggtgg 67920
gcatggacag tgtccaccta agcgagggac agacccgagt gtccctgcag tagacctgag 67980
agcgctgggc ccacagcctc ccctcggggc cctgctgcct cctcaggtca gccctggaca 68040
tcccgggttt ccccaggcct ggcggtaggt ttgaagtgag gtctgtgtca ctgtggtatt 68100
actatgatag tagtggttat tactaccaca gtgtcacaga gtccatcaaa aactcatgcc 68160
tgggagcctc ccaccacagc cctccctgcg ggggaccgct gcatgccgtg ttaggatttt 68220
gatcgaggac acggcgccat gggtatggtg gctaccacag cagtgcagcc catgacccaa 68280
acacacgggg cagcagaaac aatggacagg cccacaagtg accatgatgg gctccagccc 68340
accagcccca gagaccatga aacagatggc caaggtcacc ctacaggtca tccagatctg 68400
gctccaaggg gtctgcatcg ctgctgccct cccaacgcca aaccagatgg agacagggcc 68460
ggccccatag caccatctgc tgccgtccac ccagcagtcc cggaagcccc tccctgaacg 68520
ctgggccacg tgtgtgaacc ctgcgagccc cccatgtcag agtaggggca gcaggagggc 68580
ggggctggcc ctgtgcactg tcactgcccc tgtggtccct ggcctgcctg gccctgacac 68640
ctgagcctct cctgggtcat ttccaagaca ttcccaggga cagccggagc tgggagtcgc 68700
tcatcctgcc tggctgtcct gagtcctgct catttccaga cctcaccagg gaagccaaca 68760
gaggactcac ctcacacagt cagagacaac gaaccttcca gaaatccctg tttctctccc 68820
cagtgagaga aaccctcttc cagggtttct cttctctccc accctcttcc aggacagtcc 68880
tcagcagcat cacagcggga acgcacatct ggatcaggac ggcccccaga acacgcgatg 68940
gcccatgggg acagcccagc ccttcccaga cccctaaaag gtatccccac cttgcacctg 69000
ccccagggct caaactccag gaggcctgac tcctgcacac cctcctgcca gatatcacct 69060
cagccccctc ctggagggga caggagcccg ggagggtgag tcagacccac ctgccctcaa 69120
tggcaggcgg ggaagattca gaaaggcctg agatccccag gacgcagcac cactgtcaat 69180
gggggcccca gacgcctgga ccagggcctg tgtgggaaag gcctctggcc acactcaggg 69240
gctttttgtg aagggccctc ctgctgtgtg actacggtgg taactcccac agtgatgaaa 69300

-continued ccagcagcaa aaactgaccg gactcgcagg gtttatgcac acttctcggc tcggagctct 69360
ccaggagcac aagagccagg cccgagggtt tgtgcccaga ccctcggcct ctagggacac 69420
ccgggccatc ttagccgatg ggctgatgcc ctgcacaccg tgtgctgcca aacaggggct 69480
tcagagggct ctgaggtgac ttcactcatg accacaggtg ccctggtccc ttcactgcca 69540
gctgcaccag accctgttcc gagagatgcc ccagttccaa aagccaattc ctggggccgg 69600
gaattactgt agacaccagc ctcattccag tacctcctgc caattgcctg gattcccatc 69660
ctggctggaa tcaagagggc agcatccgcc aggctcccaa caggcaggac tcccacacac 69720
cctcctctga gaggccgctg tgttccgcag ggccaggccg cagacagttc ccctcacctg 69780
cccatgtaga aacacctgcc attgtcgtcc ccacctggca aagaccactt gtggagcccc 69840
cagccccagg tacagctgta gagagagtcc tcgaggcccc taagaaggag ccatgcccag 69900
ttctgccggg accctcggcc aggccgacag gagtggacgc tggagctggg cccacactgg 69960
gccacatagg agctcaccag tgagggcagg agagcacatg ccggggagca cccagcctcc 70020
tgctgaccag agacccgtcc cagagcccag gaggctgcag aggcctctcc agggggacac 70080
agtgcatgtc tggtccctga gcagccccca ggctctctag cactgggggc ccctggcaca 70140
gctgtctgga ccctccctgt tccctgggaa gctcctcctg acagccccgc ctccagttcc 70200
aggtgtggtt attgtcaggg ggtgccaggc cgtggtagag atggctacaa ttaccacagt 70260
ggtgccgccc atagcagcaa ccaggccaag tagacagacc cctgccacgc agccccaggc 70320
ctccagctca cctgcttctc ctggggctct caaggctgct gtctgccctc tggccctctg 70380
tggggagggt tccctcagtg ggaggtctgt gctccagggc agggatgact gagatagaaa 70440
tcaaaggctg gcagggaaag gcagcttccc gccctgagag gtgcaggcag caccacagag 70500
ccatggagtc acagagccac ggagccccca gtgtgggcgt gtgagggtgc tgggctcccg 70560
gcaggcccag ccctgatggg gaagcctgcc ccgtcccaca gcccaggtcc ccaggggcag 70620
caggcacaga agctgccaag ctgtgctcta cgatcctcat ccctccagca gcatccactc 70680
cacagtgggg aaactgagcc ttggagaacc acccagcccc ctggaaacaa ggcggggagc 70740
ccagacagtg ggcccagagc actgtgtgta tcctggcact aggtgcaggg accacccgga 70800
gatccccatc actgagtggc cagcctgcag aaggacccaa ccccaaccag gccgcttgat 70860
taagctccat ccccctgtcc tgggaacctc ttcccagcgc caccaacagc tcggcttccc 70920
aggccctcat ccctccaagg aaggccaaag gctgggcctg ccaggggcac agtaccctcc 70980
cttgccctgg ctaagacagg gtgggcagac ggctgcagat aggacatatt gctggggcat 71040
cttgctctgt gactactggg tactggctct caacgcagac cctaccaaaa tccccactgc 71100
ctcccctgct aggggctggc ctggtctcct cctgctgtcc taggaggctg ctgacctcca 71160
ggatggcttc tgtccccagt tctagggcca gagcagatcc caggcaggct gtaggctggg 71220
aggccacccc tgtccttgcc gaggttcagt gcaggcaccc aggacaggaa atggcctgaa 71280
cacagggatg actgtgccat gccctaccta agtccgcccc tttctactct gcaaccccca 71340
ctccccaggt cagcccatga cgaccaacaa cccaacacca gagtcactgc ctggccctgc 71400
cctggggagg acccctcagc ccccaccctg tctagaggag ttggggggac aggacacagg 71460
ctctctcctt atggttcccc cacctggctc ctgccgggac ccttggggtg tggacagaaa 71520
ggacgcctgc ctaattggcc cccaggaacc cagaacttct ctccagggac cccagcccga 71580
gcaccccctt acccaggacc cagccctgcc cctcctcccc tctgctctcc tctcatcact 71640

-continued ccatgggaat ccagaatccc caggaagcca tcaggaaggg ctgaaggagg aagcggggcc 71700
gctgcaccac cgggcaggag gctccgtctt cgtgaaccca gggaagtgcc agcctcctag 71760
agggtatggt ccaccctgcc tggggctccc accgtggcag gctgcgggga aggaccaggg 71820
acggtgtggg ggagggctca gggccctgca ggtgctccat cttggatgag cccatccctc 71880
tcacccaccg acccgcccac ctcctctcca ccctggccac acgtcgtcca caccatcctg 71940
agtcccacct acaccagagc cagcagagcc agtgcagaca gaggctgggg tgcagggggg 72000
ccgccagggc agctttgggg agggaggaat ggaggaaggg gaggtcagtg aagaggcccc 72060
cctcccctgg gtctaggatc cacctttggg acccccggat cccatcccct ccaggctctg 72120
ggaggagaag caggatggga gattctgtgc aggaccctct cacagtggaa tacctccaca 72180
gcggctcagg ccagatacaa aagcccctca gtgagccctc cactgcagtg cagggcctgg 72240
gggcagcccc tcccacagag gacagaccca gcaccccgaa gaagtcctgc caggggggagc 72300 tcagagccat gaaggagcaa gatatgggga ccccaatact ggcacagacc tcagctccat 72360
ccaggcccac caggacccac catgggtgga acacctgtct ccggcccctg ctggctgtga 72420
ggcagctggc ctctgtctcg gacccccatt ccagacacca gacagaggga caggcccccc 72480
agaaccagtg ttgagggaca cccctgtcca gggcagccaa gtccaagagg cgcgctgagc 72540
ccagcaaggg aaggccccca aacaaaccag gaggtttctg aagctgtctg tgtcacagtc 72600
gggtatagca gcggctacca caatgacact gggcaggaca gaaaccccat cccaagtcag 72660
ccgaaggcag agagagcagg caggacacat ttaggatctg aggccacacc tgacactcaa 72720
gccaacagat gtctcccctc cagggcgccc tgccctgttc agtgttcctg agaaaacagg 72780
ggcagcctga ggggatccag ggccaggaga tgggtcccct ctaccccgag gaggagccag 72840
gcgggaatcc cagccccctc cccattgagg ccatcctgcc cagaggggcc cggacccacc 72900
ccacacaccc aggcagaatg tgtgcaggcc tcaggctctg tgggtgccgc tagctggggc 72960
tgccagtcct caccccacac ctaaggtgag ccacagccgc cagagcctcc acaggagacc 73020
ccacccagca gcccagcccc tacccaggag gccccagagc tcagggcgcc tgggtggatt 73080
ctgaacagcc ccgagtcacg gtgggtatag tgggagctac taccactgtg agaaaagcta 73140
tgtccaaaac tgtctcccgg ccactgctgg aggcccagcc agagaaggga ccagccgccc 73200
gaacatacga ccttcccaga cctcatgacc cccagcactt ggagctccac agtgtcccca 73260
ttggatggtg aggatggggg ccggggccat ctgcacctcc caacatcacc cccaggcagc 73320
acaggcacaa accccaaatc cagagccgac accaggaaca cagacacccc aataccctgg 73380
gggaccctgg ccctggtgac ttcccactgg gatccacccc cgtgtccacc tggatcaaag 73440
accccaccgc tgtctctgtc cctcactcag ggcctgctga ggggcgggtg ctttggagca 73500
gactcaggtt taggggccac cattgtgggg cccaacctcg accaggacac agatttttct 73560
ttcctgccct ggggcaacac agactttggg gtctgtgcag ggaggacctt ctggaaagtc 73620
accaagcaca gagccctgac tgaggtggtc tcaggaagac ccccaggagg gggcttgtgc 73680
cccttcctct catgtggacc ccatgccccc caagataggg gcatcatgca gggcaggtcc 73740
tccatgcagc caccactagg caactccctg gcgccggtcc ccactgcgcc tccatcccgg 73800
ctctggggat gcagccacca tggccacacc aggcagcccg ggtccagcaa ccctgcagtg 73860
cccaagccct tggcaggatt cccagaggct ggagcccacc cctcctcatc cccccacacc 73920
tgcacacaca cacctacccc ctgcccagtc cccctccagg agggttggag ccgcccatag 73980
ggtgggggct ccaggtctca ctcactcgct tcccttcctg ggcaaaggag cctcgtgccc 74040
cggtcccccc tgacggcgct gggcacaggt gtgggtactg ggccccaggg ctcctccagc 74100
cccagctgcc ctgctctccc tgggaggcct gggcaccacc agaccaccag tccagggcac 74160
agccccaggg agccgcccac tgccagctca caggaagaag ataagcttca gaccctcagg 74220
gccgggagct gccttcctgc cacccccttcc tgccccagac ctccatgccc tcccccaacc 74280
acttacacac aagccaggga gctgtttcca cacagttcaa ccccaaacca ggacggcctg 74340
gcactcgggt cactgccatt tctgtctgca ttcgctccca gcgcccctgt gttccctccc 74400
tcctccctcc ttcctttctt cctgcattgg gttcatgccg cagagtgcca ggtgcaggtc 74460
agccctgagc ttggggtcac ctcctcactg aaggcagcct cagggtgccc aggggcaggc 74520
agggtggggg tgaggcttcc agctccaacc gctccactag ccgagactaa ggaagtgaga 74580
ggcagccaga aatccagacc attccatagc aaatggattt cattaaagtt accagacttc 74640
agtgtaagta acatgagccc catgcacaac aatcccttat gaaggggaag tcagtgtcgc 74700
ctcggatttc ttgaaaaaca caaaaactta tcaatgcctg taaaagtctg ttggaaagaa 74760
aatatgattc aagaatgtta tgcccaacaa agctggcata ttttctaccc ggacacactc 74820
agggaatgtg gtcccttgag tgcttctctc actgcgtaaa tcctacgtgg tgtttaagca 74880
tattcataaa tgtgtatgtc tatttttatg tgtaagatgg ttcattttta ttttatttat 74940
tcaatatgta caataaagaa tattgacaaa taggctggac atggtggctc ccacctgtaa 75000
tcccagccct ttgggaggcc gaggcgggca gatcacctga ggtctggagt tcgagaccag 75060
cctggccaac atgatgaaaa cccatctcta ctaaaaatac aaagattagc caggcatggt 75120
ggtgcatgcc tgtaatccca gccactcagg aggctgagac aggagaaatg cgtgaacccg 75180
gaaggcggag gttgcagtga gccgagatca caccactgca ctccagcctg gcgacagagc 75240
aagattccat ctcaaaaaaa aaaaaagaca aagaaatttg ttttttttgaa taaagacaaa 75300 tttcatcaca cgaagataaa gatgcaaagc tccagacagg aaggcacgga cagcacagtg 75360
aagcccggag cgggcgctgg ggggccaggg gcatggcggg ggtgccagcg tctctcggtt 75420
cctaccatgg ccactccagc ctgtgttctc acgaggatgg ctgtgcaatg ctaggagcgt 75480
gttcgaagct ctagggcaac cactggaagt gaggctgagg agcagagccc agaggcccgt 75540
ggagctgatg aaaagaaagc tggagaaagt gtttgctgcc tcccaacatg gtaagaaaag 75600
atagaaagag agagcacacg gcaaagggag cttgctgagg gactctttac aatggcttgc 75660
acagagctca gggggtctgg gaggctaggg ccctgcgcag ggcagtcacc ccagcctgct 75720
gaccaaggtt tgctgcaggc agctctgggg gtggttgagg cgcggtccct ggagccaccc 75780
ctcaagggaa cgaggcagca gagtgggcca aggcccaggt cggctgcaag gctgcccagg 75840
acttggggtc cttacatcag cagccactga tgcagctggc ccagagagag gcgccgagca 75900
ggttgcctcc aggggacaaa ccaggtcgga gagggtgagg cagtggatgg agccacaaca 75960
accccgggca cgggtgacac gcacgttcat gcacatctga cccttcctcc ctcaccaaac 76020
aggtccccct gccttcccca tggttgcgaa aaagcaaaat gtagacgttt tttcttttttt 76080 aattcatgtt ttaattgaca aatgaagccg tatatattta ttgtgtacaa catgatgctt 76140
taaaatatgt atacatcgtg gaacagcaac gttgagctaa tttaacacgc attacttcac 76200
atacttgtca tcttttgtgg cgagaatgct taaaatccac tctcttagta ttttttaaga 76260
atgcaataca ttgttgtcaa ctgtggtcac cgtcatgcat agccaagctc ccgacctcac 76320
cctcctgcca gctcaggctg tgcatccttt caccagcatc cccaccccg gcccctggcc 76380

```
ctggtaacta ccactctata ctctacgtat gagttcagct ttttaagatt ccacagatga  76440
atgagatcat acagtatttg ctttctatgc ctggcttatt ttagttaaca cactgtcctc  76500
cagatccatc cgttgttgca aatgacaggg tttcattctt tttaaagtct aaagagtatt  76560
ccattgtgtc aatggacctc atttgcttta tccatgcatc aactatggac atttaggttg  76620
attccatttc ttagctgttg tggatggtgc tgcagtaaac atggggctgc agatgtctct  76680
tcaacatact gacatcatgt cctttggata aatacccagt agtgggatcg ctggatcaca  76740
atgtacagtt tttttttaa tggaaacttt catttttgg tgaaattagg aaaacagata  76800
aaacccacag aatccaaaat atatgtgaag atgccaaaaa cagttgacat tgggcagagg  76860
tcacatggaa ggaagtgaat acatgacggg gtgtgagggc ccagaggcag ctgaaatacg  76920
ctttctaaac acaaggacct cttctgagag ggcagaagtt ttatcctgca catgcaatga  76980
ccagcacagc taaaatacac tttctaaaca tgaggacctc ttctgagagg gcagctttat  77040
cctgcaaatg caatgaccag cacaggaccc agaataaaga gagttgccag cggacgcctg  77100
gtgtccatgt gtccaggtga gttcgagatg cggacggcgc tggccagcca gtcacaccct  77160
aagtcaatct gctgcatgca tttgtccttg ccacagcaga aaacgagaaa gcctttgggc  77220
tgcaaagctt cacaggctcc tcttctcccg actccatgga aacagctaca aagagcaggc  77280
ccagtagagc ttaattcatg aaaatgagta ataaacttga actggaacag tatcgacttt  77340
ttagaaacgg cagcaaagtg tataaaaaat attcaccaga acaatatttc caaacgatga  77400
gatgagaatt tcagccaagt aatcctccat ggatagaaaa taatgaaggg attggattta  77460
tgaaggaaaa tcatggagct caaatacaag aaaagagaat caaaaatgaa caggaggaga  77520
taaaatatgg tttggccaaa gttacaaaat aaatttttta aaaacccttc atcatggcaa  77580
gtagaaagag cgagaggaaa aacagatccc gtggaagaca caaataggac atggggagaa  77640
aaatgaatga gatgaaacag agcagaaata aaattttacg gaactaaaga caagtgatct  77700
gaacctgcct ggggcctggg ggacctcgcc accctgaagg gaaagaacat gcctggctgg  77760
ctttgccacc tgctcattgc agagccccac agcttgcaac aaacataggc ggtagccagg  77820
gagtggttac agcaggcctt gagcaagacc cagtgttgtg ctgacttcag gtctgaccca  77880
gcactgtcat agtggtggtg tccatagtgg tagtgggggt gcttgtgtca ctccaccccc  77940
atctccagga ggctcagaac agacagagag agactccatt tgtttgggag aaagtaaggg  78000
atgagaacaa gagtctctgc ctggtaatcc agagaattat tctagatctt ggccaagatt  78060
atcaaagcag tacctctatg agtcttttgg gcttggagtc cccctaaagc agatatagct  78120
aagatcacaa cacccaagtc cttttgaata tgtgggaaga cttcccaagg acaggagcaa  78180
acaaacaagc ccagactgca aaaaaacaag ccgagactgc aataaacacc tcactcttca  78240
atgcccaggc actgaagaac atctcctagc agcaacacca tccaggaaaa catggcctca  78300
accagtgaac taaataaggc accagggacc agtctcggag aaatagaggt atgttatctt  78360
tcagagaatt caaagtagct ttgttgagga aactcaaaga aattcaagat aacacagtga  78420
aggaattcag aatcctatcc gataaattta acagagattg aagcaattaa aaagaattaa  78480
gcagaaatta tggagctgaa aaatgcaatt ggcatactga aaaatgcatc agagtatttt  78540
catagcctca tatatcaagt agaagaaaga attagtgagc ttgaaaacag gctatttgga  78600
aaagcacgat aaaaggagac aaaagagaaa agaataaata acaatgaagc atatctacag  78660
gatctagaaa atagcctcaa aaggccaaat ctaagaatta ttagccttaa agaggaggta  78720
gagaaagagg gatggagagt ttattcaaag ggataataac agaaaacttc ccaaacctag  78780
```

agaaagatat caatatccaa atgcaagaag gatgtagtac accaaggaga tttaatgcaa 78840
agaagactac ctcaaggcat tcaatactca aactcccata tgacaaggac tttaaaaaga 78900
tcctaaaagc agcaaaagaa aagaaatgaa taaaatacta tggagctcca atatgtctgg 78960
cagcagactt ttcagtgaag actttatatg ccaggagaga gtgtcataat ggatttaaag 79020
tgctgaagga aaaaactttt accctcgaac agtatagctg gtgaaattat ccttcaaaca 79080
tgaaggagaa ataatttgtt tccagacaaa tgttgaggga tttcatgaac accagacctg 79140
tcttttaaga aatgctaaag ggagtacttc aatcagaaag aaacacgtta gtgaacaata 79200
agaaatcatc tgaaggcaca aaactcaccg gtaatagtaa gtacacagaa aaacacagaa 79260
tattataaca ctgtaactgt ggtgtgtaaa ctccttttgt ttgtttgttt gtttgtttgt 79320
ttgtttttgt ttttagacgg agttttgctc cagcccaggc tggagtgcaa tggcacaatc 79380
tcagctcact gcaacttcca cctcccgggt tcaagcaatt ctcctgcctc agcctcccaa 79440
gtagctggga ttacaggcat gtgctaccat gtccagctaa ttttgtattt tagtagagac 79500
ggtgtttcac catgttggtc aggctagcct tatcttgagt agaaaaacta aatgatgaag 79560
caatgaaaaa taataactac aacttttcaa gacatagtac aataagatat aaatcataac 79620
aaaaagttaa aaggtggagg gatgaagtta aggcatagag tctttattag ttttcttttt 79680
acttgtctgt ttatgcaaac agtgttaagt tgtcatcagt ttaaaataat gggtcataag 79740
atactatttg caagcctcat ggtaacgtca aaccaaaagc aatacaacag atacacaaaa 79800
aacaaaaagc aagaagctaa attacgtcat cagagaaaat caccttcact aaaaggaaga 79860
cggagaaaag aatgaagaga gagaagacca aaagcaaata gcaatatggc aggagtaagt 79920
ccttacttat caataatacc attgaatgta aatggactaa actctccaat caaaagacat 79980
agagtggctg aatcaattaa agaaaaaaca agacccattg atctgttgtc cacaagaaac 80040
acactttatc tataaagaca cacatagact gaaaacaaag ggatggaaaa agatactcca 80100
cgccaatgga aaccaaagaa agagcaggag tagctacact tatatcaggc aaaatagatt 80160
tcaagacaaa aactataaga agagacaagg tcactaatga taaacaggtc aattcagcaa 80220
gaggatataa caattgtaaa tatatatgca cccaatgctg gagcacccag atatataaag 80280
caagtattta ctagagctaa agagagaaat agactccaat gcaataatag ctggagattt 80340
caacatccca ctttcaacat tgaacagatc ctccagatag aaaatcaaca aagaaatatt 80400
ggacttaatc tgcactatcg accaaatgga tctaacagat atttacagaa catttcatcc 80460
aacagctgca gaacacacat tcttttcctc agcacataga tcattctcaa ggatagacca 80520
tatgttgggt cacaaaacaa gttttaaaat attcaaatac attgaaataa tatcaagcat 80580
cttctgtgac cacaatggac taaaactaga aatcaataac aagaggaatt ttggaaacta 80640
tataaatata tggaaattaa tgaatgctga gtgggtcaat gaagcaatta agaaggaaac 80700
tgaaattttt cttggaacga atgatcatgg aaacagaaaa taccaaaacc tatgggatac 80760
agcaaaagca gtactaagag ggaagtttac agctacaaat gcttacatta aaaaagaaga 80820
aaaacttcaa taaaaaaacc taacaatgca tcttaaagaa ctagaaaagc aagaggaaat 80880
caaatccaaa attagtagaa gaaaacagta aaggtcagag cagaaataag taaaattgaa 80940
atgaagaaaa caatacaaaa gatcaataaa acaacaggtt gttttcttga aaagttaaac 81000
aaaattgaca aacctttagc cagactaaga aaaaaagaca gaagatccaa ataaataaaa 81060
tcagagatga aaaaggtgac attacaactt acaccacaga aattcaaagg atcattagtg 81120

-continued

```
gctactataa gcaactatat gccaataaat tggaaaatct agaagaaatg cagaaattcc  81180
tagacacata caacctccca agattaaacc aagaagaaat tcaaaacctg aacagactga  81240
taacaagtaa tgagatcaaa gccgtaataa aaagcctccc agtaaagaga agcccaggac  81300
ccgacggctt cactgctgaa ttctaccaaa catttaaagt agaactaata ccaatcctac  81360
tcaaactatt ccaaaaaata gaggtggaag gaatacttca aaactcatta tacgaggcca  81420
gtattaacct gacaccaaaa ctagacaaag acacatgaaa aaaagaaaac tacaggccaa  81480
tatgtctgat gaatattgac acaaaaatcc tcaacaaaat actagcaaac caaattcaac  81540
tacacattag aaagttcact catcatgacc aagtggaatt tatctaactt gggatgcaaa  81600
gatggttcaa catatgcaaa tcaatcaatg tgatacatca tatcaacaga atgaacaaca  81660
aaaaccattt gatcatttaa ttgatactga aaaagcattt gataaaattc aacattcctt  81720
cataataaaa attctcttct atactaggta caaaagaaac ttacctcaac ataataaagc  81780
catatatgac agtcccacag tatgatacta aatgaggaaa aactgagagc ctttcctcta  81840
cgatctggaa catgacaaag atgcccactt tcatcactgt tattcaacat agtactggaa  81900
gtcctagctg gagcgatcag acaagagaaa gatataaaag acatccaaat tggaaaggaa  81960
taagtcaaat tatcctcatt tgcatatggt atgatcttct atttagagct aactaaagac  82020
tccaccaaaa aaagttatta gaactgacga acaaattcag taaagctgca ggatacaaaa  82080
tcaacataca aaaatcagta gcatttctat atgccaacaa tgaccaatgt gaaaaagaaa  82140
ttaaaaagta accctattta caataaccac aaataaacac ctaggaatta accaaagagg  82200
taaaagattt ctgtaatgaa aactataaaa cactgatgaa agaaattgaa gagtacacca  82260
aaaaatggaa agcaattgca tgttcatgga ttagaagaat cagtgttgtt ataatgtcca  82320
tactatccaa agcaatctac agattcaatg caatccttat caaaatacca atgacatcat  82380
tcacagaaat agaaaaaaaa aatcctaaaa tttacgtgga accacaaaga cccagaatag  82440
ccaaagctct cctaagcaaa aagaacgaaa ctgtaggaat gacattgcct gtcttcaaat  82500
tctactacag agctatagat agtaaccaaa acagcgtggt actggcataa aaacagacac  82560
agagacaaac agaacaaaat ttaaaaaccc agaaataaat ccacacacct acagcaaatt  82620
catttttgac aaagttgcca agaacatact ctggggaata gataatgata tctcttcaat  82680
aaatagtgtg ggaaaactg gatatccata tacataacag tgaaactaga cccctctctc  82740
tctcactata tacaaaaatc aaatcaaaat tgtttaagga cttaaatcta agacctcata  82800
ctatgaaacc actgcaagac aaccttggcg gaaactctcc aagacatcag tccaggcaaa  82860
gatttcttga gtaatatccc acaagcacag acaaccaaag caaaaatgga caaatgggat  82920
cacatcaagt taaaaagctt ctgcacagta agggaaacaa ccaacaaaat gaagagacaa  82980
cccacagaat gggagaaaat atttgaaaaa tacccatctg gcaagggatt aaaaaccaga  83040
atatatgcag aatatataag gagctcaaac agtgctatag aaaaaaaaat ctaataatct  83100
gatttaaaaa tgggaaaaat gttagaatag acatttctta aaataagaca tacagatggc  83160
aaaccgacat ggaacggtgc tcaacatcat ggattatcac agaaacacaa tcaatcaaaa  83220
ctaaaactaa aatgtgctat catctcaccc cagttaaaat ggctgatatc cagaagacag  83280
gcaataacaa atgctggcaa ggatgtgggg aaaagggagc cccatacac tgttgctggg  83340
attgtaaatt agtacaacca ctgtggagag cagcatgaaa gttcctcaaa aaactgaaag  83400
aaagctacca taggatccag caatcccact gctgtgtata tactacaaaa gaaaggaagt  83460
cagtatatga agaggtatct gcactcccat gtttgttgca gccctgttca caacagccaa  83520
```

-continued

```
gatttggaag caacctaagt gtccatcagc agttgaatgt ataaagaaaa tgtggtgcat  83580
atacacaatg gagtattatt caataataaa aaggaatgag attgagtcat ttgcaacaac  83640
atggatggaa ctggagatca ttatgtgaag tgaaataagc caggcacaga aagacaaaca  83700
ttacaatgtt cttacttatt aatgagatct aaaaatcaaa acaattgcac ccatgttcat  83760
aaagagtaaa aggatggtta ccagatgctg agaacggtgg tggggggata gggaaaggtg  83820
gcagtggtta acgggtacaa aaaaatagaa agaatgaata agacttgcta cttgatagca  83880
cagcaaggtg gctatagtca gtaatttagt tgtatatttt taataatgaa aggtgtataa  83940
ttggattgtt tctaacacaa aggataatgc ttaagaggat ggatacccca ttttccatga  84000
tgtgattatt tcacattgca cgcctagatc aaaacatcca atgtacccca taaatatata  84060
catcttctat gtacccataa aaattctgta aaataaaata tataaaaaga ggtgacagat  84120
atggaagaca ggcaaagaag agacgacatc cacataatcc gagtacctaa gaaagaatgg  84180
agtccagtgc atctcaggag ccaccattct aagccaattt tctctggttc tctcagtcac  84240
cctaccaata cgtgggcaat cttgttttat ttcaggatag agtttttgaa attatagatt  84300
taagtatgct ttctgttcta ttacttttgg taattaattt tagaaagaac taatttgggc  84360
acaaatttga aaaaattcta aatccaaaaa aaaaaagaaa aaaacacaca cacaatcatc  84420
tataaggggg atgatgacca gtcctagatt tctcaccagc cacattcaag atcagtaaat  84480
ggtaggacaa aacctgtagg gtccttaagg gggaaagaag tagtggatag tccagagtct  84540
atatacagcc aactgttctt gaagaaaaaa ggctgctgaa aaggagttcc aaacattcta  84600
taatccataa tctcatgatg aaactactag aggaagacca ccagccatca aaaggtgctt  84660
ggagaaccca gggccaagaa ccaaaagtaa atattaagtg tccttaactg cgagactaag  84720
atagaaatga ctgtggggga ccatgtggcc tcaacagagg tgaaatggtg tctgcctgac  84780
aaagtggaca ttttacaatg atcaaaacac agaatatgag atagagagca cttctgaatt  84840
actgcctcac tccaaataac tctcagccaa aggacttcag taaaaccaaa ttgggcatat  84900
tagacagtac aaacaaattc taagaaaata atattactga ttacaatcac atgatgctag  84960
agatggaggg gaaaaggaag aggaaaccag gtaatttcat actcgtatat agtaaagaac  85020
taaagtacat tgtccaaaga agaacaaaga atattttgga aagttataaa ggtagccact  85080
acacatagaa gatagcaaag aacaagaaaa cttaagatgg aaaacttttt ggaagcataa  85140
gaatagaaaa tataaactac taagataaga ttgaagccaa acagatctat gaaaacaaca  85200
aacatcaatg gccttaactt gcctattaaa aggaagagac tttcaaattg gaccacaaga  85260
taaaacccaa ctctatatag catatgagta ttacacacaa aatgggaaaa gctgaaaaaa  85320
cttgggcaaa attcacccca agcaaattcc actgtttcct ttgggacaaa atgccaagct  85380
ccatgccagg gaagatgatt ctcctcagac cttctcctca ctctcccagt cctcttaggg  85440
aaggaattgg gtgttagagg agggagactc tgtcgattat cagctgaagc agtggtgtgc  85500
tcctgcgttg cttctgacct gggaaatgaa gcagcaagac tctttctgct gtgtctttgc  85560
ccagaagggc catcccccca gagcagagta cccaggccgg caggagcagt ggtggaagcg  85620
tggaaaccac gtctcctaca gcagagacca tcagaagcgg agcctcgggt ataagggaaa  85680
caacgcgttc tccctaacct gggagtgaca gacagcgtca ttcctcacag tgataccctg  85740
tgttctagcc atctggccca tgacagagcc agcccagagc cagcccagag ccagcccctc  85800
accatcctgg agcctggcca gctcgccaag ctgcaccata ggcctggaag gcgtggagac  85860
```

-continued

```
ctgcggcagt gccctgtcct cccgtgaggc ctgccatccc tgccaggggt cgcctctggc  85920
ttctccttct ccaggaccgc acggtccaga ggctcagtgc ctggagtagg tgttgcctcc  85980
ctgcttctag gcccagaccc tcccttgttc ctgaccccgg gcctttccct ctggcttgga  86040
catccagggc cctgtctcag ctggggagct gctcctgctc aaggactgtc ttccgcggga  86100
tcgaaaggcc gcgtcctgaa caatgcgtgg gccacgtaag cggagcaggc tctaaaggcc  86160
gcgtcctaaa cagtgcgtgg gccacgtgag cggagcaggc tctaaaggcc gcgtcctaaa  86220
cagtgcgtgg gccacgtgag cggagcaggc tctaaaggcc gcgtcctaaa cagtgcgtgg  86280
gccacgtgag cggagcaggc tctaaaggcc gcgtcctaaa cagtgcgtgg gccacgtgag  86340
cggagcaggc tctaaaggcc gcgtcctaaa cagtgcgtgg gccacgtgag cggagcaggc  86400
tctaaaggcc gcgtcctaaa cagtgcgtgg gccacgtgag cggagcaggc tctaaaggcc  86460
gcgtcctaaa cagtgcgtgg gccacgtgag cggagcaggc tctaaaggcc gcgtcctaaa  86520
cagtgcgtgg gccacgtgag cggagcaggc tctaaaggcc gcgtcctaaa cagtgcgtgg  86580
gccacgggag cggagcagac tctaaaggcc gcgtcctaaa cagtgtgtgg gccacgtgag  86640
cggagcgccc tctccactgc cctcggggcc gcagctccca gctcagctcc cagccctgct  86700
cagggcagcc aggccaggag gtaccatcca ggctaagtga ccctcagggg ggacaggtgc  86760
cccaggagat gccagctgtt gggagaggct gggggaccaa ctcgacctgg cctgtgggcc  86820
ctgccctggc cacccattgt aggatccagc cgccacgcct gtgacactcg tgtgctttcc  86880
ctggtgtgtg cttgtggcag gtgggggcag agggtcctca ggccagagag ccactccccc  86940
agcgccagac caccctcttc ctcactcccc cacctcaccc cctcacaggt gcctcccagg  87000
ccatcagggc ccaaccaccc ctaaacaaat gggttctcgg cccctcgtgg ctggaggtgg  87060
gttctctcac cattcccagc ctaagactcc atccccatgc tggcagctgt tcaaccatgt  87120
ctagagagat ccactgtccc agacagcacc tcagggtccc ccgtcctgcc tggaaccctg  87180
taggaaactc cacaaaccgc cgccattctg tccacacccc tacaggagcc ccaaccctct  87240
ccccacatcc aggcttccct cccagacccc tcatccctgc ccgcacggtg cctgaggggg  87300
ccttcttggg cagcgcctaa gcaagccccc agcacccttc ggccccttca aggcacacag  87360
gccccctttc cacccagcct caggaaacca cctgtgtcct ccaacgacag gtcccagcct  87420
cccagccttt gccttgcctg ttcctctccc tggaactctg ccccgacaca gaccctcccc  87480
agcaagcccg caggggcacc tcccctgccc ccagacaccc tgtgcccgtc agttcatccc  87540
cagcagaggc cctcaccagg cacaccccca tgctcacacc tggccccagg cctcagcctc  87600
cctgagggcc ccacccagcc cgcgtctggc cagtggtgcg tgcaaagccc ctcacccaga  87660
ctcggcggaa ggcagccagt gcaggcctgg ggaggggctc tccttagacc accttgcacc  87720
ttccctggca cccaccatgg gaagagctga gactcactga ggaccagctg aggctcagag  87780
aagggaccca gcactggtgg acacgcaggg agcccacgcc agggcgccgt ggtgagtgag  87840
gcccagtgcc acccactgag gcctcccgtt cagtgggacg acggtgaaca ggtggaacca  87900
accaggcaac ccccgccggg ccccacagac gggatcagag caggaaaggc ttcctgcccc  87960
tgcaggccag cgaggagccc tggcgggggc cgtggccctc caggcgagga ggctcccctg  88020
gccaccgcca cccgggcctc tctgctgctg ggaaaacaag tcagaaagca agtggatgag  88080
aggtggcgtg acagacccag cttcagatct gctctaattt acaaaagaaa aggaaaaaca  88140
cacttggcag ccttcagcac tctaatgatt cttaacagca gcaaattatt ggcacaagac  88200
tccagagtga ctggcagggt tgagggctgg ggtctcccac gtgttttggg gctaacagcg  88260
```

-continued

```
gaagggagag cactggcaaa ggtgctgggg gcccctggac ccgacccgcc ctggagaccg  88320
cagccacatc agcccccagc cccacaggcc ccctaccagc cgcagggttt tggctgagct  88380
gagaaccact gtgctaactg gggacacagt gattggcagc tctacaaaaa ccatgctccc  88440
ccgggacccc gggctgtggg tttctgtagc ccctggctca gggctgactc accgtggctg  88500
aatacttcca gcactggggc cagggcaccc tggtcaccgt ctcctcaggt gagtctgctg  88560
tctggggata gcggggagcc aggtgtactg ggccaggcaa gggctttggc ttcagacttg  88620
gggacaggtg ctcagcaaag gaggtcggca ggagggcgga gggtgtgttt ttgtatggga  88680
gaagcaggag ggcagaggct gtgctactgg tacttcgatc tctggggccg tggcaccctg  88740
gtcactgtct cctcaggtga gtcccactgc agccccctcc cagtcttctc tgtccaggca  88800
ccaggccagg tatctggggt ctgcagccgg cctgggtctg gcctgaggcc acaccagctg  88860
ccatccctgg ggtctccgcc atgggctgca tgccagagcc ctgctgtcac ttagccctgg  88920
ggccagctgg agcccccaag gacaggcagg gaccccgctg ggcttcagcc ccgtcaggga  88980
ccctccacag gtagcaagca ggccgagggc agggacggga aggagaagtt gtgggcagag  89040
cctgggctgg ggctgggcgc tggctgttca tgtgccgggg accaggcctg cgctttagtg  89100
tggctacaag tgcttggagc actggggcca gggcagcccg gccaccgtct ccctgggaac  89160
gtcacccctc cctgcctggg tctcagcccg ggggtctgtg tggctgggga cagggacgcc  89220
ggctgcctct gctctgtgct tgggccatgt gacccattcg agtgtcctgc acgggcacag  89280
gtttgtgtct gggcaggaac agggactgtg tccctgtgtg atgcttttga tatctggggc  89340
caagggacaa tggtcaccgt ctcttcaggt aagatggctt tccttctgcc tcctttctct  89400
gggcccagcg tcctctgtcc tggagctggg agataatgtc cgggggctcc ttggtctgcg  89460
ctgggccatg tggggccctc cggggctcct tctccggctg tttgggacca cgttcagcag  89520
aaggcctttc tttgggaact gggactctgc tgctggggca aagggtgggc agagtcatgc  89580
ttgtgctggg gacaaaatga ccttgggaca cggggctggc tgccacggcc ggcccgggac  89640
agtcggagag tcaggttttt gtgcacccct taatggggcc tcccacaatg tgactacttt  89700
gactactggg gccagggaac cctggtcacc gtctcctcag gtgagtcctc acaacctctc  89760
tcctgcttta actctgaagg gttttgctgc atttttgggg ggaaataagg gtgctgggtc  89820
tcctgccaag agagccccgg agcagcctgg ggggctcagg aggatgccct gaggcaacag  89880
cggccacaca gacgaggggc aagggctcca gatgctcctt cctcctgagc ccagcagcac  89940
gggtctctct gtggccaggg ccaccctagg cctctggggt ccaatgccca acaacccccg  90000
ggccctcccc gggctcagtc tgagagggtc ccagggacgt agcggggcgc cagttcttgc  90060
ctggggtcct ggcattgttg tcacaatgtg acaactggtt cgacccctgg ggccagggaa  90120
ccctggtcac cgtctcctca ggtgagtcct caccaccccc tctctgagtc cacttaggga  90180
gactcagctt gccagggtct cagggtcaga gtcttggagg cattttggag gtcaggaaag  90240
aaagccgggg agagggaccc ttcgaatggg aacccagcct gtcctcccca agtccggcca  90300
cagatgtcgg cagctggggg gctccttcgg ctggtctggg gtgacctctc tccgcttcac  90360
ctggagcatt ctcaggggct gtcgtgatga ttgcgtggtg ggactctgtc ccgctccaag  90420
gcacccgctc tctgggacgg gtgccccccg gggtttttgg actcctgggg gtgacttagc  90480
agccgtctgc ttgcagttgg acttcccagg ccgacagtgg tctggcttct gaggggtcag  90540
gccagaatgt ggggtacgtg ggaggccagc agagggttcc atgagaaggg caggacaggg  90600
```

-continued ccacggacag tcagcttcca tgtgacgccc ggagacagaa ggtctctggg tggctgggtt 90660
tttgtggggt gaggatggac attctgccat tgtgattact actactacta cggtatggac 90720
gtctggggcc aagggaccac ggtcaccgtc tcctcaggta agaatggcca ctctagggcc 90780
tttgttttct gctactgcct gtggggtttc ctgagcattg caggttggtc ctcggggcat 90840
gttccgaggg gacctgggcg gactggccag gaggggacgg gcactggggt gccttgagga 90900
tctgggagcc tctgtggatt ttccgatgcc tttggaaaat gggactcagg ttgggtgcgt 90960
ctgatggagt aactgagcct ctagactgag cattgcagac taatcttgga tatttgtccc 91020
tgagggagcc ggctgagaga agttgggaaa taaactgtct agggatctca gagcctttag 91080
gacagattat ctccacatct ttgaaaaact aagaatctgt gtgatggtgt tggtggagtc 91140
cctggatgat gggataggga ctttggaggc tcatttgagg gagatgctaa aacaatccta 91200
tggctggagg gatagttggg gctgtagttg gagattttca gtttttagaa taaaagtatt 91260
agctgcggaa tatacttcag gaccacctct gtgacagcat ttatacagta tccgatgcat 91320
agggacaaag agtggagtgg ggcactttct ttagatttgt gaggaatgtt ccacactaga 91380
ttgtttaaaa cttcatttgt tggaaggaga gctgtcttag tgattgagtc aagggagaaa 91440
ggcatctagc ctcggtctca aaagggtagt tgctgtctag agaggtctgg tggagcctgc 91500
aaaagtccag ctttcaaagg aacacagaag tatgtgtatg gaatattaga agatgttgct 91560
tttactctta agttggttcc taggaaaaat agttaaatac tgtgacttta aaatgtgaga 91620
gggttttcaa gtactcattt ttttaaatgt ccaaaattct tgtcaatcag tttgaggtct 91680
tgtttgtgta gaactgatat tacttaaagt ttaaccgagg aatgggagtg aggctctctc 91740
ataacctatt cagaactgac ttttaacaat aataaattaa gtttcaaata tttttaaatg 91800
aattgagcaa tgttgagttg gagtcaagat ggccgatcag aaccagaaca cctgcagcag 91860
ctggcaggaa gcaggtcatg tggcaaggct atttggggaa gggaaaataa aaccactagg 91920
taaacttgta gctgtggttt gaagaagtgg ttttgaaaca ctctgtccag ccccaccaaa 91980
ccgaaagtcc aggctgagca aaacaccacc tgggtaattt gcatttctaa aataagttga 92040
ggattcagcc gaaactggag aggtcctctt ttaacttatt gagttcaacc ttttaatttt 92100
agcttgagta gttctagttt ccccaaactt aagtttatcg acttctaaaa tgtatttaga 92160
attcattttc aaaattaggt tatgtaagaa attgaaggac tttagtgtct ttaatttcta 92220
atatatttag aaaacttctt aaaattactc tattattctt ccctctgatt attggtctcc 92280
attcaattct tttccaatac ccgaagcatt tacagtgact ttgttcatga tcttttttag 92340
ttgtttgttt tgccttacta ttaagacttt gacattctgg tcaaaacggc ttcacaaatc 92400
tttttcaaga ccactttctg agtattcatt ttaggagaaa gacttttttt ttaaatgaat 92460
gcaattatct agacttattt cagttgaaca tgctggttgg tggttgagag gacactcagt 92520
cagtcagtga cgtgaagggc ttctaagcca gtccacatgc tctgtgtgaa ctccctctgg 92580
ccctgcttat tgttgaatgg gccaaaggtc tgagaccagg ctgctgctgg gtaggcctgg 92640
actttgggtc tcccacccag acctgggaat gtatggttgt ggcttctgcc acccatccac 92700
ctggctgctc atggaccagc cagcctcggt ggctttgaag gaacaattcc acacaaagac 92760
tctggacctc tccgaaacca ggcaccgcaa atggtaagcc agaggcagcc acagctgtgg 92820
ctgctgctct taaagcttgt aaactgtttc tgcttaagag ggactgagtc ttcagtcatt 92880
gctttagggg gagaaagaga catttgtgtg tcttttgagt accgttgtct gggtcactca 92940
catttaactt tccttgaaaa actagtaaaa gaaaaatgtt gcctgttaac caataatcat 93000

-continued agagctcatg gtactttgag gaaatcttag aaagcgtgta tacaattgtc tggaattatt 93060
tcagttaagt gtattagttg aggtactgat gctgtctcta cttcagttat acatgtgggt 93120
ttgaattttg aatctattct ggctcttctt aagcagaaaa tttagataaa atggatacct 93180
cagtggtttt taatggtggg tttaatatag aaggaattta aattggaagc taatttagaa 93240
tcagtaagga gggacccagg ctaagaaggc aatcctggga ttctggaaga aaagatgttt 93300
ttagttttta tagaaaacac tactacattc ttgatctaca actcaatgtg gtttaatgaa 93360
tttgaagttg ccagtaaatg tacttcctgg ttgttaaaga atggtatcaa aggacagtgc 93420
ttagatccga ggtgagtgtg agaggacagg ggctggggta tggatacgca gaaggaaggc 93480
cacagctgta cagaattgag aaagaataga gacctgcagt tgaggccagc aggtcggctg 93540
gactaactct ccagccacag taatgaccca gacagagaaa gccagactca taaagcttgc 93600
tgagcaaaat taagggaaca aggttgagag ccctagtaag cgaggctcta aaaagcacag 93660
ctgagctgag atgggtgggc ttctctgagt gcttctaaaa tgcgctaaac tgaggtgatt 93720
actctgaggt aagcaaagct gggcttgagc caaaatgaag tagactgtaa tgaactggaa 93780
tgagctgggc cgctaagcta aactaggctg gcttaaccga gatgagccaa actggaatga 93840
acttcattaa tctaggttga atagagctaa actctactgc ctacactgga ctgttctgag 93900
ctgagatgag ctggggtgag ctcagctatg ctacgctgtg ttggggtgag ctgatctgaa 93960
atgagatact ctggagtagc tgagatgggg tgagatgggg tgagctgagc tgggctgagc 94020
tagactgagc tgagctaggg tgagctgagc tgggtgagct gagctaagct ggggtgagct 94080
gagctgagct tggctgagct agggtgagct gggctgagct ggggtgagct gagctgagct 94140
ggggtaagct gggatgagct ggggtgagct gagctgagct ggagtgagct gagctgggct 94200
gagctggggt gagctgggct gagctgggct gagctgggct gagctggggt gagctgagct 94260
ggggtgagct gagctgagct ggggtgagct gagctgagct ggggtgagct ggggtgagct 94320
gagctggggt gagctgagct gagctggggt gagctgagct ggggtgagct gagctgagct 94380
ggggtgagct gagctgagct gagctgagct gagctggggt gagctgagct gagctgagct 94440
ggggtgagct ggggtgagct gagctgagct ggagtgagct gagctgggct gagctggggt 94500
gagctgggct gagctggggt gagctgagct gagctgagct gagctggggt gagctgagct 94560
gagctggggt gagctgagct ggggtgagct gggctgagct gagctgagct gagctgagct 94620
gagctgagct gagctgagct gagctgagct gagctgagct gagctgagct gagctgagct 94680
ggggtgagct gagctgagct gggctgagct ggggtgagct gggctgagct gggctgagct 94740
gggctgagct ggggtgagct gagctggggt gagctgagct gagctgggct gagctgagct 94800
gagctggggt gagctgagct gagctggggt gagctgagct gagctgagct ggggtgagct 94860
gagctgagct gggctgagca gggctgagct ggggtgagct gagctgagct ggggtgagct 94920
gggctgagct gggctgagct gagctgagct gggctgagct gggctgagct gggctgagct 94980
gggctgagct gggctgagct ggggtgagct gagctggggt gagctggggt gagctgagct 95040
ggggtgagct gagctggggt gagctgagct gagctggggt gagctgagct ggggtgagct 95100
gagctgagct ggggtgagct gagctgagct ggggtgagct gagctagggt gaactgggct 95160
gggtgagctg gagtgagctg agctgaggtg aactggggtg agccgggatg ttttgagttg 95220
agctggggta agatgagctg aactggggta aactgggatg agctgtggtg agcggagctg 95280
gattgaactg agctgtgtga gctgagctgg ggtcagctga gcaagagtga gtagagctgg 95340

-continued

```
ctggccagaa ccagaatcaa ttaggctaag tgagccagat tgtgctggga tcagctgtac  95400
tcagatgagc tgggatgagg taggctggga tgagctgggc tagctgacat ggattatgtg  95460
aggctgagct agcatgggct ggcctagctg atgagctaag cttgaatgag cggggctgag  95520
ctggactcag atgtgctaga ctgagctgta ctggatgatc tggtgtaggg tgatctggac  95580
tcaactgggc tggctgatgg gatgcgccag gttgaactag gctcagataa gttaggctga  95640
gtagggcctg gttgagatgg ttcgggatga gctgggaaaa gatggactcg gaccatgaac  95700
tgggctgagc tgggttggga gaccatgaat tgagctgaac tgagtgcagc tgggataaac  95760
tgggttgagc taagaataga ctacctgaat tgtgccaaac tcggctggga tcaattggaa  95820
attatcagga tttagatgag ccggactaaa ctatgctgag ctggactggt tggatgtgtt  95880
gaactggcct gctgctgggc tggcatagct gagttgaact taaatgagga aggctgagca  95940
aggctagcct gcttgcatag agctgaactt tagcctagcc tgagctggac cagcctgagc  96000
tgagtaggtc taaactgagt taaaaatcaa cagggataat ttaacagcta atttaacaag  96060
cctgaggtct gagattgaat gagcagagct gggatgaact gaatgagttt caccaggcct  96120
ggaccagtta ggctaggacc tcgttctata gaggcagact gtgtgctaca gtggagtttc  96180
aagatgattc catgagtcct ccccgccccc aacataaccc accttcctcc taccctacac  96240
gcctgtctgg tgtgtaaatc ccagctttgt gtgctgatac agaagcctga gcccctcccc  96300
cacctccacc tacctattac tttgggatga gaatagttct cccagccagt gtctcagagg  96360
gaagccaagc aggacaggcc caaggctact tgagaagcca ggatctaggc ctctccctga  96420
gaacgggtgt tcatgcccct agagttggct gaagggccag atccacctac tctagaggca  96480
tctctccctg tctgtgaagg cttccaaagt cacgttcctg tggctagaag gcagctccat  96540
agccctgctg cagtttcgtc ctgtatacca ggttcaccta ctaccatatc tagccctgcc  96600
tgccttaaga gtagcaacaa ggaaatagca gggtgtagag ggatctcctg tctgacagga  96660
ggcaagaaga cagattctta cccctccatt tctcttttat ccctctctgg tcctcagaga  96720
gtcagtcctt cccaaatgtc ttccccctcg tctcctgcga gagcccccctg tctgataaga  96780
atctggtggc catgggctgc ctggcccggg acttcctgcc cagcaccatt tccttcacct  96840
ggaactacca gaacaacact gaagtcatcc agggtatcag aaccttccca acactgagga  96900
cagggggcaa gtacctagcc acctcgcagg tgttgctgtc tcccaagagc atccttgaag  96960
gttcagatga atacctggta tgcaaaatcc actacggagg caaaaacaaa gatctgcatg  97020
tgcccattcc aggtaagaac caaaccctcc cagcaggggt gcccaggccc aggcatggcc  97080
cagagggagc agcggggtgg ggcttaggcc aagctgagct cacaccttga cctttcattc  97140
cagctgtcgc agagatgaac cccaatgtaa atgtgttcgt cccaccacgg gatggcttct  97200
ctggccctgc accacgcaag tctaaactca tctgcgaggc cacgaacttc actccaaaac  97260
cgatcacagt atcctggcta aaggatggga agctcgtgga atctggcttc accacagatc  97320
cggtgaccat cgagaacaaa ggatccacac cccaaaccta caaggtcata agcacactta  97380
ccatctctga aatcgactgg ctgaacctga atgtgtacac ctgccgtgtg gatcacaggg  97440
gtctcacctt cttgaagaac gtgtcctcca catgtgctgc cagtgagtgg cctgggctaa  97500
gcccaatgcc tagccctccc agattaggga agtcctccta caattatggc caatgccacc  97560
cagacatggt catttgctcc ttgaactttg gctccccaga gtggccaagg acaagaatga  97620
gcaataggca gtagaggggt gagaatcagc tggaaggacc agcatcttcc cttaagtagg  97680
tttgggggat ggagactaag ctttttttcca acttcacaac tagatatgtc ataacctgac  97740
```

acagtgttct cttgactgca ggtccctcca cagacatcct aaccttcacc atccccccct 97800
cctttgccga catcttcctc agcaagtccg ctaacctgac ctgtctggtc tcaaacctgg 97860
caacctatga aaccctgaat atctcctggg cttctcaaag tggtgaacca ctggaaacca 97920
aaattaaaat catggaaagc cctcccaatg gcaccttcag tgctaagggt gtggctagtg 97980
tttgtgtgga agactggaat aacaggaagg aatttgtgcg tactgtgact cacagggatc 98040
tgccttcacc acagaagaaa ttcatctcaa aacccaatgg taggtatccc cccttccctt 98100
cccctccaat tgcaggaccc ttcctgtacc tcatagggag ggcaggtcct cttccaccct 98160
atcctcacta ctgtcttcat ttacagaggt gcacaaacat ccacctgctg tgtacctgct 98220
gccaccagct cgtgagcaac tgaacctgag ggagtcagcc acagtcacct gcctggtgaa 98280
gggcttctct cctgcagaca tcagtgtgca gtggcttcag agagggcaac tcttgcccca 98340
agagaagtat gtgaccagtg ccccgatgcc agagcctggg gccccaggct tctactttac 98400
ccacagcatc ctgactgtga cagaggagga atggaactcc ggagagacct atacctgtgt 98460
tgtaggccac gaggccctgc cacacctggt gaccgagagg accgtggaca agtccactgg 98520
taaacccaca ctgtacaatg tctccctgat catgtctgac acaggcggca cctgctattg 98580
accatgctag cgctcaacca ggcaggccct gggtgtccag ttgctctgtg tatgcaaact 98640
aaccatgtca gagtgagatg ttgcatttta taaaaattag aaataaaaaa aatccattca 98700
aacgtcactg gttttgatta tacaatgctc atgcctgctg agacagttgt gttttgcttg 98760
ctctgcacac accctgcata cttgcctcca ccctggccct tcctctacct tgccagtttc 98820
ctccttgtgt gtgaactcag tcaggcttac aacagacaga gtatgaacat gcgattcctc 98880
cagctacttc tagatatatg gctgaaagct tgcatgcctg caggtcgact ctagaggatc 98940
cccgggtacc gagctcgaat tcgccctata gtgagtcgta ttacaattca ctggccgtcg 99000
ttttacaacg tcgtgactgg gaaaaccctg gcgttaccca acttaatcgc cttgcagcac 99060 atccccctttt cgccagctgg cgtaatagcg aagaggcccg caccgatcgc ccttcccaac 99120
agttgcgcag cctgaatggc gaatggcgcc tgatgcggta ttttctcctt acgcatctgt 99180
gcggtatttc acaccgcata tggtgcactc tcagtacaat ctgctctgat gccgcatagt 99240
taagccagcc ccgacacccg ccaacacccg ctgacgcgaa ccccttgcgg ccgc 99294

<210> SEQ ID NO 4
<211> LENGTH: 17
<212> TYPE: DNA
<213> ORGANISM: Artificial Sequence
<220> FEATURE:
<223> OTHER INFORMATION: synthetic

<400> SEQUENCE: 4
tgcggccgat cttagcc 17

<210> SEQ ID NO 5
<211> LENGTH: 18
<212> TYPE: DNA
<213> ORGANISM: Artificial Sequence
<220> FEATURE:
<223> OTHER INFORMATION: synthetic

<400> SEQUENCE: 5
ttgaccgatt ccttgcgg 18

<210> SEQ ID NO 6

<211> LENGTH: 21
<212> TYPE: DNA
<213> ORGANISM: Artificial Sequence
<220> FEATURE:
<223> OTHER INFORMATION: synthetic

<400> SEQUENCE: 6
acgagcgggt tcggcccatt c 21

<210> SEQ ID NO 7
<211> LENGTH: 19
<212> TYPE: DNA
<213> ORGANISM: Artificial Sequence
<220> FEATURE:
<223> OTHER INFORMATION: synthetic

<400> SEQUENCE: 7
ggtggagagg ctattcggc 19

<210> SEQ ID NO 8
<211> LENGTH: 17
<212> TYPE: DNA
<213> ORGANISM: Artificial Sequence
<220> FEATURE:
<223> OTHER INFORMATION: synthetic

<400> SEQUENCE: 8
gaacacggcg gcatcag 17

<210> SEQ ID NO 9
<211> LENGTH: 23
<212> TYPE: DNA
<213> ORGANISM: Artificial Sequence
<220> FEATURE:
<223> OTHER INFORMATION: synthetic

<400> SEQUENCE: 9
tgggcacaac agacaatcgg ctg 23

<210> SEQ ID NO 10
<211> LENGTH: 19
<212> TYPE: DNA
<213> ORGANISM: Artificial Sequence
<220> FEATURE:
<223> OTHER INFORMATION: synthetic

<400> SEQUENCE: 10
tcctccaacg acaggtccc 19

<210> SEQ ID NO 11
<211> LENGTH: 20
<212> TYPE: DNA
<213> ORGANISM: Artificial Sequence
<220> FEATURE:
<223> OTHER INFORMATION: synthetic

<400> SEQUENCE: 11
gatgaactga cgggcacagg 20

<210> SEQ ID NO 12
<211> LENGTH: 24
<212> TYPE: DNA
<213> ORGANISM: Artificial Sequence
<220> FEATURE:
<223> OTHER INFORMATION: synthetic

<400> SEQUENCE: 12
tccctggaac tctgccccga caca					24

<210> SEQ ID NO 13
<211> LENGTH: 25
<212> TYPE: DNA
<213> ORGANISM: Artificial Sequence
<220> FEATURE:
<223> OTHER INFORMATION: synthetic

<400> SEQUENCE: 13
ctctgtggaa aatggtatgg agatt					25

<210> SEQ ID NO 14
<211> LENGTH: 26
<212> TYPE: DNA
<213> ORGANISM: Artificial Sequence
<220> FEATURE:
<223> OTHER INFORMATION: synthetic

<400> SEQUENCE: 14
ggtaagcata gaaggtgggt atcttt					26

<210> SEQ ID NO 15
<211> LENGTH: 30
<212> TYPE: DNA
<213> ORGANISM: Artificial Sequence
<220> FEATURE:
<223> OTHER INFORMATION: synthetic

<400> SEQUENCE: 15
atagaactgt catttggtcc agcaatccca				30

<210> SEQ ID NO 16
<211> LENGTH: 20
<212> TYPE: DNA
<213> ORGANISM: Artificial Sequence
<220> FEATURE:
<223> OTHER INFORMATION: synthetic

<400> SEQUENCE: 16
tggtcacctc caggagcctc						20

<210> SEQ ID NO 17
<211> LENGTH: 21
<212> TYPE: DNA
<213> ORGANISM: Artificial Sequence
<220> FEATURE:
<223> OTHER INFORMATION: synthetic

<400> SEQUENCE: 17
gctgcagggt gtatcaggtg c						21

<210> SEQ ID NO 18
<211> LENGTH: 30
<212> TYPE: DNA
<213> ORGANISM: Artificial Sequence
<220> FEATURE:
<223> OTHER INFORMATION: synthetic

<400> SEQUENCE: 18
agtctctgct tcccccttgt ggctatgagc				30

<210> SEQ ID NO 19
<211> LENGTH: 28
<212> TYPE: DNA

<213> ORGANISM: Artificial Sequence
<220> FEATURE:
<223> OTHER INFORMATION: synthetic

<400> SEQUENCE: 19
gatgggaaga gactggtaac atttgtac 28

<210> SEQ ID NO 20
<211> LENGTH: 26
<212> TYPE: DNA
<213> ORGANISM: Artificial Sequence
<220> FEATURE:
<223> OTHER INFORMATION: synthetic

<400> SEQUENCE: 20
ttcctctatt tcactctttg aggctc 26

<210> SEQ ID NO 21
<211> LENGTH: 27
<212> TYPE: DNA
<213> ORGANISM: Artificial Sequence
<220> FEATURE:
<223> OTHER INFORMATION: synthetic

<400> SEQUENCE: 21
cctccactgt gttaatggct gccacaa 27

<210> SEQ ID NO 22
<211> LENGTH: 23
<212> TYPE: DNA
<213> ORGANISM: Artificial Sequence
<220> FEATURE:
<223> OTHER INFORMATION: synthetic

<400> SEQUENCE: 22
ggtgtgcgat gtaccctctg aac 23

<210> SEQ ID NO 23
<211> LENGTH: 25
<212> TYPE: DNA
<213> ORGANISM: Artificial Sequence
<220> FEATURE:
<223> OTHER INFORMATION: synthetic

<400> SEQUENCE: 23
tgtggcagtt taatccagct ttatc 25

<210> SEQ ID NO 24
<211> LENGTH: 32
<212> TYPE: DNA
<213> ORGANISM: Artificial Sequence
<220> FEATURE:
<223> OTHER INFORMATION: synthetic

<400> SEQUENCE: 24
ctaaaaatgc tacacctggg gcaaaacacc tg 32

<210> SEQ ID NO 25
<211> LENGTH: 17
<212> TYPE: DNA
<213> ORGANISM: Artificial Sequence
<220> FEATURE:
<223> OTHER INFORMATION: synthetic

<400> SEQUENCE: 25
gccatgcaag gccaagc 17

<210> SEQ ID NO 26
<211> LENGTH: 24
<212> TYPE: DNA
<213> ORGANISM: Artificial Sequence
<220> FEATURE:
<223> OTHER INFORMATION: synthetic

<400> SEQUENCE: 26
agttcttgag ccttagggtg ctag 24

<210> SEQ ID NO 27
<211> LENGTH: 24
<212> TYPE: DNA
<213> ORGANISM: Artificial Sequence
<220> FEATURE:
<223> OTHER INFORMATION: synthetic

<400> SEQUENCE: 27
ccaggaaaat gctgccagag cctg 24

<210> SEQ ID NO 28
<211> LENGTH: 22
<212> TYPE: DNA
<213> ORGANISM: Artificial Sequence
<220> FEATURE:
<223> OTHER INFORMATION: synthetic

<400> SEQUENCE: 28
aactacgcac agaagttcca gg 22

<210> SEQ ID NO 29
<211> LENGTH: 18
<212> TYPE: DNA
<213> ORGANISM: Artificial Sequence
<220> FEATURE:
<223> OTHER INFORMATION: synthetic

<400> SEQUENCE: 29
gctcgtggat ttgtccgc 18

<210> SEQ ID NO 30
<211> LENGTH: 16
<212> TYPE: DNA
<213> ORGANISM: Artificial Sequence
<220> FEATURE:
<223> OTHER INFORMATION: synthetic

<400> SEQUENCE: 30
cagagtcacg attacc 16

<210> SEQ ID NO 31
<211> LENGTH: 19
<212> TYPE: DNA
<213> ORGANISM: Artificial Sequence
<220> FEATURE:
<223> OTHER INFORMATION: synthetic

<400> SEQUENCE: 31
tgagcagcac cctcacgtt 19

<210> SEQ ID NO 32
<211> LENGTH: 23
<212> TYPE: DNA
<213> ORGANISM: Artificial Sequence
<220> FEATURE:

<223> OTHER INFORMATION: synthetic

<400> SEQUENCE: 32
gtggcctcac aggtatagct gtt 23

<210> SEQ ID NO 33
<211> LENGTH: 18
<212> TYPE: DNA
<213> ORGANISM: Artificial Sequence
<220> FEATURE:
<223> OTHER INFORMATION: synthetic

<400> SEQUENCE: 33
accaaggacg agtatgaa 18

<210> SEQ ID NO 34
<211> LENGTH: 296
<212> TYPE: DNA
<213> ORGANISM: Homo sapiens
<220> FEATURE:
<223> OTHER INFORMATION: synthetic

<400> SEQUENCE: 34
caggtgcagc tggtgcagtc tggggctgag gtgaagaagc ctgggtcctc ggtgaaggtc 60
tcctgcaagg cttctggagg caccttcagc agctatgcta tcagctgggt gcgacaggcc 120
cctggacaag ggcttgagtg gatgggaggg atcatcccta tctttggtac agcaaactac 180
gcacagaagt tccagggcag agtcacgatt accgcggacg aatccacgag cacagcctac 240
atggagctga gcagcctgag atctgaggac acggccgtgt attactgtgc gagaga 296

<210> SEQ ID NO 35
<211> LENGTH: 98
<212> TYPE: PRT
<213> ORGANISM: Homo sapiens
<220> FEATURE:
<223> OTHER INFORMATION: synthetic

<400> SEQUENCE: 35

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Ala Ile Ser Trp Val Arg Gln Ala Pro Gly Gln Gly Leu Glu Trp Met
35 40 45

Gly Gly Ile Ile Pro Ile Phe Gly Thr Ala Asn Tyr Ala Gln Lys Phe
50 55 60

Gln Gly Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg

<210> SEQ ID NO 36
<211> LENGTH: 294
<212> TYPE: DNA
<213> ORGANISM: Homo sapiens
<220> FEATURE:
<223> OTHER INFORMATION: synthetic

<400> SEQUENCE: 36
caggtccagc tggtgcaatc tggggctgag gtgaagaagc ctgggtcctc ggtgaaggtc 60

-continued tcctgcaagg cttctggagg caccttcagc agctatacta tcagctgggt gcgacaggcc 120
cctggacaag ggcttgagtg gatgggaagg atcatcccta tccttggtat agcaaactac 180
gcacagaagt tccagggcag agtcacgatt accgcggaca aatccacgag cacagcctac 240
atggagctga gcagcctgag atctgaggac acggccgtgt attactgtgc gaga 294

<210> SEQ ID NO 37
<211> LENGTH: 98
<212> TYPE: PRT
<213> ORGANISM: Homo sapiens
<220> FEATURE:
<223> OTHER INFORMATION: synthetic

<400> SEQUENCE: 37

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Thr Ile Ser Trp Val Arg Gln Ala Pro Gly Gln Gly Leu Glu Trp Met
35 40 45

Gly Arg Ile Ile Pro Ile Leu Gly Ile Ala Asn Tyr Ala Gln Lys Phe
50 55 60

Gln Gly Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg

<210> SEQ ID NO 38
<211> LENGTH: 275
<212> TYPE: DNA
<213> ORGANISM: Homo sapiens
<220> FEATURE:
<223> OTHER INFORMATION: synthetic

<400> SEQUENCE: 38
caggtgcagc tggtgcagtc tggggctgag gtgaagaagc ctgggtcctc ggtgaaggtc 60
tcctgcaagg cttctggagg caccttcagc agctatgcta tcagctgggt gcgacaggcc 120
cctggacaag ggcttgagtg gatgggaggg atcatcccta tctttggtac agcaaactac 180
gcacagaagt tccagggcag agtcacgatt accgcggacg aatccacgag cacagcctac 240
atggagctga gcagcctgag atctgatgac acggc 275

<210> SEQ ID NO 39
<211> LENGTH: 91
<212> TYPE: PRT
<213> ORGANISM: Homo sapiens
<220> FEATURE:
<223> OTHER INFORMATION: synthetic

<400> SEQUENCE: 39

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Ala Ile Ser Trp Val Arg Gln Ala Pro Gly Gln Gly Leu Glu Trp Met
35 40 45

Gly Gly Ile Ile Pro Ile Phe Gly Thr Ala Asn Tyr Ala Gln Lys Phe 50 55 60

Gln Gly Arg Val Thr Ile Thr Ala Asp Glu Ser Thr Ser Thr Ala Tyr
65 70 75 80

Met Glu Leu Ser Ser Leu Arg Ser Asp Asp Thr
85 90

<210> SEQ ID NO 40
<211> LENGTH: 296
<212> TYPE: DNA
<213> ORGANISM: Homo sapiens
<220> FEATURE:
<223> OTHER INFORMATION: synthetic

<400> SEQUENCE: 40
caggtccagc tggtgcagtc tggggctgag gtgaagaagc ctgggtcctc ggtgaaggtc 60
tcctgcaagg cttctggagg caccttcagc agctatgcta tcagctgggt gcgacaggcc 120
cctggacaag ggcttgagtg gatgggaagg atcatcccta tccttggtat agcaaactac 180
gcacagaagt tccagggcag agtcacgatt accgcggaca aatccacgag cacagcctac 240
atggagctga gcagcctgag atctgaggac acggccgtgt attactgtgc gagaga 296

<210> SEQ ID NO 41
<211> LENGTH: 98
<212> TYPE: PRT
<213> ORGANISM: Homo sapiens
<220> FEATURE:
<223> OTHER INFORMATION: synthetic

<400> SEQUENCE: 41

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Ala Ile Ser Trp Val Arg Gln Ala Pro Gly Gln Gly Leu Glu Trp Met
35 40 45

Gly Arg Ile Ile Pro Ile Leu Gly Ile Ala Asn Tyr Ala Gln Lys Phe
50 55 60

Gln Gly Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg

<210> SEQ ID NO 42
<211> LENGTH: 294
<212> TYPE: DNA
<213> ORGANISM: Homo sapiens
<220> FEATURE:
<223> OTHER INFORMATION: synthetic

<400> SEQUENCE: 42
caggtccagc tggtgcagtc tggggctgag gtgaagaagc ctgggtcctc ggtgaaggtc 60
tcctgcaagg cttctggagg caccttcagc agctatgcta tcagctgggt gcgacaggcc 120
cctggacaag ggcttgagtg gatgggaggg atcatcccta tctttggtac agcaaactac 180
gcacagaagt tccagggcag agtcacgatt accacggacg aatccacgag cacagcctac 240
atggagctga gcagcctgag atctgaggac acggccgtgt attactgtgc gaga 294

<210> SEQ ID NO 43
<211> LENGTH: 98
<212> TYPE: PRT
<213> ORGANISM: Homo sapiens
<220> FEATURE:
<223> OTHER INFORMATION: synthetic

<400> SEQUENCE: 43

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Thr Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg
```

<210> SEQ ID NO 44
<211> LENGTH: 296
<212> TYPE: DNA
<213> ORGANISM: Homo sapiens
<220> FEATURE:
<223> OTHER INFORMATION: synthetic

<400> SEQUENCE: 44

```
caggtgcagc tggtgcagtc tggggctgag gtgaagaagc ctgggtcctc ggtgaaggtc      60

tcctgcaagg cttctggagg caccttcagc agctatgcta tcagctgggt gcgacaggcc     120

cctggacaag ggcttgagtg gatgggaggg atcatcccta tctttggtac agcaaactac     180

gcacagaagt tccagggcag agtcacgatt accgcggaca aatccacgag cacagcctac     240

atggagctga gcagcctgag atctgaggac acggccgtgt attactgtgc gagaga        296
```

<210> SEQ ID NO 45
<211> LENGTH: 98
<212> TYPE: PRT
<213> ORGANISM: Homo sapiens
<220> FEATURE:
<223> OTHER INFORMATION: synthetic

<400> SEQUENCE: 45

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg
```

<210> SEQ ID NO 46
<211> LENGTH: 233
<212> TYPE: DNA
<213> ORGANISM: Homo sapiens
<220> FEATURE:
<223> OTHER INFORMATION: synthetic

<400> SEQUENCE: 46
agaagcctgg gtcctcggtg aaggtctcct gcaaggcttc tggaggcacc ttcagcagct 60
atgctatcag ctgggtgcga caggcccctg gacaagggct tgagtggatg ggaaggatca 120
tccctatctt tggtacagca aactacgcac agaagttcca gggcagagtc acgattaccg 180
cggacgaatc cacgagcaca gcctacatgg agctgagcag cctgagatct gag 233

<210> SEQ ID NO 47
<211> LENGTH: 77
<212> TYPE: PRT
<213> ORGANISM: Homo sapiens
<220> FEATURE:
<223> OTHER INFORMATION: synthetic

<400> SEQUENCE: 47

Lys Pro Gly Ser Ser Val Lys Val Ser Cys Lys Ala Ser Gly Gly Thr
1 5 10 15

Phe Ser Ser Tyr Ala Ile Ser Trp Val Arg Gln Ala Pro Gly Gln Gly
20 25 30

Leu Glu Trp Met Gly Arg Ile Ile Pro Ile Phe Gly Thr Ala Asn Tyr
35 40 45

Ala Gln Lys Phe Gln Gly Arg Val Thr Ile Thr Ala Asp Glu Ser Thr
50 55 60

Ser Thr Ala Tyr Met Glu Leu Ser Ser Leu Arg Ser Glu
65 70 75

<210> SEQ ID NO 48
<211> LENGTH: 296
<212> TYPE: DNA
<213> ORGANISM: Homo sapiens
<220> FEATURE:
<223> OTHER INFORMATION: synthetic

<400> SEQUENCE: 48
caggtccagc tggtgcaatc tggggctgag gtgaagaagc ctgggtcctc ggtgaaggtc 60
tcctgcaagg cttctggagg caccttcagc agctatacta tcagctgggt gcgacaggcc 120
cctggacaag ggcttgagtg gatgggaagg atcatcccta tccttggtac agcaaactac 180
gcacagaagt tccagggcag agtcacgatt accgcggaca aatccacgag cacagcctac 240
atggagctga gcagcctgag atctgaggac acggccgtgt attactgtgc gagaga 296

<210> SEQ ID NO 49
<211> LENGTH: 98
<212> TYPE: PRT
<213> ORGANISM: Homo sapiens
<220> FEATURE:
<223> OTHER INFORMATION: synthetic

<400> SEQUENCE: 49

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

-continued

```
Thr Ile Ser Trp Val Arg Gln Ala Pro Gly Gln Gly Leu Glu Trp Met
        35                  40                  45

Gly Arg Ile Ile Pro Ile Leu Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg
```

```
<210> SEQ ID NO 50
<211> LENGTH: 296
<212> TYPE: DNA
<213> ORGANISM: Homo sapiens
<220> FEATURE:
<223> OTHER INFORMATION: synthetic

<400> SEQUENCE: 50

caggtgcagc tggtgcagtc tggggctgag gtgaagaagc ctgggtcctc ggtgaaggtc      60

tcctgcaagg cttctggagg caccttcagc agctatgcta tcagctgggt gcgacaggcc     120

cctggacaag ggcttgagtg gatgggaagg atcatcccta tccttggtat agcaaactac     180

gcacagaagt tccagggcag agtcacgatt accgcggaca aatccacgag cacagcctac     240

atggagctga gcagcctgag atctgaggac acggccgtgt attactgtgc gagaga         296
```

```
<210> SEQ ID NO 51
<211> LENGTH: 98
<212> TYPE: PRT
<213> ORGANISM: Homo sapiens
<220> FEATURE:
<223> OTHER INFORMATION: synthetic

<400> SEQUENCE: 51

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg
```

```
<210> SEQ ID NO 52
<211> LENGTH: 296
<212> TYPE: DNA
<213> ORGANISM: Homo sapiens
<220> FEATURE:
<223> OTHER INFORMATION: synthetic

<400> SEQUENCE: 52

caggtccagc tggtgcagtc tggggctgag gtgaagaagc ctgggtcctc agtgaaggtc      60

tcctgcaagg cttctggagg caccttcagc agctatgcta tcagctgggt gcgacaggcc     120

cctggacaag ggcttgagtg gatgggaggg atcatcccta tccttggtat agcaaactac     180
```

gcacagaagt tccagggcag agtcacgatt accgcggaca aatccacgag cacagcctac 240
atggagctga gcagcctgag atctgaggac acggccgtgt attactgtgc gagaga 296

<210> SEQ ID NO 53
<211> LENGTH: 98
<212> TYPE: PRT
<213> ORGANISM: Homo sapiens
<220> FEATURE:
<223> OTHER INFORMATION: synthetic

<400> SEQUENCE: 53

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Ala Ile Ser Trp Val Arg Gln Ala Pro Gly Gln Gly Leu Glu Trp Met
35 40 45

Gly Gly Ile Ile Pro Ile Leu Gly Ile Ala Asn Tyr Ala Gln Lys Phe
50 55 60

Gln Gly Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg

<210> SEQ ID NO 54
<211> LENGTH: 296
<212> TYPE: DNA
<213> ORGANISM: Homo sapiens
<220> FEATURE:
<223> OTHER INFORMATION: synthetic

<400> SEQUENCE: 54
caggtccagc tggtgcagtc tggggctgag gtgaagaagc ctgggtcctc ggtgaaggtc 60
tcctgcaagg cttctggagg caccttcagc agctatgcta tcagctgggt gcgacaggcc 120
cctggacaag ggcttgagtg gatgggaagg atcatcccta tccttggtac agcaaactac 180
gcacagaagt tccagggcag agtcacgatt accgcggacg aatccacgag cacagcctac 240
atggagctga gcagcctgag atctgaggac acggccgtgt attactgtgc gagaga 296

<210> SEQ ID NO 55
<211> LENGTH: 98
<212> TYPE: PRT
<213> ORGANISM: Homo sapiens
<220> FEATURE:
<223> OTHER INFORMATION: synthetic

<400> SEQUENCE: 55

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Ala Ile Ser Trp Val Arg Gln Ala Pro Gly Gln Gly Leu Glu Trp Met
35 40 45

Gly Arg Ile Ile Pro Ile Leu Gly Thr Ala Asn Tyr Ala Gln Lys Phe
50 55 60

Gln Gly Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg

<210> SEQ ID NO 56
<211> LENGTH: 296
<212> TYPE: DNA
<213> ORGANISM: Homo sapiens
<220> FEATURE:
<223> OTHER INFORMATION: synthetic

<400> SEQUENCE: 56
caggtccagc tggtgcagtc tggggctgag gtgaagaagc ctgggtcctc ggtgaaggtc 60
tcctgcaagg cttctggagg caccttcagc agctatgcta tcagctgggt gcgacaggcc 120
cctggacaag ggcttgagtg gatgggaggg atcatcccta tctttggtac agcaaactac 180
gcacagaagt tccagggcag agtcacgatt accgcggacg aatccacgag cacagcctac 240
atggagctga gcagcctgag atctgaggac acggccgtgt attactgtgc gagaga 296

<210> SEQ ID NO 57
<211> LENGTH: 98
<212> TYPE: PRT
<213> ORGANISM: Homo sapiens
<220> FEATURE:
<223> OTHER INFORMATION: synthetic

<400> SEQUENCE: 57

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Ala Ile Ser Trp Val Arg Gln Ala Pro Gly Gln Gly Leu Glu Trp Met
35 40 45

Gly Gly Ile Ile Pro Ile Phe Gly Thr Ala Asn Tyr Ala Gln Lys Phe
50 55 60

Gln Gly Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg

<210> SEQ ID NO 58
<211> LENGTH: 296
<212> TYPE: DNA
<213> ORGANISM: Homo sapiens
<220> FEATURE:
<223> OTHER INFORMATION: synthetic

<400> SEQUENCE: 58
caggtccagc tggtgcagtc tggggctgag gtgaagaagc ctgggtcctc agtgaaggtc 60
tcctgcaagg cttctggagg caccttcagc agctatgcta tcagctgggt gcgacaggcc 120
cctggacaag ggcttgagtg gatgggaggg atcatcccta tctttggtac agcaaactac 180
gcacagaagt tccagggcag agtcacgatt accgcggacg aatccacgag cacagcctac 240
atggagctga gcagcctgag atctgaggac acggccgtgt attactgtgc gagaga 296

<210> SEQ ID NO 59
<211> LENGTH: 98

<212> TYPE: PRT
<213> ORGANISM: Homo sapiens
<220> FEATURE:
<223> OTHER INFORMATION: synthetic

<400> SEQUENCE: 59

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 60
<211> LENGTH: 305
<212> TYPE: DNA
<213> ORGANISM: Homo sapiens
<220> FEATURE:
<223> OTHER INFORMATION: synthetic

<400> SEQUENCE: 60
gagcccactc ccaggtgcag ctggtgcagt ctggggctga ggtgaagaag cctggggcct 60
cagtgaaggt ctcctgcaag gcttctggat acaccttcac cggctactat atgcactggg 120
tgcgacaggc ccctggacaa gggcttgagt ggatgggacg gatcaaccct aacagtggtg 180
gcacaaacta tgcacagaag tttcagggca gggtcaccag taccagggac acgtccatca 240
gcacagccta catggagctg agcaggctga gatctgacga cacggtcgtg tattactgtg 300
cgaga 305

<210> SEQ ID NO 61
<211> LENGTH: 98
<212> TYPE: PRT
<213> ORGANISM: Homo sapiens
<220> FEATURE:
<223> OTHER INFORMATION: synthetic

<400> SEQUENCE: 61

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Arg Ile Asn Pro Asn Ser Gly Gly Thr Asn Tyr Ala Gln Lys Phe
    50                  55                  60

Gln Gly Arg Val Thr Ser Thr Arg Asp Thr Ser Ile Ser Thr Ala Tyr
65                  70                  75                  80

Met Glu Leu Ser Arg Leu Arg Ser Asp Asp Thr Val Val Tyr Tyr Cys
                85                  90                  95

Ala Arg

<210> SEQ ID NO 62
<211> LENGTH: 307
<212> TYPE: DNA
<213> ORGANISM: Homo sapiens
<220> FEATURE:
<223> OTHER INFORMATION: synthetic

<400> SEQUENCE: 62
gagcccactc ccaggtgcag ctggtgcagt ctggggctga ggtgaagaag cctggggcct 60
cagtgaaggt ctcctgcaag gcttctggat acaccttcac cggctactat atgcactggg 120
tgcgacaggc ccctggacaa gggcttgagt ggatgggatg gatcaaccct aacagtggtg 180
gcacaaacta tgcacagaag tttcagggca gggtcaccat gaccagggac acgtccatca 240
gcacagccta catggagctg agcaggctga gatctgacga cacggccgtg tattactgtg 300
cgagaga 307

<210> SEQ ID NO 63
<211> LENGTH: 98
<212> TYPE: PRT
<213> ORGANISM: Homo sapiens
<220> FEATURE:
<223> OTHER INFORMATION: synthetic

<400> SEQUENCE: 63

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg

<210> SEQ ID NO 64
<211> LENGTH: 307
<212> TYPE: DNA
<213> ORGANISM: Homo sapiens
<220> FEATURE:
<221> NAME/KEY: variation
<222> LOCATION: (124)...(124)
<223> OTHER INFORMATION: n=a, g, t, or c

<400> SEQUENCE: 64
gagcccactc ccaggtgcag ctggtgcagt ctggggctga ggtgaagaag cttggggcct 60
cagtgaaggt ctcctgcaag gcttctggat acaccttcac cggctactat atgcactggg 120
tgcnacaggc ccctggacaa gggcttgagt ggatgggatg gatcaaccct aacagtggtg 180
gcacaaacta tgcacagaag tttcagggca gggtcaccat gaccagggac acgtccatca 240
gcacagccta catggagctg agcaggctga gatctgacga cacggccgtg tattactgtg 300
cgagaga 307

<210> SEQ ID NO 65
<211> LENGTH: 98

<212> TYPE: PRT
<213> ORGANISM: Homo sapiens
<220> FEATURE:
<221> NAME/KEY: VARIANT
<222> LOCATION: (38)...(38)
<223> OTHER INFORMATION: Xaa=any amino acid

<400> SEQUENCE: 65

Gln Val Gln Leu Val Gln Ser Gly Ala Glu Val Lys Lys Leu Gly Ala
1 5 10 15

Ser Val Lys Val Ser Cys Lys Ala Ser Gly Tyr Thr Phe Thr Gly Tyr
20 25 30

Tyr Met His Trp Val Xaa Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg

<210> SEQ ID NO 66
<211> LENGTH: 294
<212> TYPE: DNA
<213> ORGANISM: Homo sapiens
<220> FEATURE:
<223> OTHER INFORMATION: synthetic

<400> SEQUENCE: 66
caggtgcagc tggtgcagtc tggggctgag gtgaagaagc ctggggcctc agtgaaggtc 60
tcctgcaagg cttctggata caccttcacc ggctactata tgcactgggt gcgacaggcc 120
cctggacaag ggcttgagtg gatgggatgg atcaacccta acagtggtgg cacaaactat 180
gcacagaagt ttcagggctg ggtcaccatg accagggaca cgtccatcag cacagcctac 240
atggagctga gcaggctgag atctgacgac acggccgtgt attactgtgc gaga 294

<210> SEQ ID NO 67
<211> LENGTH: 98
<212> TYPE: PRT
<213> ORGANISM: Homo sapiens
<220> FEATURE:
<223> OTHER INFORMATION: synthetic

<400> SEQUENCE: 67

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Trp Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg

<210> SEQ ID NO 68
<211> LENGTH: 346
<212> TYPE: DNA
<213> ORGANISM: Homo sapiens
<220> FEATURE:
<223> OTHER INFORMATION: synthetic

<400> SEQUENCE: 68
aggatgtggg ttttcacact gtgtctctcg cacagtaata cacgaccgtg tcgtcagatc 60
tcagcctgct cagctccatg taggctgtgc tgatggacgt gtccctggtc atggtgaccc 120
tgccctgaaa cttctgtgca tagtttgtgc caccactgtt agggttgatc cgtcccatcc 180
actcaagccc ttgtccaggg gcctgtcgca cccagtgcat atagtagccg gtgaaggtgt 240
atccagaagc cttgcaggag accttcactg aggccccagg cttcttcacc tcagccccag 300
actgcaccag ctgcacctgg gagtggacac ctgtggagac tcgcga 346

<210> SEQ ID NO 69
<211> LENGTH: 98
<212> TYPE: PRT
<213> ORGANISM: Homo sapiens
<220> FEATURE:
<223> OTHER INFORMATION: synthetic

<400> SEQUENCE: 69

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Arg Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Val Val Tyr Tyr Cys
85 90 95

Ala Arg

<210> SEQ ID NO 70
<211> LENGTH: 150288
<212> TYPE: DNA
<213> ORGANISM: Artificial Sequence
<220> FEATURE:
<223> OTHER INFORMATION: synthetic

<400> SEQUENCE: 70
gcgcgccctg gcatggagga aatgacaaag attattagat tgaagacttt ctcagaaaat 60
gatattaagt cattaaggaa aaggaacaat ataaacgtgt atttgagaaa ttttaattat 120
ttgagagatt tttcatacaa tatttattct gcaagcaaat ttcagggatt gaattaataa 180
aactgataca gaacttcctc tgtaggtatc tgtgtaaaca tcaatttctg aatcagtgtt 240
gtaaatattt tggaacacac acacaaatca cattttatct ctacttttat ctctattttt 300
aaaaatgcca aaaaaactca ttttgtgcat gtagcatttt gaattcccac catcaatgca 360
tgatagttct tggttttcca cattcatatt gccatttatc attatgagaa ttgtgtgttt 420
taaccattct aataggtgag taatggtatc taatttttag ttaaatgcac atttccctaa 480
taaaaattca catttaacaa ttttcatata atttttgcca agatgcctct tctcatattt 540

```
ggttcatttt taactgcatt gttttctttt gattagttgt aagtttactt gcatattgat    600
tataaaatca tttaacaaat taaaagaatt catttaacaa atatgtgact tggaagtatt    660
ttctccaagt ctgcggctgt cttttactcc cttatcagta tgtattgcag aaaagtgtgt    720
gtgtgtgtgt gtgtgtgtgt ttatacaaat ttagatttaa aaaatgtaaa atgttattca    780
tccacagatc atgtctttgg tattatatct gaaatctcat tataaaatac agtaatagca    840
attacttttt ccacgtctct aatctcaggc tacaatcaac tcatgagtgt ttaagcttca    900
cctacttgat tagaggacta tcaacctaac atatttggaa tacttctgta aaaagatgtg    960
ttcctcttcc tattatttct ttatttgatc acttattaat atgtgtattg gtttatggat   1020
gtctatttca tactctgaag aagatccatg ctacattatt cattttattt ttcaaaccac   1080
cacggcttta ttatgtgctg ggagctcatt gagtttggat cctgcatcct tacagctcac   1140
ctcatgcttt tgtttttgaa cacttccctg tttcctgcta ttataataaa ttctaaactc   1200
atttctata ttatcttttt catacataga atcagccatt tttctaaaga ttgcttgctt   1260
ctgatgttaa agaatagtat ttaaaaaatt gtaatactgg gtatgtgcat tgttaatgtg   1320
gtataagtac ttgcaggacc tctcaaccaa ctggcctagt aaactatgta tctaaccttc   1380
tgtaatgtga ttacattaaa aatgagaaca cactggtctc tctacccaat tatgctacca   1440
catggatctt tctagccttc cttccttgac tgtctataac ctctcactgc aaaatgagga   1500
accccatcca accatatgcc attttattac ttagctgcac aatttcagga cacatgcata   1560
gcagtatcag aaatgtaaag ctgtaccctt gtaggaaaca tgtttatcta ctagaataga   1620
gtgcttatgt tcagtttctt tacactttaa acttacagag tttcctcatt ttcaaagttc   1680
cttaggtcag caacttcatt ttccactttc ttcagtgagg tcatttcaat gacactgtat   1740
aatttgattt atttgaaatt ctataaaagc caaaactgta gtcaagtgaa caacaacata   1800
tagaggatat tcgaggagtt tagagactgg tataaaataa gttaaaaaga cactgtttaa   1860
gaagattaaa attattttta gtgatatgca atggttcaga tatgacacaa ttaatttgtc   1920
taagcacata gttttgtgat ggaaaatata aacctaaata tatacaatta aaaaaaaatt   1980
tagcagttca ttaacccaag gatcaaatgc agattgtata aaattatctc attacttatt   2040
ttgtgagggt ggagatttca tgagatgtat gcaacaaaga atgaggtaat tttcctgatt   2100
tgcatataag atgttgccat tcactaaaga cctttaattt tttaaattgt ttttttttta   2160
aatcaatttt ctatgtgacc caggtttttt tctcttgaca agcaaataac ccacaggatt   2220
attttctttc cttggttgag aaatatttcc ccaaacttca gctcagttca ggcatacact   2280
gtccctgaat gggcatttac cctcagatgg gtacacacac ctgtcaacat gtggactctt   2340
ctgtcagaca aacgcacctt tactcacgtg gattcttctc tcagacaaac acacatgtcc   2400
ccacgtggac tctttcctca gactaccaca tatgttctta catttactct ttcctcagaa   2460
aacagacatt tcctcatgtg gactcttgtc tcagacaagc aaacatgtct ccatgtgaac   2520
tcttcactca cataagtaca catatgtcca cattgactgt ttccttacac aagtacatat   2580
atccaatgtc gaattgttct gtggcaaaat gatctcaaga taatgataat cataaacccc   2640
ctccctgaca aggcatagat ctgtattttt ttcattgcaa cctaactttg ccttattgtc   2700
aagaacagta gtttgcagct ctaaatatac caattagaga caggtgtcca ttttctctgg   2760
aaacgtattt ttatgttctt actggacata tttgttgata atgtttgcta ttatgaagat   2820
accccaacag tgtccacatt agagaataaa aaatagtaat gggcagatta actctgtgca   2880
```

-continued

```
tccagaccca gaaatccttt gaccttgact tccctgaaat gtagacacag aggatggatg   2940

agcaatgctg agcagtgcac ccatgaccac aaaaagaaag acgtggaaat gtgtcccctc   3000

cacttctcat gaaaggcagc tcatcccctg ttccctcagg ccctggcgag gagccacccc   3060

atgtctgtgc ccttcctcag tgtccacacc gtggggtctg cattgatctg gattctcttc   3120

tcatccccgt caatattagt gtccttcgta aatcaggtcc agctgtggct tctcctcacg   3180

gggctgttct cagtctgttt gctgtgttca cggaagtcct gtgtgaagtt tactgatgga   3240

gtcagagggg gaaaaaattt acagcccagt ggtgagactc tcctgcaaag cctctggttt   3300

cacctttact ggttacagca tgagcttggt ccagcacgct tcacaacagg gataggtgtg   3360

ggtgccaaca gtgagtgatc aagtatgaat tctcagggtt actttccatg agtacaaata   3420

aattaacaat ctcaagcaac accctttttaa gtgcagtctg ccttacaatg accaatctga   3480

aagccaagga caaggtcatg tattactgtg agtgacacag tgagggaaac cctgtgtgag   3540

cccagacaca aagctcaccg cagggagaca ggaggggact atgtggtaga tgctgctcag   3600

aaccaccagg gggcatcagg accatcaggg agggtgcaca gaaccaccag gaggggctca   3660

ggacaccagg gggcgctcag aaccaccagg gggccctcag gacaccagag ggtgctcaga   3720

accaccagga ggcgctcagg acaccagggg gcgctcagaa cactaggagg tgctatgaat   3780

cactaggggg cgctcaggac acaagggagc actcagaacc accagggata gctcaggata   3840

ccagggggca ctcggaaccg ccagggggcg ctcaggacac tagggggcgc tcagaaccac   3900

cagggggcac tcaggaccat cagggagggt gcacagaacc accaggaggg gctcaggaca   3960

ccagggggcg ctcaggacca caagggggcc ctcaggacac caggggggcac tcggaaccac   4020

caggggggcac tcagaaccat cagggagggt gcacagaacc accaggaggg gctcaggacc   4080

accaggaggt gctcaggaca ccagggggcg ctcagaacac taggaggtgc tatgaatcac   4140

tagggggcgc tcaggacaca agggagcact cagaaccacc agggatagct caggacacca   4200

gggggcactc ggaaccgcca gggggcgctc aggacactag gggcgctca gaaccaccag   4260

gaggcactca ggaccatcag ggagggtgca cagaaccacc aggaggtgct caggacacca   4320

gggggcgctc agaacactag gaggtgctat gaatcactag gggcgctca ggacacaagg   4380

gagcactcag aaccaccagg gatagctcag gataccaggg ggcactcgga accgccaggg   4440

ggcgctcagg acactagggg gcgctcagaa ccaccagggg gcactcagga ccatcaggga   4500

gggtgcacag aaccaccagg aggggctcag gacaccaggg ggcgctcagg accacaaggg   4560

ggccctcagg acaccagggg gcactcggaa ccaccagggg gcactcagaa ccatcaggga   4620

gggtgcacag aaccaccagg aggggctcag gaccaccagg aggtgctcag gacaccaggg   4680

ggcgctcaga acactaggag gtgctatgaa tcactagggg gcgctcagga cacaagggag   4740

cactcagaac caccagggat agctcaggac accagggggc actcggaacc gccagggggc   4800

actcaggaca ctagggggca ctcagaaccg ccaaggggcg ctcagaagaa gcagggggtg   4860

ctcagaacac cagagggtgc tcagaagcac cagggggcgc tcaggacacc aaagggcact   4920

catgagactg tggcaagggg gtgctgagaa ccacaggatg tgaccaagac accaaggggc   4980

actcagaact gccagggggt gctcaggaca ccagaggatt ctcagaacca ccaggggatg   5040

ctcaggaaac tagcgggtgc tcagaaccac cggaggacac tcagaaaacc aggggatgct   5100

caggaaccac caggggggcgc ccacgacacc agagggcagt cagaaccacc ggggcatgct   5160

cagaaccacc agggggcgct caggacacca ggggatgctc aggacactag ggcgctcag   5220

gaaccaccag gggacgctca ggacactagt agggtctcag aaccaccagg ggatgctcag   5280
```

gacactaggg ggcgctcagg aaccaccagg ggtcacccag gacaccaggg gtcgctcagg 5340
aaaccagagg gtgcccagga aaccagggga ggttcaggaa ccaccagggg gcactgagga 5400
caccaagggg tgctcagaac caccaggggg cgctcaggaa ccaccagggg gcgctcagga 5460
cactagtagg cactgaggaa ccaccagggg gcgctcagga cactagtagg cactgaggaa 5520
ccaccagggg gggctcagga cactagtagg cactgaggaa ccaccagggg gcgctcagga 5580
cactagtagg cactgaggaa ccaccagggg gggctcagga caccagaggt cgctcagaaa 5640
accagggggt gctcagaacc accagggggc actcaggaac caccagtggg tgttcaggac 5700
agcaagaatg gctcaggaca ccagggagca ctcaggacct ccaaggggct ctttggaggc 5760
agctccatat caggtacctg ggaggatga ggtttccttt tccaccttgg tgattcctga 5820
cctggtcaag caaaagtctt ccccaggatc tcttacgatg tcttccttgt aactcatggt 5880
ttctttcacc tataaaacat taacttagaa caggggttca attcaacttt taactctgcc 5940
tattttcaga gttatactag caatgatata tctcagtata ttttttttaa ttgtgtatat 6000
tcaatccaaa gtctggctct atgcacaatt tttttgtttt ctgtgctgtc agacacacta 6060
ttgtaaatgc ttttctaaca actcagcata tgcatggggt ccagtttctt ttcctttcat 6120
cggctgtttg tgcagatgaa acaccacttt aagggctcct gtcctccact ttggcccctg 6180
gtgttctgct tctcaaactt tctccatctt ctctttttct gtcaaaatat tttatcttcc 6240
tcagtctcca tgcaggaaac aggaagtcct tttacttcct gtcctccatg tctggtaaat 6300
cagttcactt cttttcatga tcactgaagc caaccaagtt taggagagta acagttctcc 6360
ttagaataca ctctacctgc agaccctctg ccctcatcac acttttctag ggtcctgcag 6420
acataacccc cacccattcc tctttttccc taagtaccac agactaggct ctgcaactta 6480
tgctaccctc tgtgtgctca gcccaggggc tcagtagtgc tttcatgaag tccaaatccc 6540
taatgtgttt gcccactctc agaccaccct ccagcaagct gccattgtga ttgaatcctg 6600
caaagcatgg gctgctttca gtttcctatt gctggatgtt ctttattata aaggcatatt 6660
ggcaaataac gactagagtt tgtattgaaa attaacgcca aaaagttttt taaaaagttt 6720
ttcaaataga aaagttctat cctgcctagt ttaaaaaaat acaatgttac tttaatcaat 6780
gatttaataa aaatttaagt gatgtttgtc ttattagtta ttcaatttat taataactga 6840
ctgatattta aaaagtaaat actggctggg cgcagtggct cacgcctgta atctcagcac 6900
tttgggaggg tgaggtgggt ggatcacctg aggtcgggaa ttcgagacca gcctgaccaa 6960
catggagaaa ccccctctct actaaaaata caaaattagc tgggcgtggc ggggaagctg 7020
aggcaggaga atcgcttgaa cctgggaggc ggaggttgcg gtgagccgag aacacgccat 7080
tgcactccag cctgggcgac aagaccaaaa ctctgtctca aaaaaaaaaa aaagtaaata 7140
ccattgtaca cttaagtaat atatttggca agaatggcat ttacattcat tcaaaaatga 7200
aactgcaaat acgagttaca ttcaattaaa taattaaaat aatatagaaa aaaatgggtg 7260
tgttgttttg gtgtttaata tacattcatt tttgcatgga cgggtatatg tgtcattgct 7320
gggctgttgt gtatgtgtgc gtgtgtgtgt gtgtctgtgt gtacaactat gaagtttaaa 7380
atatattatt aaattacgta gttatattaa tccaaattta tcatgttaaa atattaggaa 7440
aaaaacacca gtagagaaat tacagagaac atcagcaatg cctacagcat ttacaagagt 7500
cacattaata acaaacaaac tagttcaaat gtttagatat gacacatgca gtagaaaacg 7560
ttcacatggt attaacacaa aaatggtgca caactgagga aattataata cgttcatgat 7620

-continued

```
attggctaca taaatgctta tgatagtaat gcttttcatc catcaaatgc ttatgataat   7680
gcttttcatc catcatatta tagatgataa aacaactcta taaacacttc catcactagc   7740
gtttaatatg agatgcctca catctttttc tgaaataaat aaacatctgt ccaccacttc   7800
gatgatcatt tcaggattat cctctgaaat aattatccat aataatttta gtaacaatat   7860
tattttcaga agcctatttt ataaggtctt tgaactatta tttttatgat tgttacttta   7920
tattttacac actttttatt tggaataatt ataggttatc agaacaattg taaggaaaat   7980
acagtgtgtt cacatccatc tccaagtttt cactaaagtt aatatgtcaa aaaaaacatg   8040
ggacatggga ctaatatatt tacattgata agtttctgtt tattcagctc tgggatttat   8100
ttgaattttg ccaattttta acagtttcct tttttccttt ttcttttctt tttgagataa   8160
ggtgtcactt tcctattgct ttttgtttgt ttctttgttc aacccacgta accacatcaa   8220
attcagtcac catgttcctc tcatatcttc tggttaatca cagtttgggt tcctgctgtc   8280
ttcccattga atattctata aatgaaacta gtcaaataag ttgattctgg tcacttatat   8340
atttacctat tttatcacgt ttgttttgtc aatcacagta agtgtcgaat tcgctatctg   8400
ttatagatgt tagcctattt tctatcccag atccattggt taaatctttg gtgatgcctt   8460
ttagaaaact gatcccttta ccctatgtaa tatgcccctt gattcctgaa agtcttatgt   8520
ctaccttgtc tgaatttaac atagctaagc acgctttctt ttcgttcata ttttcatggt   8580
ccatgttttc ctgtatttaa cttttctatg tagagcaaat ttctgtacag agctagtagt   8640
tgggtcttgc tttttaaatc aactataata attctatttt aaaactggta ttactatttt   8700
tctgttaatt tctgttttaa tttggcattt tatgatcatg tttatttctc tattaactta   8760
ttgtttagtt catcttttat gaatattgta ttggccctaa gatatacaat aagaattgtg   8820
tataatcaga ttctaattca aataacgtaa aacctcttca taggttgtag agctattata   8880
acttattctt ctaaacactc tttctcatcc gttgtcttag tttattctca gtttgcactt   8940
atatgtgcta taaaatataa tatgtgcatt tttatcatta catagacata tattagaaca   9000
attaaaaata taaaaactac atttcaactt catttttttca ttcttgacca catgttttat   9060
ttggatagat tcatgtttcg gatgtatatc atatggctac tcaccctggc agaaaatttg   9120
ccaaagcacc tactgaagga tgaatgcact agcaataaat tttctcagaa tcgatttgtc   9180
ttacagggta ttcatttgac tttcgcttta aatgaaattt ttaatatata tagaattcca   9240
gtttgacttt aatttgtaat ttattttctt gtactcatgt attcattatt ttcttcctga   9300
agatggtcac acattccatt ctgctgggcc ttcattatag atatttgtgt gtatctattc   9360
agggctatat ttgcaattta tggatgccac aattatcaga gttgaagtca gcttctgctg   9420
tccacagaga tttcaagttc ctcccatgat acttgctttt gtgtccctgt ttgatcctgg   9480
gtctttatat ttagttttcc ccagggaggc tgtctgtttc agctgtggaa agtgcaccct   9540
actgacagtt taaattgatg actgtgtggt gaaggaggtt ggacaaagcg ggacttcctc   9600
caaccttctg actgagtctc cttcttatgc aggagtagta agcatagttc tggggagtgg   9660
ccttccacat tgtcctgtcc ttaactcttt ccccagggct ggaacgtctt ttcccagaca   9720
caactgtttt tcaccagtgt ccccagcttt ttacccacta tccttaccct aaagagtaag   9780
gatttctttc ctgaggaagg agatgggagg tgtttctgga tcaagtttcc ttggtgtcgt   9840
ctgtttcctt ttgtttctgt tgacttcacc acagctcata tgacacatgc tttggtggat   9900
ttcccctgga ggtagtggag gtgcattcag gcattccaca ggagctgctg ttcttttccc   9960
cagtcaacac cacaagacac cagatgagga agttgtccgt ggatttttca agttctctag  10020
```

gaaaagcttg caagcactag gccaatctaa caccattagt acatgcatac taaaaaaaaa 10080
aaagtcatta agtatttcta ggttagtctg tttctatctc aaatgccatc cagtggcacc 10140
tgccctacgt acactagcag gtaggtcctg gttctctctg caggctccta tcttctcaga 10200
tttcagtttt cttgtttgct tggtgaaatc aactcagata tgttgaatgt tttttctctc 10260
ttttatttgt agctgttcag cttcgttgtt aatgaggtca gaataaaatc acagttttct 10320 cattttttc acattcccac actgaatagc tgctttccgt ataaaagcca gaaactgaga 10380
gaacacattg aatatccatt acaggtgaat gttaaacaat ttgagatatg tttgtgtact 10440
ggaataaaat gctgcattac aatcaagtca tcactcattc acataaaaca tggccacatt 10500
ctcaaataat gtagggacct gagtgcccct ccatctactg gcctctcctg gggccctagc 10560
ctggccacac cttcttgcag ggcagtcttg gacgccctgg gatcccgcac caaaatttct 10620
gccctggcag aacatgcctg actggtggag agctccaatc gggcagccct catgtgcaca 10680
caccagctta cacacttcct ccgaatactg taggttcacc caggcccacg taacttccca 10740
catcactttg cagtcacatg tctgtatagg tgggttttgc ttttcttgtc ccaccattgc 10800
gtggagtgca gtcccctccc cccaccccaa ccaccatggc agaggaagct ttggtgggga 10860
aaaagccagg gccgctcctg tcagcgtccc gcacttgcgc taattctgca cagagaatag 10920
cagatcatct cacacattca gaaatcactc ctgcttgtgg ggcatgaata cggcacccgg 10980
gcctgtgccc acaagtgtcc catccctgag ccaacacctc ctccagtgtg accttgaaca 11040
cagtcaccaa cagggcccca cagacgcaat gcctctgcca ctgtggcgaa cacctgcagg 11100
gaggcaggca cccagacacc cactagcact ctgccacagc tgccacacct ccaacagccc 11160
aggacagtgg attcctaacc ttaaggagcc ggagaaccaa gtcagggact agtataactt 11220
cccccagagt cagagcacac agtctaggtg ttgggagctg agcactggcc acctaaattt 11280
ttccagaaat gaagccagtt ggctgaatcc accttatacc acaatcaaac cctcaaggtc 11340
atccaatagg gtaaaagaaa ataaaaatgt atccaaaggt cagcaacttc aaagattgaa 11400
ggtggataag cccacaaaga tgagaaagaa ccagtgcaaa agtcctgaaa acaaaaaggg 11460
cgccctcttt cctccaaaca accacagcac ctcttcaaca gcagttctga atggggctga 11520
gatggctgaa atgacagaaa cagaactcag aatatggaga gtgaaaatgt agatgaatac 11580
agctatttat ggagaatact ataaatgttc ctcaaaaaat aaagaaacaa aatctactgt 11640
agaatccagc agtctcactg ctggctatgt atccaaagga aatgaaatca acatgtcaaa 11700
gagatatctg cactccatgt tcacgttcat tgcagcatta tttaaaatag taaagatatg 11760
gaaacatcct aaattcccat gaatggatga atgaataaag aaaatgcata cagacacaac 11820
agagtaatgt tcatccttaa ataagaagga aaccctgcct ctgtgacagc atgcatgaat 11880
ctagaggacc ttatgccaag tgaaacaagc caggaacaga ggaagagtca ttcatgattt 11940
cactgtatat attaaagcag tagacttgca gaggtagagt agaatgttgg ttaccagggc 12000
ctagaggggt ggactgggaa agggagatgt gggttaaagt gcacaacgtt ccagttagac 12060
cggaggtata agttatgcct ttctaatgca cagcatgtca actatagctg ataaggtagt 12120
atatatttca aaattactaa aaaaataaac attagaattt ccccactaag aaatgataaa 12180
tttgtgaggt gatgaatata agcggcttga gttacccagt tcataatgta tacatgtatc 12240
ataactaaac aacatatgtc ataaatatat gcaaaaatta tttgtaattt ataataaaat 12300
aagtttcata tttaaataat tacattaaga aaatgaacag aaactttcag atttcaagaa 12360

-continued

```
tattttatat atatatatat atatcttaaa acaaacttgc aacagaatat agaaataagt  12420
tttacgactc aatggaaaag aacagaattc aataaaaact ggctaaaaga aacaacagct  12480
gcatcattat agaaaattct ggaataatca gccatataaa gattctcact ctcttagaac  12540
tagaattccg taggacttgt aattcctcct gacctgggtg ggaggcaaaa ggaagaacag  12600
ctaatggtga ttcagtgagt tttatacctg tgtgtacttc tgtgctcact cagcagaaag  12660
aaaagaagaa aagaaagaaa gagagaaaga aagaaacaga aagaaagaaa gaaagaagaa  12720
agaaagaaag aaagaaagaa agaaagaaag aaagaaagaa agaaagagaa agaaagaaga  12780
aggaagaagg aaggaaagaa aagaaagaaa gaaagagaga gagggagaga gggaaggaag  12840
ggacagcaga agtcattgtg gtgtgtgtga aagcacaatc cttgggctcc cccacatcca  12900
tctctactcc agtcccatca atgtccagca aatacatttt ctaagatgaa gtattttaaa  12960
ctttctaaat cctgctagaa aacccctcag ctctttcagt tttgctctat cacttgaatt  13020
attgaattaa atctagtttt tgtgggccta tcaataccat aagccaaaat aacacatgaa  13080
gaaattgcac tgagacacat gaaaaccttc tgaaagctcc ataatttcag atctgcattc  13140
ttatttcccc gaacctaaat cactgaatag agactcagaa cgagttgatc ttgttcctga  13200
acgtgcacag agccaaggac atcctgtctg tctggaacag ctcaggtttg ttcctgtttc  13260
tcctagagga tataaaatct tgagttaggg aaaaacagcc agggacaccc tgggctttgt  13320
tcttctctcc cctggaggca ggatgtcctt cagagctttg tcccagtggg taacacagct  13380
gctgaggtgt acaacccacg tggcctcgtt ttggtcactt ttgcatggtg agcctgcttt  13440
gcaccatggc ctacaatatg cgtgtgtaac taatctgtct ccatcttcaa aatgacatta  13500
ttccacatca aatctagtgc aggtgcctca cacagaacat tctcaattac ctccatcatt  13560
cataaaattg atgccattaa tttcaagtat acatacatca gactcattta acgtattgtt  13620
attctcattg tttgaaacat aacttttaga tcaaataatt aacaataata aaaatataaa  13680
ttttgaagtc aggtaatgtg atttctctag ttgtgttctc tttgctcaga atggcttggg  13740
ctgttctgca tcttttgttt ttccacatat attttaggat tttttaaaaa tttctgtgaa  13800
gaatatcatt gttgttttca tagggattgt actgagtctg tagattgctt taagtattat  13860
ggacatttta acaatattga atctttgaat tcataaacat ggaatattgt tccatcttgt  13920
gtcctcttta tttcctcaat gttttataga tttattgtag ttttttttta ctttgttcat  13980
tacacattgt atgcctgtac caaaacatca catataccca acaaatagaa atatatatac  14040
tattatgtgc ttataacaat taaaaattat gtatgtatat tgaatctatt caaaatcaga  14100
aactatttct ttttactgtt tgtaaggtct tgtctctagg ctataaaaag aatttgtaaa  14160
actcaacaga aagcataata taaacagaat tctaaaatga gtgaaaatct gaacaaacac  14220
ctcaccaaga aaaaatgtta tctgaaaata agaatatata aaattgttca gtatcaattg  14280
tcataaactg atactcatat ttaccaaata caaaagtaaa catgatgtat ttcaacagaa  14340
ttgattctca aatatttgta tactcataca gtggaatact atcagtcata aaaactatgg  14400
gttattaatt cagaagacaa cattttaaca ttttttctaa gtgaaggaag atggacaaaa  14460
gagactaagt attgtacaat tccattcatg agacctgcta aatacagtaa aattaaaagg  14520
attttaaaaa caggtttgtg ataggcaggg cttttgggga aagacaagag actgacttgg  14580
caaagctcag gggatatttt tagggtaaaa caaactgtgt gccattgtga tatgcctaat  14640
ttcttattat atttgttcag agttaatagt gtacgtttca accaactcgg tgattttata  14700
ttttctattt gctgatagag acatgttcat ttttgtcaat cactttgcta aatgtggctg  14760
```

```
agaggctgtt gaaatgaacg ctgagcaaat gtattcacca aatctacaag agcaaattat  14820
ttgccaattg ctgattgagt ggggtctata atgtatttga gattgggtgt ggggatgtta  14880
ttgtgtgaga tcatgatgtt tagaccatga cactctctgg tgagggatca ctcattcatt  14940
gcacatttaa tgaaaggcag gtaggaggag cagaagggga tgagtcacac tcctgaccac  15000
agccacaggt tattgaaggc agaactgatg taatccccta aggtagacca ctgcccctcc  15060
aaggtgacct tatcctagag ttgacacaca tcctgggaca ccagagacaa ctccttctct  15120
cccctttctc tgcacttcag ctggaagcaa ctgtctcacc gagcaccttg tgttaaggaa  15180
tgagagttcc tgttccaggt gtgagggccc aggtgcatcc acttgatcca gcacaagagc  15240
aagaacagcc ttccagaaaa tgacatcgcc tgaggtataa ccagctctca cctgctgcag  15300
cttcctctga ataaaaagga aactgttgaa acttcctcat aagtgtcctg ctgtgccatt  15360
ccctttgtcc ccacatgttc agttgtgtct gtccagatgt cacttttgtg tagggagatt  15420
agggttctgc ttccagtacc agaacacaca tgacctctta ggggacttca gggttttgct  15480
gacatatgtg atgatcttaa aagtcattag ctccatttct acatcaaaaa acatctgaac  15540
caaaggagca cataggctca ggcctgtaat cccagcactt tgggaagcca aggcagagga  15600
atcacttgag gtcaggaatt tgagaccagc ctggtgaaca tggtgaaacc ccgtctctac  15660
taaaaaatat atacaaaaat tagccaggcg tggtggcact agcctgtaat cccagctact  15720
tgaaaggctg aggcaggaga attgcttgaa cccaggaggt ggagattgaa gtgagctgag  15780
atcgcaccac ttcactccag cctgggcgac agagtgagcc tccatctaaa aaaaaaaaaa  15840
atttatatat atatatatat atatatatat ataataaata tatattatat atcatatata  15900
tattttatat aatatatatg tatattttta tatattatac atacatatca atatatgata  15960
tataatatgt atatataata tataatatgt atattcatat attatataat atgtatattg  16020
atatatatta cacatatata ttttgatata tatatatctc caaaccatct aaatatcaag  16080
tattttttaa tccatctaag agctgaaatt gctgaaaaaa ctactccctc caaaagctgt  16140
agagacaggc acatccacag tcacagcaga gacttgctga cttggaagag aagctcctgg  16200
agacacattg gtgagaacat ttacctggtg attatgctga atgtctggag gacaaatgtg  16260
gactaggggg agggtgagca ctcctagagg ctgtacaccc cacacttgtg tggacttgcc  16320
ctccagggcc ttcaggttct cgtggaagca attaaaatag attccctata gccatgaact  16380
ggggaggagt aatcacggag aaaagatgca caaaaagact tttctagaaa gctcatccaa  16440
gggaaggtat tctccaaaat cttagtttat gtgggggaag gaaatacttc caaattacag  16500
acccctcctc ctcagccttc ctctatcacg caaatgataa aattagccaa gaggagtcag  16560
attcaaggcg gtagccctgg gtgcagcatc tgcagaaggg aggaaagaga gaaaatcagc  16620
tgtatcactg gagattcctt gtgaaggtca ctgctcagga gaagagggca accaaaccag  16680
ggagagtcaa ctgtaagaac ataccatgct cccctgcccc acacattacc tcctcaacag  16740
catcattaat atggattaaa gagggcagtg tgattgcttt agatctgttt gagaaagaaa  16800
gtcacatact gaggcctagg gtcagggtcg gcggcacttc ccgtgagtaa gatactacga  16860
agaaggaaaa attaggggtc cataactgtg aaaatcagcc acagtgtgtg tgagaatgtt  16920
tgtgtttgtg tttctgtgtg tttgagtagg agttattgga acagcggacg tggagtgagc  16980
tttaatccac atccatctgc agcttcaggt attctcagat gcagtattca tctgcaagag  17040
ccgaaatgag aaaagagcca cctccaaccc ccccagagtt ttagcctccc tttgtttcca  17100
```

-continued

```
gtgatccagt gcatctagac ctccaggaag tggactccct ggtgatttta gcgattcttc  17160
tcttggagcc accctgaaga ggacattggg tttccaaagg cccattcact atttcaagaa  17220
gtggtgccat cagctcatgt tgtcactgaa ggagcattct gagccagggc acagtcactt  17280
cctagtgagc tacagaggct gagagaaaaa tgctctgtga gacccaatgg gaagctccct  17340
gcagtgcaag gtctgggtgg cagggagcgc tagggcctcg cccagcacag gctgcagccc  17400
tggagcaggt gcaagggagg ctggggaggg gttcctccca gggtctgatg tcttcctttt  17460
ctcggacaaa catgctttaa taagttaaac aagactttag taaagactat tgatgtgtct  17520
ttgtgtcttt cagtatacag ttctatttgt aggatttatc taacctaaca agtcaatgag  17580
aatcacatgt aaaaggagaa atttctagga ttttcagata tcttaatagg taggagatgg  17640
agaaaaggga tggttttatt aattcagtgc ttgccaatct taacagagac agtagtaaga  17700
catgcagaaa gcaaagccca gaaaagtatg aaggtgtcaa agtgccattt aagtatgggt  17760
tcacttggag gaccatgttc tgcgggaact tgttttcagc agacaatcta ttttagcaga  17820
gttctgggca tacaagggga cacacatcat taaacaagga ttgggacagg gacttcagcg  17880
tcccactgtt gcatggccca taaattatgt gtgttctctt tctcatcttg gatcaagtct  17940
agagctatga aatagtatcc ctcatgaata tgcaaataac ctgagattta ctgaagtaaa  18000
tacagatctg tcctgtgccc tgagagcatc acccagcaac cacatctgtc ctctagagaa  18060
tcccctgaga gctccgttcc tcaccatgga ctggacctgg aggatcctct tcttggtggc  18120
agcagccaca ggtaagaggc tccctagtcc cagtgatgag aaagagattg agtccagtcc  18180
agggagatct catccacttc tgtgttctct ccacaggagc ccactcccag gtgcagctgg  18240
tgcagtctgg ggctgaggtg aagaagcctg gggcctcagt gaaggtctcc tgcaaggctt  18300
ctggatacac cttcaccggc tactatatgc actgggtgcg acaggcccct ggacaagggc  18360
ttgagtggat gggatggatc aaccctaaca gtggtggcac aaactatgca cagaagtttc  18420
agggcagggt caccatgacc agggacacgt ccatcagcac agcctacatg gagctgagca  18480
ggctgagatc tgacgacacg gccgtgtatt actgtgcgag agacacagtg tgaaaaccca  18540
catcctgagg gtgtcagaaa cccaagggag gaggcagctg tgctggggct gagaaatgaa  18600
agggattatt atttttaatg ttgtttacag tatgtcatta ataaattgaa aaaaagtaac  18660
aatagaagta tatactctaa ttatatggga actttgtttt ttcagttttt tcattttttt  18720
ttttttttt ggtttgtttg tgacagagtc tcactctgcc acccaggctg gagtgtaacg  18780
gcacaatctc agctcactac aacctccacc tcccaggttc aagcaattct cctgcctcgg  18840
cctccagagt agttgggatt acaggcaccc gccaccatgc ccggtgaatt tttgtatttt  18900
tagtagagac ggggtttcac catgttagct aggctggtct caaactgctg atctcaggtg  18960
atctaccctc ctcagcctcc caaagtcctg ggattacagg cgtgagccac tgcgcctggc  19020
ccaattatat gggaattgtt tatataatta tcaccctata agcaaaattc atggaggagg  19080
aaaagctcta ctgaagaaag ctgataccgg cattcccatg aaagtatctg tgtagaagta  19140
agtattaaaa tcagttgaat aggcaaggca tggtggctca cgcctataat cccagcactt  19200
tgggagaccg aggcaggtgg atcacaaggt aaggagttca agatcagcct gcccaagatg  19260
gtgaaacccc ttctctacta aaaatacaaa gaattagctg ggcgtggtgg tgggtgcctg  19320
taatcgcagc tattcgggag gctgaggcag agaattgctt gaacctggga ggtgaaggtt  19380
gcagtgagcc gagatcacgc cactgcactc cagcctgggc gacagagtga aactccatct  19440
caaaacaaaa caaaacaaaa caaaacaaaa aaacagttga ataaagtacc ttagagtcat  19500
```

```
ctgttcaatt aacatgttta actccaaaga aatactgaaa atattttcca aaaaggaagt  19560
gccattttac gttcctacca acagtgaata agattttctt ttctggagcc ttgtcagtat  19620
tcactaatgc tttgctgtgc agccgttgta atattatagt aaatgagtag cagtatttaa  19680
tggttgtttt aaatatacat attcttaata caaagtcttg atgaacactt ttttatacat  19740
tgttttatga ggtgtgtgtt cagatctatg tatgccagaa atgcctggca gcgttaattt  19800
aagcacactg tgagaatgac cctatagttt atgaagaatg tatgttcaga gctctgagct  19860
aagaaatcca ggagctgtca acccagaagt ttattccttg tctgtgaagg acatctgaat  19920
ccctggccta tcccttggaa cacaggatgt ccaggtgatt gatgctcttt gttaaatctg  19980
gaggttgcta ggtagagggt gctaagtgaa aatcataata taaactacac gtgttttaca  20040
aatggtagtg gttttcctgt ccaacacact tttcctgggc cacattgtat gcaagtcctc  20100
aatacaccct aggtcttgtt catgggctcc aggtctcctc ttcagccttt tggacatggt  20160
gccatgccta ttacagtcaa taggggtcta gcatgacaac tggtaggccc agaacaaggt  20220
caaagaaaat cctgcaagct cttagacaac agtgtcaagg aaggggagac ctgtggggaa  20280
atcccaggca ggccatgcac atctctgtgg gcccaacagc tgcaatcctt gatggatggg  20340
gcccgctgca tgtgtacggg gatgcctcca aaatgccaaa agttctggag gacctgttgc  20400
ctgaggtgga tgtgacaatg tgacaaagtg acagtcagat tcctgagctg tggcagctgt  20460
tggccactcc tgactgcact ctgagcaacc actgaggcag agctcattgc acaggctagg  20520
gtgtgtcagc cacgagaaca gttgtaacta taatgagatg ccgcctgtag ggataggata  20580
gcaaattgga gaccattgtt tatttggtag gccatttaaa gtgttgctga ctgccacacc  20640
aatgcattag gactactatg actacgtcat cctgggagcc taagtcctgg cgtccgatgt  20700
agagctccag tgggaaggag atgaaggtta ggatgagtcc ataaaggttc ttgctctgca  20760
gcccctgctt tgctgtctca cttggtgaac agagaatggg aggtcaatgc ggacaaagtc  20820
cagggtccag gcttatcagt caaatacttg gtgtcatctg gttacataag actatagtta  20880
ttccatattt catcatagat aagataagat gcaggtctac tcatgtccca ccacaccaaa  20940
gcagttggaa acctcccaag gcctcctggg acattggcga tcctttattc cccatttcgg  21000
caaacccctt gggcccccat ggcacttaga caagaaggtg ccccactgcg actgttccaa  21060
aagggaggat gagggctctg aagaagctga agtcacagtg aaatgaatac aaaccttggg  21120
agttctagtg cagggacagc cctgtgaatt ggatgtagtc agttaccctg aggggtttag  21180
gtggggactg tgttaaaggc aaggacataa gtgtgtgtcc ctaagaccct ggtctcaaag  21240
acagaaggaa gctgaagtga gatatactgt ttaggagtag caactgcact acatgtcatg  21300
ccttacgagt gtaggatgtg acaaagaggg ccactccaca tccggaacaa cctttagcag  21360
gctggctaaa ggatgccttc cagacacaaa agccttggaa tgccaggaca cagtctgtag  21420
ccaaatggta cttgtggtgg tcaccaccaa cataaaagtg ggccaactgt gccagcagaa  21480
gttagcccca cagaactttc ccccacctaa gagaaggcag tgcaccacaa tgcggaattc  21540
caccactgtg gaattggggg agcttagaat tggattcaga cacaagggga gagagtggat  21600
cacagggtgg cttctctatg ggataggggg tggagagtat tatactctct ggactcaaga  21660
tgagtaaaat gacacccatc acaaaccatc cagccctatg atggcacctt tatggtaagt  21720
ggttgcaggc tccaaggggg ccgggtccaa tgaggaagat gcccccacag ctcgttctca  21780
atggcagact atagaagagt tgcaggatat cttctgggag tcgagatgag gcatgctaat  21840
```

-continued

```
tatgctgaga attattgaag tcccaacaat gaattgttta ctgcaaaata aaagctacag  21900
ttatgtattc agtgcctacc caatggcatg gtgcactgat ttccacgtta agccccctgg  21960
gagggcagcc aacatttcat gtgccccagg tagttgctga cttaggagaa aagaagaaac  22020
tgagtaagca agggatgcac cctactgtga tgaagaacaa tggcaccaaa ggaagagaga  22080
cagccaagga gccagtcagg gtggccagac aacgaatgtg ctctaactgg caacacctac  22140
cagttctctg ggcccatagc ggcaataggt ggttatggaa gggccacgga agtcagaccg  22200
gttgaactag tgatacgacc tgggggactg ccacccagac cctgtgtagt atacacagct  22260
tccatcctag aacacatgag aatggatatc ttcttaggcg tgaccctcca aacaacggcc  22320
agggaattcc aacggagagt tagagtggtg atatgtgtga ccaagcagaa ggcaaactgg  22380
atgccagtag agctgccaac ccatggggag tcccacagct ggagcaacac cacccgccct  22440
gggaggggaa gatgatccaa tcatgaagat tgttaaggag ctagcccagg taggcattag  22500
gaggccactg catggttcct acaacagacc tgcatggccc atgcagaggc cagttgagac  22560
atggagaatg acagtagatt actgggagtt aaataaggtg gtctcccgag tgaatgcagc  22620
tgttcctaat atctcctcca gtctgacgag aataggagag gtgttagcca cgtagcattt  22680
ccttatcagt ttagtcaata ccttcttcag catttctgtt gccccagagt caagatcaat  22740
ttgcattaac ctaaaaagaa caatggactt ttactgtctt gttccaggga tatttacaca  22800
gcccaaatct cacagcctag tgacctccaa cctcagtcga tgggctgacc caaaggggat  22860
acatgttttc cactacattg gtgttatcat gataacctct gagtcttttt tcagcttata  22920
aattacagcc cctgtcttgc tgtctcactt gctgaataga ggatgggagg ttaatacaga  22980
caaaatccag ggtccaggct tatcagtcaa atagttggtg tcatctggtt gggtaaaact  23040
aaagtcattc catctgccat catagataag gtgcaggcct acccacgtcc caccacaaca  23100
aagcagctgc aaactctcaa ggccttctgg agcatcagtg tccttttatt ccttttattt  23160
gacatccctg aaggaggctg ctaggggaga ctgtgtccct cctaaattca tgtgctgaag  23220
tcccaaccct tggtccttca gaatgaaatc atacttggat tagtgtcctt taaagaggtg  23280
aataagttaa agtgagattc ctggagtggg gccctaatgc aatctgactg ttgttataag  23340
aagaggaagc aggagggagg gtgcacaggc cccgagggac ggccatgtta ccacagaaca  23400
gtgagaaggc gccatctgca tgccagggag cgagacctca gaggaaaccc acccagctgg  23460
cagcttgatc ttaggctttc atcctccata agtgtgagga aattggtttt gtattgtaag  23520
ccatccgatc tgtggtattt cgttataaaa gccctataaa atgaatacag taggtaatag  23580
gagagcttct atacattgaa aaagtcggat ggccagaaaa acctagacac tcctgttcag  23640
acctgagcag ggtgatggac ctgctttggg acaggagagg ggaagagatg aacccagcac  23700
ccagacccag ctgagcccat tcctcagcag gccgtccctg ggccggagct tgcacaggtg  23760
tgaaagagcc tgtcttggtc ttcaggggct catggagttg gacggagaat ggtgtagact  23820
caagaacacg tcatcggtgt gcccgtgttt atctgaatgg gatgtgtttc tagggtgtgc  23880
tcatccccaa agaagaatta atcaggtctc ttgggctaaa aagaggttgt ggcatttgtg  23940
tgtattaata actgtggtcg gacagtaaat tatgttaaac tgcttatggg aaggcacaat  24000
ggaaagaaac actttgttac agaaggaaaa aaaaggtgat tatttaaatg aggtgccttt  24060
gaaggtcacc atgccaagag gagcccatca catgatagtg ctggctttca tgttcaggag  24120
atcaggaggg tccgtccgct ggcttttatg acaccctaga cagagctgag agtgtaatgt  24180
atgaatggag gggaagtgga gagaggggag gccaaatgtt tggtgggaat ggagggtcac  24240
```

tattggagcc attaggaaat acacaagcat gaattatgct ggaggacaga acagtgttcc 24300
tggggaatat tgtgttgctt tgggagctgc tgaacataca ggagtttcac tgttcctagt 24360
tctcaaattc tctagactct ctggacaacc cagttttaaa tattgggaat ataggtaaga 24420
cacattcgtt attaaaaatt attaagagaa gatgtaggaa gaaatttaaa gtaatccatt 24480
tggttatgaa aatttagtta cagcgaactg tgatgtccgt ttcttacttg gaataatgga 24540
atgtaagtca ttagtcatct caacggttca tttttccata accatcaatt acaaaactgc 24600
tgagtaattt cctgaattgc ccaccataga aactgacctc acatttcctc aatgagaaac 24660
tgccagtccc gttgatccag cctcgttctt cccatcaggg attttgtatc tctgtggacg 24720
tgtggcacag tgctgcatat ccatcggcat atggcctcag gaaaggcgcc agcctatcca 24780
tgcatgatga agcttactta ggggatgaag cccgcatgct gggtgagcca gtgccaacag 24840
ctgaaagaat caactgcctg gtgtatgatg cttttatgaa aacaagccca gggcctcttg 24900
cattcttctg tattagattc tctggtgaag atttttattc atttctgcct gaaattgcca 24960
catataatta cctggaagca ttacaataaa ctgatttgga agttaactga cttcctggtg 25020
aggttaaaat gagtgtcagg tgcatagtga gacagaccgg agacatggat gcatagcaaa 25080
cttgtgctca ccatggtttc tatcttagtt agggaaactt ctgtaccttc cttagatgtt 25140
caggcactcc attgaggacc ctggcataac attatttatt gacagaccat agctcaaagt 25200
atagaactgg atactaccaa ggaggatata ctattactat tttatcttta tcttaaaata 25260
tactcttcca tctgaggtga aaattaatcc agatggtaga acttattgca gttactacag 25320
cattttagca aatcaaaagc cgcagaacaa acatatggac agatggcagg tatgttttcg 25380
gaatcgtaaa caagttcgtg atgactgtaa aaccaagggg tgtctcacga gggctggaaa 25440
cctctcacaa tgaaacaaca caatgaggat ctttgaaaag tactctgacc tcctggtgag 25500
ctggctgata tggaggctga gctccatgta gaaagccaaa ggaatttctg caggacgtca 25560
tcatgccaag cacagccgta acctgggtcc cagccctttt cacacgctca atggttagat 25620
cttgggaggg aatcaaagaa gccatagtaa aatatcaaaa tttaaacccc gattttgaat 25680
ttaaaaagtg ttaaaatatg gttgtggcct acactcagaa aatctgtgtc cttcagatgg 25740
tttctcagtg gcaccagatg gtttcaagtg gctattcatt aagtttctca gtgaaattac 25800
cagacataga ataaataaat tgtcactgtc ttaaatcaac ccatgggaaa ggaaaactgt 25860
gtaaatacag cagagaggaa acattgctca agggaaaaac aatctccaga aagtattgtt 25920
aaagaaacag aggccctctt tccagccagc gccgagcgat gggcacctct cgggacaact 25980
ggcacaaggg ccgcaaagct gggggcaaga gaaggccctg ccacaagaag cggaagtatg 26040
agttggggcg cccagctgcc aacagcaaga ctgacccgtg ccgcatccac acagtccgtg 26100
tgcgaggagg taacaagaaa tactgtgccc cgaggctgga cgtggggaat ttctcctggg 26160
gctcagaatg ctgcgctggt gaaacaaggg tcatcgatgt tgtctacaat gcatccaata 26220
acgagctggt tcgtaccaag accgtggtga agaattgcat cgtgcccatc gacagcacgc 26280
cctaccgaca gtggtacgag tcccactgtg cactgcccct gggccgcaag aagggagcca 26340
agctgactcc tgaggaagaa gagattttaa acaaaaaacg atctaaaaaa attcagaaga 26400
aatatgatga aaggaagaag aatgccaaaa tgagcagtct cctgggggag cagttccagc 26460
agggcaagct tcttgcgtgc atggcttcaa ggccgggaca gtgtggccga gcagatggct 26520
atgtgctaga gggcaaagag ttggagttct atcttaggaa aatcaaggcc cagaaaggca 26580

-continued

```
aataaatcct tgttttgtct tcacccatgt aataaaggtg tttattgttt tgttcccaaa  26640
aaaaaaaaag aaagaaaaag aaacagaggc atcacactta ctagaaaaac atattctatt  26700
tcatatatta tggggatatg acgtgatgtt ttgacatatg cgggcattgt gaaattatta  26760
aatcaagtaa ataaacatgt ccatcacctc acatacttat tttttatggt gtaaacgtgt  26820
aaaatctact ctcttatcag ttttcaagta tatagtacat tagtatcatg gaagtcacca  26880
tgctgtgcaa tagatcttca aacgaattcc ttctatctaa ccaaaactct gtaccctttc  26940
accaacgtct cagctttcac atgcccctga cgccagcccc tggtaggcac cattctactc  27000
tctactctga gttcaacatt tttagattgc atgtgtaagt gagatcatgg agtaattttt  27060
tatacctggc ttatttcact caacataaag agtcaaatgc tcaacatcac taatcatcag  27120
ggaaatgcaa attaaaacca cgataagata tcacctcaca catgttacaa tggcttagtc  27180
tcagtctgtc tttttgttac tataaccgaa taccagagac tgggcaattt ctaaagaaaa  27240
ggaatttatg ctttatggtg cttgagtcag agaagtctaa tatcaaggca ctggcatctc  27300
acaagggcct tctcactgcc tcatctcaca gcagaggtgg gtgagcaaga gaccatttgt  27360
ccacgagaga aaagagacca tcttttatta gaaattcact cctataataa ctaacccact  27420
ccattgatag tgacagtaat ccattcatga ggacagagcc ttcatgactt gatcacataa  27480
taaaggtccc acctctcaac actgttgcat taaagattat ttccagatcc taaactttgg  27540
gagacacatt taaaccatag cattccattc ctaatatcaa aatttatgtc cttatcacaa  27600
tgcaaattac attcattcca tcccaattgt ctccaaagtc ttatccagca tcagtgcaaa  27660
agtctgaagt ccaaagtctc atctaaatca gatatgagtg tgactcgagg cacaatttag  27720
cctgatataa attgtttcca tctgcgagcc tataaagtca aaacaagtta tctactttca  27780
aatacagtga acaatggggc aggtatggga tagaaattcc cattccaaag ctcagagaga  27840
ggcaaggaga aagcggtgcc tagttcaaaa cccaacaggg aaaaaaacat taagtcttat  27900
agctggaaaa tcatcctctt taacggcatc ttgtgcacac tggggagggg gatgggcccc  27960
caaggcctcc ggcagtcttg cctctatata ttttctgggt tcagtccact cagccgctct  28020
cacaggtggg actctcaggc ctctagctct cctaggctga ctggaaactc tttgtggtac  28080
ctccaaaccc acatttctgc ttggcattgt gctaagggcc cagtgtggtg actctgtctc  28140
tgcaacaagt cactgcccga gaccttaggc tgtccttagg ctgcccgaga ccttaggccg  28200
tccacagcat tctttgaaat ctaggtggag aaagccatgc cctcgtggtt cttgtattct  28260
gcacacctgc agaattaaca acacatggat gccatggaag ttgatgactt gtaccattaa  28320
agtgatggct tgagccacac ctaggtcctc ctgagccaca gcatgggcag ccaaggagtg  28380
ctgtgcctgg acaccgggaa cagagtccta aagtgcctgc tagaagtcag gccatagatt  28440
tccttcaaat ttctcccacc atataacctc gttcatggct ctgaacttcc accttacaga  28500
aggacctagg gatgaacaca attcagccac gttctttgcc actttatggc aaggatggcc  28560
tttgctccat tttccgatga gctattcttc tttttctcct gagacctcat cagaacggcc  28620
tttattgtcc acggttctac tgacattcta atggtcatca cctaaataat ctctaagaag  28680
tttcagaatt tcctcacagc tctcttcttc tgagtcctca aaagaatcac ctctagtgtt  28740
ctattcaggg caatccagac tttttatagt ctgatcctcc aaattattcc agtctttgtg  28800
cattactaca tccacttcta cattttgggg tatttgttat cgcaacagcc ccacctcttg  28860
atactgattt ttcgtcttag tccactttgt ggtgcaatga gtgaatacca cacactggct  28920
aaagtataag gaaaagaaat ttattttctc gcagctctag aggctgggaa gtcaatatca  28980
```

-continued

```
aggtgttagc atctggcaag agccttcttg ctgtgatgtc catgtggaag gcaggagagc  29040
aggtgcgaag gatggaaagg ggtttaaact cattttttaa tgaggaaccc aggcctgtag  29100
taactaatct gctaccacaa tgagtaacct actctgacga taatggcatt cattgcttca  29160
tgagggcaga gccctcatga cctaatcatt tcttaacatt cccacctctg gacactatgg  29220
aatttgggat taagtttcca atacacatcc tttctaaaca gcaggggctt tttaataggt  29280
tgaccaccca aggctgcagg aggctctgaa gcagtggcct gaggttggct gtcctttgtg  29340
agaatggaga gaagtgaact gactcatgga gacacaagta gatgaggtaa aggcattcat  29400
tgcttcatta catggatggt gaggtcgatt gaaggcatta acggattaaa gatggtggca  29460
aaaccgtctg aggtggagac cacggggagt ccatcagaaa tggaggacac gtcccaataa  29520
atggtgcttc atttccctgc aaagcagaag aaagcaaaga acaaaacaca acatcatagt  29580
gtacactgag cagtggattg agagaagagt ttcctaaggc ataactgaca gagtggagaa  29640
gacacacaaa tctttgcatg atgctaacat ttggactgtg gcttcattat ttcttattaa  29700
tattttactg aaatatcgct agaaggagac tgaaaatgaa gtgtgaaaag ttaaatggga  29760
tttctgctct atgtcctttt cagatgagag gaactaggga attccaggga agaaacaata  29820
atagctgctg agcaaggctt ttgcagggca ggacaaggaa tccccaaaga gaaaacggaa  29880
acctcagctt cactttgcat ctgctcctga gccaggtcct gagcgacccc tgtaggtcct  29940
gagtgcccct ccgtaggttc tgagcatccc ttggttgctg ggcgccctct ggtggtgtct  30000
gagcccctct ggtggtttct gagccccccg ccttatgtct gatcctccct ggtggtgtcc  30060
gagtgcccct gctagtgtct gagcccccctg gtggtgtctg agtccccttc ttagtgtctg  30120
agccacccta ttagtgtctg aggacccctg atggtgtctg agcccccagt tagtgtctga  30180
gccaccctat tagtgtctga gcccccctgg tggtgtctga gcacaggaga gctcctctga  30240
aggaagggtc tacatgggga caggcgtgct tgtctcaggg aagggtccat gtggggacag  30300
gtgtgcttgt ctgaaggaag gttccacatg gagacaggtg tgcttgtctc agggaagggt  30360
ccacatgggg acaggtgagc ctgtctgagg ggacagaagt gcttgtctca aggaagggtc  30420
ctcatgtgga caggtgagct cttttgaggg aagggttgac ctggggacag gcatgcttgt  30480
ctgaggtaag ggtcctcctg gggacaggtg tgcttctctc agggaagggt ccacgtgggg  30540
acagaggtgc ttgtctaagg caagaatcca agtagggaca ggtgagctcg tctcagggaa  30600
gggtccaggt ggggacagtt gtgctcatct gagagaagcg ttgaagtggg gacaggtgtg  30660
cttgtctcaa ggaagggtcc atgtggggac aggtgtgcta gtatcaagaa agggtccaca  30720
tagggacagg tgtgcttctc tcagggaagg gtgcatgtgg ggacaggtgt gcacatcgga  30780
gagaatggtc cacctgggga caggtgttct tgcctcaggg aagagtccac cttctcaggg  30840
aagaagtgtg ctcctctgag ggaagggtgc acatggggac aggtgtgctt gtctcaggga  30900
agggtccatg tgggaacagg tgagctcatc tgagggaaga gtccacgtgg ggacaggtga  30960
gctcatctga gggaagggtc cacatgggga caagtgacct cgtctgaggg aagggtccac  31020
gtggggacag gtgagctcgt ctgaaggaag ggtccacttg gggaccggtg tgctcctctg  31080
agggaagggt ccacgtgggg acaggtgtgc tcctctggag ggaagggtcc acgtggggac  31140
aggtgagttc atctgaagga agggtccaca tggggacagt tatgctcctc tgagggaagg  31200
gtccatgtgg ggacaggtgt gcttgtctca gggaaaggtc cacgtgggga caggtgtgct  31260
caccttgggg aagaggacag atgagctcat ctcagggaag gggccatgtg gggacaggac  31320
```

-continued caagggttgg gacttcagca caagaattta ggaggaacac agtcttccct agcagcctcc 31380
ttcagggatg tcaaatattt tccttctgtt ccctgtgaaa gccttaaagg ggtagggaaa 31440
gggcgttcaa cctgcacact cgtagagggg aaaccagctt cattagtaat cgttcatctg 31500
tggtaaaaag gcaggatttg aagcgatgga agatgggagt acggggcgtt ggaagacaaa 31560
gtgccacaca gcgcagcctt cgaaacacac cacggtcacg ttaagtttaa atggagtgac 31620
cacattcgcc aggaaaggga aatatttaca cttttgaaga aacagtaatt tgtgtttctg 31680
attatgatct ggccttggat tttccctccc ctcataagca atgacagaat tggcagaaat 31740
atgtgaaacg ttagttctca gacatgagac acccacagag ggccccctgt gcccttccct 31800
gagagctgat cagctcctgc atctgaagaa atgaccaaag accaggagag aaccacacag 31860
aagcatcgga gggacagcac ctggggctct gatggggtca ggaatagcat ctgttcccaa 31920
tagatggact aagtaaaaag tatcataatt cacaagagtt ttacatagca cagaagaaaa 31980
agttacccta tatcaactgt tgatcttgtg aatccaggaa ctctggattc aaggtggtcg 32040
ggcacatctt gatttacgca tttcagggac acatgagaca tcagtcaata taagtaagaa 32100
ggacattagt tccatccaga aaggctgaga caactcaaag caagtcctcc ccacttaggg 32160
cttccaggtc acaggtaggt gagagacaga tggttgcatt cttttgagtt tctgataagt 32220
gtttgcaaag gaggccatga ggatatgcac ctgtctctgt gagcagaggg acaactttaa 32280
atagactggg aggcagattt gtcctgagtg gtttccagct tgacggggcc caagatattt 32340
tcctttcaca atctggtaac ttcaaacaaa acttcaaagc cacaacaaaa caacacaaca 32400
acaaaaagaa taagacatgg gtacttatta agagtagaaa aacattcagt ccccaaggaa 32460
aatattggca gtgtctacct ccacatgaca aaggagtaag cagtgtgagc cacagaaagg 32520
agcactatta acccacagag caaccgagaa taacacgggt gatgcgaggg cattggacgc 32580
acatcattgc attttgtaga ttcagaaaga aacggaaaag attgacggtg gtaaaagaga 32640
cagccctgct tccctctccc ttttccctcc ccgatgaggc ctcacagcca tgaccctcag 32700
cctcatcccg cagtgcagca gctgccgtcc tgtccaggcc cacccccctgc cccgccctgg 32760 gactgttacc tcattccctc ccggagtcca ggtgcccccc ggggtgtggt gcgggagcct 32820
ggggaggccc tttgttctct gtcagggtct ccctgggagg gacgcagcca ccgcagctgg 32880
ttggggcctg gcttcgccca ggacagtcct ttcctttccc attgtctttg gatgactatc 32940
gctgggctgg gacatgaggc gggcagaggc gcgggtcacc cttaggaccc ccctcttgct 33000
gctggggctc tgggcgctcc tggctccggt ccggtgttct caaggccgtc ccttgtggca 33060
ctatgcctcc tccgaggtgg tgattcccag gaaggagaca caccatagca aaggccttca 33120
gtttcccggc tggctgtcct acagcctgtg ttttggggtc aaagacacgt cattcacatg 33180
cggaggaaac accttctttg gcctagacat ctgctggtga caactcagga tgaccaagga 33240
gtcttgcaga tgggtgaccc ctacatccct ccagactgct agtacctcgg ctacctggag 33300
gaggtgcctc tgtccatggt caccgtcgac acgtgctatg ggacctcag aggcatcatg 33360 aggctggacg accttgcgta cgaaatcaaa cccctccagg attcccgcag gtttgaacat 33420
gttgtttttc agatagtggc cgagcccaac gcaacagggc ccacatttag agatgatgac 33480
aatgagacag accccctgtt ctctgaagca aatgacagca tgaatcccag gatatctaat 33540
tcgctgtata gttctcatag aggcaatata aaaggccacg ttcaatgttc caattcatat 33600
tatcgcatat atggcaatat tacaacttgt tccaaagagg tggtccagat gttcagtctc 33660
attgacagca ttgctcaaaa tattgatctg cggtactata tttatctttt gaccatatat 33720
aataatcgtg acccagcccc tgtgaatgaa tatcgaattc agagtgcaat gtttacctat 33780
tttaaaacaa ctttttttga tacttttcat gttcattcat ccacactact tattaaatac 33840
gtgccacatg aatctaacta tgaacctgaa aggtataact tctgttcccg tatagccctg 33900
ttacacattg gtactccagg cagacattat ttattggtag ccgtcataat aacccagaca 33960
cagatgagaa gtattggtct ggagtatgat gataactact gcacatgtca gagaagggcc 34020
tcctgcatta tgcagcgatt tcctgggatg acagatgcgt tcagtaactg ttcttatgga 34080
catgcacaaa attgttttat acattcaggc cggtgtgttt ttgaaacact tgctcctgtg 34140
tataacgaaa ccatgacaac ggttcgctgt ggaaacctca tagtggaggg gagggaggaa 34200
tgtgactgtg gctccttcaa gcagtgttat gccagttatt gctgccaaag tgactgtcac 34260
ttaacaccgg ggagcatctg ccatatagga gagtgctgta caaactgcag cttctcccca 34320
ccagggactc tctgcagacc tatccaaaat atatgtgacc ttccagagta ctgtcacggg 34380
accaccgtga catgtcccgc aaacgtttat atgcaagatg gaaccccgtg cactgaagaa 34440
ggctactgct atcgtgggaa ctgcactgat cgcaatgtgc tctgcaaggc gatctttggt 34500
gtcagtgctg aggatgctcc cgaggtctgc tatgacataa atcttgaaag ctaccgattt 34560
ggacattgta ttagacaaca aacatatctc agctaccagg cttgtgcagg aatagataag 34620
ttttgtggaa gactgcagtg taccaatgtg acccatcttc cccggctgca ggaacgtgtt 34680
tcattccatc actcagtgag aggagggttt cagtgttttg gactggatga acaccatgca 34740
acagacacga ctgatgttgg gcgtgtgata gatggcactc cttgtgttca tggaaacttc 34800
tgtaataaca cccagtgcaa tgtgactatc acttcactgg gctacaactg ccaccctcag 34860
aagtgcggtc atagaggagt ctgcaacaac agaaggaact gccattgcca tataggctgg 34920
gatcctccac tgtgcctaag aagaggtgct ggtgggagtg tcaacagcgg gccacctcca 34980
aaaagaacac gttccgtcaa acaaagccag caatcagtga tgtatctgag agtggtcttt 35040
ggtcgtattt acgccttcat aattgcactg ctctttggga cagccaaaaa tgtgcgaact 35100
atcaggacca ccaccgttaa ggaagggaca gttactaacc ctgaataaca ctaattcagc 35160
ctcccgatcc ctgtaaagat acagagaata taacagcaaa atctatgaaa caggatcagg 35220
ggaagggatg gcaaagctca agtccacatt tcttgaagtc cacaggaagc acagggtcct 35280
gtttcacatc acagggaaac gggaggcatt ggcttctgtc ccaggttctt gtaggtcgct 35340
gatgctcact ctgaaataaa tcttcaaaaa cacacattgg tgccttccac atttcttag 35400 actcctctgg gagcccaaac ttggccagaa cctcttgcct ggagagacat gaatgagcat 35460
ctggctcttg tcctgaggtc tctggtccca gaattaacgg aagttgccac cagctcctta 35520
cagggaacat tcatgacatt tctccagaag agagctccag agcaatgagc ttcctcattc 35580
cccaggtaat ctgtccttct ctaaacccga agtcagttta gggtgatcca gggctactcc 35640
ctgttccctg tctgttcctc acgggggtgc tgtgggcttt gcagtgagag ggacttgggt 35700
tcaaatcccc caccaagcaa atccccctac ctggggccga gcttcccgta tgtgggaaaa 35760
tgaatccctg aggtcgattg ctgcatgcaa tgaaattcaa ctagaaaaat aggtagacgt 35820
gaggggcaag ctgtctgtca tttagtgtga gctctgtgag tggcagctgc cccctttctt 35880
cctgccccca catttccttg aactgaaaca ggaagggaag ctgagtaagt cgtgatgagg 35940
aagagaaacc aggcttgtag cagcacaggc tggtccgggt ggaaaacagg gctaggtgta 36000
tcactgagtt attgtaaagg aaaatggaag ttaaatgtat aaataactga atgagataac 36060

```
attttatttt aacttaaaat tcacactaat attgactttt aaaatgcagt gtagatatgt  36120
cagagagaat ttcaaaggca aagcccaccg acggaagaaa tcacccttcc cataccatcc  36180
acagaaaact gttggtattc tagggtagta ctgagatcta gcatttttct gaatacatct  36240
gtggttctag atgtcctgct tccatagata ttgtttagaa ttcccacccc tttctccaaa  36300
cacagcttga tatcctttct ctgaacctgt tagaaatttc ctccattcag ctgtcataaa  36360
gatgcgagca atccattcct gtgcctctgt cagtgtgttc tattattttg tggctgaacg  36420
ctaatggaca gttaagtgtg aggtcagtga atacagtgcc ctccctctat gtgtccttcg  36480
ggtgtgaggg gttttgctga tagagcagca ggccccatcc caccctttat gcatctccgc  36540
cccccacctc acgctccagc tgacctctcc cctgtggcct ggggcgttcc ccagggggaa  36600
tgacctctcc tctctccagg gcccacccac tcagtgcccg tgcaagacca ccacgcttgg  36660
cacggcccca cctcgtgtca gggcctgtgt cccctgcccc accccctaaa cagatgggaa  36720
ccactgggac tctgctcagg gcagggggcg gaggtatgtg tgaaaggaag gcaaatgtgc  36780
actctgttgg agaaatatta taggtagttt gagcaaaaaa tctaatgcca tgggaacttt  36840
tagaatgata cgtattttaa caaagaacat gaccaataga gtttgtattg aagccaggaa  36900
aacactattt agagcaacag caatatcaaa aacacaagcc aacagttcac caagaaaaac  36960
caccattaac cccatggaaa tggtcttcca agagcatcgg cacttaaatc ctggaaatct  37020
gcctgcctca gcacctgttg tcctgacctg ccctcctgtg tgtcctaatc actcccaaac  37080
acggggcctg cactgtggga gattcacact gtgccaggtg gagggagcag gacaactgct  37140
aacaggttgt tggtgtggat gccgaggcca cccaagcagg tgtaaactcc cacctgtggg  37200
gcagggaaga gtgcacggga gacatgtccc gggcataggg tgagggagag ctgtgggggc  37260
tctgggttct gaagtgggtt ctgaagaggg ttctggcctg gcagggataa gaccaaccag  37320
catgtgaggc caggctggag tctggacctc tgaagctgca agggtcatgg gctgcttggc  37380
cccaggggct gtcctggttc tctatggagt actttcaaac attctttctt cttccaatcc  37440
ccctccttct ctcccaaagc ctgcatctcc caaatcctct ttgtcggatc ctcggcttca  37500
ctctgcatcc gtcctgagca tcgatcttcc aattccatcc tcttctcttc tgctatgtct  37560
aagctgctgt gaagccacct gctgtaattt actgctttat atttaatatt gtaccgtaca  37620
tctgttctgt ttccctcatc ataaatgctt catttcatgc tcagcatctg agaacacaag  37680
gccttgtcag ctgtcacctc cttccgttct ctgtttcctt cctcctatcc ccatattgct  37740
catcatgtcc agtctcctgc catcctgaat gcttctgatg gaaggtctga gatgtctcat  37800
gagcactgtg aagattcttt gtaatgtgag cttgttccag gcaggaattc tccttcaccc  37860
agccctggaa gccaagtata ggcagatggc catgctcaat caaagactga gctaacttaa  37920
cagtggcttt ggttttaagg tttctccaat ccccagggca caggatttca gggaattcag  37980
gtgagagtct gggtgttacc cttcaggagg ctgtaaactc catttcacct agtctacacc  38040
acagactatg gaaactatat atatatatag ttctgtccct ctagagaaac ctaatatgta  38100
tatatacaat atataatacg tattatatat tatatataat acgtattata tattatatat  38160
attatatata tattagagtt tattgaggag tattaaactc acaatcacaa ggtcccacag  38220
taggccatct gcaagctgag gagcaaggaa gccagtccga gtcccaaagc tgaagaattt  38280
gaagtctgat gttcgacggc aggaagcatc cagcacagga gaaagatgta ggctgggagg  38340
ctaagccagt ctagtctttt cacgtttttc tgcctgcttt atatcctggc cacactggca  38400
gctgattaga tggtgcccac ctagattaag ggtgggtctg cctttcccag tttactggct  38460
```

-continued

```
caaatgttaa tctcctttgg caacaccctc acagacacac ccaggatcaa tactttgcat  38520
gcttcaatcc aatcaagttg acactcagta tcaaccatca caagtccacc ccttgtcaac  38580
ttgaacccat acaaatctcc tgagatcata cataatcttc aaataaagac aataataagg  38640
tcataattac acctaatgta atacaactat cttttgtaca accagaaatg caccaatccc  38700
caacccaaat gctattatgt aaagttaaga acacttaaat gctgatatga agtcaataaa  38760
ttttatgtca catgataaag gaaaaaagaa atgaaggaat tttcttagta caagtgtgta  38820
catgcacaaa catgttttta acaaaagaag aaggaaatac tgatgacaat tacagtcctc  38880
atttctgcaa ctgatcacgt ggttgtagct ggtattgatg actaccttct tctactaccc  38940
attctgtatt ccctttgcct tcagcaagca tcacagcagg tagagttttt tctcctagtg  39000
gagtgatgca aaccttcatt cctgaagggt ctgggccatt tgtagtcctg cctggattgg  39060
gctgttgtag tttcccgttg accttaatga cagggcatgg taatgttaag agacgcccta  39120
atggatctcc tgtattccat acatattctt ccttacctcc attgtggagt aatagactga  39180
ttgcatcttg atagtccagg tcaatcagcc cagccaacac tgtaactccc ctcttagcct  39240
gtggacttaa aggtaggagg ggcccaaagt ggccaggtgg aaatctttac ttccagttta  39300
atggaattgt tgttgtttct cctgatggca gcattattcc cactggaact aagacctcta  39360
ggccaacaga atgtaatgtc atgggaccag gaagcaaaaa ttttgctagt ggatcactag  39420
gggtgatggt gaatggtgcc atttccactt ccaccccttg attcctggat ccatgaatta  39480
tggctatggg agaaagagta ccatatattg gatgctgatt tggagcatac atggcctttt  39540
ggagagcttt gccccagccc tgcaaagtat tggagcctag ttgacattgt aattgtgact  39600
ttgaaaggcc attccattct tctatcaatc cagctgcttc aggatgatgg ggaaaatggt  39660
aagacaagtg aatcccatga gcatgagccc actgccacac ttctttagcc gtaaagggag  39720
tgccttggtc agaggcaatg ctatgtggaa tactgtgaca gtggataagg cattccatga  39780
ctccacagat ggtagtcttg gcagaagcat tgcatgcata tctgcagtaa gtgtctattt  39840
cagtgaggac aaacctctgc cctttccagg atggaagagg tccaatataa tccaacctgc  39900
catcaggtag ctcactgatc accctgagga atggtgtcat ttgggtagag acccagagcc  39960
aaaccagatc acgccaccca acccctccca aatctcatgt cctctttgca tttcaaaacc  40020
aatcatgcct tcccaacagt cccccaacat cttaactcat ttcagtatta actcaaaagt  40080
ccaaatccaa agtcacattg gagacaaggc aagtcccttt catctatgaa cctgtaaaat  40140
gaaaaacaag tcagttactt ccaagacaaa atgggggtac aggcattaga tacatgctcc  40200
catttcagtt gggagaaatg agccagaata aaggggcttc aggtcacatg caagcccaaa  40260
ctccagtggg gcagtcatta aatcttaaag cttcaaaata atctcctttg actccattcc  40320
tcacattcag ggcatgctta tgcaaagtgg gggctcctac aaccttggga agctctcacc  40380
ctgtggcttt gcagctctga ccccatggct gctctcatgg gctttgcaga gttcagccct  40440
cctggctgct ctcattgagt gcatgcagct tttccaggtg cacagtgcaa gccgttaatg  40500
gatctaccat tctggggtct gaaagatggt ggccctcttc tcacagcccc attagtcact  40560
gtctccagtg gggactctgt gtgggggctc caaccccaca tttcccttct gcactgccct  40620
agcagaggct ctccatgaag gctttgcccc tggcgcagac ttctggctgg acatccagtc  40680
atttctataa atcctctgag atctgggtgg aggatcacaa agctgaactc ttctcttccg  40740
cacatcccta ggcccaacat catgtagaag ccaccaatga ttggggcttt ctgaagcaat  40800
```

```
ggcctgagct gtacattgga ctttttttagc cacagctaga cctggagcag ctgggacaca  40860
gggcaccaag tcccaaggct ccaaagagaa gctgggccct ggacccagcc catgaaaaca  40920
tttttccctg ataggcctcc aggcctgtga ttggaagggc tgctgcaaag atctccgaca  40980
tgccctggaa acattttccc cattgtcttg attattaata ttcatctctt cattacttat  41040
gcaaatttct gcagccaact tgaatttctc cctagcaaat gtgtttttct ttactaccac  41100
atggccaggc tgcaaatttt ccaaactttt atgctctgtt tcccttttaa aaataagttc  41160
ctatttcaga tcatctctct caagggcaaa gttccacaga tttctagggc agggacaaaa  41220
ttccatcaag cttggtttta tacattttag agaggcatga gacatcaatc aaatacattt  41280
aagagacaca ttggtttggt ccagaaaggt ggaacaactc aaagctaggg cttccaggct  41340
ataggtgaat ttaaatattt tctggttgac aattggttga gtttgtctaa agacctggga  41400
tagatagaaa ggtaatgttc aggttaagat aaagattgta gagtccaaag ttcttttgaa  41460
gtcttatagt ggctgccctt agagataata ggtgacaaat gtttcctatt caaatcttag  41520
ttgaactctt taggattggg aggttctaga agaaaaagat ctagctatgt taatagagat  41580
tctttacaga tgcaaatttt cccccacaaa gaacagcttt gcagggccct ttctttcttt  41640
ctttctttct ttctttcttt ctttctttct ttctttcttt ctttctttct tttttagatg  41700
gagttttgct cttgttgccc aggctagagt ataatggcac gatcttgtct caccacaacc  41760
tccacctcct gggttcaagt aattctcctg cctcagtctc ccgagtagct atgattacag  41820
gcatgcacca ccacacccgg ctaattctgt atttttagta gacacagggt ttctccatgt  41880
tggtgaggct ggtctcgaac tcccaacctc aggtgatccg cccacctcag cctcccaaag  41940
tgctgggatt acaggcatga gccaccatgc ccggcctgca gggccatctc agagtatggc  42000
aaagaaacat gttttggggt aaaatatttt gattttctta tttgtctcat aatgttatgc  42060
cagagtcagt ttggaaagta aatcatgata tataggttta aataaaaccc atctgatgag  42120
aatttatgat ttgtagagca tgcctcccca gactctttag ataggaattt gggcaagatg  42180
aaaaaaaaat cagagtttag tcctcactac ctaagaccag ctcagcttgg acttcactgt  42240
tcatgtcact atcagcattt tagtcaaaac cactcaataa gtctctagga agttccaaac  42300
tttcccacat cttcccttct cctttcaagt tctccaaact gttccaaccg ctgccaggag  42360
gtacccagtt ccaaagttgc ttccagattt tgagttatct ttatagcagt tccccactcc  42420
tggtaccaat ttactatatt agtctgtttc cacagtgcta taaagaactg cccgaaagtg  42480
gttaatttgt aaagaaaaga ggtttaattg actcacagtg ctgtgtggtt agggtcggag  42540
gctcaggaaa cttgcaatca tggtggaagt ggaagcaggc atgtgacaca tggcagcagg  42600
tgagagagag aaagagagag agagggaatg aaggaggaac caccatacat ggataaaacc  42660
atcagatctc atgagaactc actcactatc aggagaacat gaggacagca tgggggaaac  42720
cacccctatg acccagtcac ctcccaccag gtccacccct tgacacataa ggattactat  42780
ttgagatgag atttgtttaa tgacacagag ccaaaccaca tcagcatgtg acaaaggtct  42840
aatatcaaga atctatgagg gggcagttcc aaaatggctg aataggaaca gctccagtct  42900
acagctccca gcatgagcta cacagaagac aggtgatttc tgcatttcca actgaggtac  42960
tgggttcatc tcacgggggc ttgttggaca gtgggggcag gacagtgggt gcagcccacc  43020
aagagtgagc tgaagcaggg cgaggcattg cctaacccag gaagtgcaag gggtcaggga  43080
attcccgttc ctagccaagg gaagcggtga tggacggcac ctggaaaatc cggtcactcc  43140
caccctaata ctgcactttt ccaacggtct tagcaaatgg cacaccagga gattatatcc  43200
```

```
tatgcctggc ttggaggttc ccatgcccac ggaacctcgc ttattgctag cacagcagtc  43260
tgagatcaaa ctgcaaggtg gcagtgaggc tgggggaggg gtgcccacaa ttgctgaggc  43320
ttgagtaagt aaacaaagtg gctgggaagc tcaaactggg tggagtccac tgcagctcaa  43380
ggagacctgt ctgcctctgt agactccacc tctgggggca gggcatagct gaacaaaagg  43440
cagcagaaac ctctgcagac ttaaatgtcc ctgtctgaca gctttgaaga gagtagtgtt  43500
tctcccacat ggactttgag atctgagaat ggacagactg cctcctcaag tgggtccctg  43560
acccccgagt agcctaactg ggaggcaccc tccagtaggg gcagactgac accttacacg  43620
gctgggtgcc cctctgagat gaagcttcca gaggaattat caggcagcaa catttgctgt  43680
tcagcaatat tcgctgttct gcagcctctg ctgctgatac ccaggaaaat agggtctgca  43740
gtagacctcc agcaaactcc aacagacctg cagctgaggg tcctgactgt cagaaggaaa  43800
actaacaaac agaaaggaca tccacatgaa aaccccatct gtacatcacc attatcaaag  43860
acaaaaggta gataaaacca caaagatggg gaaaaaacag ggcagaaaag ctgaaaattc  43920
taaaaatcaa agtgcctctc cccctccaaa ggaatgcagc tcctcgccag caatggaaca  43980
aagctggatg gagaatgact ttgatgagtt gagagaaggt ttcagatgat caaacttctc  44040
cgagctaaag gaggaagttg gaacccattg caaagaagct aaaaaccttg aaaaaagatc  44100
agatgagtag ctaactagaa taatcagtgt agagaagtcc ttaaatgacc tgatggagct  44160
gaaaaccatg gtatgagaac tacgtgatga atgcacaagc ttcagtagcc gattcgatca  44220
actggaagaa agggtatcag tgattgaaga tcaaatgaaa gaaatgaagg gagaagagaa  44280
gtttagagga aaaaaaagta aaaagaaaga aacaaaccct ccaagaaata tcagactatg  44340
tgaaaagacc aaatctatgt ctgattggtg cacctgaaag tgacagggag aatggaacca  44400
agttggaaaa caccctgcag tatattatcc agcagaactt ccccaaccta gcaagacagg  44460
ccaacattca aattcaggaa atacagagaa ccccacaaag atactcctcg agaagagcaa  44520
ctccaagaca cataattgtt agattcacca aagttgaaat gaaggaaaaa atattaaggg  44580
cagccagaga gaaaggtcgg gttaccctca aagggaagcc catcagacta acagctgatc  44640
tctcagcaga aactctacaa gccagaagag agtgggggcc aatattcaac attcttaaag  44700
aaaagaaatt tcaacccaga atttcatatc catccaaact aagcttcata agtgaaggag  44760
aaataaaatc ctttacagac aaacaaatgc tgatagattt tgtcatcacc aggcctgccc  44820
tacaggagct cctgaaggaa gcactaaaca tggaaaggaa caactggtac cagccactgc  44880
aaaaacatgc caaatcataa agaccaccaa agcgaggaag aaactgcatc aactaacgag  44940
ccaaataacc agctaacatc ataatgacag gatcaaattc acacataaca atattaacct  45000
ttaatgtaaa tgggctaaat gctccaatta aaagacacag actggcaaat tggataaaga  45060
gtcaagaccc atcagtgtgc tgtattcagg agacccatct cacatgcaga gacacacata  45120
ggctcaaaat aaaggcatgg aggaagatct accaagcaac tggaaaacaa aaaaaggcag  45180
gagttgcaat cctagtctct gataaaagag actttaaacc aacaaagatc aaaagagacg  45240
aagaagacca ttacataatg gtaaagggat caattcaaca agaagagcta actatcctaa  45300
atatatatgc atccaataca ggagcaccca gattcataaa gcaagtcctt ggagacctac  45360
aaagagactt agattcccac acaataataa tgggagactt taacacccca ctgtcaacat  45420
tagacagatc aacgagacag aaagttaata aggatatcca gcaactgaac tcggctctgc  45480
accaagcaga cctaatagac atctacagaa ctctccaccc caaatcaaca gaatatacat  45540
```

-continued

```
tcttttcagc accacaccac acctattcca aaattgacca catagatgga agtaaagcac  45600
tcctcagcaa atgtaaaaga acagaaatta taacaaactg tctctcagag cacagtgcaa  45660
tcaaactaga actcaggatt aagaaactca ctcaaaacca ctcaactaca tggaaactga  45720
acaacctgct cctgaatgac tactgggtac ataatgaaac gaaggcagaa ataaagatgt  45780
tctttgaaac cagtgagaac aaagacacaa cataccagaa tctctgggac acattcaaag  45840
cagagtgtag agggaaattt atagcactaa atgcccacaa gagaaagcag gaaaaatcta  45900
aaattgacac cctaacatca caattaaaag agctagagaa gcaagtgcaa acacattcaa  45960
aagccagcag aaggcaagac ataactaaga tcagagcaga actgaaggaa acagagacac  46020
aaaaaaaccc ttcaaaaaat caatgaatcc aggagctggt tttttgaaaa gatcaacaaa  46080
attgatagac cactagcaag actaataaag aagaaaagag agaagaatca aatagatgca  46140
ataaaaaatg ataaagggga tatcaccacc gatcccacag aaatacaaac taccatcaga  46200
gaatactata aacacctcta cggaaataaa ctagaaaatc tagaagaaat ggataaattt  46260
ctcgacacat acaccatccc aagactaaac caggaagaag ttgaatctct gaatagacca  46320
ataacaggct ctgaaattga ggcaataatt aatagcttaa caaccaaaaa aagtccagga  46380
acagatggat tcacagccga attctaccag agctacaagg aggagctggt accattcctt  46440
ctgaaactat tccaatctat agaaaaagag ggaatcctcc ctaactcatt ttatgaggcc  46500
agcatcatcc taataccaaa gcctggcaga gacacaacaa aaaaaaagag aattttaggc  46560
caataaccct gatgaacatc aatgcaaaaa tcctcaataa aatactggca aaccgaatcc  46620
agcagcacat caaaaagctt atccaccatg atcaagtggg cttcatccct gggatgcaag  46680
tctggttcaa catacgcaaa tcaataaacg taatccagca tataaacaga accaacgaca  46740
aaaaacacat gattatctca atagatgcag aaaaggcctt tgacaaaatt caacaacact  46800
tcatgctaaa aactctcaat aaattagata ttgatgggac gtatctcaaa ataataagag  46860
ctatctatga caaacccaca gccaatatca tactgaatgg gcaaaaacta caagcattcc  46920
ctttgaaagc tggcacaaga cagagacacc ctctctcacc actcctattc aacatagtgt  46980
tggaagttct ggccagggca atcaggcagg agaaggaaat aaagggtatt caattaggaa  47040
aagaggaagt caaattgtcg ctgtttgcag atgacatgat tgtatatcta gaaaacccca  47100
tcgtctcagc ccaaaatctc cttaagctga taagcaactt cagcaaagtc tcaagataca  47160
aaatcaatgt gcaaaaatca cacgcatttc tataacccaa taacagacaa acagagagcc  47220
aaatcatgag tgaactccca ttcacaattg cttcaaagag aataaaatac cttggaatcc  47280
aacttacaag ggacgtgaag gacctcttca aggagaacta caaaccactg ctcaatgaaa  47340
taaaagagga tacaaacaaa tggaaaaaca ttccatgctc atgggtagga aggatcaata  47400
tcctgaaaat ggccatactg cccaaggtaa tttatagatt caatgacatc cccatcaagc  47460
taccaatgac tttcttcaca gaattgggaa aaactgcttt aaagttcata tggaaccaaa  47520
aaagagcctg caatgtcaag tcaatcctaa gccaaaagaa caaagctgga ggcatcacgc  47580
tacctgactt caaactatac tacgaggtta cagtaaccaa aacagcatgg tactggtacc  47640
aaaacagaga tacagaccaa tggaacagaa cagagccctc agaaataatg ccgcatatct  47700
acaactatct gatttttggc aaacctgaca aaaacaagaa atgggaaaac gattccctat  47760
ttaataaatg gtgctgggaa aactggctag ccatatgtag aaagctgaaa ctggatccct  47820
tccttacaca ttatacaaaa attaattcaa gaggattaaa gacttaaatg ttagacctaa  47880
aaccataaaa accctagaag aaaacctagg caataccatt caggacatag gcatgggcaa  47940
```

ggacttcatg tctaaaacac caaaagcaat gacaacaaaa gccaaaattg acaaatggga 48000
tctaattaaa ctaaagagct tctgcacagc aaaagaaact accatcagag taaacaggca 48060
acctacagaa tgggagaaaa tttttgcaat ctacttatct gacaaagggc taatatccag 48120
aatctacaat gaactcaaac aaatttacaa gaaaaacaaa caaccccatc aaaaagtggg 48180
caaaggatat gaatagacac ttctcaaaag aagacattta tggagccaaa agacacatga 48240
aaaaatgctc atcatcacta gccatcagag aaatgcaaat caaaaccaca atgagatacc 48300
atctcacacc agttagaacg gcgatcatta aaaagtcagg aaacaacagg tgctggagag 48360
gatgtggaga aataggaaca cttttacact gttggtggga ctgtaaacta gttcaaccat 48420
tgtggaagtc agtgtggcga ttcctcaggg atctagaact agaaatacca tttgacccag 48480
ccatcccatt actgggtata tacccaaagg attataaaac atgctgctat aaagacacat 48540
gcacacgtat gtttattgcg gcactattca caatagcaaa gacttggaac caacccatat 48600
gtccaacaat gatagactgg attaagaaaa tgtggcacat atacaccatg gaatactctg 48660
cagccataaa aaggatgag ttcatgtcct ttgtagggac atggatgaag ctggaaacca 48720
tcattctcag caaactatca caaggacaaa aagacaaaca ctgcatgttc tcattcatag 48780
gtgggaattg aacaatgaga acacttggac acaggaaggg gaacatcaca caccagggcc 48840
tgttgtgggg tggggggagt ggggagggat agcattagga gatataccta atgttaattg 48900
atgagtttat gggtgcagca caccaacatg gcacatatat acatatgtaa caaacctgca 48960
cgttgtgcac atgtacccta aaacttaaag tataataaaa aaatttttaa aaaaagaaac 49020
acctgctttt ttctgttttc catttgctta gtagattttt ctccatcctt ttactttgag 49080
cctggggatg tcattgcatg tgagatgggt ctcttgaaga cagcatacat ttgggtcttg 49140
cttctttctc caacttggca attctctgcc ctttaattgg ggcatttagc ccatttacat 49200
tcaaggttaa tattgatatg tgcatatttc atcctgttat catgttgtta gctgctcaat 49260
atgcagattt gattgtatag ttgatttata gtggcaatcg ttatgtactt aagtgtgttt 49320
ttgtggtggc cagtaacgtt cttccattat catatttagc aatcccttaa gggcctcttg 49380
taaggcaatc tagtggtgat gaataccctt agcatttgct tgtctgaaaa ggatcttatt 49440
tctccttcac ttgtgaagct tcatttggct agatatgaaa ttcttgcttg gaatttcttt 49500
tctttaagaa tgctgaatat aggcccccaa tctcttctgg attgtacagt ttctgctgaa 49560
acctccattg ttagcctcat tgggttccct ttgtatgtga cctgaacctt ctttctagct 49620
gcctctaata tttttttcc tttcaacctt taagagtctg atgtctgatg gctatatgtc 49680
ttagggatgg ttgtcatgta taatatcatg cagaggttat ttgcatttct tgaatttgaa 49740
tgttggcctc tctggtgagg ttggagaaat tttcatggag gatagcctga aatgtttttc 49800
aagtttcttt ttttctcttt ctcttcttaa gggataccaa tgtgtcatag atctggtctt 49860
tttacataat tgcacatttc tctgaggttt tatgccttct tttttattct ttgttcttta 49920
tttttgtctg actgagttaa ttcagagaat cagtttttaa gctctgtgat tctttcctca 49980
gcttggtcta ttctgctgtt aatacttgta attgtattct gaaattcttg aagtgagttt 50040
tttagctcta tcaaatcagt ttggttcttt cttaaaatgg ccatttcatc tttcagcttc 50100
tgtatcattt tactttattt cttagctccc ttggattggg tttcaacatt ctcctgaatc 50160
tcagtgatct tctttcctgt gcatattctg aattctatgt ctgtcatttc agccatttca 50220
gtcaggttaa gaaccattgc tgggaaacca gtgtgattat ttggaggtaa gaagacactc 50280

-continued tggattttag agttgcagag tttcttgcat taattctttc tcatctttgt gggctgtttc 50340
tttaatcttt gaagtggctg tcctttggat gtttttgtct tttttgttgt tttttggtgt 50400
gtgtttttgt ttgtttgttc atttgtttgt tttttgctct tatcttcttt gatactcttg 50460
caggtttgat tgtggtataa agtggattca gttagctgtg tttcttgaaa atcttagagg 50520
gtccaggctc acctcagcac tcttgtggtg tgttctctgc tctgggactg ggcccctggc 50580
tttattctct ggccccttga gtttagaaac ttgctgcatt ggaggggctg aggtgttccc 50640
agtccattgg ccacaacact atagtagggg gtgccggcca aagcacttca ttagagtggt 50700
ggcagtggga tccattctta ctcatgggtg ccagcagttg tggagtcatg gcagggtgca 50760
catgcatctg ctggggtggg ggtactggca ggagcagagt ggcagcatcc ctacataggt 50820
tcctgctggc agtcacagcg cagtgaggtg cccgtgtgtt ggcagggaca gggtggtggg 50880
gcacacatgc acatgcttgc tggtggtaga gggagttgtg atctgctgtg cactcatgcc 50940
agcaaagcag ttgggaggta ctatgggtgg actggtgcac atcagcagag gctggcctgc 51000
tggaggtctc caatggttag gcatggtctg ctggcaaagg agctatgatg agggccccca 51060
ggaaacaccc tggttgggct tccaaggctg tactgcaagc aggcacagcc agcctggggc 51120
cccaggagag gccagaaggc aaggaaattc tcatttcaga tgggccctgt cccatggaca 51180
agaccaccct gctttattca ggtcccatag tcactctaag gttaaaatct cctagaggag 51240
gttggtgagc cttgggggat gggtgtcccc tggctgtgct ccactacagc cattctcatg 51300
tcaaacactc tgggctttac acagactgga gtcctgcccc tggcatctct ctaagcagct 51360
gtcccttcca gcacaagtgt ccatgggggt catggggtct cctgctgcta ggattctgga 51420
ggcccatggc aacagcaggc cactcctcac ctgttcaact caacctttcc ccaggagttg 51480
ctgggagcca ggaatgagtc ctggtgcttg gcatccccat gcagggttcc catcttcctc 51540
caccttcagc tcagcatctg tgtcctcccc cgtctactct caatccactc tcaatgcctc 51600
cccttcaaag atctgcttgg aaagcacccg tcttcctgat gtctcactcc ctccatggca 51660
gatattcctc ctggctgcat ctagtcagcc atcttgactc gcctccaaag tctttttaat 51720
taccacttcg gttaaattag taactatcat tttacaatgg cctgtgattc tgttttgatc 51780
aaatattttg agccttttag catctataac aaatgttctc aaaaatcaaa atcctaaatc 51840
aagtctctgc cttagtctta tttctggggc ttattaaggc tataaaaatt aatcaccata 51900
aggttgtaca agctttttac agcttccagt caggctatga actccagtat caccacctcc 51960
agcctgataa ttacatatat tggaagaaaa tcagttaaag gactccctct agacccttga 52020
aagggtgtga gagacaacat ggtttcgcct gccttcatgt gtcccagtcc atccctgtgg 52080
ctgcctctgt ccacctcagc ttgcccactg tctttccttc ccaactgtct gccctgctga 52140
cttctggcct cagtgacaga tgcaaagaca aggcgacagc cccacataga ccgtttaacc 52200
agtcccacat ttgcataagc taaatggtca tgtcacagtc tgttgcccag gctggtctca 52260
aactcctggg ctcaagtgat ccacccacct tgacccccaa ggtgctggga ttacaggctt 52320
gagccacagt gcccagccaa gaacccgttt ttgagtgggc accttggcac acacctgtaa 52380
acgcaacact ttgggaggcc aaggtgggag tgtggcttga ggccaggagg ttgaggttgc 52440
agtgagctat gatggcacca cctcactcca gcgtgggtgg cagagtgaga tcctttagaa 52500
aaaaaaaaaa aaaaaacttg ttttctctgc agccgggctc cgtgaccaaa cacaaacaca 52560
aacttcccct ccagagggtc caggaggggc tgggctgcag gaggtgctta gggcctctta 52620
gggaatggta agtgaccacc caacgcaggc actcagcccc aggggcatat gcagagagag 52680

-continued

```
ggtccaggag gagctgggct gcaggaggtg cttagggcct cttagggaat ggtaagtgac  52740
cacccaacgc aggcactcag ccccaggggc atatgcagag agagggtcca ggaggagctg  52800
ggctgcagga ggtgattagg gcctcttagg gaatggtaag tgaccatcca acgcaggcac  52860
tcagccccag gggcatatgc agagagaggc tgggaggaca ctttcagtga ctggggttac  52920
aaaccccaac cataagacat tgctggctct gtgagccgcc acctccagaa atctcccact  52980
tagttcttag cacttatcca ctcttccctt ttcctactct caattcctgg aggatgccct  53040
cctttctcag gctcagacca acctaccagc tccactctag acctgaacac atgactcctc  53100
cctctgtctc cacctggaaa tctcatcagt gcctcacatt tacactcctg aaaatcaggt  53160
cctgcctacc caccctcttg ctccacctga ttcctgccct gtttcagcca gagaccttgc  53220
agtctccttt aactctcaaa cccacccatg tcgtgtgagc atactgactg tgttctatgc  53280
aagaaagagc agtttcttgg tggtcctgcg gttttattag tccagaggca aagcgttggc  53340
agagctggtt tcttctgaac cctgggaggg agattctgtt ttcatgcctt ttccagattc  53400
tagaacccat attccttgct ctgtgtcccc ttcttccatc ttcaaaggcc atcctctcat  53460
ctctgtgtcc atcatcacat cacccttccc ctgactctgg ttctcctgct tccacttata  53520
agcacccttg tgattacatc atacccaccc agacaatgca gggccatatt ctcccctctc  53580
gagattaatt taatcacatc tacaaagttc ctcgtgccat atgaggtcac taaaccacat  53640
gttctggggg tttgaatgta aacatttggg ggatgcatta ttcagccacc cacaagcact  53700
gctccccact ggccacacac tatgcacagc cgagatcatg caagtgaggc acgttcatca  53760
acagcagctt cagcaggaaa ctatatgctc cactttcctg ccatttgtat ctggattttt  53820
ttttcgctat cattgtagaa agagtggtat tgtaaaatta aagatggatt attttctttc  53880
tagaacactt tggcaatcta tccaacatta tttatcccct tctgagtgtc aagtgtgagg  53940
tcattctttc attgagagct caatgcctac aattatgata atgcatattg ggtactttca  54000
cacatcagaa agttcttctt tcttaaaatc tgttcttgaa ttattcattc ttctctagct  54060
ttttgttgat ctattttata attttagaaa aatcagaaag taacttgaag tatctgtcat  54120
ctctacaggt ttacctccct ctttgtggcc ttcagaatgt catgacacgc ttttcccttg  54180
ctcatcacat ggtttctatg tatgagacct catcacagga gctgtggtcc cccgggagca  54240
ggcatctgtg gatggtgcct tgctcctggc tgctgggacc tgtgtgctgc cagtggcact  54300
ccacgacagt gatttcccag ctcagttttg cagctccaga tggtgggtga gacactagga  54360
ccactttgtg aacagcgagg gcttggggtt tgcttttcta ccatgtccag ggctgctgtt  54420
catgagggaa tgtttctaac ctgacatcat ggctgaagcc aacttagaac ctctctagcc  54480
gtatggggag taggtgagtg atacagatgt taattagctc agtggagcca ctcccctatg  54540
tagacatgtt acaaaacatt atgctgtaca gaataaatat aggtcatttt tatgtgtcaa  54600
tcaaaagaga aactaattat ttaaaaaaaa aaaaaaaacc tctctactca agccgaaacc  54660
tcagctccag tcccacaagt cacacaaggc tgctcccgtc ctgtgtatgt taaacctacc  54720
tcagaaatgc aagggggcat tcaggtttca ttctcaattc aaatgccctt tttaattttg  54780
tctattccta gcacctggca acttccagct ctttttttcg gggctcattc attatttaaa  54840
gcacgtataa tttttcaccc acattctaac acatgtagta ctgtagagaa tccttcccta  54900
ggaggatcta cagcattaga aaagaattaa gaactccaat atttacaaga aggaaaaagc  54960
aaaaagagat caaaaaatgg gcaacttcta gaaatagaaa accctcatga gtatgatgat  55020
```

-continued

```
aaatcgctgg cacacatgtg aatagttact tgatgcttat agtgatgtct gggaaaataa  55080
catgaaatac ttataatctg tttctcacac atgtaattca aaagaataga gagaagatga  55140
tttgaaatat tcttaagttt gtaggaaaaa agctacttcc atatgcataa ttgcatgtat  55200
tttgatactg ccattattaa gaactatcta agagggtcca ttaaaaataa aatttcttgg  55260
ctgggcacag tggctcatgc ctgtatccca gcactttgga aggccgaggc aggtggctca  55320
cctgaggtca gaagttcaaa accagcctgg ccaacatggt gaaacgctgt atctaccaaa  55380
aatacaaaaa ttagctgggc atggtggcat gcacctgtag tctgagctac ttggggggct  55440
gaggcaggat aatcgtttga acccaagagg tgtaggttgc agtgagctaa gatcatacca  55500
ccgcactcca gcctgacaga caaagcaaga ctctgtctca aaaatattaa aataaaattt  55560
ctcattccta ttacagagta atttaattca ttaatgccct gccctgttac aaaactcatt  55620
tgtaaaatac taattgtaat tgtgaaaaaa tggcaattga tactaatttt aaattctaaa  55680
aacagggcac ccatattaaa gattattctg cagtaagaga attagctata acattttgta  55740
ataaggtgga gaaaacattc tccaacttac aatggttggt gagaagaaag tttccagcac  55800
ggtagatgga ccctaagagc ccttgttgaa ataataagac aaaaagatat acagagagat  55860
gagccagatg aagggagaca gagagagaga gagagagaga gagagaggca cagaaatgag  55920
agatacaaag tgaaagaggg caacctgtgg ggtcatcaga tatttgtttt ctgttttgtt  55980
tattctaaca taaaggcagt ggtgggtcat cgatgtattt agagtttgca caatcactgt  56040
ggaacacaga cagacacagg ggaagaggag aaacacaggg cggtggcttg cccttggact  56100
gttcttagtt cctcaaaacg taacagcttt gcccaaccta agggaacttt cagcagctgc  56160
tcttctgcca taggcctctt tcctgccttg ttttcatgtg gctgactgtt tctgttcctg  56220
caggtcttag ctcatcagac aggcatttat tacctctgtg tcaacagtgg gagcttccat  56280
tactctctag catgacactc cccttcctct tttaggaaat ttaacatgga agtgagtttg  56340
ccatcggcct tctccccaca gtgttaacag tggtgaggaa gccagcctgt tccaccttgc  56400
ccctcccatg attccaacac tgagttcaga cttgtcacat ggaacttatc tttgcatgtt  56460
tgtggcacag acagatggac ccaaccatgg attagtggat ggatggatgg atggatggat  56520
ggatggatgg atggatggat ggatagatgg atggatggat ggctgagtag gtgtgtggat  56580
ggaagagtga aaagatagat ggatgcatgt atgggtggat gggtaggttg atggatgcat  56640
ggatgggtgg atggatgggt gagtggatga atgggtgggt aggtgggtgg ctacatgcat  56700
ggatgagtac ttggatagat aagtgagtgg atggatggat ggatggatga atgggtatgt  56760
gaagggatgg atgtattaga gtgggtagtt aggcaggcat gagctgatag tcaagtgatt  56820
gttaaactgc ctctctaaaa taataattgg tctcggctgg acgcggtggc tcatgtctgt  56880
aatcccaaca ctttgggagg ctgaggtggg cggatcacaa ggtcaagaga ttgagaccat  56940
cctgaccaac atggtgaaac cctgtcttta ctaaaaatac aaaaattagc tgggcgtggt  57000
ggcgtgcatc tatagttcca gctactcggg aggctgaggc aggagaattg cttgaacctg  57060
ggaggaagag gctgcagtga gctgagattg tgccactgca ctccagcctg gtgacagagc  57120
aaagctctgt ctcaaataat aataataata ataaataata attgatctca gccagcgcca  57180
agaaaaggca gtctcccaat agatagaaaa cacccgaaac tggtcatcag cagcttcctg  57240
ataagatctc aggcattggg tgagtgggct caagcatatg cactaagagg caaagtggca  57300
gagtttaact ggcacataat cttcctctag gaacactcta atagtaagag aaggacacct  57360
caaatgagca tgtgcacatt tcattaaacc cactgtgtat gcagcccctc ccaagtgctg  57420
```

gcaggccact gtacatgtgg gcagcccact ccaagggaag aatcaaggga gaagaaatac 57480
aaatcccaga accatgtcaa tgtataaaac cccaagtcaa gggccggaca gagcacttag 57540
atctctcaag tcgcccactt agccctcttc caagtgtact ttacttcctt tagttcccac 57600
tttaaaactt taataaacat ttactcctgc tctaaaactt gcttgggtct ctcactcttc 57660
tgtatgcccc ttggccaaat tctttcctcc aaggaggcga gaatcaagtt gctgcagacc 57720
tgtatggatt cgctcctgct aacagatagc tggatgggtg gacagatgca tgaattagtg 57780
gatggacgtt tggatgtgtg ggtgggtggg tggattgtgg gatggctgga tgaatgcatg 57840
gctggatggg tggacagatg catgaattag tggatggatg tttggatgtg tgagtgggtg 57900
ggtggattgt gggatggctg gatgaatgca tggctggatg ggtggacaga tgcatgaatt 57960
cgtggatgga cgtttggatg tgtgggtggg tgggtggatt gtgggatggc tggatgaatg 58020
catggctgga tgggtggaca gatgcatgaa ttcgtggatg gacgtttgga tgtgtgggtg 58080
ggtgggtgga ttgtgggatg gctggatgaa tgcatggctg gatgggtgga cagatgcatg 58140
aattcgtgga tggacgtttg gatgtgtggg tgggtgggtg gattgtggga tggctggatg 58200
aatgcatggc tgggtgggtg gatggatgca tggataagtg gtggacggat ggacgggtga 58260
gtggatgggt ggatgtgtgt gtggatgggt ggataggaaa gccctctaat tgattacagg 58320
gctcagtgtg tgcttcaaca tcatgatggc atcatcacat tggtccctgt atgaagcagt 58380
gggggaggag agtgtaccag gggagcagga atgacttttc tccagaatcg acctctccca 58440
ccctgcagcc tgggctgtgc aggccacatt ggagaaggtg cggtcgacta ctcctaaatg 58500
ttgttgtgtc caatggcttg ttgacgttga tgtaggaatg agcctacatc tccaccatag 58560
atggaactgt ttgggtcccc aaagcagaaa gcctcttctg ttgcaggtgc tgaagtttcc 58620
atcttcttct gcttatacgg aagctcacgc atcccttgga tggcaggcgt caggttcctg 58680
tgcgcactga gttcccccct tacatgcttt ggacagaagt gtgagacaca caagattgct 58740
gcaggaagtc cacctgtggg gatgctgcga cttctccagc aagaacacga gtctgctcat 58800
tgaccatcac cacacataac aaattaagtg tcccttttt gataacacgt cattgtttca 58860
cagagtattc ttttaaagtg tataagttga ctgcagttat tattttttac ttctgttact 58920
aatttactca taattaggca caatttacac ttaagaaatt tcttaatagt tttttcctcc 58980
ttaaggtgaa ctacagtcag ataacatact tatcaattgt ctctagctct tgtcagaaaa 59040
acatatagat gtgtgtgtgc gtgtgtcttg gcctttccaa tgatgaatta agatgtgcat 59100
tgagaaggca ttcactttat ttgacgttaa ggaagtacca agaagacgct ctccacagac 59160
cctgggaaag ccagcagctg caccccgagg ctgtgccagg cagggaacaa ggaggcagca 59220
ccacctgctg ggcagggaaa atgtcctccc agtccctgcc gcttctctgc agaggcacaa 59280
agagctgccc cttctcctgg gccttctcct gggctgatga gattgctccc cgatatgcca 59340
aatcagggtt gtgcatctga ggctctgtct agactctcag ctccttccta ctcctgcaaa 59400
gtgaagaaaa caatgccaag ggtcctgga ggcgtctcta cccctggaga gttttgactc 59460
tcttcaatag tctccactac cctgccctca ctccatgtcc tccgtttctc cctaaagcgg 59520
tgcccagtct gattgcactg tggcagggat aacgaggggc caggacatca ggggagagaa 59580
gtttctacct gagtcacagc agcggctgcc ctgcagactc ctgaagacac aagacacatt 59640
tccatcccag agacccagcg aaatgcaacc tcaggctaga gacagccagt tattttttct 59700
tgttctgtcc tggagaggcc actgagaaag tcgagcccct tgttgaggaa aacatgagat 59760
ctctgtgtgt cgtcctctgc ctgatggctg tacctccatg tgagtgtctc agagatttca 59820
gaacgggggc tgtgggctgt ggtgtccgct tgtgactcat ctctttgctt cttgtccctg 59880
agtgtcctgc atcagatgca gctactggag tcatgcccag ggctggtgag gtcctcacag 59940
acctctgggc ctggacccag cagccctctg ggaaggcgct ggggcacctc agctccaggg 60000
gcagcacaca cttcagccca gcctttctgg gccaactctc catctgtaga gacacatcca 60060
aggcccagtt atccctgcag ctgagctccg tgatggccaa gggcagggcc gcacattccc 60120
gtgggagaca gaatggggac ctcagcgtga gcccagacac aaacctccct gcagggaagc 60180
acaagaccac caggcggcgc tccagaccac acagcggccc cagaagcagg ttttaggggg 60240
cggggcagac gtgtccgcgt tgagtcaggt cattggtttt actttccctg agcaaacggc 60300
ctctgccaag gactcactgc acctctcacc ttcacagttg tttttttttt ttttttaatc 60360
accctgtaga gttttgctag ctaatttaga tattgaggag tgcttcatac ttccttgggc 60420
ctctgcttgc agaaacatag caattgtaag gaggcacgtg ggaaagcccc ggctcggtga 60480
cccgggggat gctgctgtgg ccctggcaag agggcgtcgg gccgcagtaa caaaggtgca 60540
gacggctctc agcctgcgcc cgcggagtac aacacataag ggctgtaacc taacgaaaaa 60600
agaatcgcag tgcaactgtc ctgcatttga gtttgtgatc agttttgccc tttgtcttta 60660
acaggttcta acataaaatt ttgaatgttg gttcaagccc tgtgggtaaa atgcacttac 60720
ccacattcct taaacaaata gaacactgag gtggaaatgt tttgaaaaag tagttttcag 60780
acatttggaa acaagcatca caggatcata acccctgaga aaagaaaaac aaatgaacga 60840
atcctgctat tgcctgaaag cagctgccag gacacacgga aaggcttagt gagctgagcg 60900
gacagagagc agagttcaag gcagcagcag cccgagggga ggagcaccgg ggagcaggct 60960
gctgtgcagc caggatgggc cggggtgggg cggggggaga acagctggag acttgccgca 61020
gggaggggga tccctcaggt ttggggctga gaactgactt atgcctgact tatgcctgca 61080
tgaaaagaaa ctactcgata tcagggggaa atcaccagaa acctgtggac ccaaaactac 61140
acagagccta cacaaggaaa gcattgtttg tgttctccca gccagggtgg aaagaccttg 61200
agatatgtaa agcttcaagc aatcttccga agtaatctcg tgagtagtgg tgccacatta 61260
attcaggact aaaggctgct ctgaactgaa cctaagaaat gcttcaagtg tagcctggag 61320
cccgggtgca gtggctcaca cctgtaatcc cagcactgtg ggaggccgag gcaggcggat 61380
cacttgaggt caggactttg agaccagcct ggccaacatg gcaaaacctg tctctactaa 61440
aaacacaaaa attagctggg cgtggtggca gatgcctgta atcacctccc acctggaccc 61500
ttccttgata catcagaatt acaactagag atgagattgg ggtggggaca cagagccaaa 61560
ccgtatcaca taggaaccta aaaggataat aaagtaggaa aacttcccac atcagtaacc 61620
ctttatccga tagtaatccc aatctgcaaa gtaaaactgt gtgattttac taagataacg 61680
gaatcttctc tacagaagga ctttccagtg caaaagctcc ccaccctcac catgaaatgc 61740
acgtgaccat ttccaatttg tgtaaagtcc tcagttagta ctgagacttc ggaaggttag 61800
aaatcccttt gctcatgctg catggtccgg atgagatgta agaatcatta gctaatagac 61860
atgcaacagc ttttgtgtga aagatgttat gagacattta aggtatttgc ttgtgattac 61920
taagcattca ttgtatcatt ggagcacatg tgcttttata ccctggagaa attccagtaa 61980
ttgaattgct gggttgaatg ggattttgat ttggattaaa tttaaactat agattttatt 62040
tagggaaaac tggcatctta attatgttat tggggggccc ttgctcccag agctcccaag 62100
atggtggcag gccgcttcca aaatgaccgc aggccacttc caagatggtg gcaagcctca 62160

-continued tgttctctga cctggggttc ttggcctcac ggattccaag gaatggaagc ttgggccatg 62220
cagtgagtgt tatagctcta ttagaagccg tgggtcacgg aagagaaccg tggaacccag 62280
tgactagtgt tcagctcgat taggacgaac ccaggcactt agccgtgcag gaacaatggc 62340
gagcatttgg cccgatcgag agtggcaatg ggcgcctcgc tggatcagga gcacagcgga 62400
taccctgatg gatccggagg gatggaagcc agcggtgggt ctcccacggg ggcaaacagc 62460
agtggtggac ggtgagcgaa agcgaagctc gagccgtaac aaacatggac cagaagagtg 62520
cagttgcaag atttagtaga gtgaagacag agctcccata caaagggagg ggacccaaag 62580
agggtagctg ttaccggctc gaatgcctgg gtttatatcc cgatcattgt ccctcccgct 62640
gtgctctcag gtgatagatg attggctatt tctttacctc ctgcttttgc ctaattagca 62700
ttttagtgag ctctctttac tatctgattg gtcgggtgtg agctgagttg caagccccgt 62760
gtttaaaggt ggaagtggtc accttcccag ctgggcttag ggattcttag tcggcctagg 62820
aaatccagct agtcctgtct ctcaattaca ctgagttttc caatccatgc atccaatatg 62880
tggtgtatct cttcatatgt tcatagcctc tgagcaatgt tttacaattt tctgtgtaaa 62940
gaactccaca tcgttttatg tttcttctaa ggtatatcct gattgctttt tatgtcttca 63000
caagtttttt cctttcaaaa ttaattttcc aattgtttgg tgctaatatg ctcaaatgtc 63060
cttgattttc ttagtttgaa cagtccgttt ttgttttggg gatttatttt tttttcagat 63120
tctttaagat tttctatgtc tataaccata taatctctga acagagacag ttttgctttt 63180
tcctttcaac ttgaggtagg ttttctgggt agttcaggac gcgcaggcac tgggtgggtg 63240
gtgttagcag ctgcacgatg ccttggagag gacactctcg ggggactgtg gccgctgctc 63300
agctgtgacc gttcttatag caccagcagc tgcggccacc attcttatcc aatttccaaa 63360
gccacaccac aggccctctc aagaacgagg cgtggaggct atgccctctc ctggacacat 63420
catcattccc aagccccacg atgtgggccc catgggacgc acacctttgt ctgtccagac 63480
ctcagcccca cctcctcatc ctgcaccaga actcttcaga gcccagtgca tgaaatgggc 63540
taccaaggaa atgagggtag gttcctgaga ggaaactggc cctgcatttg ggagctagga 63600
gtctgctaat tcgcctggca gccctgtgca gccctccgtg gctacagtcc accccgtgcc 63660
catcagtgcc tccttcctgt gcaagcctgg acctcgccct gggctcagga tgggctgtag 63720
accgagaatg caggcgggaa agtctttgtc tatcggggcc atagtcaggt tctacagtga 63780
gtcagggaaa gacctgtgga ggtgtggatg aggacaatgg gtccaccatc aacaggagga 63840
cacgggttcg accccttgca gaggcacagt cccacatcac tgggaggcag ccacactcac 63900
tgcctcgccc tctcctcaca cagtgcagtt tccacgttca cagccccagc cagtcaccag 63960
gaatgccctg gggcggcct ttccccagtg cactccgagc cctcccttgg ctgtgcggtg 64020
agctccatgc ccaggagata tccacccata gtcctccgga aagcagctga cctgccatgc 64080
cctggaacca caaatcccca cagatcagcc agcctgcagt gggccttgga tgtggtgagg 64140
agtggtggca cccccgttcc caccccacag atgcaacgcc tgtgggtgac gcatgtgagt 64200
actgaggagt agagggtaga actgtaggcc ccgagaacca cagaaactcg ggtgttacac 64260
tctggggcca tgtaaggaga aagtgtcact ggacagaaac aggcccctcc tagacactgt 64320
gtgcgccata gtcacctgtc attagctctc actcttgcag attcatgatt gaggtggtta 64380
aaaaaaaaaa agctcctact cacccatcca accccatcct ggggtgtttc caccacccctt 64440 ggggtttggg atgagctgcc cttgcccact gtgctctgtg gacctccctt tagaagctca 64500

-continued

```
cagctccctg cactcggctc catcctgccc caccacacag aagcaaaacc cctctccttt  64560
ccactgcagg cttttcctgg accagaatgc tgacctgctg cccttcactc ccgaagtggt  64620
gggactgcct ggggtggtgt gggtgttgag ccttcttact ctagggacct ggcacctggc  64680
cccaggggca cagggatggt gcatctgcct agggatgcct cctcatgcca gggggtgggg  64740
gttagtacca tcggccctca ggatttgttg catgaatgag tgaatgggtg aataaatgaa  64800
ggggatctga tctatgaata agggtatata gactttggtt gatgtaggac gccaaatgct  64860
ggaatttcag agtcatcaca cccaggggcc ctgcctctga gctcctcttt gcatccaatc  64920
tgctgaagaa catggctcta gggaaaccca gttgtagacc tgagggcccc ggctcttcaa  64980
tgagccatct ccgtcccggg gccttatatc agcaagtgac gcacacaggc aaatgccagg  65040
gtgtggtttc ctgtttaaat gtagcctccc ccgctgcaga actgcagagc ctgctgaatt  65100
ctggctgacc agggcagtca ccagactcga gtgccatttc attacctctt tctccgcacc  65160
cgacatagat tctcactcac ctgtgccatc tccggggaca gtgtctctag caacagtgct  65220
gcttggaact ggatcaggca gtccccatcg agaggccttg agtggctggg aaggacatac  65280
tacaggtcca agtggtataa tgattatgca gtatctgtga aaagtcgaat aaccatcaac  65340
ccagacacat ccaagaacca gttctccctg cagctgaact ctgtgactcc cgaggacacg  65400
gctgtgtatt actgtgcaag agacacagtg aggggaagtc agtgtgagcc cagacacaaa  65460
cctccctgca gggatgctca ggaccccaga aggcacccag cactaccagc gcagggccca  65520
gaccaggagc aggtgtggag ttaagcaaaa atggaacttc ttgctgtgtc ttaaactgtt  65580
gttgtttttt tttttttttt ggctcagcaa cagagatcat agaaaaccct ttttcatatt  65640
tttgaaatct gttcttagtc taatggagat tctctaatat gtgacaatgt ttttctcttg  65700
ctgtttttgg aattctttgt ctttgacttt tgacaacttg acttttgaca gtgtgcctca  65760
aagaagttct attttgggtt ctgtgaacct cctggatctg ggaagttttc agctatgatt  65820
tcattaaacg tgttttctac accatttccc tactcttttg gaatacccat aatgcaaata  65880
tttgttcact taattgtgtc ccataaatgc tggggatttt cttcattcct ttttactctt  65940
tttttctttt tattcatctg cctgaattat ttcaaaagat ctgtcttcaa cttcagaaac  66000
tcttttgctt ggcctagtct aatcttgaag gtctcaattg tacttttaat ttcattcatt  66060
gaattcttca actctggaat ttctgttggt tcttttttat gatacttatc tctttgttga  66120
attcctcatt caaatgataa attgttttcc tgatttcact gaattttcta tctgtacact  66180
attgtatctc cctgagtttc ttagagatta tccttttgaa ttatttttct gacattctgt  66240
atatttcctt atgattgggg tctgctactg gagaatgact gttgtctttt tcaggtgtcg  66300
tgtttcctgg ccttttcatg ttttatgtgt tcctacgttg atttctacac atctggcgga  66360
ccagtcatcc cttgcaattt aatggagtag gttttgcagg aaaagacttc ctagtacaga  66420
cgggtctcag ggtgtcagtg tggcggggcg tgctggcttt agttctaggt tgacgcagta  66480
gcgtagtctc catgtcgttt cttcagctgc cgtccacatt ggtgacgttt gcgagtgtct  66540
cagtggcctg ggctgagagg tttgtggcag tggaagtgca acgttgctag aggtggactc  66600
accaggctgt ttctgaggtc gaggcacatg catgcacatg gtggattgac caacttggtg  66660
ccaggctcac tagggttggg gacatggggc tgtttctcag gcccaggatg caaacacaag  66720
tctctttggc tggcctgggg gtgtggcttc tgagggcaat ccacagggct gtttctcagg  66780
ttcaggacac aagtgcatgg ccgctcaact ggcctgggca tgtgtctccc agggccaccc  66840
catgggctct ttctcagacc caggacatgg ccacatggct tcctcagctg gcctgggtgt  66900
```

gtgtctgctg gggggctgca ggggcacagg gttatttctc aggccggggt catgggcgca 66960
cagctgcttg ctggcttata ggagtgcctg ccaggggtgg cccatgatgc tgtttctcag 67020
gcctaatttc aggtgcagag cctttgggca ggtcaacggc atacctgtgg aaattggagt 67080
ggatgccaca gggctatttc tcaggtgcct gagtgtgggc acatatccac tctgccagcc 67140
tggagttagt atcaggtgct cggtggctca ggggcctctc ctgctcaggg gagggccctc 67200
agcagcttgg ccaaatcaat ggtggattca ccctgggcag gcctggcagg ctcttcctcc 67260
agctggatgt gcagcagcag gggttgggtt ttttgctgtg cagggccaga gtcacggcca 67320
atcctcagcc taggctctgc acagccaggg ttgtggcatt cagccaccca gatatgggca 67380
tcctgaagat ggagccccaa tgctagaaag gggcagtggc taccagcctc agggcaggat 67440
gcactccaga ggcggctccg gtctcaaggt ggcgctgggc tgcagcagct aggctcacag 67500
tggatgaatg gggggcaggga gtacacacct tgtgctccta atctgggatc attcctggca 67560
gctcccaaac ttggctgagg gcttgcaaaa cctgtggaat tctcctgttg caagggctgt 67620
agatgtttgc agtggcagtg ggtgctggcg ggaaatctgc ttaccttttc cctacatggg 67680
aagtccctcc tgtgtccaga ccaatccgat ctgggtgggg aagacaaggc tgcaaaggcc 67740
aggtgcctcc atgctgccct ccgatcacca cgggtgcgtt tccacacctc cactgcactc 67800
cgtcagtctc ccttcaacac tccagtcaaa ccttagctgt ttcttctttg ccttattcct 67860
tcctcatggg gagggtgtgg gtgaacacca ggcttctcta agttcttcat ccatcttgct 67920
gatgtcattc tccatccagg catgggtttt taagaagtag tgaatactga aatttcagca 67980
gaggacacct ctataaaaat tctgcaactg gaaaacctcc ttaaattggc tgattgtcat 68040
tacaattgga ggaaaactgc caataatttc aaatttagaa ggctgagact ctataaacaa 68100
agactaacaa tatgttttct gatatttttc cccaaaataa tacttttcca agacgaaaat 68160
ttttccaggg tatataagca catgtgctcc aatgatacaa caaatactta ctaatcataa 68220
gcaaatacct taaatgtctt ataacatctt tcacacaaaa gctgttgcat gtctattagc 68280
taaaaattct tatgtctcgt ccagatcatg cagcatgagc aaagggattt ttgaccttca 68340
aaagtctcag tactaactga ggactttaca caaattggaa atggtcacct gcatttcatg 68400
gtggtggtgg ggagcttttg cactggaaaa tccttctgta gagaagattc cattatcttg 68460
gtaaaattac atagttttat tttgcagatt gggattacca actgataaag ggttactgat 68520
gtggaagttt tcctacttta ttctcctatt aggttcctat gtgatatggt ttggctctgt 68580
gtccccaccc caatctcatc tccaattgta attcccatgt gtccagggag ggtccaggtg 68640
ggagtgatta gatcaagggt ggtttttccc aggctgtttt catgataggg tgttatcatg 68700
agatatgatg gtttaaaagt ggcaggttcc cctgctctct ctctcgcctg ctgccacata 68760
agacgtgcct tgctttccct tcaccttctg ccatgattgt aagtttcctg aggcctcccc 68820
agccatgcgg aactatgagt caattaaacc tcctctcttt ataaattacc cagtctcagg 68880
tagtatcttt atagcggtgt gaaaatggac taatacacta tggctttgaa ttaataattt 68940
aaaatttgtc agcttggcaa taaaacatcc tgttgacatt tattttttag gtaatatttt 69000
aaattggcag tttcattcat gtttttacaa attcttattt tcagggtgtt taaggccttt 69060
gctttgaact tggtggttcc ttacactcca tgctgttagt gaagagggac caggttggga 69120
ggcattggtt tgggtggtgg tcaggaaggg cagagtgatt tgagtagggt ctgagtggat 69180
aatagctcat cagtttggaa tttataaatg accagggatg atttaaggag attcctgcca 69240

-continued

```
gacacctatg ccatggccat gccctatctg gatctccagc cgtgagatga gaacccagcc  69300
atgcggggga gtctgttcgt tctgctcaat gttgtaagtg gcacatgcta ttggataatg  69360
tagaattgaa tggatatcat tttattatta taatttacaa acttcctaca ataaacttat  69420
cacctttata catagaaaca aatataagta cattttccct cccctatgtc attttgagcc  69480
ctctctccaa accatcctcc cactctgcga ctcactgtcc tgcatttggc tatgctctgg  69540
caagtcctgc ttagacaagc actcaccaga ccacctactc agcctccctt cagcgcccac  69600
ctggcccacc tgctcaaata catgttgagt ggtcacacac atggactgaa caccatctat  69660
tccatgcact gccccagtga ccgcactgag cagcaagaga gaaatgatcg cattagctat  69720
caattatgcc aattcaaatg ctggagtctt tctcagatac ttttcaatgt tcaagaattg  69780
ttgattgtga attctatacc caatgaaact atccttcaga aatgagcaga aaatggatac  69840
cttctcaaat aaacaaaaac taaaagaatt cttgctacaa gatgtactct taaagactgg  69900
ctaaaggaag ttcttcaaac agcaaggaaa ttgaattgat cttatgtcct gcacacttgc  69960
taaatttcct ctcaatttta gcagcactgt ttagattcca taggattttc catacaaaca  70020
gtcatgtggt ctatatatag agacagattt tcctcttttc cagtggggat aaatttatgt  70080
ctttttcttt ctgtgttaca gcaggtagga cctccagtac aatgttaaac agaagtggtg  70140
aaaacagaca ttcttgcctg tttcctaacg ttggagtttg gtcttttact atggtgtcag  70200
atgttagctg tagggttttt ataaatgccc ttcatcacat tgaggaagtt tgctcctatg  70260
cctaattttc tgagagtctt ttaatgtgac actcatgcta gaatttatta aatgctttct  70320
gtctactaag atgattatgc agttcttata ttaacatgaa taattacatt tatttattct  70380
ttaatatcaa ggcaattttg cattcctgag acaaacccca tttagtcatc atgtgttgtt  70440
attgttacat attgttggat tcaatttcct caaaatttgt taagaattgt tacatctatg  70500
tttacaagga agattagtct gtagggtatt ttttcttata ataactttgc ctagttttgc  70560
aatcagggta atgctggact cacagaatga gttgggaagc tatttcctcc tcttcatttt  70620
tctgaaagaa tttgtataaa attggaatta tatcttcctt aaaggtttgc aagatttcat  70680
aatgaagtca ttggcctaga gttttctttg tgggaaagtc tttgtttgtt tgttttgtgg  70740
tttgggtttt tttttaagag acacagtctc actctgttgc ccaggctgga atgcagtggt  70800
gtaatcatag ctcacagcag cctcaacctc ctgggctcaa gcaatcctcc tacctcagcc  70860
ttcagagtag ctgggactac gggcatgtac caccacaccc agctgtttgt ttgtttgttt  70920
atcgctttgt cttgttttttg aggtcttatt atgttgccca ggctggtctt gaactcctgg  70980
cctcaagtaa tcctcatgcc tcagcctccc acagtgctgg aattacaggc atgagccact  71040
gcacacagac tgtgggaaag tttttaacta aaaattcaat tttctcttcc ttttccagtg  71100
agctttccag tgtctttcaa ttaatgtatc tattttatct aagttgttga atttattgtc  71160
aaaatttttt taaacaatat tcctctctta gaggttgaac atctgtagaa tctgtagtga  71220
tggcacctct taaatccctg atcttgctca tctgtgtcgt ctctctttct ctaatcagta  71280
tgcctaaagt ttaatttcat tgattttctt aaaaaaactgg ttttggtttt attgattttt  71340
ttccctagtt ttttgtgtta catttcattg acttctgctc tgatatttac tatttccttt  71400
ctactgccta cagtaagttt aatttgctat tttcttagtt tcctaaagtg gaagctaagt  71460
ttattgactt gaggcctttc ctctgtctgg atgcggatat ttgctgctaa acatttccct  71520
ccaacaccat gctgtgagtt ttagttacag cgggcttgga gttggcctga gaaattctac  71580
ttaaacagct gcacctatca tgtaagtgat aaatgatgta cctgcctggc cctcacccct  71640
```

ggtcaaagaa tgggatgtac taatgagcaa tgttgctgcg tagctgtgga tttcaaggta 71700
ttttctgtgt ggttttatca tcagcattgt ttgttgatga ctgcaagact gatgatttgc 71760
acctggcctc ggtgagatcc ccgaaagacc ctgcagatgg gctggttact tagcagaaaa 71820
tatgacaacg tggccagcag gaaacaggaa ggtacaatcg gctgcaggtg agctgttgga 71880
agtaagttcc aattttccta ttttgtattt gcattttaat agtgagactg cgcttatgtt 71940
atttgtgtga aacagcttta ttcatagcac tgtaatttaa agagaaaacc cattcatggg 72000
aacaacaaac gacctagaca ccaaggtagc tcatgccatc caaggctata ctgtgcagtg 72060
attgggaaaa tgggcactgg tcccagaagt ctgatcgaca ctctgccact ggctagtccc 72120
gtgctggggg gcgaggatcc acactctgcc actggttagt cccatgctgg ggacaagtat 72180
ccacactctg ccactggcta gtcccgtgct ggggggcgag gatccacact ctgccactgg 72240
ttagtcccat gctggggaca agtatccaca ctctgccact ggctagtccc gtgctggggg 72300
gcaaggatcc acactctgcc actgattagt gttgtgaaga tttaaataaa gaacccacac 72360
catattcttt gacttgtgct ttccgtatac tgagagatag taagagtaca ttattattat 72420
ttataaagta aactagaaag cacatgggaa gacaagaaga aaacctgaat aaacatgaat 72480
taccccattt tcctcaggag aaaactttca cactctgaag gtacacaaat tagcctacaa 72540
atttaatgta aagcaaatag actgttgtag gtaccaattc tcaatgtcac agtgttacat 72600
ggaaagtaaa atacacaaga acagcccaaa agatggaaac aatggacgtg gtcaaatgac 72660
atcagtacaa catccatatg gtcctaagta gccatcttta aaatgggtta gaaatgcctt 72720
caatcattca cacagacaca tgcattgaac aaactctaag aagtgttctt acacgggaaa 72780
agcaagttac agatgcatgg gcatgatatg gatgtagatg tgtgtatgtg catcccactc 72840
atacacaaaa tacccagcat cgcccacatg cctgctgtgt gcgtaagtgt gagcgagtgc 72900
acagacaaca gcgtgcagaa attcaaacca agctgtgggt acttgttacc actgggaagg 72960
gagtcggtca cagagggaaa gagaaacagg acatcagcct ttgacttcag aactgttcct 73020
gccttttcac atcctgtgct gttttcagca tcatcggagc ccttaacaca catcacggga 73080
gtaagagtgt gttagaggga gcattcggtg ggacagatat tgccatggct tgtggataga 73140
gttcacagtc cttaataatc cccgagatgg cagccaagag ctacgttctc aatcacgcag 73200
cttcacccca gaaactgaca gaaacccaac aaccaaaagg tgtccattct gacagcctca 73260
gcctgtgctg gctcagatga gcaaaaatgt acagatatta ataatgatgt tgatttgaag 73320
agcacagagg ggggtatgca tgataagggt ccaaattttt accttaaaaa agaatacatt 73380
tacttctcaa tcacctacat aacgatcatt ttttaaaaaa ctgatcaaat ttggtgttac 73440
aagggcacgt tgcaaattct tctggctact tttctctgac tattctaatt acgttaccgt 73500
gttttctcct gtatgtgccc gttcatgtga atgtcatttc tggctacttt tctctgacta 73560
ttctaattac gttaccgtgt tttctcctgt atgtgcccgt tcatgtgaat gtcatttctg 73620
gctacttttc tctgactatt ctaattacat taccgtgttt tcctgtatgt gcccgttcat 73680
gtgaatgtca tttctggcta cttttctctg actattctaa ttacgttacc atggtttctc 73740
ctatatgtgc ccgttcatgt gaatgtcatt tctggctact tttctctgac tattctaatt 73800
acgttaccgt gttttctcct gtatgtgccc gttcatgtga atgtcatttc tggctacttt 73860
tctctgacta ttctaattac attaccgtgt tttcctgtat gtgcccgttc atgtgaatgt 73920
catccaggca gatttcccaa atccggcttc ctgtaaccaa gggctgaaag agggaacggt 73980

-continued

```
ttcctgggaa tcctttttgc agtttatttt acccggaggc agaagcccac ggttccgtga  74040
agagtctatt gctctcccct ctctcctttt gtgtctctat ttttaattga caaaaaagca  74100
aatgtgaaga ttcctggggt acaatgcaaa gtgacaatgc ctgtctatat tgtgggatga  74160
ttaaaacaag gtaagtggca tatccatcac ctcacacact tatcattttg tggtgagaac  74220
atttaaaatc tcatctttta gcaattttga aatagtcatt attgttaact atagtcacca  74280
tgctgtgcaa cagatcaaaa gaactgactc ctcccatcag cagaaacttc atgccctttg  74340
accagcatct ctcctttccc cgtccacgac taacccccag cccaagagaa cagccaacac  74400
ccacctcgct gctgccacac gacatgtcgg gctttgatgg gatggaggtg agggtgggga  74460
agacaattcc aaagctggag cactggcctc acagctcaga cactcttcta cttatcctga  74520
gagaatgatg tgctgagacc aactaaacct cccctgctct tcccacatgg cagaaaagag  74580
gcaacccagg gaagccattg ccaggacatc atggtcaccc aacccttgtg cagaaaggaa  74640
gcacctgccc aggatgccat agcacccaac cctcatcccc aaggaaacac agcccagggc  74700
accatggaca cccaaccgtc atccccaggg gaggacacag cccagggcac catggacacc  74760
caaccctcat ccccagggga ggacacagcc cagggtatct tggacaccca gccctcattc  74820
ctaggggagt acacagccca gggcatcttg gacatccaac cctcatcccc agggaaggac  74880
acagcccagg gcatcttgga cacccaaccc tcattcccat aagagcacac agcccagggc  74940
atcgtggagg cccgaccctc atccctaggg gaggacacag cccagggcac catggacacc  75000
caaccctcat ccccagggga agacacaacc caggccacca ttaacaccca atcatgtgca  75060
gggagggtgt ccttggagcc tgggactctt gccagtgaag cggtggacaa gaaactgagg  75120
atgcgatcag cacacagaaa tctcaggcag cctaggatac atgaggcctc tcacccctgg  75180
gaacactgag cagccaccag gagcccacac cttgaggtac agcaggagcc atgcgctctt  75240
gctcttgctc actcacactc ctgcacacag ccactgacac acgccctcgt gcacgttgca  75300
gattaactcc actggccttg cacttgcaac gctggaggct gagaggtatc cccaggttct  75360
tttctcgtga gaggggcagg ctgactttca ctctcctcca tgtgctagag gcagctccac  75420
caacactggc tgccctgagt ggatgcacct ggctctggaa ttcctgtcat ttgctttgga  75480
tccaggagcc cctgcctcat gtagctactt aacagaaagg aggaatccac ccaggacatg  75540
cccagacggg agcctcacag gatggacagt ggtgtctggg gtcacgggca gccctgaccc  75600
agcagcgcca gcaccagcac acccagtggg gaaggcgggg aggcccaaac gccacccaca  75660
gtttgttact ccactgggtg ggacccggca cccctgcctt cctgacaccc tggagtccct  75720
gcctcctcct agagccccca agcccatctg cctcagagca tccagagaca gacctgggga  75780
gccatttcct caggccctgg acaaggaaac agggaattcc aggttatggg tgcctggggc  75840
aggtctcagg caggtgctgg gaaccagaga gaggggtcac cgcgaggcct caggcctggc  75900
accagcactt tgagcctcag tttaccagcc cacgaggtgc tgagtctgga ctggatgacc  75960
ttcccacccc cagtgacctc tgccctttcc cgagcatgtc agctctgctc cagcatcctg  76020
gtgtgagcgc aatgccactt tttttctcaa caaatacgaa aggaggaagg tgcccccagg  76080
gccctgtgcc ctgaggatgc ctgtgtggag gggtccattt catcactggt gtcactcaca  76140
ggaagggacg aagccacctg ccttgacgga gcttactcca cctccgccga aggccgggga  76200
ggtccctcac agagaacctg aggcccagca ggctgcagag gtgctggcat ggaatgactg  76260
ctcagacgcc cggggccggc agagaggacg gatgtggggg aggtgcacac tgaggagcct  76320
ctccttggag gtggagacac gtgcaccaca tggaccagga cacagtccac gaagcctcgc  76380
```

-continued atccccctga gctgcagctc aagggcctct ctctgagccc agagtcccac ccctgggagg 76440
cagctgcccc agctctgagg gaggagggca tccaccaggc cctccatctc ctgggggcac 76500
cagcccagcc cagaggctct gcaggactct gcacctccaa ttcatggcca ggactttctg 76560
gatgtatctt aaggactgag gactccacat cagggaccac acaagaccgg ggtcccggac 76620
acgggggttg ggggtgagca tgtcaccggg atgggctgtg gcgtcactct ggtacttcat 76680
ccggacagcc agggaccaaa gccacgccct cagccccacc ccacccctgc ctcacatggc 76740
aacgcagggt ctgcagatgc aggagagtga gaagcatggt agccaggcag actagaggac 76800
ccgagctggg gttgagcacc tccctgtcta cccagggcat ggcctgtgag actgcaggtg 76860
gcctagtgtg tgctgcaggc tcaaggtcct gccccaggga gcatgacatt caggcccaga 76920
aattgcatcg tgctgcacac agtccaaggg gataaccctg tgaagttcag gtcaccagca 76980
ggcttggggt caagaccgag ctgcagagga caggtttctg gaaggcacag catcatgggt 77040
ggagggactt ggagcaaggt ccttagcccc gggaccagtg aatgtgtgcc cttataggga 77100
aagggggtct gtgcagaagc aagttagctg aaaatcatga agtggagagg ctcccctgga 77160
ttaaaggggt gagccctaat gtaatcacaa gtgtccttct aggaggttgg cagagggaga 77220
ctgacataga cagaagccag gtgaggtggg aagcggaggc agaggccgag agagcagacg 77280
ctacgccctg gccctgaaga cggaggagga gccgagagct cagggatgga gagactggag 77340
gaggcaggga agttctcccc gcaagcctgg agggagcatg gcctccagca cccccagacc 77400
ttggccctgc aggattcatc tggacctgtg gtataaatgg tgtttaagcc actgggctgt 77460
gcaaattgtc atagcagcca tggcgcattc ctagagggag ccctggtggg gacccagcag 77520
gcagcgacgg ggccctcaca agcctgtgag ccactcagag ccgcgagagt ggctaggctt 77580
ggtgaggtgc aggccacgcg cacctccact aaggcagcct tagggcccac acttcctctc 77640
tctctctctc tctctctatc tctctccctc cctccttccc tccctcccgc tctcttggtt 77700
ggacagctct ccatcatccc cctggacatg accacctccc aaggccgagc tggggcgctt 77760
tgctcgaggt gagcactgac atcctggggg tgtgaggggc acctgcccag cggccccgtg 77820
tgcaggatgg gcggtgggcc ctagctggca ctgggcatat ggcccggctg gtgcctgcag 77880
gctgcagctt ttctggggtg gctgggatca gtgaaggcct ccagagtctg ggcctgggat 77940
ccctgcagtg ctggctgagg acaggcgggg ctgggcagtg agggcactgg gtcactatca 78000
ccacccacgg tttattactt cactaggtgg gacctggcac ccctgccttc ctgacaccct 78060
ggaatccctg cctcctccta cagcccccaa gcccatctcc ctcagagcct ccagagacag 78120
acctggggag gcatttcttc tgcccccagc agaagcccgg gaggccggga aggcacagtg 78180
ggtctaaagg agaggatccc aggactgcct gaggggtgac tccgacgagg caagcataga 78240
gcccactgag aagcggggtg ggagccccac cagggatggg ctagttcctc atgaaggacc 78300
aggacccagg aaggacaagg gggcctgctg gggcagggtc tgctatgccg gagtccctgt 78360
gagcctggcc cagacctgcc tctctctttc ctcattggtc cccacaggtc cgtggtggtt 78420
gccgtatcgg gaggccccat ggtggcaggg gtgggacacc tggtatacgt cgccaggtgt 78480
gtccaatagg ctcatgctca caccttctcc tggcacctgg gcaaagcctg agcacccagg 78540
cactgaagtg agggcaaggc ctcggggccc cacaggatgg ccgaggagac agctgcaggg 78600
cgcctgggac ccctgggctc aggaggtaga aggatacagc ctgaaaaccc acaccacaag 78660
ctcaccggcc agtgcaggcc cacagagctc gaggaggcag ccctgagcct cccagggaga 78720
gatgctctgt gcacgccggc acaggccctg ggttacaaac cctaggcaca gcccaggaga 78780
ggcccaggcc ccagtccagc aaggggttgc aggaagcaag aggtccccgg ccacagcatg 78840
agataagccc atcaagccag ggccaggtgg gcaatgggag gcaggcaggg cttgggggtg 78900
agtccctgct gcagcgccgt ccactgtcga ccggaggagt ttcttccctg tgcggagtcc 78960
acgggcctcc tgtgagtgtg tgcatgggca caagtgtgtg tgtggctctg ctgtgtgtct 79020
gtacacacat atgttttggg ttttttgtg tctcagacca cagagtctgc ccctcccacc 79080
aaagcccagg cagaaggatg aacccacgcc cctggggccc aggcctcagc agcctctgcg 79140
ggatcattgt tcccagttgt cacttgcctt tgccacagcc ctatttctcc acaattcctt 79200
aaagtcctca acatgcattt aaggcacaaa ggtgaaactg cccagaaaca tctgactccg 79260
ccgtggaacc caggagcaag ctgggttagc taaggagcgg ggccgttggc agaggctggg 79320
gatccaggct gaactttgga ggaggcatgt cccagcatgg gctcctgact atgtcctcct 79380
gggacaaacc caaacccgct ctttgaatat gggagggact ttgctggccc cggccctgac 79440
cgcagcactt ggaaactgag gagtggtcgc ctcctccgtg tcacagctgc ccgttcacca 79500
tcatagaagc aactctgtca cctccatggg cccctctgtg gctgctgcct gggtccaagc 79560
tgagcccagc tgcccaggcc cagaaggaaa gcccaggcca ggtgcccagc acagaggcag 79620
tcacataccc cggggagagc cacagcaagc agccaatatt gcccaggaga ggagtagctg 79680
acaaggcaga acgtgagctg ccatcggctc gagaggcttt gctggtcctc ctggggctct 79740
ggacatgacc aggaggagcg agggaagaag tcgcatggtg gtcccatcct gggtggggcc 79800
tgatggcagc tggccacccg tcccagagtg gcagccagat gccagcgcca ttcccacagt 79860
cacatcattg gtcacagaat gcaggacata gagtgtcttc tttccatcac agtgctgtcc 79920
agacccatag cctagggtag acctggaaga ttcaatgtcc acacccgggg ctggagcgta 79980
gccatgagcc acgcccctg cccgtgcatg gaaagccagc ccaagctctg ctccatccct 80040
agccaaagtc agtgtccttt ccccttctcc caagtgagct ctagccacct gcctaccctg 80100
ccatctgagg atgacagcct tcattccatt ggaacctggc tctgccacca gcaggcttgc 80160
agtcctgggc agactccgtc acctctctat gcctcagcct ttccatctgc acaggaggaa 80220
gatgatgatg gtggtgatga tgatggcgat ggtttccttt tgcatctgag gcaaggacta 80280
attgagatga tacacatcag gcactgggta tggtgctggt ccttcctgag cactcaatct 80340
atgtgagctg tccttgtgaa atgggtgtca ccacatttcc ccacgcagaa catcctttgt 80400
ctgccatact tgaaacgtct gccccaatac taacagctcc tcatggaaga tgtgcacacc 80460
cacccaccct catactccca aaggtgcccg tgctttatca agccaaagtc cagccaggaa 80520
ctttacagca gcatcccttt ccctctccaa gcaccaagga gcaaggcaaa gcactacatc 80580
ttccatctgg aggcaatgcc accctcttct cccattttca ctgccatccc taagaggcag 80640
tgcttcccca aaaggttcca tagcagcctg cctacagcaa ctctgttcac acgagtttca 80700
gcatccttgc agtggctccc ctgccatgct gtggctcttc attcaccctc ttctcctgct 80760
ccccgtgaca ggcatagatt ctgagtgatc tggatacatt gctttgttta ataacattac 80820
agcttctgtg ctgaaaaaga tacagcagat agagaaggca attgttgaac acaaaatagt 80880
gacagcagag atgacggcaa gttggcattt ttcttttcta gcaataaaac ttaaagctga 80940
ctcaaggaga aatggaaatc ataattggaa cagtaatcct caagaaagca ttaagattat 81000
taaataattg ccctcacaga tgacttcagg ccaagatggc tttatgggtg aagtttagac 81060
tttcacaaaa ctaatcagtt cccataagaa ctgctccagg atttggagga acatgggaaa 81120
gtctattaaa gggatcacaa ttcacagtcc ccagagtaaa acatgggcta acttgcattt 81180
tggcaaagag ccaaatgtta taaatgacat cctagaaggc caaattctgt ccatctcgtt 81240
gaacaaggac ttacaccagg aatttagaac tatttatagc tcatcccacc actcaggcca 81300
atgatgaccc atgatcatct caccagaaat ggaaagactc agatgattaa tagagtctca 81360
atttctctga gacatctaag agcccagccc aagcccagac ccaggagggc acccaggcct 81420
ggacagagaa cactgatatc acaccagccc tccagaggga agcagagact ccttcaagct 81480
ctggaaacac aggcccagac agctgcccaa agttgggcag gcttcactgc aaacccaaat 81540
catgaagcta ggtaacacct ttacagattc tttacattta aaaatcatca aaacaagagt 81600
aaataataaa ctcaaataat attaatctaa tatgtaaagg tcttgtacca ttattatgca 81660
aacaacatac ataagctaat aagaaaaaga acaaatccct taagaaatcg gcaaaaagga 81720
tataacacaa tttctaaaag aaaacaaatg gctagcacac ataaggaaaa cactttgtga 81780
acagacattc ttcagaacat tatttataat tataaaatag ttgaaagcaa gatagtgcct 81840
gaagaaatta tggtgcatac attagtggga ctattctgca aacattccca attatacttg 81900
tcacatatct gtgataacgt gacagccagc attcatgggg tgacctcatt tggtaaaagg 81960
gtgcaaagct caacacgcat tgtgagatga ctgtggtgta aaattagtgg gattattccg 82020
caaacattcc caattatact taccgcatat ctgtgataac atgacagcat tcatggggtg 82080
acctcatttg gtaaaagggt gcaaagctca acacgcattg tgagatgact ggtgtaaata 82140
caaagaccaa actgtgaaaa ggagtccatc aattaatcga tgcttacctt cagttttggg 82200
ctaattttta aagtatgcta taagcatatg ctcctgttat aacagaatgg agggattatg 82260
agagatgatg caggtgtgtc ctgggcctcc cctggcccac tgggccctag agatgccttc 82320
ccaggcatcg ctgtcagggc ttccctcaga gggagtcctg tattgacctc accaccaagg 82380
tctggagcag gggatcctta gatattggtt ggggttatct caccttaggt ctgaatatgg 82440
ggttgtctta gactgttttg tgctgttaga atagaatacc caagactggg aaatttatac 82500
tgaacggaaa tttatttctc acagttctag aggctgtgaa gtccaagagc acaggtgcca 82560
gagcaagtcc aagagcaagg gaaagtccaa agcaagtcca ggagcatctg gcgaggacct 82620
tcttgctgtg tcatcacatg gcggaaggca agaaagagag caagaggggg ccgaactcac 82680
ccttttataa cagcaccaat cccacccatg aggtggggac cttatgacct aatcactctt 82740
catactgtta caatggcaat gaaatttcaa catgagtttt ggaggagaga agcattcaaa 82800
ccacagcaag ggtgctccta cctcctctct cagggcatct gcagaaagag ctgcaactgc 82860
acgtccttcc tccgtccatc ctccatccct tcccaatgtc cgtgcatatc ctgtgaccca 82920
ggaggtctgg catagggggt gctcctgcct taggtctgag gccctgtctg aagaggggta 82980
ggtgaggagg ccatctgatg gtctgggcca agacagtcac aggacgcatc atttatcatc 83040
aaggaggctg agggttgagt ctccaggtcc agggaactcc ccacaaagtg ggaaccctgc 83100
ccagctccac acagcctctg ctgggggacc ctgctctggt gcagagcctg gggacaggtc 83160
ttgagctcag ccagagtctg cctccctgtc atttaggaac taaaccaagc ggcaggatgc 83220
tggagcccag cccccatctg accttacagg gccaaggctg gggccctggg ttcccctcaa 83280
ggcgcagcag gactggagcc ccaggcagtg caggagtggc caaagctggg gcttcctcca 83340
gagcccccaa gcatcacggc accaagaagg gtaggaccct ggcctgagga attggcacca 83400
aagccccaga aactaccctg gacaccatgg agagaggcct ggaggggaag caccaggcac 83460

-continued

```
tgcctcccct tctgatccca cctgaggtgg ctgccaagcc cagagagccg ctctgatgtc  83520
ccccagccct gcagcccagg gatacctgta ctgtgcccct gggggacccc tggccagtct  83580
gtgcaaagaa gtcaccaccc tacactcaga gacagtgggg gtcctcgtcc cacatcctca  83640
gagcatggcc cggctgctgc agggatggtc tcctggtcct cagagcatgg cccggctgct  83700
gcagggatgg tctcctggtc ctcagagcat ggcccagctg ctgcagggat ggtctcctgg  83760
aggcccccca gtgctctatt gtcagggctc cctccacccc cccgcaccaa gagagagcca  83820
gaccccagca aggcttccag tggcttcagg tcacacccct aggctgaccc cagccccatt  83880
aacacctgcc tgagaaagct ccacgcacca gaactgaccg tctgctccaa ctcttgacct  83940
cccgttctca gggcgtctgc tgaaaaggct gcaactgcac atccttcctc cgtccgttcc  84000
cgatgtccgt gtgtctcctg tggccaggaa ggtctttctc gggacctgag agccgctccc  84060
tgaagtgtcc ccattgggaa ggatggggcc tgtgtctcca ggctctggga ggacagaatc  84120
ctgacctcaa cagtggccgg cacggacaca actggcccca tcccggggac gctgaccagc  84180
gctgggcaac ttttcccttc cccgacgact gagccccgag caccctccct gctcccctac  84240
cacctccctt tacaaggctg tggcctctgc acagatgata atggagcttg gctcattccc  84300
ctagagtcgg tagggagtta aggacaaaac tcagtttcct ccacctgaac tcaagtctgc  84360
ctatgtttac ctaatcacac ctggtggaca gtttggacaa acttgcacac tcagagacac  84420
agacacttct agaaatcatt atctccctgc cccggggacc ccactccagc agaagtctgc  84480
taggcactgg cctgggccct cctgctgtcc taggaggctg ctgacctcct gcctggctcc  84540
tgtccccagg tccagagtca gagcagactc cagggacgct gcaggctagg aagccgcccc  84600
ctccaggcca gggtctagtg caggtgccca ggacaagaaa gattgtgaat gcaggaatga  84660
ctgggccaca cccctcccgt gcacgccccc tcttgccctg caccccacag cccagccccc  84720
cgtgctggat gcccccccac agcagaggtg ctgttctgtg atcccctggg aaagacgccc  84780
tcaacctcca ccctgtccca cggcccaagg aagacaagac acaggccctc tcctcacagt  84840
ctccccacct ggctcctgct gggaccctca aggtgtgaac agggaggatg gttgtctggg  84900
tggcccctag gagcccagat cttcactcta cagaccccaa cccaagcacc cccttctgca  84960
gggcccagct catccccctc ctcctccctc tgctctcctc tcgtcgcctc tacgggaaat  85020
ccgggactca gcagtaaccc tcaggaagca gggcccaggc gccgtttaat aggaggcttc  85080
ctcacaatga aacttttaga aagccttgac tacaatgatg accttggtgt ggctgtgaac  85140
actgtcagct cccacagctg ctgcagcaaa aaatgtccat agacagggtg ggggcccggg  85200
gtcgtctgct gtcctgctca gcccacagca cgcatggagg atctgaggtg ccacacctga  85260
cgcccaggcc agaacatgcc tccctccagg gtgacctgcc atgtcctgca ttgctggagg  85320
gacaggggca gcctatgagg atctggggcc aggagatgaa tcctattaac ccagaggaaa  85380
actaacagga cccaagcacc ctccccgttg aagctgacct gcccagaggg gcctgggccc  85440
accccacaca ccggggcgga atgtgtacag gccccggtct ctgtgggtgt tccgctaact  85500
ggggctccca gtgctcaccc cacaactaaa gcgagcccca gcctccagag cccccgaagg  85560
agatgccgcc cacaagccca gcccccatcc aggaggcccc agagctcagg gcgccggggc  85620
agattctgaa cagccccgag tcacggtggg tacaactgga acgaccaccg tgagaaaaac  85680
tgtgtccaaa actgtctcct ggcccctgct ggaggccgcg ccagagaggg gagcagccgc  85740
cccgaaccta ggtcctgctc agctcacacg acccccagca cccagagcac aacggagtcc  85800
ccattgaatg gtgaggacgg ggaccagggc tccagggggt catggaaggg gctggacccc  85860
```

atcctactgc tatggtccca gtgctcctgg ccagaactga ccctaccacc gacaagagtc 85920
cctcagggaa acgggggtca ctggcacctc ccagcatcaa ccccaggcag cacaggcata 85980
aaccccacat ccagagccga ctccaggagc agagacaccc cagtaccctg ggggacaccg 86040
accctgatga ctccccactg gaatccaccc cagagtccac caggaccaaa gaccccgccc 86100
ctgtctctgt ccctcactca ggacctgctg cggggcgggc catgagacca gactcgggct 86160
tagggaacac cactgtggcc ccaacctcga ccaggccaca ggcccttcct tcctgccctg 86220
cggcagcaca gactttgggg tctgtgcaga gaggaatcac agaggcccca ggctgaggtg 86280
gtgggggtgg aagaccccca ggaggtggcc cacttccctt cctcccagct ggaacccacc 86340
atgaccttct taagataggg gtgtcatccg aggcaggtcc tccatggagc tcccttcagg 86400
ctcctccccg gtcctcacta ggcctcagtc ccggctgcgg gaatgcagcc accacaggca 86460
caccaggcag cccagaccca gccagcctgc agtgcccaag cccacattct ggagcagagc 86520
aggctgtgtc tgggagagtc tgggctcccc accgcccccc cgcacacccc acccacccct 86580
gtccaggccc tatgcaggag ggtcagagcc ccccatgggg tatggactta gggtctcact 86640
cacgtggctc ccctcctggg tgaaggggtc tcatgcccag atccccacag cagagctggt 86700
caaaggtgga ggcagtggcc ccagggccac cctgacctgg accctcaggc tcctctagcc 86760
ctggctgccc tgctgtccct gggaggcctg gactccacca gaccacaggt ccagggcacc 86820
gcccataggt gctgcccaca ctcagttcac aggaagaaga taagctccag acccccaaga 86880
ctgggacctg ccttcctgcc accgcttgta gctccagacc tccgtgcctc ccccgaccac 86940
ttacacacgg gccagggagc tgttccacaa agatcaaccc caaaccggga ccgcctggca 87000
ctcgggccgc tgccacttcc ctctccattt gttcccagca cctctgtgct ccctccctcc 87060
tccctccttc aggggaacag cctgtgcagc ccctccctgc accccacacc ctggggaggc 87120
ccaaccctgc ctccagccct ttctccccg ctgctcttcc tgcccatcca gacaaccctg 87180
gggtcccatc cctgcagcct acaccctggt ctccacccag acccctgtct ctccctccag 87240
acacccctcc caggccaacc ctgcacatgc aggccctccc cttttctgct gccagagcct 87300
cagtttctac cctctgtgcc taccccctgc ctcctcctgc ccacaactcg agctcttcct 87360
ctcctggggc ccctgagcca tggcactgac cgtgcactcc cacccccaca ctgcccatgc 87420
cctcaccttc ctcctggaca ctctgacccc gctcccctct tggacccagc cctggtattt 87480
ccaggacaaa ggctcaccca agtcttcccc atgcaggccc ttgccctcac tgcccggtta 87540
cacggcagcc tcctgtgcac agaagcaggg agctcagccc ttccacaggc agaaggcact 87600
gaaagaaatc ggcctccagc accctgatgc acgtccgcct gtgtctctca ctgcccgcac 87660
ctgcagggag gctcggcact ccctgtaaag acgagggatc caggcagcaa catcatggga 87720
gaatgcaggg ctcccagaca gcccagccct ctcgcaggcc tctcctggga agagacctgc 87780
agccaccact gaacagccac ggagcccgct ggatagtaac tgagtcagtg accgacctgg 87840
agggcagggg agcagtgaac cggagcccag accataggga cagagaccag ccgctgacat 87900
cccgagcccc tcactggcgg ccccagaaca ccgcgtggaa acagaacaga cccacattcc 87960
cacctggaac agggcagaca ctgctgagcc cccagcacca gccctgagaa acaccaggca 88020
acggcatcag agggggctcc tgagaaagaa aggaggggag gtctccttca ccagcaagta 88080
cttcccttga ccaaaaacag ggtccacgca actcccccag gacaaaggag gagccccctg 88140
tacagcactg ggctcagagt cctctcccac acaccctgag tttcagacaa aaaccccctg 88200
gaaatcatag tatcagcagg agaactagcc agagacagca agaggggact cagtgactcc 88260
cgcggggaca ggaggatttt gtgggggctc gtgtcactgt gaggatattg tagtagtacc 88320
agctgctata cccacagtga cacagcccca ttcccaaagc cctgctgtaa acgcttccac 88380
ttctggagct gaggggctgg ggggagcgtc tgggaagtag ggcctagggg tggccatcaa 88440
tgcccaaaac gcaccagact ccccccaga catcacccca ctggccagtg agcagagtaa 88500
acagaaaatg agaagcagct gggaagcttg cacaggcccc aaggaaagag ctttggcggg 88560
tgtgcaagag gggatgcggg cagagcctga gcagggcctt ttgctgtttc tgctttcctg 88620
tgcagatagt tccataaact ggtgttcaag atcgatggct gggagtgagc ccaggaggac 88680
agtgtgggaa gggcacaggg aaggagaagc agccgctatc ctacactgtc atctttcaag 88740
agtttgccct gtgcccacaa tgctgcatca tgggatgctt aacagctgat gtagacacag 88800
ctaaagagag aatcagtgaa atggatttgc agcacagatc tgaataaatt ctccagaatg 88860
tggagccaca cagaagcaag cacaaggaaa gtgcctgatg caagggcaaa gtacagtgtg 88920
taccttcagg ctgggcacag acactctgaa aagccttggc aggaactccc tgcaacaaag 88980
cagagccctg caggcaatgc cagctccaga gccctccctg agagcctcat gggcaaagat 89040
gtgcacaaca ggtgtttctc atagccccaa actgagaatg aagcaaacag ccatctgaag 89100
gaaaacaggc aaataaacga tggcaggttc atgaaatgca aacccagaca gccagaagga 89160
caacagtgag ggttacaggt gactctgtgg ttgagttcat gacaatgctg agtaattgga 89220
gtaacaaagg aaagtccaaa aaatactttc aatgtgattt cttctaaata aaatttacag 89280
ccggcaaaat gaactatctt cttaagggat aaactttcca ctaggaaaac tataaggaaa 89340
atcaagaaaa ggatgatcac ataaacacag tggtcgttac ttctactggg gaaggaagag 89400
ggtatgaact gagacacaca gggttggcaa gtctcctaac aagaacagaa caaatacatt 89460
acagtacctt gaaaacagca gttaaaattc taaattgcaa gaagaggaaa atgcacacag 89520
ctgtgtttag aaaattctca gtccagcact gttcataata gcaaagacat taacccaggt 89580
tggataaata aacgatgaca caggcaattg cacaatgata cagacataca ttcagtatat 89640
gagacattga tgatgtatcc ccaaagaaat gactttaaag agaaaaggcc tgatatgtgg 89700
tggcactcac ctccctgggc atccccggac aggctgcagg cacactgtgt ggcagggcag 89760
gctggtacct gctggcagct cctggggcct gatgtggagc aggcacagag ccgtatcccc 89820
ccgaggacat ataccccaa ggacggcaca gttggtacat tccggagaca agcaactcag 89880
ccacactccc aggccagagc ccgagaggga cgcccatgca cagggaggca gagcccagct 89940
cctccacagc cagcagcacc cgtgcagggg ccgccatctg gcaggcacag agcatgggct 90000
gggaggaggg gcagggacac caggcagggt tggcaccaac tgaaaattac agaagtctca 90060
tacatctacc tcagccttgc ctgacctggg cctcacctga cctggacctc acctggcctg 90120
gacctcacct ggcctagacc tcacctctgg gcttcacctg agctcggcct cacctgactt 90180
ggaccttgcc tgtcctgagc tcacatgatc tgggcctcac ctgacctggg tttcacctga 90240
cctgggcttc acctgacctg ggcctcatct gacctgggcc tcactggcct ggacctcacc 90300
tggcctgggc ttcacctggc ctcaggcctc atctgcacct gctccaggtc ttgctggaac 90360
ctcagtagca ctgaggctgc aggggctcat ccagggttgc agaatgactc tagaacctcc 90420
cacatctcag ctttctgggt ggaggcacct ggtggcccag ggaatataaa aagcctgaat 90480
gatgcctgcg tgatttgggg gcaatttata aacccaaaag gacatggcca tgcagcgggt 90540
agggacaata cagacagata tcagcctgaa atggagcctc agggcacagg tgggcacgga 90600
cactgtccac ctaagccagg ggcagacccg agtgtccccg cagtagacct gagagcgctg 90660
ggcccacagc ctcccctcgg tgccctgcta cctcctcagg tcagccctgg acatcccggg 90720
tttccccagg cctggcggta ggtttggggt gaggtctgtg tcactgtggt attacgattt 90780
ttggagtggt tattataccc acagtgtcac agagtccatc aaaaacccat ccctgggaac 90840
cttctgccac agccctccct gtggggcacc gccgcgtgcc atgttaggat tttgactgag 90900
gacacagcac catgggtatg gtggctaccg cagcagtgca gcccgtgacc caaacacaca 90960
gggcagcagg cacaacagac aagcccacaa gtgaccaccc tgagctcctg cctgccagcc 91020
ctggagacca tgaaacagat ggccaggatt atcccatagg tcagccagac ctcagtccaa 91080
caggtctgca tcgctgctgc cctccaatac cagtccggat ggggacaggg ctggcccaca 91140
ttaccatttg ctgccatccg gccaacagtc ccagaagccc ctccctcaag gctgggccac 91200
atgtgtggac cctgagagcc ccccatgtct gagtaggggc accaggaagg tggggctggc 91260
cctgtgcact gtccctgccc ctgtggtccc tggcctgcct ggccctgaca cctgggcctc 91320
tcctgggtca tttccaagac agaagacatt cccaggacag ctggagctgg gagtccatca 91380
tcctgcctgg ccgtcctgag tcctgcgcct ttccaaacct cacccgggaa gccaacagag 91440
gaatcacctc ccacaggcag agacaaagac cttccagaaa tctctgtctc tctccccagt 91500
gggcaccctc ttccagggca gtcctcagtg atatcacagt gggaacccac atctggatcg 91560
ggactgcccc cagaacacaa gatggcccac agggacagcc ccacagccca gcccttccca 91620
gacccctaaa aggcgtccca ccccctgcat ctgccccagg gctcaaactc caggaggact 91680
gactcctgca caccctcctg ccagacatca cctcagcccc tcctggaagg gacaggagcg 91740
cgcaagggtg agtcagaccc tcctgccctc gatggcaggc ggagaagatt cagaaaggtc 91800
tgagatcccc aggacgcagc accactgtca atgggggccc cagacgcctg gaccagggcc 91860
tgcgtgggaa aggcctctgg gcacactcag gggctttttg tgaagggtcc tcctactgtg 91920
tgactacagt aactaccaca gtgatgaacc cagcagcaaa aactgaccgg actcccaagg 91980
tttatgcaca cttctccgct cagagctctc caggatcaga agagccgggc ccaagggttt 92040
ctgcccagac cctcggcctc tagggacatc ttggccatga cagcccatgg gctggtgccc 92100
cacacatcgt ctgccttcaa acaagggctt cagagggctc tgaggtgacc tcactgatga 92160
ccacaggtgc cctggcccct tccccaccag ctgcaccaga ccccgtcatg acagatgccc 92220
cgattccaac agccaattcc tggggccagg aatcgctgta gacaccagcc tccttccaac 92280
acctcctgcc aattgcctgg attcccatcc cggttggaat caagaggaca gcatccccca 92340
ggctcccaac aggcaggact cccacaccct cctctgagag gccgctgtgt tccgtagggc 92400
caggctgcag acagtccccc tcacctgcca ctagacaaat gcctgctgta gatgtcccca 92460
cctggaaaat accactcatg gagcccccag ccccaggtac agctgtagag agagtctctg 92520
aggcccctaa gaagtagcca tgcccagttc tgccgggacc ctcggccagg ctgacaggag 92580
tggacgctgg agctgggccc atactgggcc acataggagc tcaccagtga gggcaggaga 92640
gcacatgccg gggagcaccc agcctcctgc tgaccagagg cccgtcccag agcccaggag 92700
gctgcagagg cctctccagg gggacactgt gcatgtctgg tccctgagca gccccccacg 92760
tccccagtcc tgggggcccc tggcacagct gtctggaccc tctctattcc ctgggaagct 92820
cctcctgaca gccccgcctc cagttccagg tgtggttatt gtcagggggt gtcagactgt 92880
ggtggataca gctatggtta ccacagtggt gctgcccata gcagcaacca ggccaagtag 92940

-continued

```
acaggcccct gctgtgcagc cccaggcctc cagctcacct gcttctcctg gggctctcaa  93000
ggctgctgtt ttctgcactc tcccctctgt ggggagggtt ccctcagtgg gagatctgtt  93060
ctcaacatcc cacggcctca ttcctgcaag gaaggccaat ggatgggcaa cctcacatgc  93120
cgcggctaag atagggtggg cagcctggcg gggacaggac atcctgctgg ggtatctgtc  93180
actgtgccta gtggggcact ggctcccaaa caacgcagtc cttgccaaaa tccccacggc  93240
ctcccccgct aggggctggc ctgatctcct gcagtcctag gaggctgctg acctccagaa  93300
tggctccgtc cccagttcca gggcgagagc agatcccagg ccggctgcag actgggaggc  93360
cacccccctcc ttcccagggt tcactgcagg tgaccagggc aggaaatggc ctgaacacag  93420
ggataaccgg gccatccccc aacagagtcc accccctcct gctctgtacc ccgcaccccc  93480
caggccagcc catgacatcc gacaacccca caccagagtc actgcccggt gctgccctag  93540
ggaggacccc tcagccccca ccctgtctag aggactgggg aggacaggac acgccctctc  93600
cttatggttc ccccacctgg ctctggctgg gacccttggg gtgtggacag aaaggacgct  93660
tgcctgattg gcccccagga gcccagaact tctctccagg gaccccagcc cgagcacccc  93720
cttacccagg acccagccct gcccctcctc ccctctgctc tcctctcatc accccatggg  93780
aatccagaat ccccaggaag ccatcaggaa gggctgaggg aggaagtggg gccactgcac  93840
caccaggcag gaggctctgt ctttgtgaac ccagggaggt gccagcctcc tagagggtat  93900
ggtccaccct gcctatggct cccacagtgg caggctgcag ggaaggacca gggacggtgt  93960
gggggagggc tcagggcccc gcgggtgctc catcttggat gagcctatct ctctcaccca  94020
cggactcgcc cacctcctct tcaccctggc cacacgtcgt ccacaccatc ctaagtccca  94080
cctacaccag agccggcaca gccagtgcag acagaggctg gggtgcaggg gggccgactg  94140
ggcagcttcg gggagggagg aatggaggaa ggggagttca gtgaagaggc ccccctcccc  94200
tgggtccagg atcctcctct gggacccccg gatcccatcc cctccaggct ctgggaggag  94260
aagcaggatg ggagaatctg tgcgggaccc tctcacagtg gaatacctcc acagcggctc  94320
aggccagata caaaagcccc tcagtgagcc ctccactgca gtgctgggcc tgggggcagc  94380
cgctcccaca caggatgaac ccagcacccc gaggatgtcc tgccaggggg agctcagagc  94440
catgaaggag caggatatgg gacccccgat acaggcacag acctcagctc cattcaggac  94500
tgccacgtcc tgccctggga ggaacccctt tctctagtcc ctgcaggcca ggaggcagct  94560
gactcctgac ttggacgcct attccagaca ccagacagag gggcaggccc cccagaacca  94620
gggatgagga cgccccgtca aggccagaaa agaccaagtt gcgctgagcc cagcaaggga  94680
aggtccccaa acaaaccagg aagtttctga aggtgtctgt gtcacagtgg agtatagcag  94740
ctcgtcccac agtgacactc gccaggccag aaaccccatc ccaagtcagc ggaatgcaga  94800
gagagcaggg aggacatgtt taggatctga ggccgcacct gacacccagg ccagcagacg  94860
tctcctgtcc acggcaccct gccatgtcct gcatttctgg aagaacaagg gcaggctgaa  94920
gggggtccag gaccaggaga tgggtccgct ctacccagag aaggagccag gcaggacaca  94980
agccccctcc ccattgaggc tgacctgccc agagggtcct gggcccaccc aacacaccgg  95040
ggcggaatgt gtgcaggcct cggtctctgt gggtgttccg ctagctgggg ctcacagtgc  95100
tcaccccaca cctaaaacga gccacagcct ccggagcccc tgaaggagac cccgcccaca  95160
agcccagccc ccacccagga ggccccagag cacagggcgc cccgtcggat tctgaacagc  95220
cccgagtcac agtgggtata actggaacta ccactgtgag aaaagcttcg tccaaaacgg  95280
tctcctggcc acagtcggag gccccgccag agaggggagc agccacccca aacccatgtt  95340
```

-continued ctgccggctc ccatgacccc gtgcacctgg agccccacgg tgtccccact ggatgggagg 95400
acaagggccg gggctccgg cgggtcgggg caggggcttg atggcttcct tctgccgtgg 95460
ccccattgcc cctggctgga gttgaccctt ctgacaagtg tcctcagaga gtcagggatc 95520
agtggcacct cccaacatca accccacgca gcccaggcac aaaccccaca tccagggcca 95580
actccaggaa cagagacacc ccaataccct gggggacccc gaccctgatg actcccgtcc 95640
catctctgtc cctcacttgg ggcctgctgc ggggcgagca cttgggagca aactcaggct 95700
taggggacac cactgtgggc ctgacctcga gcaggccaca gacccttccc tcctgccctg 95760
gtgcagcaca gactttgggg tctgggcagg gaggaacttc tggcaggtca ccaagcacag 95820
agcccccagg ctgaggtggc cccaggggga accccagcag gtggcccact acccttcctc 95880
ccagctggac cccatgtctt ccccaagata ggggtgccat ccaaggcagg tcctccatgg 95940 agccccctc aggctcctct ccagacccca ctgggcctca gtccccactc taggaatgca 96000
gccaccacgg gcacaccagg cagcccaggc ccagccaccc tgcagtgccc aagcccacac 96060
cctggaggag agcagggtgc gtctgggagg ggctgggctc cccaccccca cccccacctg 96120
cacaccccac ccacccttgc ccgggccccc tgcaggaggg tcagagcccc catgggatat 96180
ggacttaggg tctcactcac gcacctcccc tcctgggaga aggggtctca tgcccagatc 96240
cccccagcag cgctggtcac aggtagaggc agtggcccca gggccaccct gacctggccc 96300
ctcaggctcc tctagccctg gctgccctgc tgtccctggg aggcctgggc tccaccagac 96360
cacaggtcta gggcaccgcc cacactgggg ccgcccacac acagctcaca ggaagaagat 96420
aagctccaga cccccaggcc cgggacctgc cttgctgcta cgacttcctg ccccagacct 96480
cgttgccctc ccccgtccac ttacacacag gccaggaagc tgttcccaca cagaccaacc 96540
ccagacgggg accacctggc actcaggtca ctgccatttc cttctccatt cacttccaat 96600
gcctctgtgc ttcctccctc ctccttcctt cgggggagca ccctgtgcag ctcctccctg 96660
cagtccacac cctggggaga cccgaccctg cagcccacac cctggggaga cctgaccctc 96720
ctccagccct ttctccccg ctgctcttgc cacccaccaa gacagccctg gggtcctgtc 96780
cctacagccc ccacccagtt ctctacctag acccgtcttc ctccctctaa acacctctcc 96840
caggccaacc ctacacctgc aggccctccc ctccactgcc aaagaccctc agtttctcct 96900
gcctgtgccc acccccgtgc tcctcctgcc cacagctcga gctcttcctc tcctagggcc 96960
cctgagggat ggcattgacc gtgccctcgc acccacacac tgcccatgcc ctcacattcc 97020
tcctggccac tccagcccca ctcccctctc aggcctggct ctggtatttc tgggacaaag 97080
ccttacccaa gtctttccca tgcaggcctg ggcccttacc ctcactgccc ggttacaggg 97140
cagcctcctg tgcacagaag cagggagctc agcccttcca caggcagaag gcactgaaag 97200
aaatcggcct ccagcgcctt gacacacgtc tgcctgtgtc tctcactgcc cgcacctgca 97260
gggaggctcg gcactccctc taaagacgag ggatccaggc agcagcatca caggagaatg 97320
cagggctacc agacatccca gtcctctcac aggcctctcc tgggaagaga cctgaagacg 97380
cccagtcaac ggagtctaac accaaacctc cctggaggcc gatgggtagt aacggagtca 97440
ttgccagacc tggaggcagg ggagcagtga gcccgagccc acaccatagg gccagaggac 97500
agccactgac atcccaagcc actcactggt ggtcccacaa caccccatgg aaagaggaca 97560
gacccacagt cccacctgga ccagggcaga gactgctgag acccagcacc agaaccaacc 97620
aagaaacacc aggcaacagc atcagagggg gctctggcag aacagaggag gggaggtctc 97680

-continued

```
cttcaccagc aggcgcttcc cttgaccgaa gacaggatcc atgcaactcc cccaggacaa  97740
aggaggagcc ccttgttcag cactgggctc agagtcctct ccaagacacc cagagtttca  97800
gacaaaaacc ccctggaatg cacagtctca gcaggagagc cagccagagc cagcaagatg  97860
gggctcagtg acacccgcag ggacaggagg attttgtggg ggctcgtgtc actgtgagga  97920
tattgtacta atggtgtatg ctatacccac agtgacacag ccccattccc aaagccctac  97980
tgcaaacgca ttccacttct ggggctgagg ggctgggggga gcgtctggga aatagggctc  98040
aggggtgtcc atcaatgccc aaaacgcacc agactcccct ccatacatca cacccaccag  98100
ccagcgagca gagtaaacag aaaatgagaa gcaagctggg gaagcttgca caggccccaa  98160
ggaaagagct ttggcgggtg tgtaagaggg gatgcgggca gagcctgagc agggcctttt  98220
gctgtttctg ctttcctgtg cagagagttc cataaactgg tgttcgagat caatggctgg  98280
gagtgagccc aggaggacag cgtgggaaga gcacagggaa ggaggagcag ccgctatcct  98340
acactgtcat ctttcgaaag tttgccttgt gcccacactg ctgcatcatg ggatgcttaa  98400
cagctgatgt agacacagct aaagagagaa tcagtgagat ggatttgcag cacagatctg  98460
aataaattct ccagaatgtg gagcagcaca gaagcaagca cacagaaagt gcctgatgca  98520
aggacaaagt tcagtgggca ccttcaggca ttgctgctgg gcacagacac tctgaaaagc  98580
cctggcagga actccctgtg acaaagcaga accctcaggc aatgccagcc ccagagccct  98640
ccctgagagc ctcatgggca aagatgtgca caacaggtgt ttctcatagc cccaaactga  98700
gagcaaagca aacgtccatc tgaaggagaa caggcaaata aacgatggca ggttcatgaa  98760
atgcaaaccc agacagccac aagcacaaaa gtacagggtt ataagcgact ctggttgagt  98820
tcatgacaat gctgagtaat tggagtaaca aagtaaactc caaaaaatac tttcaatgtg  98880
atttcttcta aataaaattt acaccctgca aaatgaactg tcttcttaag ggatacattt  98940
cccagttaga aaaccataaa gaaaaccaag aaaaggatga tcacataaac acagtggtgg  99000
ttacttctgc tggggaagga agagggtatg aactgagata cacagggtgg gcaagtctcc  99060
taacaagaac agaacgaata cattacagta ccttgaaaac agcagttaaa cttctaaatt  99120
gcaagaagag gaaaatgcac acagttgtgt ttagaaaatt ctcagtccag cactgttcat  99180
aatagcaaag acattaaccc aggtcggata aataagcgat gacacaggca attgcacaat  99240
gatacagaca tatatttagt atatgagaca tcgatgatgt atccccaaat aaacgacttt  99300
aaagagataa agggctgatg tgtggtggca ttcacctccc tgggatcccc ggacaggttg  99360
caggctcact gtgcagcagg gcaggcgggt acctgctggc agttcctggg gcctgatgtg  99420
gagcaagcgc agggccatat atcccggagg acggcacagt cagtgaattc cagagagaag  99480
caactcagcc acactcccca ggcagagccc gagagggacg ccccacgcaca gggaggcaga  99540
gcccagcacc tccgcagcca gcaccacctg cgcacgggcc accaccttgc aggcacagag  99600
tgggtgctga gaggaggggc agggacacca ggcagggtga gcacccagag aaaactgcag  99660
acgcctcaca catccacctc agcctcccct gacctggacc tcactggcct gggcctcact  99720
taacctgggc ttcacctgac cttggcctca cctgacttgg acctcgcctg tcccaagctt  99780
tacctgacct gggcctcaac tcacctgaac gtctcctgac ctgggtttaa cctgtcctgg  99840
aactcacctg gccttggctt cccctgacct ggacctcatc tggcctgggc ttcacctggc  99900
ctgggcctca cctgacctgg acctcatctg gcctggacct cacctggcct ggacttcacc  99960
tggcctgggc ttcacctgac ctggacctca cctggcctcg ggcctcacct gcacctgctc 100020
caggtcttgc tggagcctga gtagcactga gggtgcagaa gctcatccag ggttggggaa 100080
```

tgactctaga agtctcccac atctgacctt tctgggtgga ggcagctggt ggccctggga 100140
atataaaaat ctccagaatg atgactctgt gatttgtggg caacttatga acccgaaagg 100200
acatggccat ggggtgggta gggacatagg gacagatgcc agcctgaggt ggagcctcag 100260
gacacaggtg ggcacggaca ctatccacat aagcgaggga tagacccgag tgtccccaca 100320
gcagacctga gagcgctggg cccacagcct cccctcagag ccctgctgcc tcctccggtc 100380
agccctggac atcccaggtt tccccaggcc tggcggtagg tttagaatga ggtctgtgtc 100440
actgtggtat tacgatattt tgactggtta ttataaccac agtgtcacag agtccatcaa 100500
aaacccatgc ctggaagctt cccgccacag ccctccccat ggggccctgc tgcctcctca 100560
ggtcagcccc ggacatcccg ggtttcccca ggctgggcgg taggtttggg gtgaggtctg 100620
tgtcactgtg gtattactat ggttcgggga gttattataa ccacagtgtc acagagtcca 100680
tcaaaaaccc atccctggga gcctcccgcc acagccctcc ctgcagggga ccggtacgtg 100740
ccatgttagg attttgatcg aggagacagc accatgggta tggtggctac cacagcagtg 100800
cagcctgtga cccaaacccg cagggcagca ggcacgatgg acaggcccgt gactgaccac 100860
gctgggctcc agcctgccag ccctggagat catgaaacag atggccaagg tcaccctaca 100920
ggtcatccag atctggctcc gaggggtctg catcgctgct gccctcccaa cgccagtcca 100980
aatgggacag ggacggcctc acagcaccat ctgctgccat caggccagcg atcccagaag 101040
cccctccctc aaggctgggc acatgtgtgg acactgagag ccctcatatc tgagtagggg 101100
caccaggagg gaggggctgg ccctgtgcac tgtccctgcc cctgtggtcc ctggcctgcc 101160
tggccctgac acctgagcct ctcctgggtc atttccaaga cagaagacat tcctggggac 101220
agccggagct gggcgtcgct catcctgccc ggccgtcctg agtcctgctc atttccagac 101280
ctcaccgggg aagccaacag aggactcgcc tcccacattc agagacaaag aaccttccag 101340
aaatccctgc ctctctcccc agtggacacc ctcttccagg acagtcctca gtggcatcac 101400
agcggcctga gatccccagg acgcagcacc gctgtcaata ggggccccaa atgcctggac 101460
cagggcctgc gtgggaaagg cctctggcca cactcgggct ttttgtgaag ggccctcctg 101520
ctgtgtgact acagtaacta ccatagtgat gaacccagtg gcaaaaactg gctggaaacc 101580
caggggctgt gtgcacgcct cagcttggag ctctccagga gcacaagagc cgggcccaag 101640
gatttgtgcc cagaccctca gcctctaggg acacctgggt catctcagcc tgggctggtg 101700
ccctgcacac catcttcctc caaatagggg cttcagaggg ctctgaggtg acctcactca 101760
tgaccacagg tgacctggcc cttccctgcc agctatacca gaccctgtct tgacagatgc 101820
cccgattcca acagccaatt cctgggaccc tgaatagctg tagacaccag cctcattcca 101880
gtacctcctg ccaattgcct ggattcccat cctggctgga atcaagaagg cagcatccgc 101940
caggctccca acaggcagga ctcccgcaca ccctcctctg agaggccgct gtgttccgca 102000
gggccaggcc ctggacagtt cccctcacct gccactagag aaacacctgc cattgtcgtc 102060
cccacctgga aaagaccact cgtggagccc ccagccccag gtacagctgt agagacagtc 102120
ctcgaggccc ctaagaagga gccatgccca gttctgccgg gaccctcggc caggccgaca 102180
ggagtggacg ctggagctgg gcccacactg ggccacatag gagctcacca gtgagggcag 102240
gagagcacat gccggggagc acccagcctc ctgctgacca gaggcccgtc ccagagccca 102300
ggaggctgca gaggcctctc cagggagaca ctgtgcatgt ctggtaccta agcagccccc 102360
cacgtcccca gtcctggggg cccctggctc agctgtctgg gccctccctg ctccctggga 102420
agctcctcct gacagccccg cctccagttc caggtgtggt tattgtcagg cgatgtcaga 102480
ctgtggtgga tatagtggct acgattacca cagtggtgcc gcccatagca gcaaccaggc 102540
caagtagaca ggcccctgct gcgcagcccc aggcatccac ttcacctgct tctcctgggg 102600
ctctcaaggc tgctgtctgt cctctggccc tctgtgggga gggttccctc agtgggaggt 102660
ctgtgctcca gggcagggat gattgagata gaaatcaaag gctggcaggg aaaggcagct 102720
tcccgccctg agaggtgcag gcagcaccac ggagccacgg agtcacagag ccacggagcc 102780
cccattgtgg gcatttgaga gtgctgtgcc cccggcaggc ccagccctga tggggaagcc 102840
tgtcccatcc cacagcccgg gtcccacggg cagcgggcac agaagctgcc aggttgtcct 102900
ctatgatcct catccctcca gcagcatccc ctccacagtg gggaaactga ggcttggagc 102960
accacccggc cccctggaaa tgaggctgtg agcccagaca gtgggcccag agcactgtga 103020
gtaccccggc agtacctggc tgcagggatc agccagagat gccaaaccct gagtgaccag 103080
cctacaggag gatccggccc cacccaggcc actcgattaa tgctcaaccc cctgccctgg 103140
agacctcttc cagtaccacc agcagctcag cttctcaggg cctcatccct gcaaggaagg 103200
tcaagggctg ggcctgccag aaacacagca ccctccctag ccctggctaa gacagggtgg 103260
gcagacggct gtggacggga catattgctg gggcatttct cactgtcact tctgggtggt 103320
agctctgaca aaaacgcaga ccctgccaaa atccccactg cctcccgcta ggggctggcc 103380
tggaatcctg ctgtcctagg aggctgctga cctccaggat ggctccgtcc ccagttccag 103440
ggcgagagca gatcccaggc aggctgtagg ctgggaggcc accccctgccc ttgccggggt 103500 tgaatgcagg tgcccaaggc aggaaatggc atgagcacag ggatgaccgg gacatgcccc 103560
accagagtgc gccccttcct gctctgcacc ctgcaccccc caggccagcc cacgacgtcc 103620
aacaactggg cctgggtggc agccccaccc agacaggaca gacccagcac cctgaggagg 103680
tcctgccagg gggagctaag agccatgaag gagcaagata tggggccccc gatacaggca 103740
cagatgtcag ctccatccag gaccacccag cccacaccct gagaggaacg tctgtctcca 103800
gcctctgcag gtcgggaggc agctgacccc tgacttggac ccctattcca gacaccagac 103860
agaggcgcag gccccccaga accagggttg agggacgccc cgtcaaagcc agacaaaacc 103920
aaggggtgtt gagcccagca agggaaggcc cccaaacaga ccaggaggtt tctgaaggtg 103980
tctgtgtcac agtggggtat agcagcagct ggtaccacag tgacactcac ccagccagaa 104040
accccattcc aagtcagcgg aagcagagag agcagggagg acacgtttag gatctgagac 104100
tgcacctgac acccaggcca gcagacgtct cccctccagg gcaccccacc ctgtcctgca 104160
tttctgcaag atcaggggcg gcctgagggg gggtctaggg tgaggagatg ggtcccctgt 104220
acaccaagga ggagttaggc aggtcccgag cactctcccc attgaggctg acctgcccag 104280
agagtcctgg gcccacccca cacaccgggg cggaatgtgt gcaggcctcg gtctctgtgg 104340
gtgttccgct agctggggct cacagtgctc accccacacc taaaatgagc cacagcctcc 104400
ggagcccccg caggagaccc cgcccacaag cccagccccc acccaggagg ccccagagct 104460
cagggcgccc cgtcggattc cgaacagccc cgagtcacag cgggtataac cggaaccacc 104520
actgtcagaa tagctacgtc aaaaactgtc cagtggccac tgccggaggc cccgccagag 104580
agggcagcag ccactctgat cccatgtcct gccggctccc atgaccccca gcacgcggag 104640
ccccacagtg tccccactgg atgggaggac aagagctggg gattccggcg ggtcggggca 104700
ggggcttgat cgcatccttc tgccgtggct ccagtgcccc tggctggagt tgacccttct 104760
gacaagtgtc ctcagagaga caggcatcac cggcgcctcc caacatcaac cccaggcagc 104820

-continued acaggcacaa accccacatc cagagccaac tccaggagca gagacacccc aataccctgg 104880
gggaccccga ccctgatgac ttcccactgg aattcgccgt agagtccacc aggaccaaag 104940
accctgcctc tgcctctgtc cctcactcag gacctgctgc cgggcgaggc cttgggagca 105000
gacttgggct taggggacac cagtgtgacc ccgaccttga ccaggacgca gacctttcct 105060
tcctttcctg gggcagcaca gactttgggg tctgggccag gaggaacttc tggcaggtcg 105120
ccaagcacag aggccacagg ctgaggtggc cctggaaaga cctccaggag gtggccactc 105180
cccttcctcc cagctggacc ccatgtcctc cccaagataa gggtgccatc caaggcaggt 105240
gctccttgga gccccattca gactcctccc tggaccccac tgggcctcag tcccagctct 105300
ggggatgaag ccaccacaag cacaccaggc agcccaggcc cagccaccct gcagtgccca 105360
agcacacact ctggagcaga gcagggtgcc tctgggaggg gctgagctcc ccaccccacc 105420
cccacctgca caccccaccc accccgccc agcggctctg caggagggtc agagccccac 105480
atggggtatg gacttagggt ctcactcacg tggctcccat catgagtgaa ggggcctcaa 105540
gcccaggttc ccacagcagc gcctgtcgca agtggaggca gaggcccgag ggccaccctg 105600
acctggtccc tgaggttcct gcagcccagg ctgccctgct gtccctggga ggcctgggct 105660
ccaccagacc acaggtccag ggcaccgggt gcaggagcca cccacacaca gctcacagga 105720
agaagataag ctccagaccc ccagggccag aacctgcctt cctgctactg cttcctgccc 105780
cagacctggg cgccctcccc cgtccactta cacacaggcc aggaagctgt tcccacacag 105840
aacaacccca aaccaggacc gcctggcact caggtggctg ccatttcctt ctccatttgc 105900
tcccagcgcc tctgtcctcc ctggttcctc cttcggggga acagcctgtg cagccagtcc 105960
ctgcagccca caccctgggg agacccaacc ctgcctgggg cccttccaac cctgctgctc 106020
ttactgccca cccagaaaac tctggggtcc tgtccctgca gtccctaccc tggtctccac 106080
ccagacccct gtgtatcact ccagacaccc ctcccaggca aaccctgcac ctgcaggccc 106140
tgtcctcttc tgtcgctaga gcctcagttt ctccccccctg tgcccacacc ctacctcctc 106200
ctgcccacaa ctctaactct tcttctcctg gagcccctga gccatggcat tgaccctgcc 106260
ctcccaccac ccacagccca tgccctcacc ttcctcctgg ccactccgac cccgcccccct 106320
ctcaggccaa gccctggtat ttccaggaca aaggctcacc caagtctttc ccaggcaggc 106380
ctgggctctt gccctcactt cccggttaca cgggagcctc ctgtgcacag aagcagggag 106440
ctcagccctt ccacaggcag aaggcactga aagaaatcgg cctccagcac cttgacacac 106500
gtccgcccgt gtctctcact gcccgcacct gcagggaggc tccgcactcc ctctaaagac 106560
aagggatcca ggcagcagca tcacgggaga atgcagggct cccagacatc ccagtcctct 106620
cacaggcctc tcctgggaag agacctgcag ccaccaccaa acagccacag aggctgctgg 106680
atagtaactg agtcaatgac cgacctggag ggcaggggag cagtgagccg gagcccatac 106740
catagggaca gagaccagcc gctgacatcc cgagctcctc aatggtggcc ccataacaca 106800
cctaggaaac ataacacacc cacagcccca cctggaacag ggcagagact gctgagcccc 106860
cagcaccagc cccaagaaac accaggcaac agtatcagag gggctcccg agaaagagag 106920
gaggggagat ctccttcacc atcaaatgct tcccttgacc aaaaacaggg tccacgcaac 106980
tcccccagga caaaggagga gccccctata cagcactggg ctcagagtcc tctctgagac 107040
accctgagtt tcagacaaca acccgctgga atgcacagtc tcagcaggag aacagaccaa 107100
agccagcaaa agggacctcg gtgacaccag tagggacagg aggattttgt gggggctcgt 107160

-continued

```
gtcactgtga ggatattgta gtggtggtag ctgctactcc cacagtgaca cagacccatt 107220
cccaaagccc tactgcaaac acacccactc ctggggctga ggggctgggg gagcgtctgg 107280
gaagtagggt ccaggggtgt ctatcaatgt ccaaaatgca ccagactccc cgccaaacac 107340
caccccacca gccagcgagc agggtaaaca gaaaatgaga ggctctggga agcttgcaca 107400
ggccccaagg aaagagcttt ggcgggtgtg caagagggga tgcaggcaga gcctgagcag 107460
ggccttttgc tgtttctgct ttcctgtgca gagagttcca taaactggtg ttcaagatca 107520
gtggctggga atgagcccag gagggcagtc tgtgggaaga gcacagggaa ggaggagcag 107580
ccgctatcct acactgtcat ctttcaaaag tttgccttgt gaccacacta ttgcatcatg 107640
ggatgcttaa gagctgatgt agacacagct aaagagagaa tcagtgagat gaatttgcag 107700
catagatctg aataaactct ccagaatgtg gagcagtaca gaagcaaaca cacagaaagt 107760
gcctgatgca aggacaaagt tcagtgggca ccttcaggca ttgctgctgg gcacagacac 107820
tctgaaaagc cttggcagga tctccctgcg acaaagcaga accctcaggc aatgccagcc 107880
ccagagccct ccctgagagc gtcatgggga aagatgtgca gaacagctga ttatcataga 107940
ctcaaactga gaacagagca aacgtccatc tgaagaacag tcaaataagc aatggtaggt 108000
tcatgcaatg caaacccaga cagccagggg acaacagtag agggctacag gcggctttgc 108060
ggttgagttc atgacaatgc tgagtaattg gagtaacaga ggaaagccca aaaaatactt 108120
ttaatgtgat ttcttctaaa taaaatttac accaggcaaa atgaactgtc ttcttaaggg 108180
ataaactttc ccctggaaaa actacaagga aaattaagaa aacgatgatc acataaacac 108240
agttgtggtt acttctactg gggaaggaag agggtatgag ctgagacaca cagagtcggc 108300
aagtctccaa gcaagcacag aacgaataca ttacagtacc ttgaatacag cagttaaact 108360
tctaaatcgc aagaacagga aaatgcacac agctgtgttt agaaaattct cagtccagca 108420
ctattcataa tagcaaagac attaacccag gttggataaa taaatgatga cacaggcaat 108480
tgcacaatga tacagacata catttagtac atgagacatc gatgatgtat ccccaaagaa 108540
atgactttaa agagaaaagg cctgatgtgt ggtggcactc acctccctgg gatccccgga 108600
caggttgcag gcacactgtg tggcagggca ggctggtaca tgctggcagc tcctggggcc 108660
tgatgtggag caagcgcagg gctgtatacc cccaaggatg gcacagtcag tgaattccag 108720
agagaagcag ctcagccaca ctgcccaggc agagcccgag agggacgccc acgtacaggg 108780
aggcagagcc cagctcctcc acagccacca ccacctgtgc acgggccacc accttgcagg 108840
cacagagtgg gtgctgagag gaggggcagg gacaccaggc agggtgagca cccagagaaa 108900
actgcagaag cctcacacat ccacctcagc ctcccctgac ctggacctca cctggtctgg 108960
acctcacctg gcctgggcct cacctgacct ggacctcacc tggcctgggc ttcacctgac 109020
ctggacctca cctggcctcc ggcctcacct gcacctgctc caggtcttgc tggaacctga 109080
gtagcactga ggctgcagaa gctcatccag ggttggggaa tgactctgga actctcccac 109140
atctgacctt tctgggtgga ggcatctggt ggccctggga atataaaaag ccccagaatg 109200
gtgcctgcgt gatttggggg caatttatga acccgaaagg acatggccat ggggtgggta 109260
gggacatagg gacagatgcc agcctgaggt ggagcctcag gacacagttg gacgcggaca 109320
ctatccacat aagcgaggga cagacccgag tgttcctgca gtagacctga gagcgctggg 109380
cccacagcct cccctcggtg ccctgctgcc tcctcaggtc agccctggac atcccgggtt 109440
tccccaggcc agatggtagg tttgaagtga ggtctgtgtc actgtggtat tatgattacg 109500
tttgggggag ttatcgttat acccacagca tcacacggtc catcagaaac ccatgccaca 109560
```

gccctccccg caggggaccg ccgcgtgcca tgttacgatt ttgatcgagg acacagcgcc 109620
atgggtatgg tggctaccac agcagtgcag cccatgaccc aaacacacag ggcagcaggc 109680
acaatggaca ggcctgtgag tgaccatgct gggctccagc ccgccagccc cggagaccat 109740
gaaacagatg gccaaggtca ccccacagtt cagccagaca tggctccgtg gggtctgcat 109800
cgctgctgcc ctctaacacc agcccagatg ggacaaggc caaccccaca ttaccatctc 109860
ctgctgtcca cccagtggtc ccagaagccc ctccctcatg gctgagccac atgtgtgaac 109920
cctgagagca ccccatgtca gagtaggggc agcagaaggg cggggctggc cctgtgcact 109980
gtccctgcac ccatggtccc tcgcctgcct ggccctgaca cctgagcctc ttctgagtca 110040
tttctaagat agaagacatt cccggggaca gccggagctg ggcgtcgctc atcccgcccg 110100
gccgtcctga gtcctgcttg tttccagacc tcaccaggga agccaacaga ggactcacct 110160
cacacagtca gagacaaaga accttccaga aatccctgtc tcactcccca gtgggcacct 110220
tcttccagga cattcctcgg tcgcatcaca gcaggcaccc acatctggat caggacggcc 110280
cccagaacac aagatggccc atggggacag ccccacaacc caggccttcc cagaccccta 110340
aaaggcgtcc cacccccctgc acctgcccca gggctaaaaa tccaggaggc ttgactcccg 110400
catacccctcc agccagacat cacctcagcc ccctcctgga ggggacagga gcccgggagg 110460
gtgagtcaga cccacctgcc ctcgatggca ggcggggaag attcagaaag gcctgagatc 110520
cccaggacgc agcaccactg tcaatggggg ccccagacgc ctggaccagg gcctgcgtgg 110580
gaaaggccgc tgggcacact caggggcttt ttgtgaaggc ccctcctact gtgtgactac 110640
ggtgactacc acagtgatga aactagcagc aaaaactggc cggacaccca gggaccatgc 110700
acacttctca gcttggagct ctccaggacc agaagagtca ggtctgaggg tttgtagcca 110760
gaccctcggc ctctagggac accctggcca tcacagcgga tgggctggtg ccccacatgc 110820
catctgctcc aaacaggggc ttcagagggc tctgaggtga cttcactcat gaccacaggt 110880
gccctggccc cttccccgcc agctacaccg aaccctgtcc caacagctgc cccagttcca 110940
acagccaatt cctggggccc agaattgctg tagacaccag cctcgttcca gcacctcctg 111000
ccaattgcct ggattcacat cctggctgga atcaagaggg cagcatccgc caggctccca 111060
acaggcagga ctcccgcaca ccctcctctg agaggccgct gtgttccgca gggccaggcc 111120
ctggacagtt cccctcacct gccactagag aaacacctgc cattgtcgtc cccacctgga 111180
aaagaccact cgtggagccc ccagccccag gtacagctgt agagagactc cccgagggat 111240
ctaagaagga gccatgcgca gttctgccgg gaccctcggc caggccgaca ggagtggaca 111300
ctggagctgg gcccacactg ggccacatag gagctcacca gtgagggcag gagagcacat 111360
gccggggagc acccagcctc ctgctgacca gaggcccgtc ccagagccca ggaggctgca 111420
gaggcctctc caggggggaca ctgtgcatgt ctggtccctg agcagccccc cacgtcccca 111480
gtcctggggg cccctggcac agctgtctgg accctccctg ttccctggga agctcctcct 111540
gacagccccg cctccagttc caggtgtggt tattgtcagg gggtgtcaga ctgtggtgga 111600
tacagctatg gttaccacag tggtgctgcc catagcagca accaggccaa gtagacaggc 111660
ccctgctgtg cagccccagg cctccacttc acctgcttct cctggggctc tcaaggtcac 111720
tgttgtctgt actctgccct ctgtggggag ggttccctca gtgggaggtc tgttctcaac 111780
atcccagggc ctcatgtctg cacggaaggc caatggatgg gcaacctcac atgccgcggc 111840
taagataggg tgggcagcct ggcgggggac agtacatact gctggggtgt ctgtcactgt 111900

-continued gcctagtggg gcactggctc ccaaacaacg cagtcctcgc caaaatcccc acagcctccc 111960
ctgctagggg ctggcctgat ctcctgcagt cctaggaggc tgctgacctc cagaatgtct 112020
ccgtccccag ttccagggcg agagcagatc ccaggccggc tgcagactgg gaggccaccc 112080
cctccttccc agggttcact ggaggtgacc aaggtaggaa atggccttaa cacagggatg 112140
actgcgccat cccccaacag agtcagcccc ctcctgctct gtaccccgca ccccccaggc 112200
cagtccacga aaaccagggc cccacatcag agtcactgcc tggcccggcc ctggggcgga 112260
cccctcagcc cccaccctgt ctagaggact tggggggaca ggacacaggc cctctcctta 112320
tggttccccc acctgcctcc ggccgggacc cttggggtgt ggacagaaag gacacctgcc 112380
taattggccc ccaggaaccc agaacttctc tccagggacc ccagcccgag cacccccctta 112440 cccaggaccc agccctgccc ctcctcccct ctgctctcct ctcatcaccc catgggaatc 112500
cggtatcccc aggaagccat caggaagggc tgaaggagga agcggggccg tgcaccaccg 112560
ggcaggaggc tccgtcttcg tgaacccagg gaagtgccag cctcctagag ggtatggtcc 112620
accctgcctg gggctcccac cgtggcaggc tgcggggaag gaccagggac ggtgtggggg 112680
agggctcagg gccctgcggg tgctcctcca tcttcggtga gcctcccccct tcacccaccg 112740 tcccgcccac ctcctctcca ccctggctgc acgtcttcca caccatcctg agtcctacct 112800
acaccagagc cagcaaagcc agtgcagaca aaggctgggg tgcagggggg ctgccagggc 112860
agcttcgggg agggaaggat ggagggaggg gaggtcagtg aagaggcccc cttcccctgg 112920
gtccaggatc ctcctctggg acccccggat cccatcccct cctggctctg ggaggagaag 112980
caggatggga gaatctgtgc gggaccctct cacagtggaa tatccccaca gcggctcagg 113040
ccagacccaa aagcccctca gtgagccctc cactgcagtc ctgggcctgg gtagcagccc 113100
ctcccacaga ggacagaccc agcaccccga agaagtcctg ccagggggag ctcagagcca 113160
tgaaagagca ggatatgggg tccccgatac aggcacagac ctcagctcca tccaggccca 113220
ccgggaccca ccatgggagg aacacctgtc tccgggttgt gaggtagctg gcctctgtct 113280
cggaccccac tccagacacc agacagaggg gcaggccccc caaaaccagg gttgagggat 113340
gatccgtcaa ggcagacaag accaaggggc actgacccca gcaagggaag gctcccaaac 113400
agacgaggag gtttctgaag ctgtctgtat cacagtgggg tatagcagtg gctggtacca 113460
cagtgacact cgccaggcca gaaaccccgt cccaagtcag cggaagcaga gagagcaggg 113520
aggacacgtt taggatctga ggccgcacct gacacccagg gcagcagacg tctcccctcc 113580
agggcaccct ccaccgtcct gcgtttcttc aagaataggg gcggcctgag gggtccagg 113640 gccaggcgat aggtcccctc taccccaagg aggagccagg caggacccga gcaccgtccc 113700
cattgaggct gacctgccca gacgggcctg ggcccacccc acacaccggg gcggaatgtg 113760
tgcaggcccc agtctctgtg ggtgttccgc tagctggggc ccccagtgct caccccacac 113820
ctaaagcgag ccccagcctc cagagccccc taagcattcc ccgcccagca gcccagcccc 113880
tgcccccacc caggaggccc cagagctcag ggcgcctggt cggattctga acagccccga 113940
gtcacagtgg gtataactgg aacgaccacc gtgagaaaaa ctgtgtccaa aactgactcc 114000
tggcagcagt cggaggcccc gccagagagg ggagcagccg gcctgaaccc atgtcctgcc 114060
ggttcccatg acccccagca cccagagccc cacggtgtcc ccgttggata atgaggacaa 114120
gggctggggg ctccggtggt ttgcggcagg gacttgatca catccttctg ctgtggcccc 114180
attgcctctg gctggagttg acccttctga caagtgtcct cagaaagaca gggatcaccg 114240
gcacctccca atatcaaccc caggcagcac agacacaaac cccacatcca gagccaactc 114300
caggagcaga gacaccccaa cactctgggg gaccccaacc gtgataactc cccactggaa 114360
tccgccccag agtctaccag gaccaaaggc cctgccctgt ctctgtccct cactcagggc 114420
ctcctgcagg gcgagcgctt gggagcagac tcggtcttag gggacaccac tgtgggcccc 114480
aactttgatg aggccactga cccttccttc ctttcctggg gcagcacaga ctttggggtc 114540
tgggcaggga agaactactg gctggtggcc aatcacagag cccccaggcc gaggtggccc 114600
caagaaggcc ctcaggaggt ggccactcca cttcctccca gctggacccc aggtcctccc 114660
caagataggg gtgccatcca aggcaggtcc tccatggagc cccccttcaga ctcctcccgg 114720
gaccccactg gacctcagtc cctgctctgg gaatgcagcc accacaagca caccaggaag 114780
cccaggccca gccaccctgc agtgggcaag cccacactct ggagcagagc agggtgcgtc 114840
tgggaggggc taacctcccc accccccacc ccccatctgc acacagccac ctaccactgc 114900
ccagaccctc tgcaggaggg ccaagccacc atggggtatg gacttagggt ctcactcacg 114960
tgcctcccct cctgggagaa ggggcctcat gcccagatcc ctgcagcact agacacagct 115020
ggaggcagtg gccccagggc caccctgacc tggcatctaa ggctgctcca gcccagacag 115080
cactgccgtt cctgggaagc ctgggctcca ccagaccaca ggtccagggc acagcccaca 115140
ggagccaccc acacacagct cacaggaaga agataagctc cagaccccag ggcgggacct 115200
gccttcctgc caccacttac acacaggcca gggagctgtt cccacacaga tcaaccccaa 115260
accgggactg cctggcacta gggtcactgc catttccctc tccattccct cccagtgcct 115320
ctgtgctccc tccttctggg gaacaccctg tgcagcccct ccctgcagcc cacacgctgg 115380
ggagacccca ccctgcctcg ggccttttct acctgctgca cttgccgccc acccaaacaa 115440
ccctgggtac gtgaccctgc agtcctcacc ctgatctgca accagacccc tgtccctccc 115500
tctaaacacc cctcccaggc caactctgca cctgcaggcc ctccgctctt ctgccacaag 115560
agcctcaggt tttcctacct gtgcccaccc cctaacccct cctgcccaca acttgagttc 115620
ttcctctcct ggagcccttg agccatggca ctgaccctac actcccaccc acacactgcc 115680
catgccatca ccttcctcct ggacactctg accccgctcc cctccctctc agacccggcc 115740
ctggtatttc caggacaaag gctcacccaa gtcttcccca tgcaggccct tgccctcact 115800
gcctggttac acgggagcct cctgtgcgca gaagcaggga gctcagctct tccacaggca 115860
gaaggcactg aaagaaatca gcctccagtg ccttgacaca cgtccgcctg tgtctctcac 115920
tgcctgcacc tgcagggagg ctccgcactc cctctaaaga tgagggatcc aggcagcaac 115980
atcacgggag aatgcagggc tcccagacag cccagccctc tcgcaggcct ctcctgggaa 116040
gagacctgca gccaccactg aacagccacg gaggtcgctg gatagtaacc gagtcagtga 116100
ccgacctgga gggcaggggga gcagtgaacc ggagcccata ccatagggac agagaccagc 116160
cgctaacatc ccgagcccct cactggcggc cccagaacac cccgtggaaa gagaacagac 116220
ccacagtccc acctggaaca gggcagacac tgctgagccc ccagcaccag ccccaagaaa 116280
cactaggcaa cagcatcaga gggggctcct gagaaagaga ggaggggagg tctccttcac 116340
catcaaatgc ttcccttgac caaaaacagg gtccacgcaa ctcccccagg acaaaggagg 116400
agccccctgt acagcactgg gctcagagtc ctctctgaga caggctcagt ttcagacaac 116460
aacccgctgg aatgcacagt ctcagcagga gagccaggcc agagccagca agaggagact 116520
cggtgacacc agtctcctgt agggacagga ggattttgtg ggggttcgtg tcactgtgag 116580
catattgtgg tggtgactgc tattcccaca gtgacacaac cccattccta aagccctact 116640

-continued gcaaacgcac ccactcctgg gactgagggg ctgggggagc gtctgggaag tatggcctag 116700
gggtgtccat caatgcccaa aatgcaccag actctcccca agacatcacc ccaccagcca 116760
gtgagcagag taaacagaaa atgagaagca gctgggaagc ttgcacaggc cccaaggaaa 116820
gagctttggc aggtgtgcaa gaggggatgt gggcagagcc tcagcagggc cttttgctgt 116880
ttctgctttc ctgtgcagag agttccataa actggtattc aagatcaatg gctgggagtg 116940
agcccaggag gacagtgtgg gaagagcaca gggaaggagg agcagccgct atcctacact 117000
gtcatctttt gaaagtttgc cctgtgccca caatgctgca tcatgggatg cttaacagct 117060
gatgtagaca cagctaaaga gagaatcagt gaaatgcatt tgcagcacag atctgaataa 117120
atcctccaga atgtggagca gcacagaagc aagcacacag aaagtgcctg atgccaaggc 117180
aaagttcagt gggcaccttc aggcattgct gctgggcaca gacactctga aaagcactgg 117240
caggaactgc ctgtgacaaa gcagaaccct caggcaatgc cagccctaga gcccttcctg 117300
agaacctcat gggcaaagat gtgcagaaca gctgtttgtc atagccccaa actatggggc 117360
tggacaaagc aaacgtccat ctgaaggaga acagacaaat aaacgatggc aggttcatga 117420
aatgcaaact aggacagcca gaggacaaca gtagagagct acaggcggct ttgcggttga 117480
gttcatgaca atgctgagta attggagtaa cagaggaaag cccaaaaaat acttttaatg 117540
tgatttcttc taaataaaat ttacacccgg caaaatgaac tatcttctta agggataaac 117600
tttcccctgg aaaaactata aggaaaatca agaaaacgat gatcacataa acacagtggt 117660
ggttacttct actggggaag gaagagggta tgagctgaga cacacagagt cggcaagtct 117720
cctaacaaga acagaacaaa tacattacag taccttgaaa acagcagtta aacttctaaa 117780
tcgcaagaag aggaaaatgc acacacctgt gtttagaaaa ttctcagtcc agcactgttc 117840
ataatagcaa agacattaac ccaggttgga taaataagcg atgacacagg caattgcaca 117900
atgatacaga catacattca gtatatgaga catcgatgat gtatccccaa agaaatgact 117960
ttaaagagaa aaggcctgat gtgtggtggc aatcacctcc ctgggcatcc ccggacaggc 118020
tgcaggctca ctgtgtggca gggcaggcag gcacctgctg gcagctcctg gggcctgatg 118080
tggagcaggc acagagctgt atatccccaa ggaaggtaca gtcagtgcat tccagagaga 118140
agcaactcag ccacactccc tggccagaac ccaagatgca cacccatgca cagggaggca 118200
gagcccagca cctccgcagc caccaccacc tgcgcacggg ccaccacctt gcaggcacag 118260
agtgggtgct gagaggaggg gcagggacac caggcagggt gagcacccag agaaaactgc 118320
agaagcctca cacatccacc tcagcctccc ctgacctgga cctcacctgg cctgggcctc 118380
acctgacctg gacctcacct ggcctgggct tcacctggcc tgggcttcac ctgacctgga 118440
cctcacctgg cctcgggcct cacctggcct gggcttcacc tggcctgggc ttcacctgac 118500
ctggacctca cctggcctgg gcctcacctg acctggacct cacctggcct gggcttcacc 118560
tggcctgggc ttcacctggc ctgggcttca cctgacctgg acctcacctg gcctgggctt 118620
cacctgacct ggacctcacc tggcctcggg cctcacctgc acctgctcca ggtcttgctg 118680
gagcctgagt agcactgagg ctgtagggac tcatccaggg ttggggaatg actctgcaac 118740
tctcccacat ctgacctttc tgggtggagg cacctggtgg cccagggaat ataaaaagcc 118800
ccagaatgat gcctgtgtga tttgggggca atttatgaac ccgaaaggac atggccatgg 118860
ggtgggtagg gacagtaggg acagatgtca gcctgaggtg aagcctcagg acacaggtgg 118920
gcatggacag tgtccaccta agcgagggac agacccgagt gtccctgcag tagacctgag 118980
agcgctgggc ccacagcctc ccctcggggc cctgctgcct cctcaggtca gccctggaca 119040

-continued tcccgggttt ccccaggcct ggcggtaggt ttgaagtgag gtctgtgtca ctgtggtatt 119100
actatgatag tagtggttat tactaccaca gtgtcacaga gtccatcaaa aactcatgcc 119160
tgggagcctc ccaccacagc cctccctgcg ggggaccgct gcatgccgtg ttaggatttt 119220
gatcgaggac acggcgccat gggtatggtg gctaccacag cagtgcagcc catgacccaa 119280
acacacgggg cagcagaaac aatggacagg cccacaagtg accatgatgg gctccagccc 119340
accagcccca gagaccatga aacagatggc caaggtcacc ctacaggtca tccagatctg 119400
gctccaaggg gtctgcatcg ctgctgccct cccaacgcca aaccagatgg agacagggcc 119460
ggccccatag caccatctgc tgccgtccac ccagcagtcc cggaagcccc tccctgaacg 119520
ctgggccacg tgtgtgaacc ctgcgagccc cccatgtcag agtaggggca gcaggagggc 119580
ggggctggcc ctgtgcactg tcactgcccc tgtggtccct ggcctgcctg gccctgacac 119640
ctgagcctct cctgggtcat ttccaagaca ttcccaggga cagccggagc tgggagtcgc 119700
tcatcctgcc tggctgtcct gagtcctgct catttccaga cctcaccagg gaagccaaca 119760
gaggactcac ctcacacagt cagagacaac gaaccttcca gaaatccctg tttctctccc 119820
cagtgagaga aaccctcttc cagggtttct cttctctccc accctcttcc aggacagtcc 119880
tcagcagcat cacagcggga acgcacatct ggatcaggac ggcccccaga acacgcgatg 119940
gcccatgggg acagcccagc ccttcccaga cccctaaaag gtatccccac cttgcacctg 120000
ccccagggct caaactccag gaggcctgac tcctgcacac cctcctgcca gatatcacct 120060
cagccccctc ctggagggga caggagcccg ggagggtgag tcagacccac ctgccctcaa 120120
tggcaggcgg ggaagattca gaaaggcctg agatccccag gacgcagcac cactgtcaat 120180
gggggcccca gacgcctgga ccagggcctg tgtgggaaag gcctctggcc acactcaggg 120240
gctttttgtg aagggccctc ctgctgtgtg actacggtgg taactcccac agtgatgaaa 120300
ccagcagcaa aaactgaccg gactcgcagg gtttatgcac acttctcggc tcggagctct 120360
ccaggagcac aagagccagg cccgagggtt tgtgcccaga ccctcggcct ctagggacac 120420
ccgggccatc ttagccgatg ggctgatgcc ctgcacaccg tgtgctgcca aacaggggct 120480
tcagagggct ctgaggtgac ttcactcatg accacaggtg ccctggtccc ttcactgcca 120540
gctgcaccag accctgttcc gagagatgcc ccagttccaa aagccaattc ctggggccgg 120600
gaattactgt agacaccagc ctcattccag tacctcctgc caattgcctg gattcccatc 120660
ctggctggaa tcaagagggc agcatccgcc aggctcccaa caggcaggac tcccacacac 120720
cctcctctga gaggccgctg tgttccgcag ggccaggccg cagacagttc ccctcacctg 120780
cccatgtaga aacacctgcc attgtcgtcc ccacctggca aagaccactt gtggagcccc 120840
cagccccagg tacagctgta gagagagtcc tcgaggcccc taagaaggag ccatgcccag 120900
ttctgccggg accctcggcc aggccgacag gagtggacgc tggagctggg cccacactgg 120960
gccacatagg agctcaccag tgagggcagg agagcacatg ccggggagca cccagcctcc 121020
tgctgaccag agacccgtcc cagagcccag gaggctgcag aggcctctcc agggggacac 121080
agtgcatgtc tggtccctga gcagccccca ggctctctag cactgggggc ccctggcaca 121140
gctgtctgga ccctccctgt tccctgggaa gctcctcctg acagccccgc ctccagttcc 121200
aggtgtggtt attgtcaggg ggtgccaggc cgtggtagag atggctacaa ttaccacagt 121260
ggtgccgccc atagcagcaa ccaggccaag tagacagacc cctgccacgc agccccaggc 121320
ctccagctca cctgcttctc ctggggctct caaggctgct gtctgccctc tggccctctg 121380

-continued tggggagggt tccctcagtg ggaggtctgt gctccagggc agggatgact gagatagaaa 121440
tcaaaggctg gcagggaaag gcagcttccc gccctgagag gtgcaggcag caccacagag 121500
ccatggagtc acagagccac ggagccccca gtgtgggcgt gtgagggtgc tgggctcccg 121560
gcaggcccag ccctgatggg gaagcctgcc ccgtcccaca gcccaggtcc ccaggggcag 121620
caggcacaga agctgccaag ctgtgctcta cgatcctcat ccctccagca gcatccactc 121680
cacagtgggg aaactgagcc ttggagaacc acccagcccc ctggaaacaa ggcggggagc 121740
ccagacagtg ggcccagagc actgtgtgta tcctggcact aggtgcaggg accacccgga 121800
gatccccatc actgagtggc cagcctgcag aaggacccaa ccccaaccag gccgcttgat 121860
taagctccat ccccctgtcc tgggaacctc ttcccagcgc caccaacagc tcggcttccc 121920
aggccctcat ccctccaagg aaggccaaag gctgggcctg ccaggggcac agtaccctcc 121980
cttgccctgg ctaagacagg gtgggcagac ggctgcagat aggacatatt gctggggcat 122040
cttgctctgt gactactggg tactggctct caacgcagac cctaccaaaa tccccactgc 122100
ctcccctgct aggggctggc ctggtctcct cctgctgtcc taggaggctg ctgacctcca 122160
ggatggcttc tgtccccagt tctagggcca gagcagatcc caggcaggct gtaggctggg 122220
aggccacccc tgtccttgcc gaggttcagt gcaggcaccc aggacaggaa atggcctgaa 122280
cacagggatg actgtgccat gccctaccta agtccgcccc tttctactct gcaaccccca 122340
ctccccaggt cagcccatga cgaccaacaa cccaacacca gagtcactgc ctggccctgc 122400
cctggggagg acccctcagc ccccaccctg tctagaggag ttggggggac aggacacagg 122460
ctctctcctt atggttcccc cacctggctc ctgccgggac ccttggggtg tggacagaaa 122520
ggacgcctgc ctaattggcc cccaggaacc cagaacttct ctccagggac cccagcccga 122580
gcaccccctt acccaggacc cagccctgcc cctcctcccc tctgctctcc tctcatcact 122640
ccatgggaat ccagaatccc caggaagcca tcaggaaggg ctgaaggagg aagcggggcc 122700
gctgcaccac cgggcaggag gctccgtctt cgtgaaccca gggaagtgcc agcctcctag 122760
agggtatggt ccaccctgcc tggggctccc accgtggcag gctgcgggga aggaccaggg 122820
acggtgtggg ggagggctca gggccctgca ggtgctccat cttggatgag cccatccctc 122880
tcacccaccg acccgcccac ctcctctcca ccctggccac acgtcgtcca caccatcctg 122940
agtcccacct acaccagagc cagcagagcc agtgcagaca gaggctgggg tgcagggggg 123000
ccgccagggc agctttgggg agggaggaat ggaggaaggg gaggtcagtg aagaggcccc 123060
cctcccctgg gtctaggatc cacctttggg acccccggat cccatcccct ccaggctctg 123120
ggaggagaag caggatggga gattctgtgc aggaccctct cacagtggaa tacctccaca 123180
gcggctcagg ccagatacaa aagcccctca gtgagccctc cactgcagtg cagggcctgg 123240
gggcagcccc tcccacagag gacagaccca gcaccccgaa gaagtcctgc caggggggagc 123300 tcagagccat gaaggagcaa gatatgggga ccccaatact ggcacagacc tcagctccat 123360
ccaggcccac caggacccac catgggtgga acacctgtct ccggcccctg ctggctgtga 123420
ggcagctggc ctctgtctcg gacccccatt ccagacacca gacagaggga caggcccccc 123480
agaaccagtg ttgagggaca cccctgtcca gggcagccaa gtccaagagg cgcgctgagc 123540
ccagcaaggg aaggccccca aacaaaccag gaggtttctg aagctgtctg tgtcacagtc 123600
gggtatagca gcggctacca caatgacact gggcaggaca gaaaccccat cccaagtcag 123660
ccgaaggcag agagagcagg caggacacat ttaggatctg aggccacacc tgacactcaa 123720
gccaacagat gtctcccctc cagggcgccc tgccctgttc agtgttcctg agaaaacagg 123780

-continued ggcagcctga ggggatccag ggccaggaga tgggtcccct ctaccccgag gaggagccag 123840
gcgggaatcc cagccccctc cccattgagg ccatcctgcc cagaggggcc cggacccacc 123900
ccacacaccc aggcagaatg tgtgcaggcc tcaggctctg tgggtgccgc tagctggggc 123960
tgccagtcct caccccacac ctaaggtgag ccacagccgc cagagcctcc acaggagacc 124020
ccacccagca gcccagcccc tacccaggag gccccagagc tcagggcgcc tgggtggatt 124080
ctgaacagcc ccgagtcacg gtgggtatag tgggagctac taccactgtg agaaaagcta 124140
tgtccaaaac tgtctcccgg ccactgctgg aggcccagcc agagaaggga ccagccgccc 124200
gaacatacga ccttcccaga cctcatgacc cccagcactt ggagctccac agtgtcccca 124260
ttggatggtg aggatggggg ccggggccat ctgcacctcc caacatcacc cccaggcagc 124320
acaggcacaa accccaaatc cagagccgac accaggaaca cagacacccc aataccctgg 124380
gggaccctgg ccctggtgac ttcccactgg gatccacccc cgtgtccacc tggatcaaag 124440
accccaccgc tgtctctgtc cctcactcag ggcctgctga ggggcgggtg ctttggagca 124500
gactcaggtt taggggccac cattgtgggg cccaacctcg accaggacac agatttttct 124560
ttcctgccct ggggcaacac agactttggg gtctgtgcag ggaggacctt ctggaaagtc 124620
accaagcaca gagccctgac tgaggtggtc tcaggaagac cccaggaggg ggcttgtgc 124680 cccttcctct catgtggacc ccatgccccc caagataggg gcatcatgca gggcaggtcc 124740
tccatgcagc caccactagg caactccctg gcgccggtcc ccactgcgcc tccatcccgg 124800
ctctggggat gcagccacca tggccacacc aggcagcccg ggtccagcaa ccctgcagtg 124860
cccaagccct tggcaggatt cccagaggct ggagcccacc cctcctcatc cccccacacc 124920
tgcacacaca cacctacccc ctgcccagtc cccctccagg agggttggag ccgcccatag 124980
ggtgggggct ccaggtctca ctcactcgct tcccttcctg ggcaaaggag cctcgtgccc 125040
cggtcccccc tgacggcgct gggcacaggt gtgggtactg ggccccaggg ctcctccagc 125100
cccagctgcc ctgctctccc tgggaggcct gggcaccacc agaccaccag tccagggcac 125160
agccccaggg agccgcccac tgccagctca caggaagaag ataagcttca gaccctcagg 125220
gccgggagct gccttcctgc cacccccttcc tgccccagac ctccatgccc tcccccaacc 125280
acttacacac aagccaggga gctgtttcca cacagttcaa ccccaaacca ggacggcctg 125340
gcactcgggt cactgccatt tctgtctgca ttcgctccca gcgcccctgt gttccctccc 125400
tcctccctcc ttcctttctt cctgcattgg gttcatgccg cagagtgcca ggtgcaggtc 125460
agccctgagc ttggggtcac ctcctcactg aaggcagcct cagggtgccc aggggcaggc 125520
agggtggggg tgaggcttcc agctccaacc gctccactag ccgagactaa ggaagtgaga 125580
ggcagccaga aatccagacc attccatagc aaatggattt cattaaagtt accagacttc 125640
agtgtaagta acatgagccc catgcacaac aatcccttat gaaggggaag tcagtgtcgc 125700
ctcggatttc ttgaaaaaca caaaaactta tcaatgcctg taaaagtctg ttggaaagaa 125760
aatatgattc aagaatgtta tgcccaacaa agctggcata ttttctaccc ggacacactc 125820
agggaatgtg gtcccttgag tgcttctctc actgcgtaaa tcctacgtgg tgtttaagca 125880
tattcataaa tgtgtatgtc tatttttatg tgtaagatgg ttcattttta ttttatttat 125940
tcaatatgta caataaagaa tattgacaaa taggctggac atggtggctc ccacctgtaa 126000
tcccagccct ttgggaggcc gaggcgggca gatcacctga ggtctggagt tcgagaccag 126060
cctggccaac atgatgaaaa cccatctcta ctaaaaatac aaagattagc caggcatggt 126120
ggtgcatgcc tgtaatccca gccactcagg aggctgagac aggagaaatg cgtgaacccg 126180
gaaggcggag gttgcagtga gccgagatca caccactgca ctccagcctg gcgacagagc 126240
aagattccat ctcaaaaaaa aaaaaagaca aagaaatttg tttttttgaa taaagacaaa 126300
tttcatcaca cgaagataaa gatgcaaagc tccagacagg aaggcacgga cagcacagtg 126360
aagcccggag cgggcgctgg ggggccaggg gcatggcggg ggtgccagcg tctctcggtt 126420
cctaccatgg ccactccagc ctgtgttctc acgaggatgg ctgtgcaatg ctaggagcgt 126480
gttcgaagct ctagggcaac cactggaagt gaggctgagg agcagagccc agaggcccgt 126540
ggagctgatg aaaagaaagc tggagaaagt gtttgctgcc tcccaacatg gtaagaaaag 126600
atagaaagag agagcacacg gcaaagggag cttgctgagg gactctttac aatggcttgc 126660
acagagctca gggggtctgg gaggctaggg ccctgcgcag ggcagtcacc ccagcctgct 126720
gaccaaggtt tgctgcaggc agctctgggg gtggttgagg cgcggtccct ggagccaccc 126780
ctcaagggaa cgaggcagca gagtgggcca aggcccaggt cggctgcaag gctgcccagg 126840
acttggggtc cttacatcag cagccactga tgcagctggc ccagagagag gcgccgagca 126900
ggttgcctcc aggggacaaa ccaggtcgga gagggtgagg cagtggatgg agccacaaca 126960
accccgggca cgggtgacac gcacgttcat gcacatctga cccttcctcc ctcaccaaac 127020
aggtccccct gccttcccca tggttgcgaa aaagcaaaat gtagacgttt tttctttttt 127080
aattcatgtt ttaattgaca aatgaagccg tatatattta ttgtgtacaa catgatgctt 127140
taaaatatgt atacatcgtg gaacagcaac gttgagctaa tttaacacgc attacttcac 127200
atacttgtca tcttttgtgg cgagaatgct taaaatccac tctcttagta ttttttaaga 127260
atgcaataca ttgttgtcaa ctgtggtcac cgtcatgcat agccaagctc ccgacctcac 127320
cctcctgcca gctcaggctg tgcatccttt caccagcatc ccccaccccg gcccctggcc 127380
ctggtaacta ccactctata ctctacgtat gagttcagct ttttaagatt ccacagatga 127440
atgagatcat acagtatttg ctttctatgc ctggcttatt ttagttaaca cactgtcctc 127500
cagatccatc cgttgttgca aatgacaggg tttcattctt tttaaagtct aaagagtatt 127560
ccattgtgtc aatggacctc atttgcttta tccatgcatc aactatggac atttaggttg 127620
attccatttc ttagctgttg tggatggtgc tgcagtaaac atggggctgc agatgtctct 127680
tcaacatact gacatcatgt cctttggata aatacccagt agtgggatcg ctggatcaca 127740
atgtacagtt ttttttttaa tggaaacttt catttttttgg tgaaattagg aaaacagata 127800
aaacccacag aatccaaaat atatgtgaag atgccaaaaa cagttgacat tgggcagagg 127860
tcacatggaa ggaagtgaat acatgacggg gtgtgagggc ccagaggcag ctgaaatacg 127920
ctttctaaac acaaggacct cttctgagag ggcagaagtt ttatcctgca catgcaatga 127980
ccagcacagc taaaatacac tttctaaaca tgaggacctc ttctgagagg gcagctttat 128040
cctgcaaatg caatgaccag cacaggaccc agaataaaga gagttgccag cggacgcctg 128100
gtgtccatgt gtccaggtga gttcgagatg cggacggcgc tggccagcca gtcacaccct 128160
aagtcaatct gctgcatgca tttgtccttg ccacagcaga aaacgagaaa gcctttgggc 128220
tgcaaagctt cacaggctcc tcttctcccg actccatgga aacagctaca aagagcaggc 128280
ccagtagagc ttaattcatg aaaatgagta ataaacttga actggaacag tatcgacttt 128340
ttagaaacgg cagcaaagtg tataaaaaat attcaccaga acaatatttc caaacgatga 128400
gatgagaatt tcagccaagt aatcctccat ggatagaaaa taatgaaggg attggattta 128460
tgaaggaaaa tcatggagct caaatacaag aaaagagaat caaaaatgaa caggaggaga 128520

-continued taaaatatgg tttggccaaa gttacaaaat aaatttttta aaaacccttc atcatggcaa 128580
gtagaaagag cgagaggaaa aacagatccc gtggaagaca caaataggac atggggagaa 128640
aaatgaatga gatgaaacag agcagaaata aaattttacg gaactaaaga caagtgatct 128700
gaacctgcct ggggcctggg ggacctcgcc accctgaagg gaaagaacat gcctggctgg 128760
ctttgccacc tgctcattgc agagccccac agcttgcaac aaacataggc ggtagccagg 128820
gagtggttac agcaggcctt gagcaagacc cagtgttgtg ctgacttcag gtctgaccca 128880
gcactgtcat agtggtggtg tccatagtgg tagtgggggt gcttgtgtca ctccacccccc 128940
atctccagga ggctcagaac agacagagag agactccatt tgtttgggag aaagtaaggg 129000
atgagaacaa gagtctctgc ctggtaatcc agagaattat tctagatctt ggccaagatt 129060
atcaaagcag tacctctatg agtcttttgg gcttggagtc cccctaaagc agatatagct 129120
aagatcacaa cacccaagtc cttttgaata tgtgggaaga cttcccaagg acaggagcaa 129180
acaaacaagc ccagactgca aaaaaacaag ccgagactgc aataaacacc tcactcttca 129240
atgcccaggc actgaagaac atctcctagc agcaacacca tccaggaaaa catggcctca 129300
accagtgaac taaataaggc accagggacc agtctcggag aaatagaggt atgttatctt 129360
tcagagaatt caaagtagct ttgttgagga aactcaaaga aattcaagat aacacagtga 129420
aggaattcag aatcctatcc gataaattta acagagattg aagcaattaa aaagaattaa 129480
gcagaaatta tggagctgaa aaatgcaatt ggcatactga aaaatgcatc agagtatttt 129540
catagcctca tatatcaagt agaagaaaga attagtgagc ttgaaaacag gctatttgga 129600
aaagcacgat aaaaggagac aaaagagaaa agaataaata acaatgaagc atatctacag 129660
gatctagaaa atagcctcaa aaggccaaat ctaagaatta ttagccttaa agaggaggta 129720
gagaaagagg gatggagagt ttattcaaag ggataataac agaaaacttc ccaaacctag 129780
agaaagatat caatatccaa atgcaagaag gatgtagtac accaaggaga tttaatgcaa 129840
agaagactac ctcaaggcat tcaatactca aactcccata tgacaaggac tttaaaaaga 129900
tcctaaaagc agcaaaagaa aagaaatgaa taaaatacta tggagctcca atatgtctgg 129960
cagcagactt ttcagtgaag actttatatg ccaggagaga gtgtcataat ggatttaaag 130020
tgctgaagga aaaaactttt accctcgaac agtatagctg gtgaaattat ccttcaaaca 130080
tgaaggagaa ataatttgtt tccagacaaa tgttgaggga tttcatgaac accagacctg 130140
tcttttaaga aatgctaaag ggagtacttc aatcagaaag aaacacgtta gtgaacaata 130200
agaaatcatc tgaaggcaca aaactcaccg gtaatagtaa gtacacagaa aaacacagaa 130260
tattataaca ctgtaactgt ggtgtgtaaa ctccttttgt ttgtttgttt gtttgtttgt 130320
ttgtttttgt ttttagacgg agttttgctc cagcccaggc tggagtgcaa tggcacaatc 130380
tcagctcact gcaacttcca cctcccgggt tcaagcaatt ctcctgcctc agcctcccaa 130440
gtagctggga ttacaggcat gtgctaccat gtccagctaa ttttgtattt tagtagagac 130500
ggtgtttcac catgttggtc aggctagcct tatcttgagt agaaaaacta aatgatgaag 130560
caatgaaaaa taataactac aacttttcaa gacatagtac aataagatat aaatcataac 130620
aaaaagttaa aaggtggagg gatgaagtta aggcatagag tctttattag ttttcttttt 130680
acttgtctgt ttatgcaaac agtgttaagt tgtcatcagt ttaaaataat gggtcataag 130740
atactatttg caagcctcat ggtaacgtca aaccaaaagc aatacaacag atacacaaaa 130800
aacaaaaagc aagaagctaa attacgtcat cagagaaaat caccttcact aaaaggaaga 130860

```
cggagaaaag aatgaagaga gagaagacca aaagcaaata gcaatatggc aggagtaagt 130920
ccttacttat caataatacc attgaatgta aatggactaa actctccaat caaaagacat 130980
agagtggctg aatcaattaa agaaaaaaca agacccattg atctgttgtc cacaagaaac 131040
acactttatc tataaagaca cacatagact gaaaacaaag ggatggaaaa agatactcca 131100
cgccaatgga aaccaaagaa agagcaggag tagctacact tatatcaggc aaaatagatt 131160
tcaagacaaa aactataaga agagacaagg tcactaatga taaacaggtc aattcagcaa 131220
gaggatataa caattgtaaa tatatatgca cccaatgctg gagcacccag atatataaag 131280
caagtattta ctagagctaa agagagaaat agactccaat gcaataatag ctggagattt 131340
caacatccca ctttcaacat tgaacagatc ctccagatag aaaatcaaca aagaaatatt 131400
ggacttaatc tgcactatcg accaaatgga tctaacagat atttacagaa catttcatcc 131460
aacagctgca gaacacacat tcttttcctc agcacataga tcattctcaa ggatagacca 131520
tatgttgggt cacaaaacaa gttttaaaat attcaaatac attgaaataa tatcaagcat 131580
cttctgtgac cacaatggac taaaactaga aatcaataac aagaggaatt ttggaaacta 131640
tataaatata tggaaattaa tgaatgctga gtgggtcaat gaagcaatta agaaggaaac 131700
tgaaattttt cttggaacga atgatcatgg aaacagaaaa taccaaaacc tatgggatac 131760
agcaaaagca gtactaagag ggaagtttac agctacaaat gcttacatta aaaaagaaga 131820
aaaacttcaa taaaaaaacc taacaatgca tcttaaagaa ctagaaaagc aagaggaaat 131880
caaatccaaa attagtagaa gaaaacagta aaggtcagag cagaaataag taaaattgaa 131940
atgaagaaaa caatacaaaa gatcaataaa acaacaggtt gttttcttga aaagttaaac 132000
aaaattgaca aacctttagc cagactaaga aaaaaagaca gaagatccaa ataaataaaa 132060
tcagagatga aaaaggtgac attacaactt acaccacaga aattcaaagg atcattagtg 132120
gctactataa gcaactatat gccaataaat tggaaaatct agaagaaatg cagaaattcc 132180
tagacacata caacctccca agattaaacc aagaagaaat tcaaaacctg aacagactga 132240
taacaagtaa tgagatcaaa gccgtaataa aaagcctccc agtaaagaga agcccaggac 132300
ccgacggctt cactgctgaa ttctaccaaa catttaaagt agaactaata ccaatcctac 132360
tcaaactatt ccaaaaaata gaggtggaag gaatacttca aaactcatta tacgaggcca 132420
gtattaacct gacaccaaaa ctagacaaag acacatgaaa aaaagaaaac tacaggccaa 132480
tatgtctgat gaatattgac acaaaaatcc tcaacaaaat actagcaaac caaattcaac 132540
tacacattag aaagttcact catcatgacc aagtggaatt tatctaactt gggatgcaaa 132600
gatggttcaa catatgcaaa tcaatcaatg tgatacatca tatcaacaga atgaacaaca 132660
aaaaccattt gatcatttaa ttgatactga aaaagcattt gataaaattc aacattcctt 132720
cataataaaa attctcttct atactaggta caaaagaaac ttacctcaac ataataaagc 132780
catatatgac agtcccacag tatgatacta aatgaggaaa aactgagagc ctttcctcta 132840
cgatctggaa catgacaaag atgcccactt tcatcactgt tattcaacat agtactggaa 132900
gtcctagctg gagcgatcag acaagagaaa gatataaaag acatccaaat tggaaaggaa 132960
taagtcaaat tatcctcatt tgcatatggt atgatcttct atttagagct aactaaagac 133020
tccaccaaaa aaagttatta gaactgacga acaaattcag taaagctgca ggatacaaaa 133080
tcaacataca aaaatcagta gcatttctat atgccaacaa tgaccaatgt gaaaaagaaa 133140
ttaaaaagta accctattta caataaccac aaataaacac ctaggaatta accaaagagg 133200
taaaagattt ctgtaatgaa aactataaaa cactgatgaa agaaattgaa gagtacacca 133260
```

aaaaatggaa agcaattgca tgttcatgga ttagaagaat cagtgttgtt ataatgtcca 133320
tactatccaa agcaatctac agattcaatg caatccttat caaaatacca atgacatcat 133380
tcacagaaat agaaaaaaaa aatcctaaaa tttacgtgga accacaaaga cccagaatag 133440
ccaaagctct cctaagcaaa aagaacgaaa ctgtaggaat gacattgcct gtcttcaaat 133500
tctactacag agctatagat agtaaccaaa acagcgtggt actggcataa aaacagacac 133560
agagacaaac agaacaaaat ttaaaaaccc agaaataaat ccacacacct acagcaaatt 133620
catttttgac aaagttgcca agaacatact ctggggaata gataatgata tctcttcaat 133680
aaatagtgtg gggaaaactg gatatccata tacataacag tgaaactaga cccctctctc 133740
tctcactata tacaaaaatc aaatcaaaat tgtttaagga cttaaatcta agacctcata 133800
ctatgaaacc actgcaagac aaccttggcg gaaactctcc aagacatcag tccaggcaaa 133860
gatttcttga gtaatatccc acaagcacag acaaccaaag caaaaatgga caaatgggat 133920
cacatcaagt taaaaagctt ctgcacagta agggaaacaa ccaacaaaat gaagagacaa 133980
cccacagaat gggagaaaat atttgaaaaa tacccatctg gcaagggatt aaaaaccaga 134040
atatatgcag aatatataag gagctcaaac agtgctatag aaaaaaaaat ctaataatct 134100
gatttaaaaa tgggaaaaat gttagaatag acatttctta aaataagaca tacagatggc 134160
aaaccgacat ggaacggtgc tcaacatcat ggattatcac agaaacacaa tcaatcaaaa 134220
ctaaaactaa aatgtgctat catctcaccc cagttaaaat ggctgatatc cagaagacag 134280
gcaataacaa atgctggcaa ggatgtgggg aaaagggagc cccatacac tgttgctggg 134340 attgtaaatt agtacaacca ctgtggagag cagcatgaaa gttcctcaaa aaactgaaag 134400
aaagctacca taggatccag caatcccact gctgtgtata tactacaaaa gaaaggaagt 134460
cagtatatga agaggtatct gcactcccat gtttgttgca gccctgttca caacagccaa 134520
gatttggaag caacctaagt gtccatcagc agttgaatgt ataaagaaaa tgtggtgcat 134580
atacacaatg gagtattatt caataataaa aaggaatgag attgagtcat ttgcaacaac 134640
atggatggaa ctggagatca ttatgtgaag tgaaataagc caggcacaga aagacaaaca 134700
ttacaatgtt cttacttatt aatgagatct aaaaatcaaa acaattgcac ccatgttcat 134760
aaagagtaaa aggatggtta ccagatgctg agaacggtgg tggggggata gggaaaggtg 134820
gcagtggtta acgggtacaa aaaaatagaa agaatgaata agacttgcta cttgatagca 134880
cagcaaggtg gctatagtca gtaatttagt tgtatatttt taataatgaa aggtgtataa 134940
ttggattgtt tctaacacaa aggataatgc ttaagaggat ggatacccca ttttccatga 135000
tgtgattatt tcacattgca cgcctagatc aaaacatcca atgtacccca taaatatata 135060
catcttctat gtacccataa aaattctgta aaataaaata tataaaaaga ggtgacagat 135120
atggaagaca ggcaaagaag agacgacatc cacataatcc gagtacctaa gaaagaatgg 135180
agtccagtgc atctcaggag ccaccattct aagccaattt tctctggttc tctcagtcac 135240
cctaccaata cgtgggcaat cttgttttat ttcaggatag agtttttgaa attatagatt 135300
taagtatgct ttctgttcta ttacttttgg taattaattt tagaaagaac taatttgggc 135360
acaaatttga aaaaattcta aatccaaaaa aaaaaagaaa aaaacacaca cacaatcatc 135420
tataaggggg atgatgacca gtcctagatt tctcaccagc cacattcaag atcagtaaat 135480
ggtaggacaa aacctgtagg gtccttaagg gggaaagaag tagtggatag tccagagtct 135540
atatacagcc aactgttctt gaagaaaaaa ggctgctgaa aaggagttcc aaacattcta 135600

-continued taatccataa tctcatgatg aaactactag aggaagacca ccagccatca aaaggtgctt 135660
ggagaaccca gggccaagaa ccaaaagtaa atattaagtg tccttaactg cgagactaag 135720
atagaaatga ctgtggggga ccatgtggcc tcaacagagg tgaaatggtg tctgcctgac 135780
aaagtggaca ttttacaatg atcaaaacac agaatatgag atagagagca cttctgaatt 135840
actgcctcac tccaaataac tctcagccaa aggacttcag taaaaccaaa ttgggcatat 135900
tagacagtac aaacaaattc taagaaaata atattactga ttacaatcac atgatgctag 135960
agatggaggg gaaaaggaag aggaaaccag gtaatttcat actcgtatat agtaaagaac 136020
taaagtacat tgtccaaaga agaacaaaga atattttgga aagttataaa ggtagccact 136080
acacatagaa gatagcaaag aacaagaaaa cttaagatgg aaaacttttt ggaagcataa 136140
gaatagaaaa tataaactac taagataaga ttgaagccaa acagatctat gaaaacaaca 136200
aacatcaatg gccttaactt gcctattaaa aggaagagac tttcaaattg gaccacaaga 136260
taaaacccaa ctctatatag catatgagta ttacacacaa aatgggaaaa gctgaaaaaa 136320
cttgggcaaa attcacccca agcaaattcc actgtttcct ttgggacaaa atgccaagct 136380
ccatgccagg gaagatgatt ctcctcagac cttctcctca ctctcccagt cctcttaggg 136440
aaggaattgg gtgttagagg agggagactc tgtcgattat cagctgaagc agtggtgtgc 136500
tcctgcgttg cttctgacct gggaaatgaa gcagcaagac tctttctgct gtgtctttgc 136560
ccagaagggc catcccccca gagcagagta cccaggccgg caggagcagt ggtggaagcg 136620
tggaaaccac gtctcctaca gcagagacca tcagaagcgg agcctcgggt ataagggaaa 136680
caacgcgttc tccctaacct gggagtgaca gacagcgtca ttcctcacag tgataccctg 136740
tgttctagcc atctggccca tgacagagcc agcccagagc cagcccagag ccagcccctc 136800
accatcctgg agcctggcca gctcgccaag ctgcaccata ggcctggaag gcgtggagac 136860
ctgcggcagt gccctgtcct cccgtgaggc ctgccatccc tgccaggggt cgcctctggc 136920
ttctccttct ccaggaccgc acggtccaga ggctcagtgc ctggagtagg tgttgcctcc 136980
ctgcttctag gcccagaccc tcccttgttc ctgaccccgg gcctttccct ctggcttgga 137040
catccagggc cctgtctcag ctggggagct gctcctgctc aaggactgtc ttccgcggga 137100
tcgaaaggcc gcgtcctgaa caatgcgtgg gccacgtaag cggagcaggc tctaaaggcc 137160
gcgtcctaaa cagtgcgtgg gccacgtgag cggagcaggc tctaaaggcc gcgtcctaaa 137220
cagtgcgtgg gccacgtgag cggagcaggc tctaaaggcc gcgtcctaaa cagtgcgtgg 137280
gccacgtgag cggagcaggc tctaaaggcc gcgtcctaaa cagtgcgtgg gccacgtgag 137340
cggagcaggc tctaaaggcc gcgtcctaaa cagtgcgtgg gccacgtgag cggagcaggc 137400
tctaaaggcc gcgtcctaaa cagtgcgtgg gccacgtgag cggagcaggc tctaaaggcc 137460
gcgtcctaaa cagtgcgtgg gccacgtgag cggagcaggc tctaaaggcc gcgtcctaaa 137520
cagtgcgtgg gccacgtgag cggagcaggc tctaaaggcc gcgtcctaaa cagtgcgtgg 137580
gccacgggag cggagcagac tctaaaggcc gcgtcctaaa cagtgtgtgg gccacgtgag 137640
cggagcgccc tctccactgc cctcggggcc gcagctccca gctcagctcc cagccctgct 137700
cagggcagcc aggccaggag gtaccatcca ggctaagtga ccctcagggg ggacaggtgc 137760
cccaggagat gccagctgtt gggagaggct gggggaccaa ctcgacctgg cctgtgggcc 137820
ctgccctggc cacccattgt aggatccagc cgccacgcct gtgacactcg tgtgctttcc 137880
ctggtgtgtg cttgtggcag gtgggggcag agggtcctca ggccagagag ccactccccc 137940
agcgccagac caccctcttc ctcactcccc cacctcaccc cctcacaggt gcctcccagg 138000

-continued ccatcagggc ccaaccaccc ctaaacaaat gggttctcgg cccctcgtgg ctggaggtgg 138060
gttctctcac cattcccagc ctaagactcc atccccatgc tggcagctgt tcaaccatgt 138120
ctagagagat ccactgtccc agacagcacc tcagggtccc ccgtcctgcc tggaaccctg 138180
taggaaactc cacaaaccgc cgccattctg tccacacccc tacaggagcc ccaaccctct 138240
ccccacatcc aggcttccct cccagacccc tcatccctgc ccgcacggtg cctgaggggg 138300
ccttcttggg cagcgcctaa gcaagccccc agcacccttc ggccccttca aggcacacag 138360
gccccctttc cacccagcct caggaaacca cctgtgtcct ccaacgacag gtcccagcct 138420
cccagccttt gccttgcctg ttcctctccc tggaactctg ccccgacaca gaccctcccc 138480
agcaagcccg caggggcacc tcccctgccc ccagacaccc tgtgcccgtc agttcatccc 138540
cagcagaggc cctcaccagg cacaccccca tgctcacacc tggccccagg cctcagcctc 138600
cctgagggcc ccacccagcc cgcgtctggc cagtggtgcg tgcaaagccc ctcacccaga 138660
ctcggcggaa ggcagccagt gcaggcctgg ggaggggctc tccttagacc accttgcacc 138720
ttccctggca cccaccatgg gaagagctga gactcactga ggaccagctg aggctcagag 138780
aagggaccca gcactggtgg acacgcaggg agcccacgcc agggcgccgt ggtgagtgag 138840
gcccagtgcc acccactgag gcctcccgtt cagtgggacg acggtgaaca ggtggaacca 138900
accaggcaac ccccgccggg ccccacagac gggatcagag caggaaaggc ttcctgcccc 138960
tgcaggccag cgaggagccc tggcgggggc cgtggccctc caggcgagga ggctcccctg 139020
gccaccgcca cccgggcctc tctgctgctg ggaaaacaag tcagaaagca agtggatgag 139080
aggtggcgtg acagacccag cttcagatct gctctaattt acaaaagaaa aggaaaaaca 139140
cacttggcag ccttcagcac tctaatgatt cttaacagca gcaaattatt ggcacaagac 139200
tccagagtga ctggcagggt tgagggctgg ggtctcccac gtgttttggg gctaacagcg 139260
gaagggagag cactggcaaa ggtgctgggg gcccctggac ccgacccgcc ctggagaccg 139320
cagccacatc agcccccagc cccacaggcc ccctaccagc cgcagggttt tggctgagct 139380
gagaaccact gtgctaactg ggacacagt gattggcagc tctacaaaaa ccatgctccc 139440
ccgggacccc gggctgtggg tttctgtagc ccctggctca gggctgactc accgtggctg 139500
aatacttcca gcactggggc cagggcaccc tggtcaccgt ctcctcaggt gagtctgctg 139560
tctggggata gcggggagcc aggtgtactg ggccaggcaa gggctttggc ttcagacttg 139620
gggacaggtg ctcagcaaag gaggtcggca ggagggcgga gggtgtgttt ttgtatggga 139680
gaagcaggag ggcagaggct gtgctactgg tacttcgatc tctggggccg tggcaccctg 139740
gtcactgtct cctcaggtga gtcccactgc agccccctcc cagtcttctc tgtccaggca 139800
ccaggccagg tatctggggt ctgcagccgg cctgggtctg gcctgaggcc acaccagctg 139860
ccatccctgg ggtctccgcc atgggctgca tgccagagcc ctgctgtcac ttagccctgg 139920
ggccagctgg agcccccaag gacaggcagg gaccccgctg ggcttcagcc ccgtcaggga 139980
ccctccacag gtagcaagca ggccgagggc agggacggga aggagaagtt gtgggcagag 140040
cctgggctgg ggctgggcgc tggctgttca tgtgccgggg accaggcctg cgctttagtg 140100
tggctacaag tgcttggagc actggggcca gggcagcccg gccaccgtct ccctgggaac 140160
gtcacccctc cctgcctggg tctcagcccg ggggtctgtg tggctgggga cagggacgcc 140220
ggctgcctct gctctgtgct tgggccatgt gacccattcg agtgtcctgc acgggcacag 140280
gtttgtgtct gggcaggaac agggactgtg tccctgtgtg atgcttttga tatctggggc 140340

-continued caagggacaa tggtcaccgt ctcttcaggt aagatggctt tccttctgcc tcctttctct 140400
gggcccagcg tcctctgtcc tggagctggg agataatgtc cgggggctcc ttggtctgcg 140460
ctgggccatg tggggccctc cggggctcct tctccggctg tttgggacca cgttcagcag 140520
aaggcctttc tttgggaact gggactctgc tgctggggca aagggtgggc agagtcatgc 140580
ttgtgctggg gacaaaatga ccttgggaca cggggctggc tgccacggcc ggcccgggac 140640
agtcggagag tcaggttttt gtgcacccct taatggggcc tcccacaatg tgactacttt 140700
gactactggg gccagggaac cctggtcacc gtctcctcag gtgagtcctc acaacctctc 140760
tcctgcttta actctgaagg gttttgctgc atttttgggg ggaaataagg gtgctgggtc 140820
tcctgccaag agagccccgg agcagcctgg ggggctcagg aggatgccct gaggcaacag 140880
cggccacaca gacgaggggc aagggctcca gatgctcctt cctcctgagc ccagcagcac 140940
gggtctctct gtggccaggg ccaccctagg cctctggggt ccaatgccca acaacccccg 141000
ggccctcccc gggctcagtc tgagagggtc ccagggacgt agcggggcgc cagttcttgc 141060
ctggggtcct ggcattgttg tcacaatgtg acaactggtt cgacccctgg ggccagggaa 141120
ccctggtcac cgtctcctca ggtgagtcct caccaccccc tctctgagtc cacttaggga 141180
gactcagctt gccagggtct cagggtcaga gtcttggagg cattttggag gtcaggaaag 141240
aaagccgggg agagggaccc ttcgaatggg aacccagcct gtcctcccca agtccggcca 141300
cagatgtcgg cagctggggg gctccttcgg ctggtctggg gtgacctctc tccgcttcac 141360
ctggagcatt ctcaggggct gtcgtgatga ttgcgtggtg ggactctgtc ccgctccaag 141420
gcacccgctc tctgggacgg gtgccccccg gggtttttgg actcctgggg gtgacttagc 141480
agccgtctgc ttgcagttgg acttcccagg ccgacagtgg tctggcttct gaggggtcag 141540
gccagaatgt ggggtacgtg ggaggccagc agagggttcc atgagaaggg caggacaggg 141600
ccacggacag tcagcttcca tgtgacgccc ggagacagaa ggtctctggg tggctgggtt 141660
tttgtggggt gaggatggac attctgccat tgtgattact actactacta cggtatggac 141720
gtctggggcc aagggaccac ggtcaccgtc tcctcaggta agaatggcca ctctagggcc 141780
tttgttttct gctactgcct gtggggtttc ctgagcattg caggttggtc ctcggggcat 141840
gttccgaggg gacctgggcg gactggccag gaggggacgg gcactggggt gccttgagga 141900
tctgggagcc tctgtggatt ttccgatgcc tttggaaaat gggactcagg ttgggtgcgt 141960
ctgatggagt aactgagcct ctagactgag cattgcagac taatcttgga tatttgtccc 142020
tgagggagcc ggctgagaga agttgggaaa taaactgtct agggatctca gagcctttag 142080
gacagattat ctccacatct ttgaaaaact aagaatctgt gtgatggtgt tggtggagtc 142140
cctggatgat gggataggga ctttggaggc tcatttgagg gagatgctaa aacaatccta 142200
tggctggagg gatagttggg gctgtagttg gagattttca gtttttagaa taaaagtatt 142260
agctgcggaa tatacttcag gaccacctct gtgacagcat ttatacagta tccgatgcat 142320
agggacaaag agtggagtgg ggcactttct ttagatttgt gaggaatgtt ccacactaga 142380
ttgtttaaaa cttcatttgt tggaaggaga gctgtcttag tgattgagtc aagggagaaa 142440
ggcatctagc ctcggtctca aaagggtagt tgctgtctag agaggtctgg tggagcctgc 142500
aaaagtccag ctttcaaagg aacacagaag tatgtgtatg gaatattaga agatgttgct 142560
tttactctta agttggttcc taggaaaaat agttaaatac tgtgacttta aaatgtgaga 142620
gggttttcaa gtactcattt ttttaaatgt ccaaaattct tgtcaatcag tttgaggtct 142680
tgtttgtgta gaactgatat tacttaaagt ttaaccgagg aatgggagtg aggctctctc 142740
ataacctatt cagaactgac ttttaacaat aataaattaa gtttcaaata tttttaaatg 142800
aattgagcaa tgttgagttg gagtcaagat ggccgatcag aaccagaaca cctgcagcag 142860
ctggcaggaa gcaggtcatg tggcaaggct atttggggaa gggaaaataa aaccactagg 142920
taaacttgta gctgtggttt gaagaagtgg ttttgaaaca ctctgtccag ccccaccaaa 142980
ccgaaagtcc aggctgagca aaacaccacc tgggtaattt gcatttctaa aataagttga 143040
ggattcagcc gaaactggag aggtcctctt ttaacttatt gagttcaacc ttttaatttt 143100
agcttgagta gttctagttt ccccaaactt aagtttatcg acttctaaaa tgtatttaga 143160
attcattttc aaaattaggt tatgtaagaa attgaaggac tttagtgtct ttaatttcta 143220
atatatttag aaaacttctt aaaattactc tattattctt ccctctgatt attggtctcc 143280
attcaattct tttccaatac ccgaagcatt tacagtgact ttgttcatga tctttttttag 143340
ttgtttgttt tgccttacta ttaagacttt gacattctgg tcaaaacggc ttcacaaatc 143400
tttttcaaga ccactttctg agtattcatt ttaggagaaa gacttttttt ttaaatgaat 143460
gcaattatct agacttattt cagttgaaca tgctggttgg tggttgagag gacactcagt 143520
cagtcagtga cgtgaagggc ttctaagcca gtccacatgc tctgtgtgaa ctccctctgg 143580
ccctgcttat tgttgaatgg gccaaaggtc tgagaccagg ctgctgctgg gtaggcctgg 143640
actttgggtc tcccacccag acctgggaat gtatggttgt ggcttctgcc acccatccac 143700
ctggctgctc atggaccagc cagcctcggt ggctttgaag gaacaattcc acacaaagac 143760
tctggacctc tccgaaacca ggcaccgcaa atggtaagcc agaggcagcc acagctgtgg 143820
ctgctgctct taaagcttgt aaactgtttc tgcttaagag ggactgagtc ttcagtcatt 143880
gctttagggg gagaaagaga catttgtgtg tcttttgagt accgttgtct gggtcactca 143940
catttaactt tccttgaaaa actagtaaaa gaaaaatgtt gcctgttaac caataatcat 144000
agagctcatg gtactttgag gaaatcttag aaagcgtgta tacaattgtc tggaattatt 144060
tcagttaagt gtattagttg aggtactgat gctgtctcta cttcagttat acatgtgggt 144120
ttgaattttg aatctattct ggctcttctt aagcagaaaa tttagataaa atggatacct 144180
cagtggtttt taatggtggg tttaatatag aaggaattta aattggaagc taatttagaa 144240
tcagtaagga gggacccagg ctaagaaggc aatcctggga ttctggaaga aaagatgttt 144300
ttagttttta tagaaaacac tactacattc ttgatctaca actcaatgtg gtttaatgaa 144360
tttgaagttg ccagtaaatg tacttcctgg ttgttaaaga atggtatcaa aggacagtgc 144420
ttagatccga ggtgagtgtg agaggacagg ggctggggta tggatacgca gaaggaaggc 144480
cacagctgta cagaattgag aaagaataga gacctgcagt tgaggccagc aggtcggctg 144540
gactaactct ccagccacag taatgaccca gacagagaaa gccagactca taaagcttgc 144600
tgagcaaaat taagggaaca aggttgagag ccctagtaag cgaggctcta aaaagcacag 144660
ctgagctgag atgggtgggc ttctctgagt gcttctaaaa tgcgctaaac tgaggtgatt 144720
actctgaggt aagcaaagct gggcttgagc caaaatgaag tagactgtaa tgaactggaa 144780
tgagctgggc cgctaagcta aactaggctg gcttaaccga gatgagccaa actggaatga 144840
acttcattaa tctaggttga atagagctaa actctactgc ctacactgga ctgttctgag 144900
ctgagatgag ctggggtgag ctcagctatg ctacgctgtg ttggggtgag ctgatctgaa 144960
atgagatact ctggagtagc tgagatgggg tgagatgggg tgagctgagc tgggctgagc 145020
tagactgagc tgagctaggg tgagctgagc tgggtgagct gagctaagct ggggtgagct 145080
gagctgagct tggctgagct agggtgagct gggctgagct ggggtgagct gagctgagct 145140
ggggtaagct gggatgagct ggggtgagct gagctgagct ggagtgagct gagctgggct 145200
gagctggggt gagctgggct gagctgggct gagctgggct gagctggggt gagctgagct 145260
ggggtgagct gagctgagct ggggtgagct gagctgagct ggggtgagct ggggtgagct 145320
gagctggggt gagctgagct gagctggggt gagctgagct ggggtgagct gagctgagct 145380
ggggtgagct gagctgagct gagctgagct gagctggggt gagctgagct gagctgagct 145440
ggggtgagct ggggtgagct gagctgagct ggagtgagct gagctgggct gagctggggt 145500
gagctgggct gagctggggt gagctgagct gagctgagct gagctggggt gagctgagct 145560
gagctggggt gagctgagct ggggtgagct gggctgagct gagctgagct gagctgagct 145620
gagctgagct gagctgagct gagctgagct gagctgagct gagctgagct gagctgagct 145680
ggggtgagct gagctgagct gggctgagct ggggtgagct gggctgagct gggctgagct 145740
gggctgagct ggggtgagct gagctggggt gagctgagct gagctgggct gagctgagct 145800
gagctggggt gagctgagct gagctggggt gagctgagct gagctgagct ggggtgagct 145860
gagctgagct gggctgagca gggctgagct ggggtgagct gagctgagct ggggtgagct 145920
gggctgagct gggctgagct gagctgagct gggctgagct gggctgagct gggctgagct 145980
gggctgagct gggctgagct ggggtgagct gagctggggt gagctggggt gagctgagct 146040
ggggtgagct gagctggggt gagctgagct gagctggggt gagctgagct ggggtgagct 146100
gagctgagct ggggtgagct gagctgagct ggggtgagct gagctagggt gaactgggct 146160
gggtgagctg gagtgagctg agctgaggtg aactggggtg agccgggatg ttttgagttg 146220
agctggggta agatgagctg aactggggta aactgggatg agctgtggtg agcggagctg 146280
gattgaactg agctgtgtga gctgagctgg ggtcagctga gcaagagtga gtagagctgg 146340
ctggccagaa ccagaatcaa ttaggctaag tgagccagat tgtgctggga tcagctgtac 146400
tcagatgagc tgggatgagg taggctggga tgagctgggc tagctgacat ggattatgtg 146460
aggctgagct agcatgggct ggcctagctg atgagctaag cttgaatgag cggggctgag 146520
ctggactcag atgtgctaga ctgagctgta ctggatgatc tggtgtaggg tgatctggac 146580
tcaactgggc tggctgatgg gatgcgccag gttgaactag gctcagataa gttaggctga 146640
gtagggcctg gttgagatgg ttcgggatga gctgggaaaa gatggactcg gaccatgaac 146700
tgggctgagc tgggttggga gaccatgaat tgagctgaac tgagtgcagc tgggataaac 146760
tgggttgagc taagaataga ctacctgaat tgtgccaaac tcggctggga tcaattggaa 146820
attatcagga tttagatgag ccggactaaa ctatgctgag ctggactggt tggatgtgtt 146880
gaactggcct gctgctgggc tggcatagct gagttgaact taaatgagga aggctgagca 146940
aggctagcct gcttgcatag agctgaactt tagcctagcc tgagctggac cagcctgagc 147000
tgagtaggtc taaactgagt taaaaatcaa cagggataat ttaacagcta atttaacaag 147060
cctgaggtct gagattgaat gagcagagct gggatgaact gaatgagttt caccaggcct 147120
ggaccagtta ggctaggacc tcgttctata gaggcagact gtgtgctaca gtggagtttc 147180
aagatgattc catgagtcct ccccgccccc aacataaccc accttcctcc taccctacac 147240
gcctgtctgg tgtgtaaatc ccagctttgt gtgctgatac agaagcctga gcccctcccc 147300
cacctccacc tacctattac tttgggatga gaatagttct cccagccagt gtctcagagg 147360
gaagccaagc aggacaggcc caaggctact tgagaagcca ggatctaggc ctctccctga 147420
gaacgggtgt tcatgcccct agagttggct gaagggccag atccacctac tctagaggca 147480
tctctccctg tctgtgaagg cttccaaagt cacgttcctg tggctagaag gcagctccat 147540
agccctgctg cagtttcgtc ctgtatacca ggttcaccta ctaccatatc tagccctgcc 147600
tgccttaaga gtagcaacaa ggaaatagca gggtgtagag ggatctcctg tctgacagga 147660
ggcaagaaga cagattctta cccctccatt tctcttttat ccctctctgg tcctcagaga 147720
gtcagtcctt cccaaatgtc ttccccctcg tctcctgcga gagcccccctg tctgataaga 147780
atctggtggc catgggctgc ctggcccggg acttcctgcc cagcaccatt tccttcacct 147840
ggaactacca gaacaacact gaagtcatcc agggtatcag aaccttccca acactgagga 147900
caggggggcaa gtacctagcc acctcgcagg tgttgctgtc tcccaagagc atccttgaag 147960
gttcagatga atacctggta tgcaaaatcc actacggagg caaaaacaaa gatctgcatg 148020
tgcccattcc aggtaagaac caaaccctcc cagcaggggt gcccaggccc aggcatggcc 148080
cagagggagc agcggggtgg ggcttaggcc aagctgagct cacaccttga cctttcattc 148140
cagctgtcgc agagatgaac cccaatgtaa atgtgttcgt cccaccacgg gatggcttct 148200
ctggccctgc accacgcaag tctaaactca tctgcgaggc cacgaacttc actccaaaac 148260
cgatcacagt atcctggcta aaggatggga agctcgtgga atctggcttc accacagatc 148320
cggtgaccat cgagaacaaa ggatccacac cccaaaccta caaggtcata agcacactta 148380
ccatctctga aatcgactgg ctgaacctga atgtgtacac ctgccgtgtg gatcacaggg 148440
gtctcacctt cttgaagaac gtgtcctcca catgtgctgc cagtgagtgg cctgggctaa 148500
gcccaatgcc tagccctccc agattaggga agtcctccta caattatggc caatgccacc 148560
cagacatggt catttgctcc ttgaactttg gctccccaga gtggccaagg acaagaatga 148620
gcaataggca gtagaggggt gagaatcagc tggaaggacc agcatcttcc cttaagtagg 148680
tttgggggat ggagactaag ctttttttcca acttcacaac tagatatgtc ataacctgac 148740
acagtgttct cttgactgca ggtccctcca cagacatcct aaccttcacc atcccccccct 148800
cctttgccga catcttcctc agcaagtccg ctaacctgac ctgtctggtc tcaaacctgg 148860
caacctatga aaccctgaat atctcctggg cttctcaaag tggtgaacca ctggaaacca 148920
aaattaaaat catggaaagc cctcccaatg gcaccttcag tgctaagggt gtggctagtg 148980
tttgtgtgga agactggaat aacaggaagg aatttgtgcg tactgtgact cacagggatc 149040
tgccttcacc acagaagaaa ttcatctcaa aacccaatgg taggtatccc cccttccctt 149100
cccctccaat tgcaggaccc ttcctgtacc tcatagggag ggcaggtcct cttccaccct 149160
atcctcacta ctgtcttcat ttacagaggt gcacaaacat ccacctgctg tgtacctgct 149220
gccaccagct cgtgagcaac tgaacctgag ggagtcagcc acagtcacct gcctggtgaa 149280
gggcttctct cctgcagaca tcagtgtgca gtggcttcag agagggcaac tcttgcccca 149340
agagaagtat gtgaccagtg ccccgatgcc agagcctggg gccccaggct tctactttac 149400
ccacagcatc ctgactgtga cagaggagga atggaactcc ggagagacct atacctgtgt 149460
tgtaggccac gaggccctgc cacacctggt gaccgagagg accgtggaca agtccactgg 149520
taaacccaca ctgtacaatg tctccctgat catgtctgac acaggcggca cctgctattg 149580
accatgctag cgctcaacca ggcaggccct gggtgtccag ttgctctgtg tatgcaaact 149640
aaccatgtca gagtgagatg ttgcatttta taaaaattag aaataaaaaa aatccattca 149700
aacgtcactg gttttgatta tacaatgctc atgcctgctg agacagttgt gttttgcttg 149760
ctctgcacac accctgcata cttgcctcca ccctggccct tcctctacct tgccagtttc 149820
ctccttgtgt gtgaactcag tcaggcttac aacagacaga gtatgaacat gcgattcctc 149880
cagctacttc tagatatatg gctgaaagct tgcatgcctg caggtcgact ctagaggatc 149940
cccgggtacc gagctcgaat tcgccctata gtgagtcgta ttacaattca ctggccgtcg 150000
ttttacaacg tcgtgactgg gaaaaccctg gcgttaccca acttaatcgc cttgcagcac 150060
atcccccttt cgccagctgg cgtaatagcg aagaggcccg caccgatcgc ccttcccaac 150120
agttgcgcag cctgaatggc gaatggcgcc tgatgcggta ttttctcctt acgcatctgt 150180
gcggtatttc acaccgcata tggtgcactc tcagtacaat ctgctctgat gccgcatagt 150240
taagccagcc ccgacacccg ccaacacccg ctgacgcgaa ccccttgc 150288

<210> SEQ ID NO 71
<211> LENGTH: 23
<212> TYPE: DNA
<213> ORGANISM: Artificial Sequence
<220> FEATURE:
<223> OTHER INFORMATION: synthetic

<400> SEQUENCE: 71
ggaaggtgtg cacaccgctg gac 23

<210> SEQ ID NO 72
<211> LENGTH: 23
<212> TYPE: DNA
<213> ORGANISM: Artificial Sequence
<220> FEATURE:
<223> OTHER INFORMATION: synthetic

<400> SEQUENCE: 72
ggaaggtgtg cacaccactg gac 23

<210> SEQ ID NO 73
<211> LENGTH: 23
<212> TYPE: DNA
<213> ORGANISM: Artificial Sequence
<220> FEATURE:
<223> OTHER INFORMATION: synthetic

<400> SEQUENCE: 73
ggaaggtgtg cacactgctg gac 23

<210> SEQ ID NO 74
<211> LENGTH: 23
<212> TYPE: DNA
<213> ORGANISM: Artificial Sequence
<220> FEATURE:
<223> OTHER INFORMATION: synthetic

<400> SEQUENCE: 74
agactgtgcg cacaccgctg gac 23

<210> SEQ ID NO 75
<211> LENGTH: 22
<212> TYPE: DNA
<213> ORGANISM: Artificial Sequence
<220> FEATURE:
<223> OTHER INFORMATION: synthetic

<400> SEQUENCE: 75
tcttatcaga cagggggctc tc 22

<210> SEQ ID NO 76
<211> LENGTH: 22

<212> TYPE: DNA
<213> ORGANISM: Artificial Sequence
<220> FEATURE:
<223> OTHER INFORMATION: synthetic

<400> SEQUENCE: 76
aagaagcaca cgactgaggc ac 22

<210> SEQ ID NO 77
<211> LENGTH: 22
<212> TYPE: DNA
<213> ORGANISM: Artificial Sequence
<220> FEATURE:
<221> NAME/KEY: variation
<222> LOCATION: (12)...(12)
<223> OTHER INFORMATION: w = a or t
<220> FEATURE:
<223> OTHER INFORMATION: synthetic

<400> SEQUENCE: 77
agtggataga cwgatggggg tg 22

<210> SEQ ID NO 78
<211> LENGTH: 22
<212> TYPE: DNA
<213> ORGANISM: Artificial Sequence
<220> FEATURE:
<223> OTHER INFORMATION: synthetic

<400> SEQUENCE: 78
agtggataga ccgatggggc tg 22

<210> SEQ ID NO 79
<211> LENGTH: 22
<212> TYPE: DNA
<213> ORGANISM: Artificial Sequence
<220> FEATURE:
<223> OTHER INFORMATION: synthetic

<400> SEQUENCE: 79
aagggataga cagatggggc tg 22

<210> SEQ ID NO 80
<211> LENGTH: 22
<212> TYPE: DNA
<213> ORGANISM: Artificial Sequence
<220> FEATURE:
<223> OTHER INFORMATION: synthetic

<400> SEQUENCE: 80
ggaagacatt tgggaaggac tg 22

<210> SEQ ID NO 81
<211> LENGTH: 22
<212> TYPE: DNA
<213> ORGANISM: Artificial Sequence
<220> FEATURE:
<223> OTHER INFORMATION: synthetic

<400> SEQUENCE: 81
ggaagatgga tacagttggt gc 22

RESTRICTED IMMUNOGLOBULIN HEAVY CHAIN MICE

CROSS-REFERENCE TO RELATED APPLICATIONS

This application claims the benefit under 35 USC § 119(e) of U.S. Provisional Application Ser. No. 61/658,459, filed Jun. 12, 2012, U.S. Provisional Application Ser. No. 61/597,969, filed Feb. 13, 2012 and U.S. Provisional Application Ser. No. 61/547,974, filed Oct. 17, 2011, which applications are hereby incorporated by reference in their entirety.

FIELD

Non-human animals that are genetically engineered at an immunoglobulin heavy chain variable (V) region locus (or in a transgene) to make antibodies from a restricted number of immunoglobulin heavy chain variable ($V_H$) segments (or a single $V_H$ segment) and/or variants thereof. Non-human animals that have a human heavy chain variable domain derived from a single immunoglobulin heavy chain variable gene segment, e.g., human immunoglobulin $V_H$1-69 gene segment or human $V_H$1-2 gene segment. Methods for making antibody sequences in non-human animals that are useful for binding pathogens, including human pathogens.

BACKGROUND

Non-human animals, e.g., mice, have been genetically engineered to be useful tools in methods for making antibody sequences for use in antibody-based human therapeutics. Mice with humanized variable region loci (e.g., $V_H$, $D_H$, and $J_H$ genes, and $V_L$ and $J_L$ genes) are used to generate cognate heavy and light chain variable domains for use in antibody therapeutics. Other mice are available that generate fully human antibodies with cognate heavy and light chains.

Human antibody therapeutics are engineered based on desired characteristics with respect to certain pre-selected antigens. Humanized mice are immunized with the pre-selected antigens, and the immunized mice are used to generate antibody populations from which to identify high-affinity cognate heavy and light variable domains with desired binding characteristics. Some humanized mice, such as those having a humanization of just variable regions at endogenous mouse loci, generate populations of B cells that are similar in character and number to wild-type mouse B cell populations. As a result, an extremely large and diverse population of B cells is available in these mice from which to screen antibodies, reflecting a large number of different immunoglobulin rearrangements, to identify heavy and light variable domains with the most desirable characteristics.

But not all antigens provoke an immune response that exhibits a very large number of rearrangements from a wide selection of variable (V) segments. That is, the human humoral immune response to certain antigens is apparently restricted. The restriction is reflected in clonal selection of B cells that express only certain V segments that bind that particular antigen with sufficiently high affinity and specificity. Some such antigens are clinically significant, i.e., a number are well-known human pathogens. A presumption arises that the V segment expressed in the human immune response is a V segment that, in combination with a human D and a human J segment, is more likely to generate a useful high affinity antibody than a randomly selected V segment that has not been observed in a human antibody response to that antigen.

It is hypothesized that natural selection, over millennia, has selected the most efficient foundation or base from which to design a most effective weapon for neutralizing human pathogens—a clonally selected V segment. There is a need in the art for more and superior antibodies that bind and/or neutralize antigens such as the pathogens discussed above. There is a need to more rapidly generate useful sequences from selected V segments, including polymorphic and/or somatically mutated selected V segments and to more rapidly generate useful populations of B cells having rearrangements of the V segments with various D and J segments, including somatically mutated versions thereof, and in particular rearrangements with unique and useful CDR3s. There is a need for biological systems, e.g., non-human animals (such as, e.g., mice, rats, rabbits, etc.) that can generate therapeutically useful antibody variable region sequences from pre-selected V segments in increased number and diversity than, e.g., can be achieved in existing modified animals. There is a need for biological systems engineered to have a committed humoral immune system for clonally selecting antibody variable sequences derived from restricted, pre-selected V segments, including but not limited to cognate human heavy and light chain variable domains, useful in the manufacture of human antibody-based therapeutics against selected antigens, including certain human pathogens.

There is a need in the art for therapeutic antibodies that are capable of neutralizing viral antigens, e.g., HIV and HCV, including antigen-specific antibodies containing heavy chains derived from a single human variable segment, and for a system that produces a diverse source of antibodies from which to select therapeutic antibody sequences. There is also a need for further methods and non-human animals for making useful antibodies, including antibodies that comprise a repertoire of heavy chains derived from a single human $V_H$ segment and having a diverse set of CDR sequences, and including such heavy chains that express with cognate human light chain variable domains. Methods are needed for selecting CDRs for immunoglobulin-based binding proteins that provide an enhanced diversity of binding proteins from which to choose, and enhanced diversity of immunoglobulin variable domains, including compositions and methods for generating somatically mutated and clonally selected immunoglobulin variable domains for use, e.g., in making human therapeutics.

SUMMARY

Genetically modified immunoglobulin loci are provided that comprise a restricted number of different heavy chain variable region gene segments (i.e., V genes, $V_H$ genes, $V_H$ gene segments, or V gene segments), e.g., no more than one, two, or three different V genes; or no more than one V gene segment family member present, e.g., in a single copy or in multiple copies and/or comprising one or more polymorphisms.

Loci are provided that are capable of rearranging and forming a gene encoding a heavy chain variable domain that is derived from a $V_H$ gene repertoire that is restricted, e.g., that is a single $V_H$ gene segment or selected from a plurality of polymorphic variants of the single $V_H$ gene segment. Modified immunoglobulin loci include loci that comprise human immunoglobulin sequences are provided, e.g., a human V segment operably linked to a human or (or human/non-human chimeric) non-human immunoglobulin constant sequence (and in operable linkage with, e.g., a D and/or a J segment). Modified loci that comprise multiple copies of a single $V_H$ gene segment, including wherein one or more of the copies comprises a polymorphic variant, are provided. Modified loci that comprise multiple copies of a single $V_H$ segment, operably linked with one or more D segments and one or more J segments, operably linked to a non-human immunoglobulin constant sequence, e.g., a mouse or rat sequence, are provided. Non-human animals comprising such humanized loci are also provided.

Non-human animals are provided that have a reduced immunoglobulin heavy chain variable gene segment complexity (i.e., a limited number of heavy chain variable gene segments, or a limited heavy chain variable gene repertoire), wherein the reduced immunoglobulin heavy chain variable gene segment complexity is characterized by the presence of no more than one or no more than two heavy chain variable gene segments, and wherein the heavy chain variable genes present are operably linked to a human or non-human constant region sequence.

Non-human animals are provided that have a reduced immunoglobulin heavy chain variable gene segment complexity (e.g., a single $V_H$ gene segment, or a limited number of $V_H$ gene segments that are polymorphic variants of a single $V_H$ gene segment), wherein the reduced immunoglobulin heavy chain variable gene segment complexity is characterized by the presence of a single $V_H$ gene segment or a plurality of $V_H$ gene segments that are polymorphic forms of a single $V_H$ gene segment (e.g., $V_H$ gene segments associated with high copy number and/or polymorphism in humans), and wherein the heavy chain variable genes present are operably linked to a human or non-human constant region sequence. In various embodiments, the heavy chain variable genes present are operably linked to one or more D and/or one or more J gene segments in the germline of the non-human animal.

Non-human animals are provided that comprise an immunoglobulin heavy chain variable locus (e.g., on a transgene or as an insertion or replacement at an endogenous non-human animal heavy chain variable locus) that comprises a single $V_H$ segment operably linked to a D and/or J gene segment. In various embodiments, the single $V_H$ gene segment is operably linked to one or more D and/or one or more J gene segments at the endogenous immunoglobulin heavy chain variable gene locus of the non-human animal.

Non-human animals are provided that are modified at their immunoglobulin heavy chain variable region loci to delete all or substantially all (e.g., all functional segments, or nearly all functional segments) endogenous immunoglobulin $V_H$ segments and that comprise a human $V_H$1-69 segment (or a human $V_H$1-2 segment) operably linked to a D and J segment or a J segment at the endogenous immunoglobulin heavy chain variable region locus of the non-human animal.

Non-human animals are also provided that are modified at their immunoglobulin heavy chain variable region loci to render the endogenous variable region loci incapable of rearranging to form a functional heavy chain comprising endogenous variable region gene segments; wherein the non-human animals comprise a single human variable gene segment (a human $V_H$1-2 or a human $V_H$1-69 gene segment) operably linked to a D and a J segment or a J segment at the endogenous immunoglobulin heavy chain variable region locus of the non-human animal.

Non-human animals are provided that comprise a restricted number (e.g., no more than one, or no more than two) of heavy chain gene segments operably linked to a human or non-human constant region sequence. In one embodiment, the no more than one or no more than two heavy chain gene segments linked to the constant region sequence are on a transgene, e.g., are at a position other than an endogenous heavy chain locus.

Methods are provided for making human immunoglobulin sequences in non-human animals. In various embodiments, the human immunoglobulin sequences are derived from a repertoire of immunoglobulin V sequences that consist essentially of a single human V segment, e.g., $V_H$1-69 or $V_H$1-2, and one or more D and J segments or one or more J segments. Methods for making human immunoglobulin sequences in non-human animals, tissues, and cells are provided, wherein the human immunoglobulin sequences bind a pathogen.

Methods are provided for making mice characterized by a restricted immunoglobulin heavy chain locus, wherein the restriction is with respect to the number of immunoglobulin $V_H$ gene segments. In various aspects, the restriction is to one or no more than two, or a single $V_H$ gene family member (e.g., one or more $V_H$ alleles, variants, or polymorphic variants thereof). In various aspects, the heavy chain locus further comprises one or more $D_H$ gene segments and one or more $J_H$ gene segments. In various aspects, the $V_H$, $D_H$ and $J_H$ gene segments are human. In various aspects, the $V_H$, $D_H$ and $J_H$ gene segments are operably linked to a non-human constant region (e.g., an IgM and/or an IgG). In various aspects, the constant region is a mouse or rat constant region.

In one aspect, a method for making a mouse having a restricted immunoglobulin heavy chain locus is provided, comprising introducing a nucleic acid construct as described herein into a mouse embryonic stem (ES) cell, and isolating or identifying a mouse ES cell that comprises the nucleic acid construct.

In one embodiment, the nucleic acid construct comprises a single human $V_H$ gene segment, one or more human $D_H$ gene segments, and one or more human $J_H$ gene segments. In one embodiment, the nucleic acid construct comprises one or more site-specific recombination sites (e.g., a loxP or a Frt site).

In one aspect, a mouse made using a targeting vector, nucleic acid sequence, or cell as described herein is provided. In various embodiments, the targeting vector, nucleic acid sequence or cell comprises a DNA sequence that contains a single human $V_H$ gene segment (or polymorphic variants thereof), one or more human $D_H$ gene segments, and one or more human $J_H$ gene segments operably linked to a non-human constant gene.

In one aspect, a method for making a mouse comprising a restricted immunoglobulin heavy chain locus is provided, comprising replacing a mouse immunoglobulin heavy chain locus with a human genomic sequence comprising a single human $V_H$ gene segment (or polymorphic variants thereof), one or more human $D_H$ gene segments, and one or more human JH gene segments, wherein the human $V_H$, $D_H$ and $J_H$ gene segments are capable of rearranging to form a chimeric heavy chain that contains a human variable domain operably linked to a non-human constant region. In one embodiment, the non-human constant region is a mouse or rat constant region.

In various aspects, the non-human animals are rodents. In various aspects, the rodents are mice and/or rats.

In one aspect, a modified immunoglobulin heavy chain locus is provided that comprises a heavy chain V segment repertoire that is restricted with respect to the identity of the V segment, and that comprises one or more D segments and one or more J segments, or one or more J segments. In one embodiment, the heavy chain V segment is a human segment. In one embodiment, the one or more D segments are human D segments. In one embodiment, the one or more J segments are human J segments. In one embodiment, the one or more D segments and one or more J segments are human D and human J segments.

In one embodiment, the modified locus is a non-human locus. In one embodiment, the non-human locus is modified with at least one human immunoglobulin sequence.

In one embodiment, the restriction is to one V segment family member. In one embodiment, the one V segment family member is present in two or more copies. In one embodiment, the one V segment family member is present as two or more variants (e.g., two or more polymorphic forms of the V segment family member). In one embodiment, the one V segment is a human V segment family member. In one embodiment, the one V segment family member is present in a number of variants as is observed in the human population with respect to that variant. In one embodiment, the V segment family member is selected from Table 1. In one embodiment, the V segment family member is present in a number of variants as shown, for each V segment, in a number of alleles from 1 allele to the number of alleles shown in the right column of Table 1.

In one embodiment, the restriction is to a human $V_H$1-69 gene segment. In one embodiment, the human $V_H$1-69 gene segment is present in two or more copies. In one embodiment, the human $V_H$1-69 gene segment is present as two or more variants (e.g., two or more polymorphic forms the human $V_H$1-69 gene). In one embodiment, the human $V_H$1-69 gene segment is present in a number of variants as is observed in the human population with respect to the human $V_H$1-69 gene segment. In one embodiment, the human $V_H$1-69 gene segment is selected from Table 2. In one embodiment, the human $V_H$1-69 gene segment is present in a number of variants as shown, for each $V_H$1-69 gene segment, in a number of alleles from one allele to the number of alleles shown in Table 2.

In one embodiment, the restriction is to a human $V_H$1-2 gene segment. In one embodiment, the human $V_H$1-2 gene segment is present in two or more copies. In one embodiment, the human $V_H$1-2 gene segment is present as two or more variants (e.g., two or more polymorphic forms the human $V_H$1-2 gene). In one embodiment, the human $V_H$1-2 gene segment is present in a number of variants as is observed in the human population with respect to the human $V_H$1-2 gene segment. In one embodiment, the human $V_H$1-2 gene segment is selected from Table 3. In one embodiment, the human $V_H$1-2 gene segment is present in a number of variants as shown, for each $V_H$1-2 gene segment, in a number of alleles from one allele to the number of alleles shown in Table 3.

In one aspect, a heavy chain immunoglobulin locus is provided that comprises a single functional human V segment. In one embodiment, the single functional human V segment is selected from a $V_H$1-2, $V_H$1-3, $V_H$1-8, $V_H$1-18, $V_H$1-24, $V_H$1-45, $V_H$1-46, $V_H$1-58, $V_H$1-69, $V_H$2-5, $V_H$2-26, $V_H$2-70, $V_H$3-7, $V_H$3-9, $V_H$3-11, $V_H$3-13, $V_H$3-15, $V_H$3-16, $V_H$3-20, $V_H$3-21, $V_H$3-23, $V_H$3-30, $V_H$3-30-3, $V_H$3-30-5, $V_H$3-33, $V_H$3-35, $V_H$3-38, $V_H$3-43, $V_H$3- 48, $V_H$3-49, $V_H$3-53, $V_H$3-64, $V_H$3-66, $V_H$3-72, $V_H$3-73, $V_H$3-74, $V_H$4-4, $V_H$4-28, $V_H$4-30-1, $V_H$4-30-2, $V_H$4-30-4, $V_H$4-31, $V_H$4-34, $V_H$4-39, $V_H$4-59, $V_H$4-61, $V_H$5-51, $V_H$6-1, $V_H$7-4-1, and a $V_H$7-81 segment. In one embodiment, the single functional human V segment is a $V_H$1-69 segment; in a specific embodiment, the single functional human V segment is present in 1, 2, 3, 4, 5, 6, 7, 8, 9, 10, 11, 12, or 13 polymorphic forms found in the human population. In one embodiment, the single functional human V segment is a $V_H$1-2 segment; in a specific embodiment, the single functional human V segment is present in 1, 2, 3, 4, or 5 polymorphic forms found in the human population.

In one embodiment, the heavy chain immunoglobulin locus is a modified locus of a non-human animal. In one embodiment, the modified non-human immunoglobulin heavy chain locus is present in the non-human animal at a position in the genome in which the corresponding unmodified non-human locus is found in the wild-type non-human animal. In one embodiment, the modified non-human immunoglobulin heavy chain locus is present on a transgene in a non-human animal.

In one embodiment, the single functional human V gene segment is a $V_H$1-69 gene segment. In one embodiment, the $V_H$1-69 gene segment comprises SEQ ID NO: 34. In one embodiment, the $V_H$1-69 gene segment is derived from SEQ ID NO: 34. In one embodiment, the $V_H$1-69 gene segment is at least 80%, at least 85%, at least 90%, at least 95%, or at least 98% identical to SEQ ID NO: 34.

In one embodiment, the single functional human V gene segment is encoded by the nucleotide sequence of SEQ ID NO: 34.

In one embodiment, the single functional human V gene segment is a $V_H$1-2 gene segment. In one embodiment, the $V_H$1-2 gene segment comprises SEQ ID NO: 60. In one embodiment, the $V_H$1-2 gene segment is derived from SEQ ID NO: 60. In one embodiment, the $V_H$1-2 gene segment is at least 80%, at least 85%, at least 90%, at least 95%, or at least 98% identical to SEQ ID NO: 60.

In one embodiment, the single functional human V gene segment is encoded by the nucleotide sequence of SEQ ID NO: 60.

In one embodiment, the single functional human V segment is operably linked to one or more D segments and one or more J segments, or one or more J segments. In one embodiment, the V segment and one or more D and/or J segments are operably linked to an immunoglobulin heavy chain constant region sequence. In one embodiment the immunoglobulin heavy chain constant region sequence is selected from a $C_H$1, a hinge, a $C_H$2, a $C_H$3 sequence, and a combination thereof. In one embodiment, the $C_H$1, hinge, $C_H$2, $C_H$3, or combination thereof are each non-human endogenous constant sequences. In one embodiment, at least one of the $C_H$1, hinge, $C_H$2, $C_H$3, or combination thereof is a human sequence. In a specific embodiment, the $C_H$1 and/or hinge are human sequences.

In one aspect, a modified endogenous non-human immunoglobulin heavy chain locus is provided, comprising a replacement of all functional V gene segments with a single human V gene segment (or a single human V gene segment present in multiple polymorphic forms or copy number), wherein the non-human immunoglobulin heavy chain locus is incapable of rearrangement to form a heavy chain variable gene that is derived from a V gene segment other than the single human V gene segment (or one of the polymorphic forms or copies).

In one embodiment, the single human V gene segment is $V_H$1-69. In one embodiment, the single human V gene segment is $V_H$1-2.

In one embodiment, the locus comprises at least one human or non-human $D_H$ gene segment, and one human or non-human $J_H$ gene segment. In a specific embodiment, the locus comprises a human $D_H$ gene segment and a human $J_H$ gene segment. In a specific embodiment, the locus comprises a human $J_H$ gene segment. In another specific embodiment, the locus comprises a human $V_H$1-69 gene segment (present as a single copy or multiple copies of different polymorphic variants), all functional human $D_H$ gene segments, and all functional human $J_H$ gene segments. In another specific embodiment, the locus comprises a human $V_H$1-2 gene segment (present as a single copy or multiple copies of different polymorphic forms), all functional human $D_H$ gene segments, and all functional human $J_H$ gene segments. In one embodiment, the human V, D, and J gene segments (or V and J gene segments) are operably linked to a mouse constant region gene at an endogenous mouse heavy chain locus. In a specific embodiment, the mouse heavy chain locus comprises a wild-type repertoire of mouse immunoglobulin constant region sequences.

In one aspect, a genetically modified non-human animal is provided, wherein the only functional immunoglobulin heavy chain V gene segment of the non-human animal is selected from a human $V_H$1-2, $V_H$1-3, $V_H$1-8, $V_H$1-18, $V_H$1-24, $V_H$1-45, $V_H$1-46, $V_H$1-58, $V_H$1-69, $V_H$2-5, $V_H$2-26, $V_H$2-70, $V_H$3-7, $V_H$3-9, $V_H$3-11, $V_H$3-13, $V_H$3-15, $V_H$3-16, $V_H$3-20, $V_H$3-21, $V_H$3-23, $V_H$3-30, $V_H$3-30-3, $V_H$3-30-5, $V_H$3-33, $V_H$3-35, $V_H$3-38, $V_H$3-43, $V_H$3-48, $V_H$3- 49, $V_H$3-53, $V_H$3-64, $V_H$3-66, $V_H$3-72, $V_H$3-73, $V_H$3-74, $V_H$4-4, $V_H$4-28, $V_H$4-30-1, $V_H$4-30-2, $V_H$4-30-4, $V_H$4-31, $V_H$4-34, $V_H$4-39, $V_H$4-59, $V_H$4-61, $V_H$5-51, $V_H$6-1, $V_H$7-4-1, and $V_H$7-81 gene segment. In one embodiment, the heavy chain V gene segment is a human $V_H$1-69 gene segment. In one embodiment, the heavy chain V gene segment is a human $V_H$1-2 gene segment.

In one aspect, a genetically modified non-human animal is provided, wherein the non-human animal comprises a single functional human $V_H$ gene segment (present as a single copy or multiple copies of different polymorphic forms), and wherein the non-human animal is substantially incapable of forming a rearranged immunoglobulin heavy chain variable domain gene that lacks the single functional human $V_H$ gene segment (or one of the polymorphic forms or copies).

In one aspect, a genetically modified non-human animal is provided, wherein the only immunoglobulin heavy chain variable region expressed in the non-human animal is derived from one of a human segment selected from a human $V_H$1-2, $V_H$1-3, $V_H$1-8, $V_H$1-18, $V_H$1-24, $V_H$1-45, $V_H$1-46, $V_H$1-58, $V_H$1-69, $V_H$2-5, $V_H$2-26, $V_H$2-70, $V_H$3-7, $V_H$3- 9, $V_H$3-11, $V_H$3-13, $V_H$3-15, $V_H$3-16, $V_H$3-20, $V_H$3-21, $V_H$3-23, $V_H$3-30, $V_H$3-30-3, $V_H$3-30-5, $V_H$3- 33, $V_H$3-35, $V_H$3-38, $V_H$3-43, $V_H$3-48, $V_H$3-49, $V_H$3-53, $V_H$3-64, $V_H$3-66, $V_H$3-72, $V_H$3-73, $V_H$3-74, $V_H$4-4, $V_H$4-28, $V_H$4-30-1, $V_H$4-30-2, $V_H$4-30-4, $V_H$4-31, $V_H$4-34, $V_H$4-39, $V_H$4-59, $V_H$4-61, $V_H$5-51, $V_H$6-1, $V_H$7-4-1, and $V_H$7-81 gene segment. In one embodiment, the human segment is a $V_H$1-69 segment. In one embodiment, the human segment is a $V_H$1-2 segment. In one embodiment, the only immunoglobulin heavy chain variable region expressed by the mouse is derived from a single V segment family member, and in one embodiment the only immunoglobulin heavy chain variable region is derived from a polymorphic variant of the single V segment family member.

In one aspect, a non-human animal comprising a restricted immunoglobulin heavy chain V gene segment repertoire is provided, wherein the non-human animal further comprises one or more human immunoglobulin κ light chain variable segments (Vκ). In one embodiment, the one or more Vκ segments are operably linked to one or more human J segments. In a specific embodiment, the J segments are human Jκ segments. In another specific embodiment, the non-human animal does not express an immunoglobulin λ light chain. In another specific embodiment, the non-human animal does not comprise a functional human or functional endogenous immunoglobulin λ light chain variable locus.

In one embodiment, the non-human animal is a rodent. In one embodiment, the rodent is a mouse.

In one embodiment, the non-human animal comprises a replacement at the endogenous non-human immunoglobulin Vκ locus of all or substantially all functional endogenous Vκ segments with one or more functional human Vκ segments. In a further specific embodiment, the replacement is with all or substantially all functional human immunoglobulin Vκ segments.

In one embodiment, the non-human animal comprises a replacement at the endogenous non-human immunoglobulin Vκ locus of all or substantially all functional endogenous Vκ gene segments with human Vκ gene segments selected from Vκ4-1, Vκ5-2, Vκ7-3, Vκ2-4, Vκ1-5, Vκ1-6, Vκ3-7, Vκ1-8, Vκ1-9, Vκ2-10, Vκ3-11, Vκ1-12, Vκ1-13, Vκ2-14, Vκ3-15, Vκ1-16, Vκ1-17, Vκ2-18, Vκ2-19, Vκ3-20, Vκ6-21, Vκ1-22, Vκ1-23, Vκ2-24, Vκ3-25, Vκ2-26, Vκ1-27, Vκ2-28, Vκ2-29, Vκ2-30, Vκ3-31, Vκ1-32, Vκ1-33, Vκ3-34, Vκ1-35, Vκ2-36, Vκ1-37, Vκ2-38, Vκ1-39, Vκ2-40, and a combination thereof.

In one embodiment, the non-human animal comprises a replacement at the endogenous non-human immunoglobulin Jκ locus of all or substantially all functional endogenous non-human immunoglobulin Jκ segments with one or more functional human immunoglobulin Jκ segments. In a further specific embodiment, the replacement is with all or substantially all functional human immunoglobulin Jκ segments.

In one embodiment, the non-human animal comprises a replacement at the endogenous non-human immunoglobulin Jκ locus of all or substantially all functional endogenous non-human immunoglobulin Jκ gene segments with human Jκ gene segments selected from Jκ1, Jκ2, Jκ3, Jκ4, Jκ5, and a combination thereof.

In a specific embodiment, the non-human animal comprises an immunoglobulin heavy chain variable region locus that comprises a repertoire of V segments consisting essentially of a single V segment and/or polymorphic variants thereof. In one embodiment, the single immunoglobulin heavy chain V segment is a human $V_H$1-69 segment, and the non-human animal further comprises a replacement of all functional non-human $D_H$ segments with all functional human $D_H$ segments, and further comprises a replacement of all functional non-human $J_H$ segments with all functional human $J_H$ segments, and wherein the immunoglobulin heavy chain variable region locus is operably linked to a human or non-human constant region gene sequence. In a specific embodiment, the constant region gene sequence is an endogenous non-human constant region gene sequence. In a specific embodiment, the non-human animal rearranges segments at the non-human immunoglobulin heavy chain locus to form a gene encoding heavy chain variable region comprising a human $V_H$1-69 sequence, a human $D_H$ sequence, a human $J_H$ sequence, and a mouse constant region sequence.

In a specific embodiment, the non-human animal comprises an immunoglobulin heavy chain variable region locus that comprises a repertoire of V segments consisting essentially of a single V segment and/or polymorphic variants thereof. In one embodiment, the single immunoglobulin heavy chain V segment is a human $V_H$1-2 segment, and the non-human animal further comprises a replacement of all functional non-human $D_H$ segments with all functional human $D_H$ segments, and further comprises a replacement of all functional non-human $J_H$ segments with all functional human $J_H$ segments, and wherein the immunoglobulin heavy chain variable region locus is operably linked to a human or non-human constant region gene sequence. In a specific embodiment, the constant region gene sequence is an endogenous non-human constant region gene sequence. In a specific embodiment, the non-human animal rearranges segments at the non-human immunoglobulin heavy chain locus to form a gene encoding heavy chain variable region comprising a human $V_H$1-2 sequence, a human $D_H$ sequence, a human $J_H$ sequence, and a mouse constant region sequence.

In one embodiment, a B cell is provided that comprises the rearranged gene. In a specific embodiment, the B cell is from a mouse as described that has been immunized with an antigen of interest, and the B cell encodes an antibody that specifically binds the antigen of interest. In one embodiment, the antigen of interest is a pathogen. In a specific embodiment, the pathogen is selected from an influenza virus, a hepatitis virus (e.g., hepatitis B or hepatitis C virus), and a human immunodeficiency virus. In a specific embodiment, the B cell encodes a somatically mutated, high affinity (e.g., about $10^{-9}$ $K_D$ or lower) antibody comprising a human light chain variable region (e.g., a human κ light chain variable region) that specifically binds the antigen of interest.

In one aspect, a non-human animal comprising a restricted immunoglobulin heavy chain V segment repertoire is provided, wherein the non-human animal comprises one or more human λ light chain variable (Vλ) segments. In one embodiment, the one or more human Vλ segments are operably linked to one or more human J segments. In a specific embodiment, the J segments are human Jλ segments. In another specific embodiment, the non-human animal does not express a κ light chain. In another specific embodiment, the non-human animal does not comprise a functional human or non-human κ light chain variable locus.

In one embodiment, the non-human animal comprises a replacement of all or substantially all functional non-human immunoglobulin Vλ segments with one or more functional human immunoglobulin Vλ segments. In a further specific embodiment, the replacement is with all or substantially all functional human immunoglobulin Vλ segments.

In one embodiment, the non-human animal comprises a replacement of all or substantially all functional non-human Vλ segments with a fragment of cluster A of the human λ light chain locus. In a specific embodiment, the fragment of cluster A of the human λ light chain locus comprises human Vλ gene segments Vλ3-27 through Vλ3-1.

In one embodiment, the non-human animal comprises a replacement of all or substantially all functional non-human Vλ segments with a fragment of cluster B of the human λ light chain locus. In a specific embodiment, the fragment of cluster B of the human λ light chain locus comprises human Vλ gene segments Vλ5-52 through Vλ1-40.

In one embodiment, the non-human animal comprises a replacement of all or substantially all functional non-human Vλ segments with a fragment of cluster A and a fragment of cluster B of the human λ light chain locus, wherein as a result of the replacement comprise human Vλ gene segments Vλ5-52 through Vλ3-1.

In one embodiment, the non-human animal comprises a replacement of all or substantially all functional non-human Vλ segments with at least 12 human Vλ gene segments, at least 28 human Vλ, gene segments, or at least 40 human Vλ gene segments.

In one embodiment, the non-human animal comprises a replacement of all or substantially all functional non-human immunoglobulin Jλ gene segments with one or more functional human immunoglobulin Jλ gene segments. In a further specific embodiment, the replacement is with all or substantially all functional human immunoglobulin Jλ gene segments. In various embodiments, the functional human Jλ gene segments include Jλ1, Jλ2, Jλ0.3 and Jλ7.

In a specific embodiment, the non-human animal comprises an immunoglobulin heavy chain variable ($V_H$) region locus that comprises only a single $V_H$ segment, wherein the single $V_H$ segment is a human $V_H$1-69 segment or a human $V_H$1-2 segment, and further comprises a replacement of all functional non-human $D_H$ segments with all functional human $D_H$ segments, and further comprises a replacement of all functional non-human $J_H$ segments with all functional human $J_H$ segments, and wherein the $V_H$ region locus is operably linked to a human or non-human constant region gene sequence. In a specific embodiment, the constant region gene sequence is a non-human constant region gene sequence, e.g., an endogenous non-human constant gene sequence. In a specific embodiment, the non-human animal rearranges segments at the non-human immunoglobulin heavy chain locus to form a gene encoding an immunoglobulin heavy chain variable region comprising a human $V_H$1-69 sequence (or a human $V_H$1-2 sequence), a human $D_H$ sequence, a human $J_H$ sequence, and an endogenous non-human constant region sequence.

In one embodiment, a B cell is provided that comprises the rearranged gene. In a specific embodiment, the B cell is from a non-human animal as described that has been immunized with an antigen of interest, and the B cell encodes an antibody that specifically binds the antigen of interest. In one embodiment, the antigen is a human protein selected from a ligand, a cell surface receptor and an intracellular protein. In one embodiment, the antigen of interest is a pathogen. In a specific embodiment, the pathogen is selected from an influenza virus, a hepatitis virus (e.g., hepatitis B or hepatitis C virus), and a human immunodeficiency virus. In a specific embodiment, the B cell encodes a somatically mutated, high affinity (e.g., about $10^{-9}$ $K_D$ or lower) antibody comprising a human light chain variable region (e.g., a human λ light chain variable region) that specifically binds the antigen of interest.

In one aspect, a non-human animal comprising a restricted immunoglobulin $V_H$ segment repertoire is provided, wherein the non-human animal comprises a human $V_H$1-69 segment (or a human $V_H$1-2 segment) on a transgene, wherein the human $V_H$1-69 segment is operably linked on the transgene to a human or non-human $D_H$ segment, and/or a human or non-human J segment, and the transgene further comprises a human or non-human constant region gene, or a chimeric human/non-human constant region (e.g., a $C_H$1, hinge, $C_H$2, $C_H$3 or combination thereof wherein at least one sequence is non-human, e.g., selected from hinge, $C_H$2, and $C_H$3 and/or hinge). In one embodiment, the non-human animal is a mouse or rat and the non-human D, J, and/or constant region gene is a mouse or rat gene or chimeric human/mouse or rat.

In one embodiment, the non-human animal comprises a transgene that comprises an immunoglobulin light chain variable region locus that comprises one or more human immunoglobulin Vλ gene segments and Jλ gene segments, or one or more human immunoglobulin Vκ gene segments and Jκ gene segments, and a human immunoglobulin κ or λ light chain constant region gene, such that the transgene rearranges in the non-human animal to form a rearranged immunoglobulin κ or λ light chain gene. In various embodiments, the human Vκ and Jκ gene segments are those described herein. In various embodiments, the human Vλ and Jλ gene segments are those described herein.

In a specific embodiment, the non-human animal comprises a transgene having an immunoglobulin heavy chain variable locus that comprises a single V segment that is a human $V_H$1-69 segment (or a human $V_H$1-2 segment), one or more human D segments, one or more human J segments, and a human constant gene operably linked to the heavy chain variable locus, such that the mouse expresses from the transgene a fully human antibody derived from the $V_H$1-69 segment (or the $V_H$1-2 segment). In one embodiment, the non-human animal does not comprise a functional endogenous immunoglobulin heavy chain variable region locus. In a specific embodiment, the non-human animal comprises a nonfunctional endogenous immunoglobulin heavy chain variable region locus that comprises a deletion of an endogenous non-human $D_H$ and/or endogenous non-human $J_H$ segment, such that the non-human animal is incapable of rearranging the endogenous immunoglobulin heavy chain variable region locus to form a rearranged non-human antibody gene. In a specific embodiment, the non-human animal comprises a deletion of a switch sequence operably linked to an endogenous mouse heavy chain constant region. In a specific embodiment, the switch sequence is a non-human (e.g., mouse) μ switch sequence. In another embodiment, the non-human animal further comprises a lack of a functional endogenous light chain variable locus selected from an immunoglobulin κ locus and an immunoglobulin λ locus. In a specific embodiment, the non-human animal comprises a deletion of a Jκ and/or a Jλ sequence, such that the non-human animal is incapable of rearranging an endogenous non-human immunoglobulin κ light chain and/or an endogenous non-human immunoglobulin λ light chain variable region to form a rearranged endogenous non-human immunoglobulin κ light chain and/or a rearranged endogenous non-human immunoglobulin λ light chain gene.

In one embodiment, the non-human animal comprises a deletion of an endogenous non-human immunoglobulin κ light chain sequence that results in a functional knockout of the endogenous non-human immunoglobulin κ light chain. In one embodiment, the non-human animal comprises a deletion of an endogenous non-human immunoglobulin λ light chain sequence that results in a functional knockout of the endogenous non-human immunoglobulin λ light chain.

In one aspect, the non-human animal comprises a functionally silenced endogenous immunoglobulin heavy chain variable gene locus, and comprises a restricted repertoire of human heavy chain variable gene segments (e.g., no more than one, or no more than two). In one embodiment, the functional silencing comprises a modification of an endogenous non-human heavy chain variable gene locus selected from a deletion, an insertion, an inversion, and a combination thereof.

In one aspect, a rodent is provided that comprises an immunoglobulin $V_H$ repertoire derived from no more than one human $V_H$ segment or one or more polymorphs thereof, from a D segment selected from a repertoire of one or more D segments, and from a J segment derived from a repertoire of one or more J segments. In one embodiment, the rodent rearranges the human $V_H$ segment, a human D segment, and a human J segment and forms a rearranged human heavy chain sequence that is operably linked to a human or a rodent constant region sequence. In one embodiment, the human and/or rodent constant region sequence is selected from a $C_H1$, a hinge, a $C_H2$, a $C_H3$, and a combination thereof. In one embodiment, the rodent expresses an immunoglobulin light chain that comprises a human variable domain, wherein the light chain is cognate with a human heavy chain domain derived from the rearranged human heavy chain sequence. In one embodiment, the rodent does not express a polypeptide sequence selected from a non-human heavy chain variable domain, a non-human light chain variable domain, and a combination thereof.

In one embodiment, the human $V_H$ segment is present in 1, 2, 3, 4, 5, 6, 7, 8, 9, 10, 11, 12, 13, 14, 15, 16, 17, 18, or 19 or more polymorphic variants, wherein each polymorphic variant is operably linked to a D and/or J segment such that each polymorphic variant is capable for rearranging and forming a rearranged heavy chain variable domain with any of the one or more D segments and any of the one or more J segments. In one embodiment, the rodent is a mouse or a rat. In one embodiment, the repertoire of D segments comprises two or more D segments. In one embodiment, the repertoire of J segments comprises two or more J segments. In one embodiment, the D and/or J segments are human segments.

In one aspect, a nucleic acid construct is provided that comprises a sequence encoding a single human immunoglobulin $V_H$ segment and/or polymorphic variants thereof and one or more $D_H$ and one or more J sequences, wherein the construct comprises at least one homology arm homologous to a non-human immunoglobulin heavy chain variable locus, or a recombinase recognition site (e.g., a lox site). In one embodiment, the V segment is a $V_H$1-69 segment or a $V_H$1-2 segment.

In one aspect, a nucleic acid construct is provided; comprising a nucleic acid sequence encoding a single human immunoglobulin heavy chain V segment, wherein the single $V_H$ segment is a $V_H$1-69 (or $V_H$1-2) segment. In one embodiment, the construct comprises a site-specific recombinase recognition site. In one embodiment, the construct comprises a first mouse homology arm upstream of the $V_H$1-69 (or $V_H$1-2) segment and a second mouse homology arm downstream of the $V_H$1-69 (or $V_H$1-2) segment, and wherein the first mouse homology arm is homologous to a region of a mouse chromosome immediately upstream of a mouse immunoglobulin heavy chain variable region but not including a functional mouse immunoglobulin heavy chain variable segment. In one embodiment, the construct comprises SEQ ID NO: 3. In one embodiment, the construct comprises SEQ ID NO: 70.

In one aspect, the restricted single $V_H$ segment is in a non-human animal, or the restricted $V_H$ segment is at a non-human immunoglobulin heavy chain locus (e.g., in situ or in a transgene), and the non-human animal or non-human immunoglobulin heavy chain locus is selected from a mouse, rat, rabbit, pig, bovine (e.g., cow, bull, buffalo), deer, sheep, goat, chicken, cat, dog, ferret, primate (e.g., marmoset, rhesus monkey) locus or animal. In a specific embodiment, the non-human animal or locus is a mouse or a rat locus.

In one aspect, a cell or tissue is provided, wherein the cell or tissue is derived from a non-human animal as described herein, and comprises a restricted $V_H$ segment repertoire. In one embodiment, the $V_H$ segment repertoire is restricted to a single $V_H$ segment family member and/or polymorphic variants thereof. In a specific embodiment, the single $V_H$ segment is a human $V_H$1-69 segment or a human $V_H$1-2 segment. In one embodiment, the cell or tissue is derived from spleen, lymph node or bone marrow of the non-human animal.

In one embodiment, the cell is an ES cell. In one embodiment, the cell is a B cell. In one embodiment, the cell is a germ cell.

In one embodiment, the tissue is selected from connective, muscle, nervous and epithelial tissue. In a specific embodiment, the tissue is reproductive tissue.

In one embodiment, the cell and/or tissue derived from a mouse as described herein are isolated for use in one or more ex vivo assays. In various embodiments, the one or more ex vivo assays include measurements of physical, thermal, electrical, mechanical or optical properties, a surgical procedure, measurements of interactions of different tissue types, the development of imaging techniques, or a combination thereof.

In one embodiment, the non-human animal is a mouse.

In one aspect, a non-human embryo is provided comprising a restricted heavy chain $V_H$ segments as described herein. In one embodiment, the embryo comprises an ES donor cell that comprises the restricted $V_H$ segment, and host embryo cells.

In one embodiment, the non-human animal is a mouse.

In one aspect, a non-human cell comprising a chromosome or fragment thereof of a non-human animal as described herein. In one embodiment, the non-human cell comprises a nucleus of a non-human animal as described herein. In one embodiment, the non-human cell comprises the chromosome or fragment thereof as the result of a nuclear transfer.

In one aspect, a nucleus derived from a non-human animal as described herein is provided. In one embodiment, the nucleus is from a diploid cell that is not a B cell.

In one aspect, a pluripotent, induced pluripotent, or totipotent cell derived from a non-human animal as described herein is provided. In a specific embodiment, the cell is a mouse embryonic stem (ES) cell.

In one aspect, a non-human induced pluripotent cell comprising a restricted $V_H$ segment repertoire is provided. In one embodiment, the induced pluripotent cell is derived from a non-human animal as described herein.

In one aspect, a hybridoma or quadroma is provided, derived from a cell of a non-human animal as described herein. In one embodiment, the non-human animal is a mouse or rat.

In one aspect, a lymphocyte of a non-human animal as described herein is provided. In one embodiment, the lymphocyte is a B cell.

In one aspect, mouse cells and mouse embryos are provided, including but not limited to ES cells, pluripotent cells, and induced pluripotent cells, that comprise genetic modifications as described herein. Cells that are XX and cells that are XY are provided. Cells that comprise a nucleus containing a modification as described herein are also provided, e.g., a modification introduced into a cell by pronuclear injection.

In one aspect, an antibody variable domain sequence made in a non-human animal as described herein is provided.

In one aspect, a human therapeutic is provided, comprising an antibody variable domain comprising a sequence derived from a non-human animal as described herein.

In one aspect, a method of obtaining an antibody variable region sequence from a non-human animal is provided, wherein the antibody variable region sequence is derived from a human $V_H$1-69 segment or a $V_H$1-2 segment, wherein the method comprises (a) immunizing a non-human animal with an antigen of interest, wherein the non-human animal comprises a replacement at the endogenous immunoglobulin heavy chain locus of all or substantially all non-human variable segments with a single human variable segment, wherein the single human variable segment is a $V_H$1-69 segment or a $V_H$1-2 segment, and wherein the non-human animal is substantially incapable of forming a immunoglobulin heavy chain variable region sequence that is not derived from a human $V_H$1-69 segment or a $V_H$1-2 segment; (b) allowing the non-human animal to mount an immune response with respect to the antigen of interest; and, (c) identifying or isolating an immunoglobulin heavy chain variable region sequence of the non-human animal, wherein the antibody binds the antigen of interest.

In one embodiment, the single human variable segment is a $V_H$1-69 segment.

In one embodiment, the antibody variable region sequence is derived from SEQ ID NO: 34. In one embodiment, the antibody variable region sequence is at least 75%, at least 80%, at least 85%, at least 90%, at least 95%, or at least 98% identical to SEQ ID NO: 34. In one embodiment, the antibody variable region sequence comprises SEQ ID NO: 34.

In one embodiment, the single human variable segment is a $V_H$1-2 segment.

In one embodiment, the antibody variable region sequence is derived from SEQ ID NO: 60. In one embodiment, the antibody variable region sequence is at least 75%, at least 80%, at least 85%, at least 90%, at least 95%, or at least 98% identical to SEQ ID NO: 60. In one embodiment, the antibody variable region sequence comprises SEQ ID NO: 60.

In one embodiment, the immune response to the antigen is characterized by an antibody titer that is about $6\times10^4$ to about $5\times10^5$ times greater than two times background as determined in an ELISA assay. In a specific embodiment, the antibody titer is about $1\times10^5$ to about $2\times10^5$ times greater than two times background as determined in an ELISA assay. In a specific embodiment, the antibody titer is about $1.5\times10^5$ times greater than two times background as determined in an ELISA assay. In one embodiment, the antigen is a human cell surface receptor.

In one aspect, a method for generating a repertoire of human antibody variable regions in a non-human animal is provided, wherein the human heavy chain variable regions of the repertoire are derived from the same $V_H$ gene family member and one of a plurality of $D_H$ segments and one of a plurality of $J_H$ segments, wherein the repertoire is characterized by having heavy chain immunoglobulin FR1 (framework 1), CDR1, FR2, CDR2, and FR3 sequences from a single $V_H$ gene family member. In one embodiment, the repertoire is further characterized by having a plurality of different CDR3+FR4 sequences.

In one embodiment, the single $V_H$ gene family is selected from $V_H$ family 1, 2, 3, 4, 5, 6, and 7. In a specific embodiment, the single $V_H$ gene family is $V_H$ family 1. In one embodiment, the single $V_H$ gene family member is selected from $V_H$1-2, $V_H$1-69, $V_H$2-26, $V_H$2-70, and $V_H$3-23. In a specific embodiment, the single $V_H$ gene family member is $V_H$1-69. In a specific embodiment, the single $V_H$ gene family member is $V_H$1-2.

In one embodiment, the repertoire comprises heavy chain FR1, CDR1, FR2, CDR2 and FR3 sequences derived from a $V_H$1-69 segment. In a specific embodiment, the repertoire comprises heavy chain FR1, CDR1, FR2, CDR2 and FR3 sequences derived from SEQ ID NO: 35. In a specific embodiment, the repertoire comprises heavy chain FR1, CDR1, FR2, CDR2 and FR3 sequences of SEQ ID NO: 35.

In one embodiment, the repertoire comprises heavy chain FR1, CDR1, FR2, CDR2 and FR3 sequences derived from a $V_H$1-2 segment. In a specific embodiment, the repertoire comprises heavy chain FR1, CDR1, FR2, CDR2 and FR3 sequences derived from SEQ ID NO: 61. In a specific embodiment, the repertoire comprises heavy chain FR1, CDR1, FR2, CDR2 and FR3 sequences of SEQ ID NO: 61.

In one aspect, a biological (i.e., in vivo) system is provided for generating a plurality of different human CDR3 sequences reflecting a plurality of rearrangements of a single human $V_H$ gene segment with a plurality of human D and J segments, wherein the system generates human heavy chain variable domains characterized by having human FR1-CDR1-FR2-CDR2-FR3 sequences that are identical but for somatic hypermutations, wherein the heavy chain variable domains are characterized by being somatically hypermutated and derived from a single human $V_H$ gene segment and a plurality of human D and J segments; wherein the system comprises a genetically modified non-human animal (e.g., a rodent, e.g., a mouse or rat) as described herein.

In one embodiment, the single human $V_H$ gene segment is selected from $V_H$1-2, $V_H$1-69, $V_H$2-26, $V_H$2-70, and $V_H$3-23. In one embodiment, the single human $V_H$ gene segment is $V_H$1-69. In one embodiment, the single human $V_H$ gene segment is $V_H$1-2. In one embodiment, the single human $V_H$ gene segment is identified in Table 1. In one embodiment, the single human $V_H$ gene segment is identified in Table 2. In one embodiment, the single human $V_H$ gene segment is identified in Table 3.

In one aspect, an in vivo method for generating a plurality of heavy chain CDR sequences derived from rearrangements of a single human $V_H$ gene segment with a plurality of human D and J segments is provided, wherein the method generates human heavy chain variable domains characterized by having human FR1-CDR1-FR2-CDR2-FR3 sequences that are identical but for somatic hypermutations, wherein the heavy chain variable domains are characterized by being somatically hypermutated and derived from a single human $V_H$ gene segment and a plurality of human D and J segments; wherein the system comprises a genetically modified non-human animal (e.g., a rodent, e.g., a mouse or rat) as described herein.

In one embodiment, the method comprises exposing a non-human animal as described herein to an antigen of interest, allowing the non-human animal to develop an immune response to the antigen, wherein the immune response generates the plurality of heavy chain CDR sequences derived from rearrangements of the single human $V_H$ gene segment with one of the human D and one of the human J segments, and identifying a set of heavy chain CDRs that bind the antigen. In one embodiment, the method comprises isolating from the animal a nucleic acid sequence that encodes a human $V_H$ domain that comprises the heavy chain CDRs.

In one embodiment, the heavy chain CDR sequences are derived from a rearrangement of a human $V_H$1-69 gene segment. In one embodiment, the heavy chain CDR sequences are derived from a rearrangement of a human $V_H$1-2 gene segment.

In one aspect, a method for generating a plurality of different CDR3 and FR4 sequences in a non-human animal is provided, comprising exposing a non-human animal that comprises an immunoglobulin heavy chain variable gene locus with a $V_H$ segment repertoire restricted to a single $V_H$ segment family member to an antigen of interest, allowing the non-human animal to develop an immune response to the antigen, wherein the immune response generates a B cell repertoire whose heavy chain variable domains are each derived from the single $V_H$ segment family member and that comprise a plurality of different CDR3 and FR4 sequences.

In one embodiment, the singe $V_H$ segment family member is human. In one embodiment, the non-human animal is selected from a mouse, a rat, and a rabbit. In one embodiment, the antigen of interest is selected from a ligand, a receptor, an intracellular protein and a secreted protein. In one embodiment, the antigen of interest is a human pathogen as described herein.

In one embodiment, the single human $V_H$ gene family member is selected from $V_H$1-2, $V_H$1-69, $V_H$2-26, $V_H$2-70, and $V_H$3-23. In one embodiment, the single human $V_H$ gene family member is $V_H$1-69. In one embodiment, the single human $V_H$ gene family member is $V_H$1-2. In one embodiment, the single human $V_H$ gene family member is identified in Table 1.

In one embodiment, the single human $V_H$ gene family member is identified in Table 2. In one embodiment, the single human $V_H$ gene family member is identified in Table 3.

In one aspect, a nucleotide sequence encoding an immunoglobulin variable region made in a non-human animal as described herein is provided.

In one aspect, an immunoglobulin heavy chain or immunoglobulin light chain variable region amino acid sequence of an antibody made in a non-human animal as described herein is provided.

In one aspect, an immunoglobulin heavy chain or immunoglobulin light chain variable region nucleotide sequence encoding a variable region of an antibody made in a non-human as described herein is provided.

In one aspect, an antibody or antigen-binding fragment thereof (e.g., Fab, $F(ab)_2$, scFv) made in a non-human animal as described herein is provided.

In one aspect, a mouse having a restricted immunoglobulin heavy chain locus characterized by the presence of a single human $V_H$ gene segment, one or more human $D_H$ gene segments, and one or more human $J_H$ gene segments is provided, wherein the single human $V_H$ gene segment is at an endogenous mouse locus and the $V_H$ gene segment is operably linked to the one or more human $D_H$ gene segments, the one or more human $J_H$ gene segments, and to an endogenous immunoglobulin heavy chain constant gene.

In one embodiment, the mouse further comprises a humanized immunoglobulin light chain locus comprising one or more human $V_L$ gene segments, and one or more human $J_L$ gene segments, wherein the human $V_L$ gene segments and the human $J_L$ gene segments are operably linked to a non-human immunoglobulin light chain constant region gene. In a specific embodiment, the human $V_L$ and $J_L$ gene segments are at an endogenous mouse light chain locus, and wherein the non-human immunoglobulin light chain constant region gene is a mouse gene.

In one embodiment, the humanized immunoglobulin light chain locus is on a transgene, and the constant region gene is selected from mouse, rat, and human.

In one embodiment, the human $V_L$ and $J_L$ gene segments are Vκ and Jκ gene segments. In one embodiment, the human $V_L$ and $J_L$ gene segments are Vλ and Jλ gene segments In one aspect, a non-human animal is provided, wherein the non-human animal has a B cell repertoire that expresses immunoglobulin heavy chain variable domains derived from a single V segment family member. In one embodiment, at least 10%, at least 20%, at least 30%, at least 40%, at least 50%, at least 60%, at least 70%, at least 80%, at least 90, or at least 95% of the B cell repertoire of the non-human animal immunoglobulin heavy chain variable domain expressed in the B cell repertoire is derived from the same V segment family member. In a specific embodiment, the percentage is at least 90%. In one embodiment, the B cell repertoire consists essentially of peripheral (blood) B cells. In one embodiment, the B cell repertoire consists essentially of splenic B cells. In one embodiment, the B cell repertoire consists essentially of bone marrow B cells. In one embodiment, the B cell repertoire consists essentially of peripheral B cells, splenic B cells, and bone marrow B cells.

In one aspect, a genetically modified non-human animal is provided, wherein more than 10%, 20%, 30%, 40%, 50%, 60%, 70%, 80%, or more than 90% of the B cells of the non-human animal that express a heavy chain immunoglobulin variable domain express a heavy chain immunoglobulin variable domain derived from a single $V_H$ gene segment family member. In one embodiment, at least 75% of the B cells of the non-human animal that express an immunoglobulin heavy chain variable domain express an immunoglobulin heavy chain variable domain derived from the single $V_H$ gene segment family member. In a specific embodiment, the percentage is at least 90%. In one embodiment, all of the B cells that express a heavy chain domain that is derived from the single $V_H$ gene family member.

In one aspect, a genetically modified mouse is provided that makes an antigen-specific B cell population in response to immunization with an antigen of interest, wherein at least 10%, 20%, 30%, 40%, 50%, 60%, 70%, 80%, or more than 90%, of said antigen-specific B cell population expresses immunoglobulin heavy chains that are all derived from the same $V_H$ gene segment. In one embodiment, at least 75% of the antigen-specific B cell population expresses immunoglobulin heavy chains derived from the same $V_H$ gene segment. In one embodiment, all of the antigen-specific B cells express a heavy chain that is derived from the same $V_H$ gene segment.

In one aspect, a non-human animal comprising a restricted $V_H$ gene segment repertoire is provided, wherein the restriction is to a human $V_H$1-69 gene segment or a $V_H$1-69 gene segment that is at least about 75.5%, 76.5%, 86.7%, 87.8%, 94.9%, 96.9%, 98%, or 99% identical to a $V_H$1-69*01 gene segment. In a specific embodiment, the restricted repertoire is selected from one or more of the $V_H$1-69 variants of FIG. 15.

In one aspect, a non-human animal comprising a restricted $V_H$ gene segment repertoire is provided, wherein the restriction is to a human $V_H$1-2 gene segment or a $V_H$1-2 gene segment that is at least about 94.9%, 95.9%, 96.9%, 98%, or 99% identical to a $V_H$1-2 gene segment. In a specific embodiment, the restricted repertoire is selected from one or more of the $V_H$1-2 variants of FIG. 18.

In one embodiment, the non-human animal is a mouse.

In one embodiment, the mouse exhibits an immunophenotype having a characteristic of a higher ratio of mature B cells to immature B cells as compared to a wild type mouse. In a specific embodiment, the ratio is calculated from B cells harvested from spleen. In one embodiment, the mouse exhibits a population of mature B cells of about $1\times10^7$. In one embodiment, the mouse exhibits a population of immature B cells of about $0.5\times10^7$. In one embodiment, the mouse exhibits a ratio of mature B cells to immature B cells in the spleen of the mouse that is about 1.5-fold to about 2-fold higher than exhibited by a wild type mouse.

In one embodiment, the ratio is calculated from B cells harvested from bone marrow. In a specific embodiment, the mouse exhibits a population of mature B cells of about $3\times10^5$. In one embodiment, the mouse exhibits a population of immature B cells of about $7\times10^5$. In one embodiment, the mouse exhibits a ratio of mature B cells to immature B cells in the bone marrow of the mouse that is about 3-fold, or about 3.3-fold higher than exhibited by a wild type mouse.

In one embodiment, the mouse exhibits an immunophenotype having a characteristic of a higher number of pro B cells in the bone marrow as compared to a wild type mouse. In a specific embodiment, the mouse exhibits a population of pro B cells in the bone marrow of the mouse that is about 2.5-fold to about 3-fold higher than exhibited in the bone marrow of a wild type mouse. In a specific embodiment, the mouse exhibits a population of pro B cells in the bone marrow of the mouse that is about 2.75-fold higher than exhibited in the bone marrow of a wild type mouse.

In one embodiment, the mouse exhibits an immunophenotype having a characteristic selected from the group consisting of a $CD19^+$ splenic B cell population that is about 80% of a wild-type B cell, a $CD3^+$ splenic T cell population that is about the same as a wild type mouse, and a combination thereof.

In one embodiment, the mouse comprises a lymphocyte population whose % $CD19^+$ B cells in spleen are about the same as a wild-type mouse. In one embodiment, the number of $CD19^+$ B cells per spleen of the mouse is at least about 50% of the number of $CD19^+$ B cells per spleen of a wild-type mouse.

In one embodiment, the non-human animal comprises at least about 75% to about 80% of $CD19^+$ B cells in bone marrow as compared with a wild-type mouse.

In one embodiment, the total number of $CD19^+$ bone cells per femur of the mouse is non less than about 30%, 40%, 50%, 60%, or 75% of the total number of CD19+ bone marrow cells in a wild-type mouse.

In one embodiment, the mouse expresses IgD and IgM at about the same level as observed in a wild-type mouse.

In one aspect, a mouse comprising a restricted human $V_H$ segment repertoire is provided, further comprising a humanized immunoglobulin light chain variable segment locus, wherein the ratio of λ to κ light chains expressed in the mouse is about the same as in a wild-type mouse.

In one aspect, a mouse is provided, comprising a restricted immunoglobulin heavy chain locus characterized by the presence of a single $V_H$ gene segment, one or more $D_H$ gene segments, and one or more $J_H$ gene segments, wherein the single $V_H$ gene segment is a polymorphic $V_H$ gene segment.

In one embodiment, the polymorphic $V_H$ gene segment is a human $V_H$ gene segment that is associated with a high copy number in human populations. In one embodiment, the human $V_H$ gene segment is selected from $V_H$1-2, $V_H$1-69, $V_H$2-26, $V_H$2-70, $V_H$3-23, or a polymorphic variant thereof. In a specific embodiment, the human $V_H$ gene segment is a $V_H$1-69 gene segment. In another specific embodiment, the human $V_H$ gene segment is a $V_H$1-2 gene segment.

In one embodiment, the single $V_H$ gene segment is operably linked to a human, mouse, or chimeric human/mouse immunoglobulin constant region gene. In a specific embodiment, the immunoglobulin constant region gene is a mouse constant region gene. In one embodiment, the immunoglobulin constant gene comprises a human sequence selected from a human $C_H1$, a human hinge, a human $C_H2$, a human $C_H3$, and a combination thereof. In one embodiment, the mouse constant gene is at an endogenous immunoglobulin heavy chain locus.

In one embodiment, the mouse further comprises a human immunoglobulin $V_L$ gene segment operably linked to a J gene segment and a light chain constant gene. In a specific embodiment, the $V_L$ gene segment and/or the J gene segment are selected from a human κ gene segment and a human λ gene segment. In one embodiment, the $V_L$ and/or J gene segments are human κ gene segments.

In various embodiments, the mouse comprises a deletion of all or substantially all endogenous $V_H$ gene segments.

In various embodiments, the non-human animal comprises an inactivated endogenous heavy chain variable gene locus. In various embodiments, the inactivated endogenous heavy chain variable gene locus is not operably linked to an endogenous heavy chain constant region gene.

In one aspect, a mouse is provided, wherein the mouse is characterized by the expression of serum immunoglobulin, wherein greater than 80% of the serum immunoglobulin comprises a human heavy chain variable domain and a cognate human light chain variable domain, wherein the human heavy chain variable domain is derived from a $V_H$ gene segment repertoire consisting essentially of a single human $V_H$ gene segment and/or polymorphic variants thereof.

In one embodiment, the single human $V_H$ gene segment is a human $V_H$1-69 gene segment and/or polymorphic variants thereof. In one embodiment, the single human $V_H$ gene segment is a human $V_H$1-2 gene segment and/or polymorphic variants thereof.

In one aspect, a mouse is provided, comprising, in its germline, a replacement at an endogenous immunoglobulin heavy chain locus of all or substantially all endogenous $V_H$ gene segments with a single human $V_H$ gene segment and/or polymorphic variants thereof. In one embodiment, the single human $V_H$ gene segment is a human $V_H$1-69 gene segment and/or polymorphic variants thereof. In one embodiment, the single human $V_H$ gene segment is a human $V_H$1-2 gene segment and/or polymorphic variants thereof.

In one embodiment, the mouse further comprises a replacement at an endogenous immunoglobulin light chain locus of all or substantially all endogenous $V_L$ gene segments with one or more human $V_L$ gene segments. In a specific embodiment, the mouse further comprises one or more human $J_L$ gene segments operably linked to the human $V_L$ gene segments.

In one aspect, use of a mouse as described herein to make an immunoglobulin variable region nucleotide sequence is provided. In one embodiment, the sequence comprises a rearranged $V_H$1-69 gene segment. In one embodiment, the sequence comprises a rearranged $V_H$1-2 gene segment.

In one embodiment, the immunoglobulin variable region nucleotide sequence is at least 80%, at least 85%, at least 90%, at least 95%, or at least 98% identical with a human $V_H$1-69 gene segment. In a specific embodiment, the immunoglobulin variable region nucleotide sequence is at least 80%, at least 85%, at least 90%, at least 95%, or at least 98% identical with SEQ ID NO: 34. In various embodiments, the human $V_H$1-69 gene segment is identified from Table 2.

In one embodiment, the immunoglobulin variable region nucleotide sequence encodes an amino acid sequence that is at least 80%, at least 85%, at least 90%, at least 95%, or at least 98% identical with SEQ ID NO: 35.

In one embodiment, the immunoglobulin variable region nucleotide sequence is at least 80%, at least 85%, at least 90%, at least 95%, or at least 98% identical with a human $V_H$1-2 gene segment. In a specific embodiment, the immunoglobulin variable region nucleotide sequence is at least 80%, at least 85%, at least 90%, at least 95%, or at least 98% identical with SEQ ID NO: 60. In various embodiments, the human $V_H$1-2 gene segment is identified from Table 3.

In one embodiment, the immunoglobulin variable region nucleotide sequence encodes an amino acid sequence that is at least 80%, at least 85%, at least 90%, at least 95%, or at least 98% identical with SEQ ID NO: 61.

In one aspect, use of a mouse as described herein to make a fully human Fab or a fully human $F(ab)_2$ is provided. In one embodiment, the fully human Fab or fully human F(ab)2 comprises a heavy chain variable region that comprises a rearranged human $V_H$1-69 gene segment. In one embodiment, the fully human Fab or fully human F(ab)2 comprises a heavy chain variable region that comprises a rearranged human $V_H$1-2 gene segment.

In one aspect, use of a mouse as described herein to make an immortalized cell line is provided.

In one aspect, use of a mouse as described herein to make a hybridoma or quadroma is provided.

In one aspect, use of a mouse as described herein to make a phage library containing human heavy chain variable regions and human light chain variable regions is provided.

In one embodiment, the human heavy chain variable regions are derived from a human $V_H$1-69 gene segment that comprises a sequence selected from SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56 and SEQ ID NO: 58.

In one embodiment, the human heavy chain variable regions are derived from a human $V_H$1-69 gene segment that comprises a sequence selected from SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57 and SEQ ID NO: 59.

In one embodiment, the human heavy chain variable regions are all derived from a human $V_H$1-2 gene segment that comprises a sequence selected from SEQ ID NO: 60, SEQ ID NO: 62, SEQ ID NO: 64, SEQ ID NO: 66 and SEQ ID NO: 68.

In one embodiment, the human heavy chain variable regions are derived from a human $V_H$1-2 gene segment that comprises a sequence selected from SEQ ID NO: 61, SEQ ID NO: 63, SEQ ID NO: 65, SEQ ID NO: 67 and SEQ ID NO: 69.

In one aspect, use of a mouse as described herein to generate a variable region sequence for making a human antibody is provided, comprising (a) immunizing a mouse as described herein with an antigen of interest, (b) isolating a lymphocyte from the immunized mouse of (a), (c) exposing the lymphocyte to one or more labeled antibodies, (d) identifying a lymphocyte that is capable of binding to the antigen of interest, and (e) amplifying one or more variable region nucleic acid sequence from the lymphocyte thereby generating a variable region sequence.

In one embodiment, the lymphocyte is derived or isolated from the spleen of the mouse. In one embodiment, the lymphocyte is derived or isolated from a lymph node of the mouse. In one embodiment, the lymphocyte is derived or isolated from the bone marrow of the mouse. In one embodiment, the lymphocyte is derived or isolated from the blood of the mouse.

In one embodiment, the labeled antibody is a fluorophore-conjugated antibody. In one embodiment, the one or more fluorophore-conjugated antibodies are selected from an IgM, an IgG, and/or a combination thereof.

In one embodiment, the lymphocyte is a B cell.

In one embodiment, the one or more variable region nucleic acid sequence comprises a heavy chain variable region sequence. In one embodiment, the one or more variable region nucleic acid sequence comprises a light chain variable region sequence. In a specific embodiment, the light chain variable region sequence is an immunoglobulin κ light chain variable region sequence. In one embodiment, the one or more variable region nucleic acid sequence comprises a heavy chain and a light chain variable region sequence.

In one embodiment, use of a mouse as described herein to generate a heavy and a κ light chain variable region sequence for making a human antibody is provided, comprising (a) immunizing a mouse as described herein with an antigen of interest, (b) isolating the spleen from the immunized mouse of (a), (c) exposing B lymphocytes from the spleen to one or more labeled antibodies, (d) identifying a B lymphocyte of (c) that is capable of binding to the antigen of interest, and (e) amplifying a heavy chain variable region nucleic acid sequence and a κ light chain variable region nucleic acid sequence from the B lymphocyte thereby generating the heavy chain and x light chain variable region sequences.

In one embodiment, use of a mouse as described herein to generate a heavy and a κ light chain variable region sequence for making a human antibody is provided, comprising (a) immunizing a mouse as described herein with an antigen of interest, (b) isolating one or more lymph nodes from the immunized mouse of (a), (c) exposing B lymphocytes from the one or more lymph nodes to one or more labeled antibodies, (d) identifying a B lymphocyte of (c) that is capable of binding to the antigen of interest, and (e) amplifying a heavy chain variable region nucleic acid sequence and a κ light chain variable region nucleic acid sequence from the B lymphocyte thereby generating the heavy chain and κ light chain variable region sequences.

In one embodiment, use of a mouse as described herein to generate a heavy and a κ light chain variable region sequence for making a human antibody is provided, comprising (a) immunizing a mouse as described herein with an antigen of interest, (b) isolating bone marrow from the immunized mouse of (a), (c) exposing B lymphocytes from the bone marrow to one or more labeled antibodies, (d) identifying a B lymphocyte of (c) that is capable of binding to the antigen of interest, and (e) amplifying a heavy chain variable region nucleic acid sequence and a κ light chain variable region nucleic acid sequence from the B lymphocyte thereby generating the heavy chain and κ light chain variable region sequences. In various embodiments, the one or more labeled antibodies are selected from an IgM, an IgG, and/or a combination thereof.

In various embodiments, the antigen of interest is a pathogen that afflicts human subjects including, e.g., a viral antigen. Exemplary viral pathogens include, e.g., mainly those of the families of Adenoviridae, bacteria Picornaviridae, Herpesviridae, Hepadnaviridae, Flaviviridae, Retroviridae, Orthomyxoviridae, Paramyxoviridae, Papovaviridae, Polyomavirus, Rhabdoviridae, and Togaviridae. Such exemplary viruses typically range between 20-300 nanometers in length. In various embodiments, the antigen of interest is a viral antigen selected from a hepatitis virus (e.g., HCV, HBV, etc.), a human immunodeficiency virus (HIV), or an influenza virus (e.g., H1N1).

In various embodiments, use of a mouse as described herein to generate a heavy and κ light chain variable region sequence for making a human antibody is provided, further comprising fusing the amplified heavy and light chain variable region sequences to human heavy and light chain constant region sequences, expressing the fused heavy and light chain sequences in a cell, and recovering the expressed heavy and light chain sequences thereby generating a human antibody.

In various embodiments, the human heavy chain constant regions are selected from IgM, IgD, IgA, IgE and IgG. In various specific embodiments, the IgG is selected from an IgG1, an IgG2, an IgG3 and an IgG4. In various embodiments, the human heavy chain constant region comprises a $C_H1$, a hinge, a $C_H2$, a $C_H3$, a $C_H4$, or a combination thereof. In various embodiments, the light chain constant region is an immunoglobulin κ constant region. In various embodiments, the cell is selected from a HeLa cell, a DU145 cell, a Lncap cell, a MCF-7 cell, a MDA-MB-438 cell, a PC3 cell, a T47D cell, a THP-1 cell, a U87 cell, a SHSY5Y (human neuroblastoma) cell, a Saos-2 cell, a Vero cell, a CHO cell, a GH3 cell, a PC12 cell, a human retinal cell (e.g., a PER.C6™ cell), and a MC3T3 cell. In a specific embodiment, the cell is a CHO cell.

In one aspect, a method for generating a reverse-chimeric rodent-human antibody specific against an antigen of interest is provided, comprising the steps of immunizing a mouse as described herein with the antigen, isolating at least one cell from the mouse producing a reverse-chimeric mouse-human antibody specific against the antigen, culturing at least one cell producing the reverse-chimeric mouse-human antibody specific against the antigen, and obtaining said antibody.

In one embodiment, the reverse-chimeric mouse-human antibody comprises a human heavy chain variable domain fused with a mouse or rat heavy chain constant gene, and a human light chain variable domain fused with a mouse or rat or human light chain constant gene. In a specific embodiment, the human heavy chain variable domain contains a rearranged human $V_H1$-69 or human $V_H1$-2 gene segment.

In one embodiment, culturing at least one cell producing the reverse-chimeric rodent-human antibody specific against the antigen is performed on at least one hybridoma cell generated from the at least one cell isolated from the mouse.

In one embodiment, the antigen of interest is a pathogen that afflicts human subjects as described herein.

In one aspect, a method for generating a fully human antibody specific against an antigen of interest is provided, comprising the steps of immunizing a mouse as described herein with the antigen, isolating at least one cell from the mouse producing a reverse-chimeric rodent-human antibody specific against the antigen, generating at least one cell producing a fully human antibody derived from the reverse-chimeric rodent-human antibody specific against the antigen, and culturing at least one cell producing the fully human antibody, and obtaining said fully human antibody.

In various embodiments, the at least one cell isolated from the mouse producing a reverse-chimeric rodent-human antibody specific against the antigen is a splenocyte or a B cell.

In various embodiments, the antibody is a monoclonal antibody.

In various embodiments, the antibody comprises a heavy chain variable domain that contains a rearranged human $V_H1$-69 or human $V_H1$-2 gene segment.

In various embodiments, immunization with the antigen of interest is carried out with protein, DNA, a combination of DNA and protein, or cells expressing the antigen. In one embodiment, the antigen of interest is a pathogen that afflicts human subjects as described herein.

In one aspect, use of a mouse as described herein to make a nucleic acid sequence encoding an immunoglobulin variable region or fragment thereof is provided. In one embodiment, the nucleic acid sequence is used to make a human antibody or antigen-binding fragment thereof. In one embodiment, the mouse is used to make an antigen-binding protein selected from an antibody, a multi-specific antibody (e.g., a bi-specific antibody), an scFv, a bi-specific scFv, a diabody, a triabody, a tetrabody, a V-NAR, a $V_{HH}$, a $V_L$, a F(ab), a $F(ab)_2$, a DVD (i.e., dual variable domain antigen-binding protein), a an SVD (i.e., single variable domain antigen-binding protein), or a bispecific T-cell engager (BiTE).

In one aspect, a method for making a human antigen-binding protein is provided, comprising exposing a genetically modified non-human animal as described herein to an antigen of interest, allowing the genetically modified non-human animal to mount an immune response to the antigen, obtaining from the genetically modified non-human animal a heavy chain variable domain nucleic acid sequence encoding a human heavy chain variable domain that specifically binds the antigen of interest, cloning the heavy chain variable domain nucleic acid sequence to a human constant region sequence, and expressing in a mammalian cell an antibody comprising the human heavy chain variable domain sequence and the human constant region sequence. In one embodiment, the mammalian cell is a CHO cell. In one embodiment the genetically modified non-human animal comprises a human $V_H$ gene segment repertoire that consists essentially of a single human $V_H$ gene segment, optionally present in two or more polymorphic variants thereof, operably linked to one or more human D and/or J segments. In one embodiment, the human $V_H$ gene segment repertoire is at an endogenous non-human $V_H$ segment locus. In one embodiment, the human $V_H$ gene segment repertoire is at a locus that is not an endogenous $V_H$ segment locus. In one embodiment, the human $V_H$ gene segment rearranges with a human D segment and a human J segment to form a rearranged human VDJ gene operably linked to a constant region sequence, wherein the constant region sequence is selected from a human sequence and a rodent sequence (e.g., a mouse or rat or hamster sequence). In one embodiment, the constant region sequence comprises a sequence selected from a $C_H1$, a hinge, a $C_H2$, a $C_H3$, and a combination thereof; in a specific embodiment, the constant region sequence comprises a $C_H1$, a hinge, a $C_H2$, and a $C_H3$. In one embodiment, the human variable domain and the constant sequence are expressed in the mammalian cell with a cognate human light chain variable domain obtained from the same mouse (e.g., sequence obtained from the same B cell as the human variable domain sequence); in one embodiment the sequence encoding the human light chain variable domain obtained from the mouse is then fused with a sequence encoding a human light chain constant sequence, and the light chain sequence and the heavy chain sequence are expressed in the mammalian cell.

In one embodiment, the antigen of interest is a pathogen that afflicts human subjects as described herein.

In one aspect, a method for making an antibody heavy chain variable domain that binds an antigen of interest is provided, comprising expressing in a single cell (a) a first $V_H$ sequence of an immunized non-human animal as described herein, wherein the first $V_H$ sequence is fused with a $C_H$ gene sequence; and (b) a $V_L$ gene sequence of an immunized non-human animal as described herein, wherein the $V_L$ gene sequence is fused with a human $C_L$ gene sequence; maintaining the cell under conditions sufficient to express an antibody; and, isolating the antibody heavy chain variable domain. In one embodiment, the $V_L$ gene sequence is cognate with the first $V_H$ sequence.

In one embodiment, the cell comprises a second $V_H$ gene sequence of an immunized non-human animal as described herein, wherein the second $V_H$ gene sequence is fused with a $C_H$ gene sequence, wherein the first $V_H$ gene sequence encodes a $V_H$ domain that specifically binds a first epitope, and the second $V_H$ gene sequence encodes a $V_H$ domain that specifically binds a second epitope, wherein the first epitope and the second epitope are not identical.

In one embodiment, the constant region sequences are all human constant region sequences. In one embodiment, the antigen of interest is a pathogen that afflicts human subjects as described herein.

In one aspect, a method for making a human bispecific antibody is provided, comprising making the bispecific antibody using human variable region gene sequences of B cells of a non-human animal as described herein.

In one embodiment, the method comprises (a) identifying a clonally selected lymphocyte of the non-human animal, wherein the non-human animal has been exposed to an antigen of interest and allowed to develop an immune response to the antigen of interest, and wherein the lymphocyte expresses an antibody that specifically binds the antigen of interest, (b) obtaining from the lymphocyte or the antibody a nucleotide sequence that encodes a human heavy chain variable region that specifically binds the antigen of interest, and (c) employing the nucleotide sequence that encodes the human heavy chain variable region that specifically binds the antigen of interest in making the bispecific antibody. In a specific embodiment, the human heavy chain variable region comprises a rearranged $V_H1$-2 or $V_H1$-69 gene segment.

In one embodiment, steps (a) through (c) are performed a first time for a first antigen of interest to generate a first human heavy chain variable region sequence, and steps (a) through (c) are performed a second time for a second antigen of interest to generate a second human heavy chain variable region sequence, and wherein the first human heavy chain variable region sequence is expressed fused with a first human heavy chain constant region to form a first human heavy chain, the second human heavy chain variable region sequence is expressed fused with a second human heavy chain constant region to form a second human heavy chain, wherein the first and the second human heavy chains are expressed in the presence of a single human light chain expressed from a rearranged human Vκ1-39 or a human Vκ3-20 gene segment. In a specific embodiment, the single human light chain comprises a germline sequence.

In one embodiment, the method comprises (a) cloning heavy chain variable regions from B cells of a non-human animal as described herein which has been exposed to a first antigen of interest, and the same non-human animal, or a different non-human animal which is genetically the same and has been exposed to a second antigen of interest; and (b) expressing in a cell the heavy chain variable regions of (a) with the same heavy chain constant region and the same light chain to make a bispecific antibody.

In one aspect, a use of a non-human animal as described herein is provided, to obtain a nucleic acid sequence that encodes a human heavy chain variable domain. In one embodiment, the heavy chain variable domain comprises a rearranged human $V_H$ gene segment selected from $V_H1$-2 and $V_H1$-69.

In one aspect, a use of a non-human animal as described herein is provided, to obtain a cell that encodes a human heavy chain variable domain. In one embodiment, the heavy chain variable domain comprises a rearranged human $V_H$ gene segment selected from $V_H1$-2 and $V_H1$-69.

In one aspect, use of a non-human animal as described herein to make a human antibody variable domain is provided. In one embodiment, the variable domain comprises a rearranged human $V_H$ gene segment selected from $V_H1$-2 and $V_H1$-69.

In one aspect, use of a non-human animal as described herein to make a human antibody is provided, comprising making the antibody using human variable region gene sequences of B cells of a non-human animal as described herein. In one embodiment, the human antibody is a human bispecific antibody. In a specific embodiment, the bispecific antibody comprises one heavy chain variable domain derived from a rearranged human $V_H$1-2 or $V_H$1-69 gene segment. In one embodiment, the human variable region gene sequences comprise a rearranged human $V_H$1-2 or $V_H$1-69 gene segment.

In one aspect, use of a non-human animal as described herein is provided to select a human immunoglobulin heavy chain variable domain. In one embodiment, the heavy chain variable domain comprises a rearranged human $V_H$ gene segment selected from $V_H$1-2 and $V_H$1-69.

In one aspect, use of the mouse as described herein for the manufacture of a medicament (e.g., an antigen-binding protein), or for the manufacture of a sequence encoding a variable sequence of a medicament (e.g., an antigen-binding protein), for the treatment of a human disease or disorder is provided. In one embodiment, the variable sequence of a medicament comprises a polymorphic human $V_H$ gene segment. In one embodiment, the variable sequence of a medicament comprises a human $V_H$1-69 gene segment. In one embodiment, the variable sequence of a medicament comprises a human $V_H$1-2 gene segment.

In one aspect, a nucleic acid construct encoding an immunoglobulin variable domain made in a mouse as described herein is provided. In one embodiment, the variable domain is a heavy chain variable domain. In a specific embodiment, the heavy chain variable domain comprises a rearranged human $V_H$ gene segment selected from $V_H$1-2, $V_H$1-69, $V_H$2-26, $V_H$2-70, or $V_H$3-23. In another specific embodiment, the heavy chain variable domain comprises a rearranged human $V_H$1-2 gene segment. In another specific embodiment, the heavy chain variable domain comprises a rearranged human $V_H$1-69 gene segment.

In one embodiment, the variable domain is a light chain variable domain. In a specific embodiment, the variable domain is a κ light chain variable domain that is cognate with a human heavy chain variable domain that comprises a rearranged human $V_H$1-69 gene segment. In a specific embodiment, the variable domain is a κ light chain variable domain that is cognate with a human heavy chain variable domain that comprises a rearranged human $V_H$1-2 gene segment.

In one aspect, use of a mouse as described herein to make a nucleic acid construct encoding a human immunoglobulin variable domain is provided. In one embodiment, the variable domain is a light chain variable domain. In one embodiment, the variable domain is a κ light chain variable domain that comprises a rearranged human Vκ gene segment selected from Vκ4-1, Vκ5-2, Vκ7-3, Vκ2-4, Vκ1-5, Vκ1-6, Vκ3-7, Vκ1-8, Vκ1-9, Vκ2-10, Vκ3-11, Vκ1-12, Vκ1-13, Vκ2-14, Vκ3-15, Vκ1-16, Vκ1-17, Vκ2-18, Vκ2-19, Vκ3-20, Vκ6-21, Vκ1-22, Vκ1-23, Vκ2-24, Vκ3-25, Vκ2-26, Vκ1-27, Vκ2-28, Vκ2-29, Vκ2-30, Vκ3-31, Vκ1-32, Vκ1-33, Vκ3-34, Vκ1-35, Vκ2-36, Vκ1-37, Vκ2-38, Vκ1-39, and Vκ2-40.

In one embodiment, the variable domain is a heavy chain variable domain. In a specific embodiment, the heavy chain variable domain comprises a rearranged human $V_H$ gene segment selected from $V_H$1-2, $V_H$1-69, $V_H$2-26, $V_H$2-70, or $V_H$3-23. In a specific embodiment, the heavy chain variable domain comprises a rearranged human $V_H$1-69 gene segment. In a specific embodiment, the heavy chain variable domain comprises a rearranged human $V_H$1-2 gene segment.

In one aspect, use of a mouse as described herein to make a human immunoglobulin variable domain is provided. In one embodiment, the variable domain is a light chain variable domain. In one embodiment, the variable domain is a κ light chain variable domain that comprises a rearranged human Vκ gene segment selected from Vκ4-1, Vκ5-2, Vκ7-3, Vκ2-4, Vκ1-5, Vκ1-6, Vκ3-7, Vκ1-8, Vκ1-9, Vκ2-10, Vκ3-11, Vκ1-12, Vκ1-13, Vκ2-14, Vκ3-15, Vκ1-16, Vκ1-17, Vκ2-18, Vκ2-19, Vκ3-20, Vκ6-21, Vκ1-22, Vκ1-23, Vκ2-24, Vκ3-25, Vκ2-26, Vκ1-27, Vκ2-28, Vκ2-29, Vκ2-30, Vκ3-31, Vκ1-32, Vκ1-33, Vκ3-34, Vκ1-35, Vκ2-36, Vκ1-37, Vκ2-38, Vκ1-39, and Vκ2-40.

In one embodiment, the variable domain is a heavy chain variable domain. In a specific embodiment, the heavy chain variable domain comprises a rearranged human $V_H$ gene segment selected from $V_H$1-2, $V_H$1-69, $V_H$2-26, $V_H$2-70, or $V_H$3-23. In a specific embodiment, the heavy chain variable domain comprises a rearranged human $V_H$1-69 gene segment. In a specific embodiment, the heavy chain variable domain comprises a rearranged human $V_H$1-2 gene segment.

In one aspect, use of a non-human animal as described herein to make a nucleic acid sequence encoding a human heavy chain variable domain is provided. In one embodiment, the human heavy chain variable domain is characterized by having human FR1-CDR1-FR2-CDR2-FR3 sequences that are derived from a polymorphic human $V_H$ gene segment. In a specific embodiment, the human $V_H$ gene segment is selected from a human $V_H$1-2, $V_H$1-69, $V_H$2-26, $V_H$2-70, or $V_H$3-23 gene segment. In one embodiment, the human $V_H$ gene segment is a human $V_H$1-69 gene segment. In one embodiment, the human $V_H$ gene segment is a human $V_H$1-2 gene segment.

In one aspect, a method for making a nucleic acid sequence encoding a human $V_H$ domain is provided, the method comprising immunizing a non-human animal as described herein with an antigen of interest, allowing the non-human animal to mount an immune response to the antigen of interest, and obtaining therefrom a nucleic acid sequence encoding a human $V_H$ domain that binds the antigen of interest. In one embodiment, the method further comprises making a nucleic acid sequence encoding a human $V_L$ domain that is cognate with the human $V_H$ domain, comprising isolating a B cell encoding the human $V_H$ domain and the human $V_L$ domain, and obtaining therefrom the sequence of the heavy and light chain variable domains. In various embodiments, the human $V_H$ domain is derived from a rearranged human $V_H$1-69 or human $V_H$1-2 gene segment. In various embodiments, the human $V_L$ domain is selected from a human Vκ or a human Vλ domain.

In one aspect, use of a non-human animal as described herein to make a human therapeutic is provided, comprising immunizing the non-human animal with an antigen of interest, allowing the non-human animal to mount an immune response, and obtaining from the animal a nucleic acid sequence encoding an immunoglobulin variable domain that binds the antigen of interest, and employing the immunoglobulin variable domain in a human therapeutic. In one embodiment, the variable domain is a heavy chain variable domain. In a specific embodiment, the heavy chain variable domain is derived from a rearranged human $V_H$1-69 or a human $V_H$1-2 gene segment. In one embodiment, the variable domain is a light chain variable domain. In a specific embodiment, the light chain variable domain is derived from a rearranged human Vκ or human Vλ gene segment.

In one aspect, a method for making a human therapeutic is provided, comprising immunizing a non-human animal as described herein with an antigen of interest, allowing the non-human animal to mount an immune response, and obtaining from the animal a nucleic acid sequence encoding an immunoglobulin variable domain that binds the antigen of interest, and employing the immunoglobulin variable domain in a human therapeutic. In one embodiment, the variable domain is a heavy chain variable domain. In a specific embodiment, the heavy chain variable domain is derived from a rearranged human $V_H$1-69 or a human $V_H$1-2 gene segment. In one embodiment, the variable domain is a light chain variable domain. In a specific embodiment, the light chain variable domain is derived from a rearranged human Vκ or human Vλ gene segment.

In one aspect, a method for making a human antigen-binding protein is provided, comprising immunizing a non-human animal as described herein with an antigen of interest, allowing the animal to mount an immune response, obtaining from the mouse a nucleic acid sequence encoding an immunoglobulin variable domain that specifically binds the antigen of interest, cloning the nucleic acid sequence in a vector suitable for expression of the nucleic acid, wherein the nucleic acid sequence is cloned in frame with a nucleic acid sequence encoding a human immunoglobulin constant region or functional fragment thereof, and inserting the vector in a mammalian cell, and maintaining the cell under conditions suitable for expressing an antigen-binding protein that comprises the immunoglobulin variable domain and the immunoglobulin constant region or functional fragment thereof. In one embodiment, the antigen-binding protein is a human antibody. In a specific embodiment, the antibody comprises a heavy chain variable domain and a light chain variable domain obtained from a mouse as described herein. In a specific embodiment, the antibody comprises a heavy chain variable domain obtained from a mouse as described herein. In various embodiments, the heavy chain variable domain is derived from a rearranged human $V_H$1-69 or a human $V_H$1-2 gene segment.

In one aspect, a nucleic acid sequence encoding a human antigen-binding domain made in a non-human animal as described herein is provided. In one embodiment, the nucleic acid sequence encodes a human immunoglobulin $V_H$ domain. In one embodiment, the nucleic acid sequence encodes a human immunoglobulin $V_H$ domain and a cognate human $V_L$ domain. In various embodiments, the human $V_H$ domain is derived from a rearranged human $V_H$1-69 or a human $V_H$1-2 gene segment.

In one aspect, a method for preparation of a human antibody is provided, comprising immunizing a non-human animal as described herein with an antigen of interest, allowing the non-human animal to mount an immune response, harvesting a lymphocyte (e.g., a B cell) from the immunized animal, fusing the lymphocyte with a myeloma cell to form a hybridoma cell, obtaining from the hybridoma cell a nucleic acid sequence that encodes a human $V_H$ domain and a human $V_L$ domain, cloning the nucleic acid sequence in frame (i.e., in operable linkage) with a human constant region sequence to create an immunoglobulin heavy chain and an immunoglobulin light chain, and expressing the heavy and light chains in a cell capable of expressing the fully human antibody. In one embodiment, the cell is a CHO cell. In various embodiments, the human $V_H$ domain is derived from a rearranged human $V_H$1-69 gene segment or a human $V_H$1-2 gene segment.

In one aspect, a method for preparation of a human antibody is provided, comprising immunizing a non-human animal as described herein with an antigen of interest, allowing the non-human animal to mount an immune response, harvesting a lymphocyte (e.g., a B cell) from the immunized animal, obtaining from the lymphocyte a nucleic acid sequence that encodes a human $V_H$ domain and a human $V_L$ domain, cloning the nucleic acid sequence in frame (i.e., in operable linkage) with a human constant region sequence to create an immunoglobulin heavy chain and an immunoglobulin light chain, and expressing the heavy and light chains in a cell capable of expressing the fully human antibody. In one embodiment, the lymphocyte is derived from the spleen of the non-human animal. In one embodiment, the cell is a CHO cell. In various embodiments, the human $V_H$ domain is derived from a rearranged human $V_H$1-69 gene segment or a human $V_H$1-2 gene segment.

In various aspects, the antigen of interest is a pathogen that afflicts human subjects as described herein. In various aspects, the antigen of interest is a virus that is capable of infecting a human. Exemplary antigens that can be employed in the methods and uses described herein include microbes or microorganisms such as a virus, bacterium, prion, or fungus or any other pathogen that causes disease in humans. A person of skill, upon reading the disclosure, will appreciate those human pathogens that will be applicable for the methods and uses described herein. The various aspects and embodiments are capable of use together, unless expressly noted otherwise or the context clearly prohibits use together.

BRIEF DESCRIPTION OF FIGURES

FIG. 13 shows the nucleotide alignment of the second exon for each of thirteen reported alleles for the human $V_H$1-69 gene. Lower case bases indicate germline nucleotide differences among the alleles. Complementary determining regions (CDRs) are indicated with boxes around the sequence. Dashes indicate artificial gaps for proper sequence alignment. $V_H$1-69*01 (SEQ ID NO: 34); $V_H$1-69*02 (SEQ ID NO: 36); $V_H$1-69*03 (SEQ ID NO: 38); $V_H$1-69*04 (SEQ ID NO: 40); $V_H$1-69*05 (SEQ ID NO: 42); $V_H$1-69*06 (SEQ ID NO: 44); $V_H$1-69*07 (SEQ ID NO: 46); $V_H$1-69*08 (SEQ ID NO: 48); $V_H$1-69*09 (SEQ ID NO: 50); $V_H$1-68*10 (SEQ ID NO: 52); $V_H$1-69*11 (SEQ ID NO: 54); $V_H$1-69*12 (SEQ ID NO: 56); $V_H$1-69*13 (SEQ ID NO: 58).

FIG. 14 shows the protein alignment of the mature heavy chain variable gene sequence for each of thirteen reported alleles for the human $V_H$1-69 gene. Lower case amino acids indicate germline differences among the alleles. Complementary determining regions (CDRs) are indicated with boxes around the sequence. Dashes indicate artificial gaps for proper sequence alignment. $V_H$1-69*01 (SEQ ID NO: 35); $V_H$1-69*02 (SEQ ID NO: 37); $V_H$1-69*03 (SEQ ID NO: 39); $V_H$1-69*04 (SEQ ID NO: 41); $V_H$1-69*05 (SEQ ID NO: 43); $V_H$1-69*06 (SEQ ID NO: 45); $V_H$1-69*07 (SEQ ID NO: 47); $V_H$1-69*08 (SEQ ID NO: 49); $V_H$1-69*09 (SEQ ID NO: 51); $V_H$1-69*10 (SEQ ID NO: 53); $V_H$1-69*11 (SEQ ID NO: 55); $V_H$1-69*12 (SEQ ID NO: 57); $V_H$1-69*13 (SEQ ID NO: 59).

FIG. 15 shows a percent identity/percent similarity matrix for the aligned protein sequences of the mature variable gene for each of thirteen reported alleles for the human $V_H$1-69 gene. Percent identity among the $V_H$1-69 alleles is indicated above the shaded boxes and percent similarity is indicated below the shaded boxes. Scores for percent identity and percent similarity were scored by a ClustalW (v1.83) alignment tool using MacVector software (MacVector, Inc., North Carolina).

FIG. 16 shows the nucleotide alignment of the second exon for each of five reported alleles for the human $V_H$1-2 gene. Lower case bases indicate germline nucleotide differences among the alleles. Complementary determining regions (CDRs) are indicated with boxes around the sequence. Dashes indicate artificial gaps for proper sequence alignment. $V_H$1-2*01 (SEQ ID NO: 60); $V_H$1-2*02 (SEQ ID NO: 62); $V_H$1-2*03 (SEQ ID NO: 64); $V_H$1-2*04 (SEQ ID NO: 66); $V_H$1-2*05 (SEQ ID NO: 68).

FIG. 17 shows the protein alignment of the mature heavy chain variable gene sequence for each of five reported alleles for the human $V_H$1-2 gene. Lower case amino acids indicate germline differences among the alleles. Complementary determining regions (CDRs) are indicated with boxes around the sequence. Dashes indicate artificial gaps for proper sequence alignment. $V_H$1-2*01 (SEQ ID NO: 61); $V_H$1-2*02 (SEQ ID NO: 63); $V_H$1-2*03 (SEQ ID NO: 65); $V_H$1-2*04 (SEQ ID NO: 67); $V_H$1-2*05 (SEQ ID NO: 69).

FIG. 18 shows a percent identity/percent similarity matrix for the aligned protein sequences of the mature variable gene for each of five reported alleles for the human $V_H$1-2 gene. Percent identity among the $V_H$1-2 alleles is indicated above the shaded boxes and percent similarity is indicated below the shaded boxes. Scores for percent identity and percent similarity were scored by a ClustalW (v1.83) alignment tool using MacVector software (MacVector, Inc., North Carolina).

DETAILED DESCRIPTION

This invention is not limited to particular methods, and experimental conditions described, as such methods and conditions may vary. It is also to be understood that the terminology used herein is for the purpose of describing particular embodiments only, and is not intended to be limiting, since the scope of the present invention is defined by the claims.

Unless defined otherwise, all terms and phrases used herein include the meanings that the terms and phrases have attained in the art, unless the contrary is clearly indicated or clearly apparent from the context in which the term or phrase is used. Although any methods and materials similar or equivalent to those described herein can be used in the practice or testing of the present invention, particular methods and materials are now described. All publications mentioned are hereby incorporated by reference.

The phrase "substantial" or "substantially" when used to refer to an amount of gene segments (e.g., "substantially all" V gene segments) includes both functional and non functional gene segments and include, in various embodiments, e.g., 80% or more, 85% or more, 90% or more, 95% or more 96% or more, 97% or more, 98% or more, or 99% or more of all gene segments; in various embodiments, "substantially all" gene segments includes, e.g., at least 95%, 96%, 97%, 98%, or 99% of functional (i.e., non-pseudogene) gene segments.

The term "replacement" includes wherein a DNA sequence is placed into a genome of a cell in such a way as to replace a sequence within the genome with a heterologous sequence (e.g., a human sequence in a mouse), at the locus of the genomic sequence. The DNA sequence so placed may include one or more regulatory sequences that are part of source DNA used to obtain the sequence so placed (e.g., promoters, enhancers, 5'- or 3'-untranslated regions, appropriate recombination signal sequences, etc.). For example, in various embodiments, the replacement is a substitution of an endogenous sequence for a heterologous sequence that results in the production of a gene product from the DNA sequence so placed (comprising the heterologous sequence), but not expression of the endogenous sequence; the replacement is of an endogenous genomic sequence with a DNA sequence that encodes a protein that has a similar function as a protein encoded by the endogenous genomic sequence (e.g., the endogenous genomic sequence encodes an immunoglobulin gene or domain, and the DNA fragment encodes one or more human immunoglobulin genes or domains). In various embodiments, an endogenous gene or fragment thereof is replaced with a corresponding human gene or fragment thereof. A corresponding human gene or fragment thereof is a human gene or fragment that is an ortholog of, a homolog of, or is substantially identical or the same in structure and/or function, as the endogenous gene or fragment thereof that is replaced.

Figure 1:
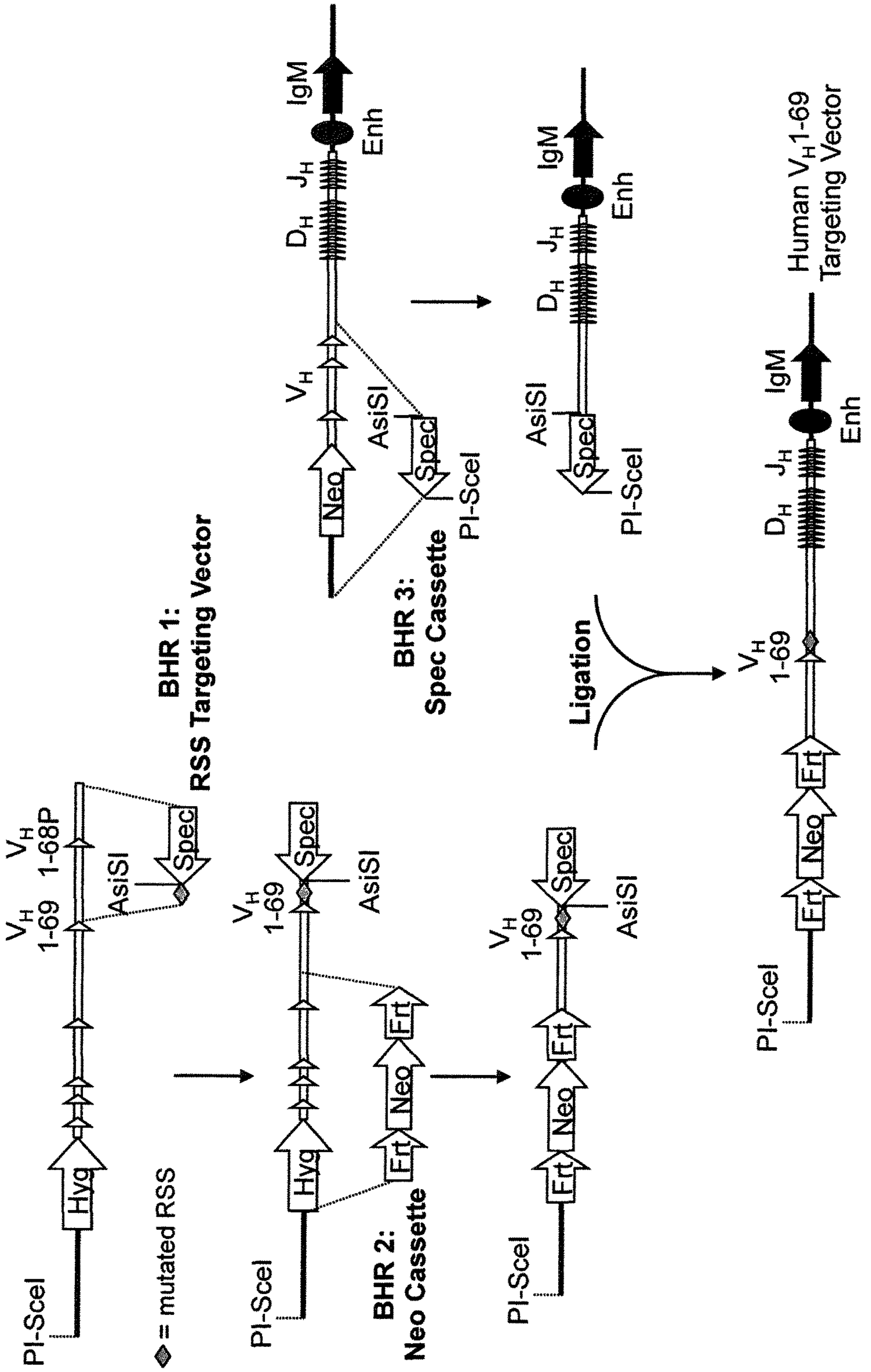
FIG. 1 shows a general illustration, not to scale, of a series of targeting and molecular engineering steps employed to make a targeting vector for construction of a modified heavy chain locus containing a single human $V_H$1-69 gene segment, twenty-seven human $D_H$ and six human $J_H$ gene segments at an endogenous immunoglobulin heavy chain locus.
Figure 2:
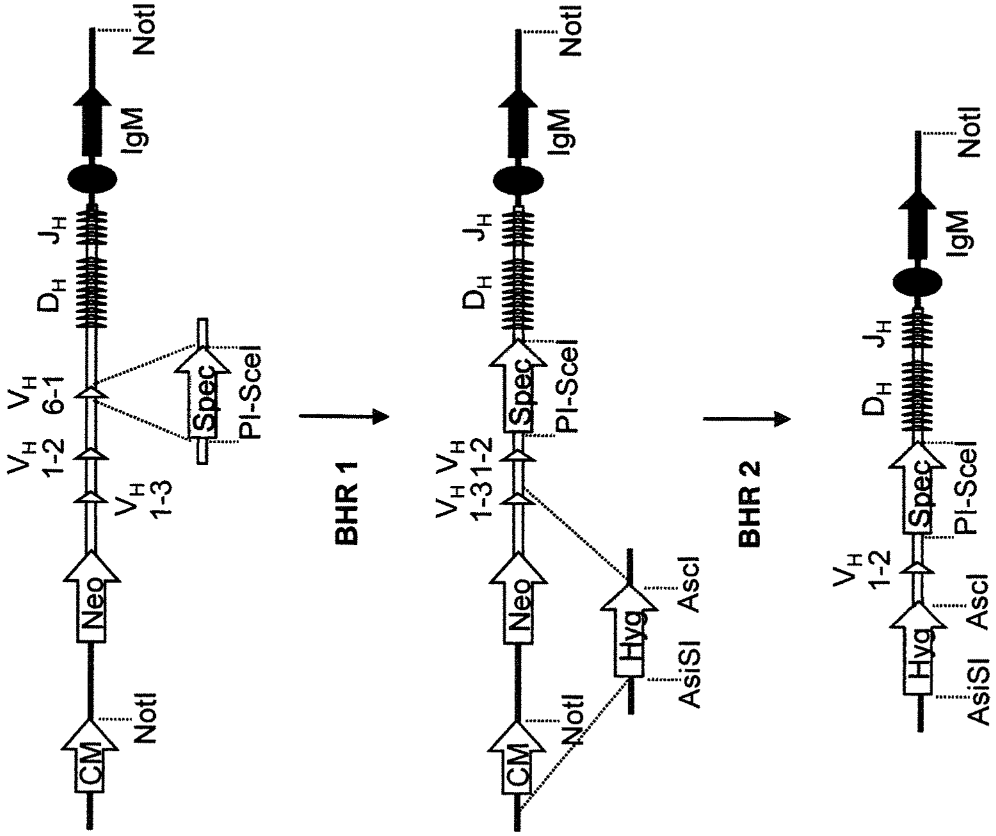
FIG. 2 shows a general illustration, not to scale, of a series of targeting and molecular engineering steps employed to make a targeting vector for construction of a modified heavy chain locus containing a single human $V_H$1-2 gene segment, twenty-seven human $D_H$ and six human $J_H$ gene segments at an endogenous immunoglobulin heavy chain locus.
Figure 3:
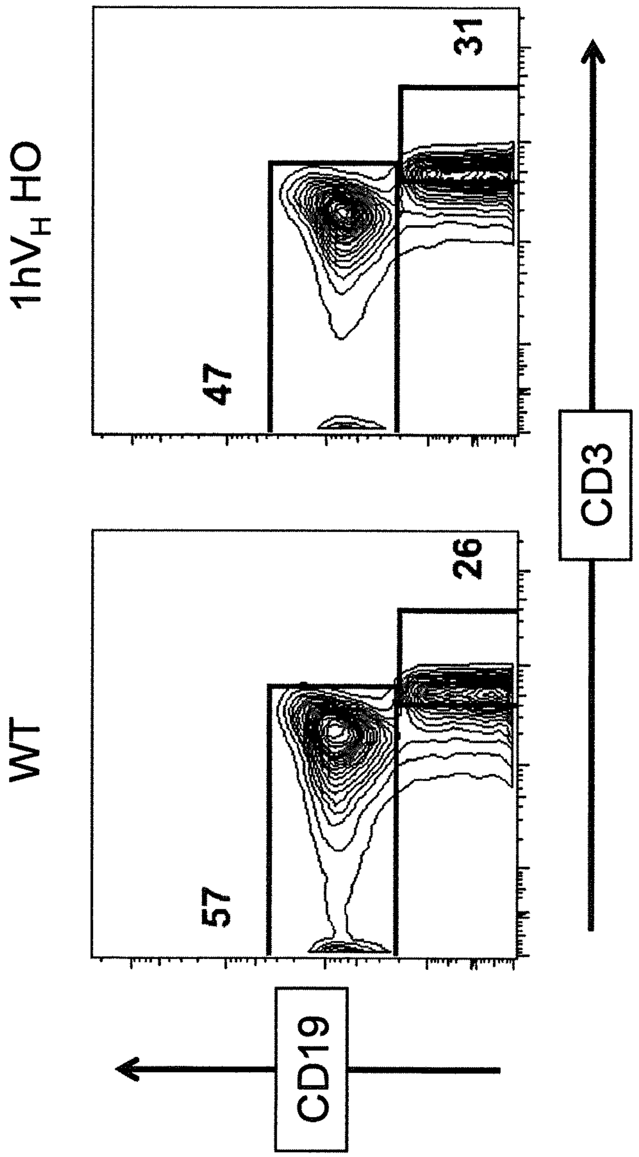
FIG. 3 shows contour plots of splenocytes gated on single lymphocytes and stained for CD19 (B cell) and CD3 (T cell) from a wild type mouse (WT) and a mouse homozygous for a single human $V_H$ gene segment, twenty-seven human $D_H$ and six human $J_H$ gene segments at the endogenous immunoglobulin heavy chain locus (1h$V_H$ HO).
Figure 4A:
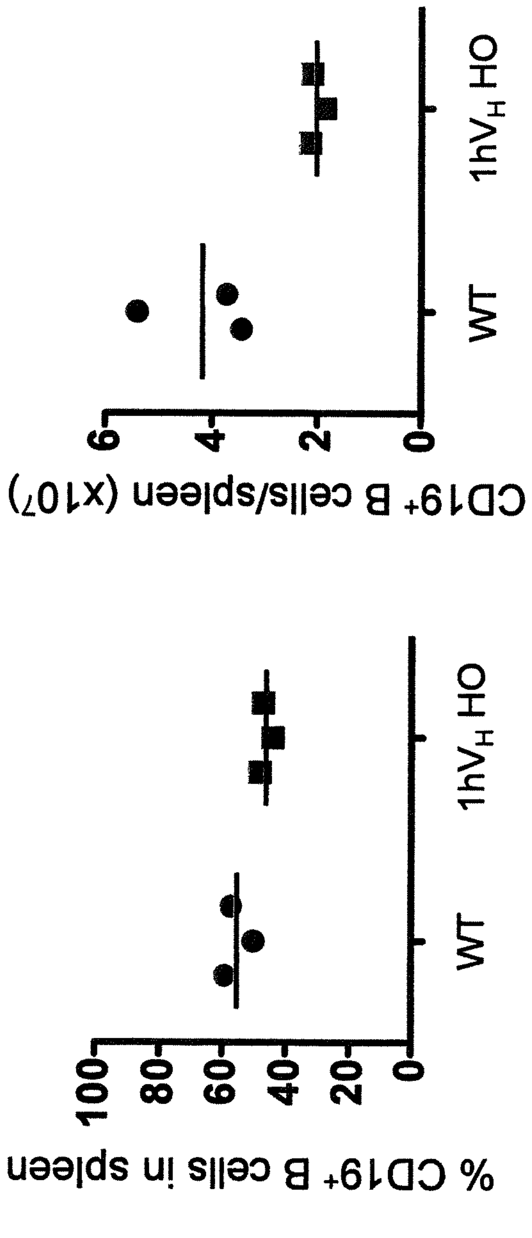
FIG. 4A shows, on the left, the percent of $CD19^+$ B cells in spleens harvested from wild type mice (WT) and mice homozygous for a single human $V_H$ gene segment, twenty-seven human $D_H$ and six human $J_H$ gene segments at the endogenous immunoglobulin heavy chain locus (1h$V_H$ HO). On the right, the number of $CD19^+$ B cells per spleen is shown for both wild type mice (WT) and mice homozygous for a single human $V_H$ gene segment, twenty-seven human $D_H$ and six human $J_H$ gene segments at the endogenous immunoglobulin heavy chain locus (1h$V_H$ HO).
Figure 4B:
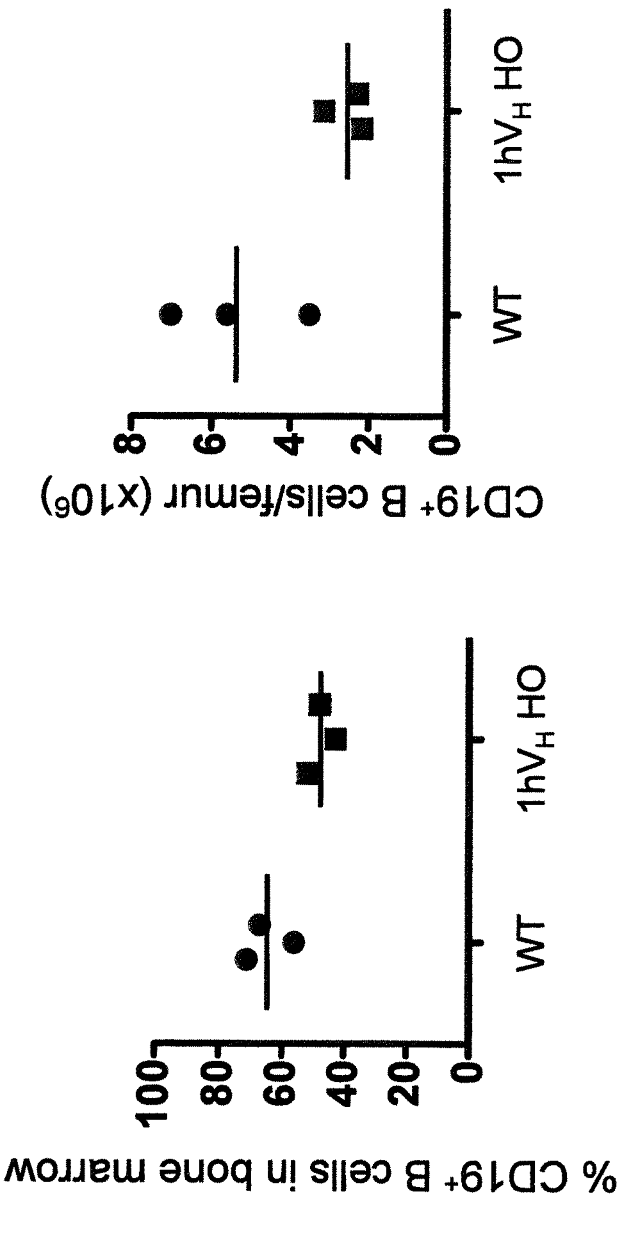
FIG. 4B shows, on the left, the percent of $CD19^+$ B cells in bone marrow harvested from femurs of wild type mice (WT) and mice homozygous for a single human $V_H$ gene segment, twenty-seven human $D_H$ and six human $J_H$ gene segments at the endogenous immunoglobulin heavy chain locus (1h$V_H$ HO). On the right, the number of $CD19^+$ B cells per femur is shown for both wild type mice (WT) and mice homozygous for a single human $V_H$ gene segment, twenty-seven human $D_H$ and six human $J_H$ gene segments at the endogenous immunoglobulin heavy chain locus ($1hV_H$ HO).
Figure 5:
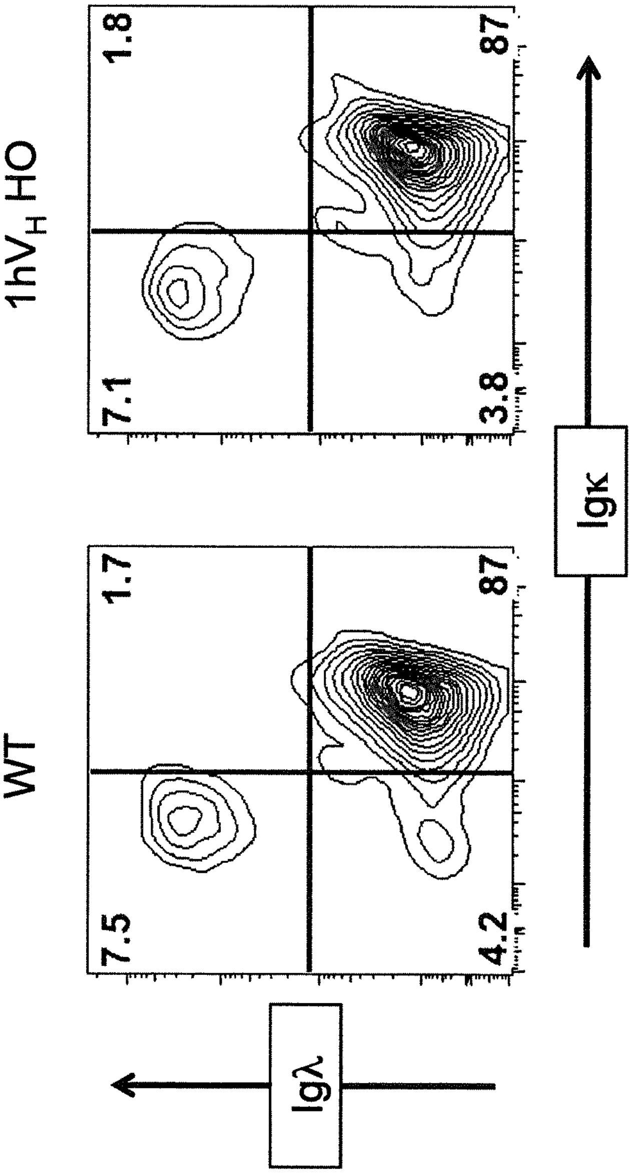
FIG. 5 shows contour plots of splenocytes gated on $CD19^+$ B cells and stained for Igλ+ and Igκ+ expression from a wild type mouse (WT) and a mouse homozygous for a single human $V_H$ gene segment, twenty-seven human $D_H$ and six human $J_H$ gene segments at the endogenous immunoglobulin heavy chain locus ($1hV_H$ HO).
Figure 6:
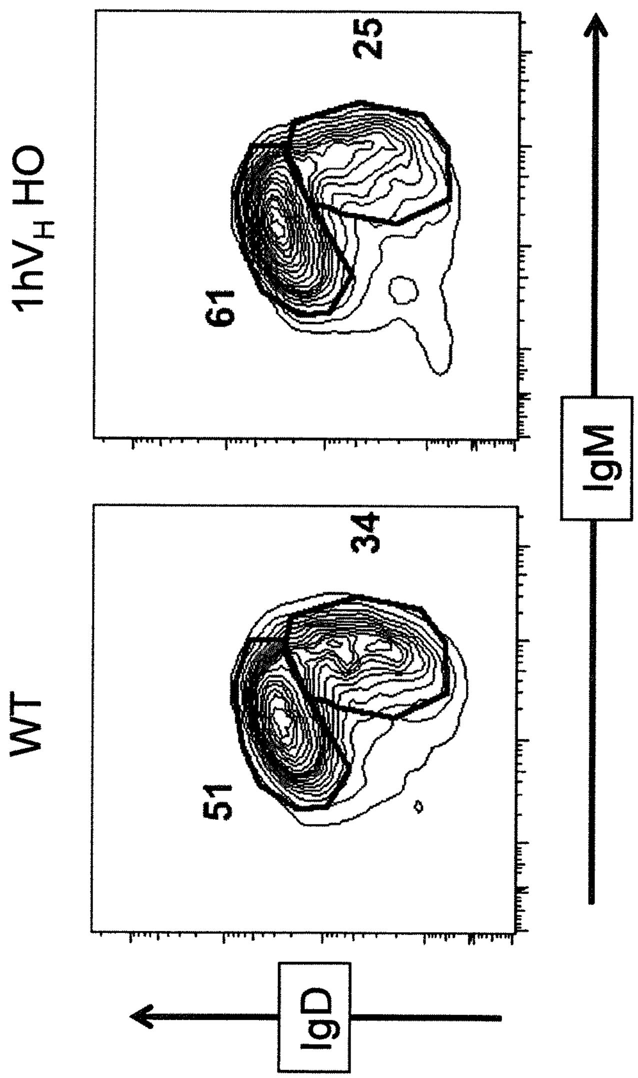
FIG. 6 shows contour plots of splenocytes gated on $CD19^+$ B cells and stained for immunoglobulin D (IgD) and immunoglobulin M (IgM) from a wild type mouse (WT) and a mouse homozygous for a single human $V_H$ gene segment, twenty-seven human $D_H$ and six human $J_H$ gene segments at the endogenous immunoglobulin heavy chain locus ($1hV_H$ HO).
Figure 7:
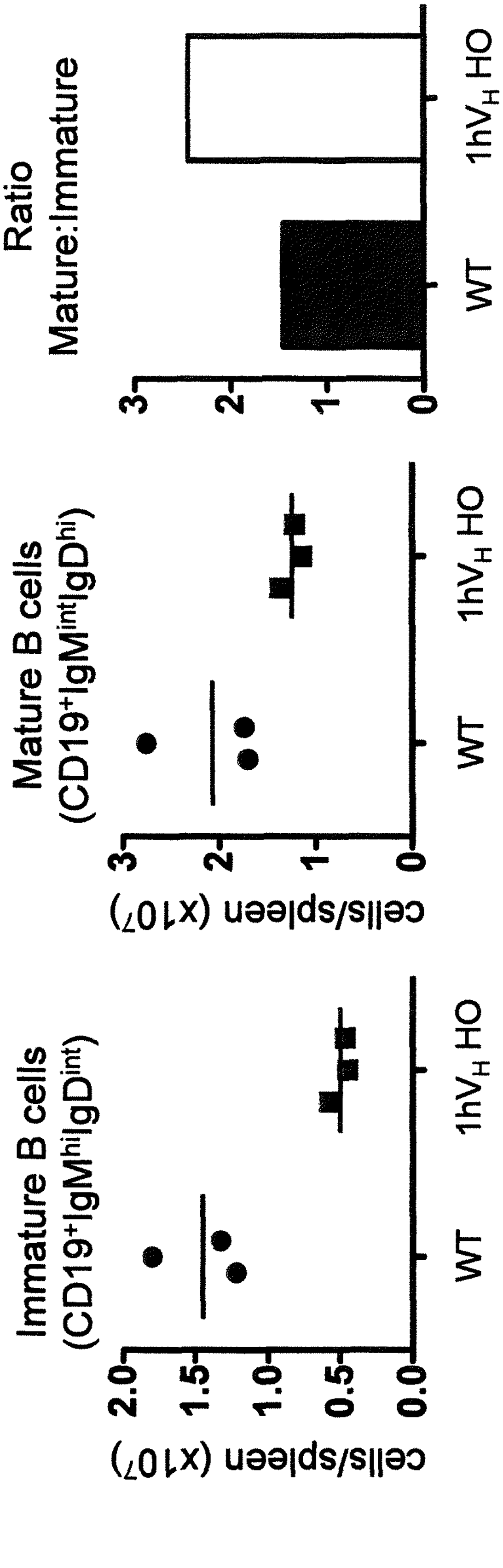
FIG. 7 shows the total number of transitional B cells ($CD19^+IgM^{hi}IgD^{int}$), mature B cells ($CD19^+IgM^{int}IgD^{hi}$), and the ratio of mature to immature B cells in harvested spleens from wild type mice (WT) and mice homozygous for a single human $V_H$ gene segment, twenty-seven human $D_H$ and six human $J_H$ gene segments at the endogenous immunoglobulin heavy chain locus ($1hV_H$ HO).
Figure 8:
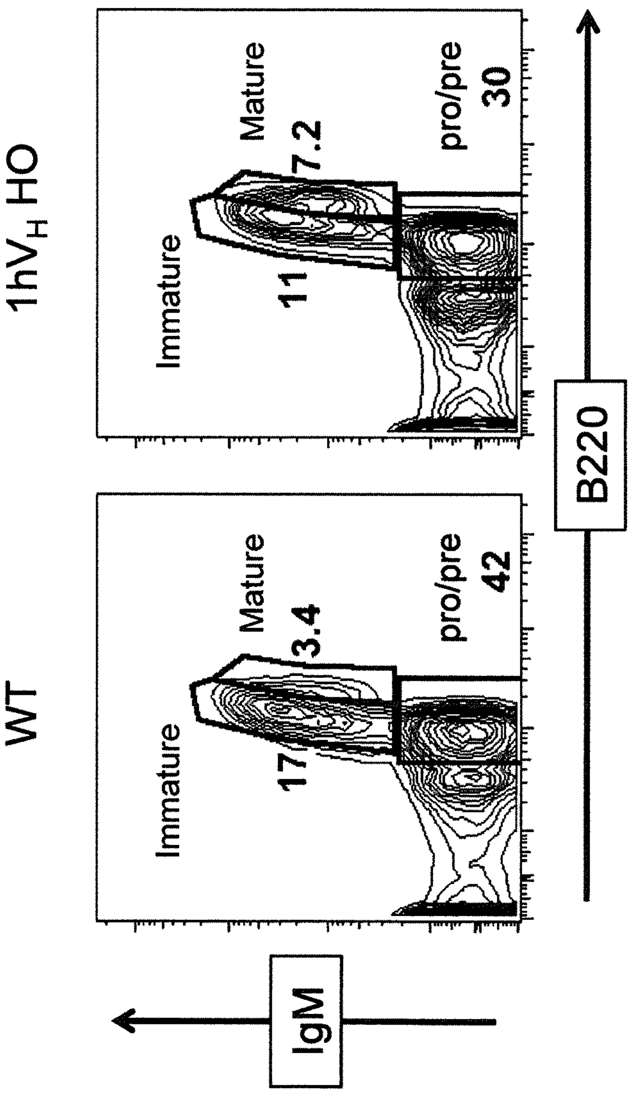
FIG. 8 shows contour plots of bone marrow gated on singlets stained for immunoglobulin M (IgM) and B220 from a wild type mouse (WT) and a mouse homozygous for a single human $V_H$ gene segment, twenty-seven human $D_H$ and six human $J_H$ gene segments at the endogenous immunoglobulin heavy chain locus ($1hV_H$ HO).
Figure 9:
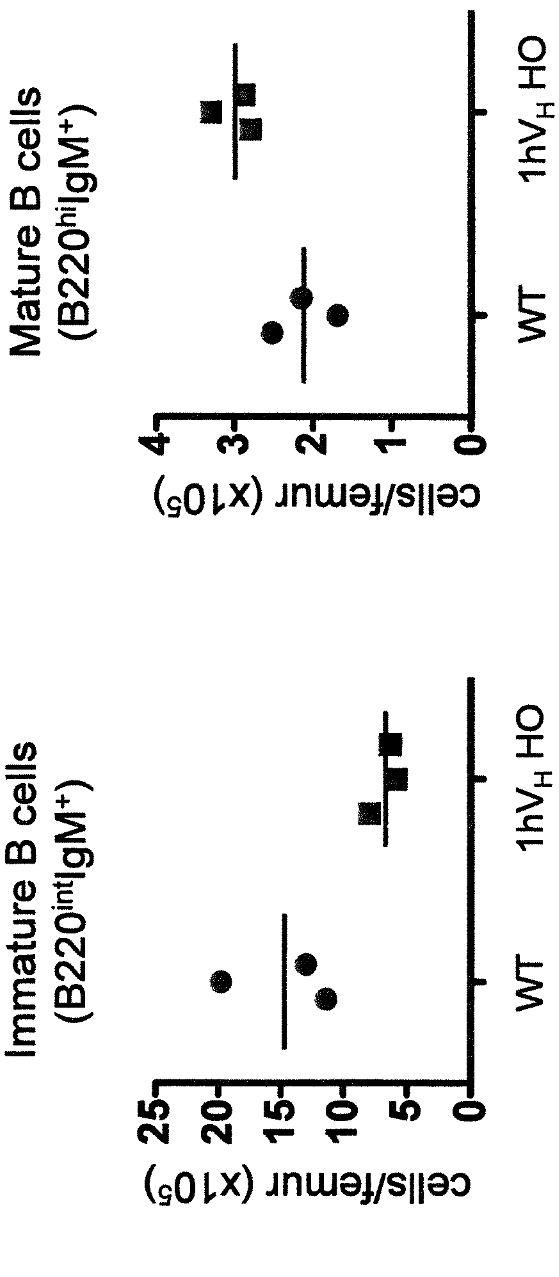
FIG. 9 shows the total number of immature ($B220^{int}IgM^+$) and mature ($B220^{hi}IgM^+$) B cells in bone marrow isolated from the femurs of wild type mice (WT) and mice homozygous for a single human $V_H$ gene segment, twenty-seven human $D_H$ and six human $J_H$ gene segments at the endogenous immunoglobulin heavy chain locus ($1hV_H$ HO).
Figure 10:
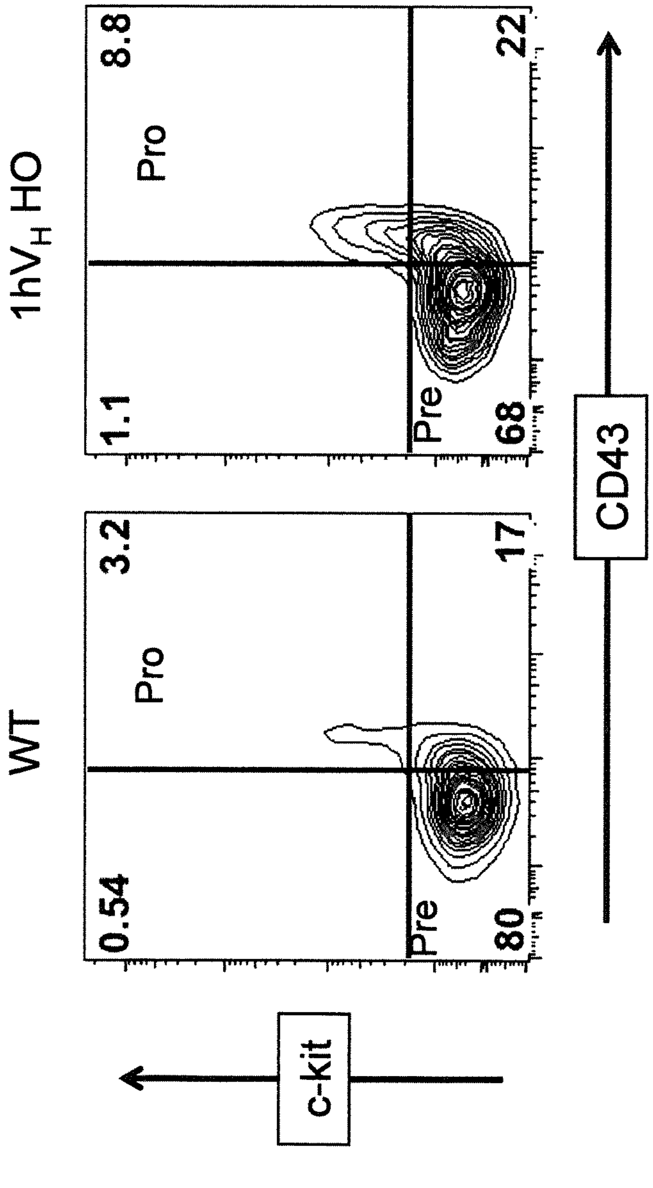
FIG. 10 shows contour plots of bone marrow gated on $CD19^+$ B cells and stained for $ckit^+$ and $CD43^+$ from a wild type mouse (WT) and a mouse homozygous for a single human $V_H$ gene segment, twenty-seven human $D_H$ and six human $J_H$ gene segments at the endogenous immunoglobulin heavy chain locus ($1hV_H$ HO).
Figure 11A:
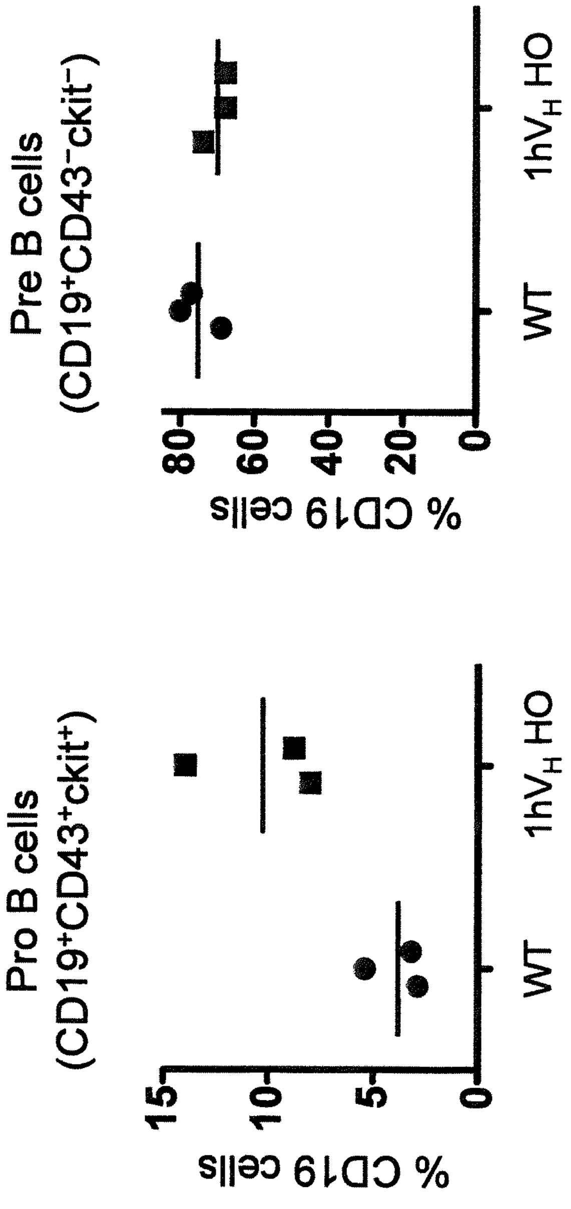
FIG. 11A shows the percent of $CD19^+$ cells in populations of pro B ($CD19^+CD43^+ckit^+$) and pre B ($CD19^+CD43^-ckit^-$) cells in bone marrow harvested from the femurs of wild type mice (WT) and mice homozygous for a single human $V_H$ gene segment, twenty-seven human $D_H$ and six human $J_H$ gene segments at the endogenous immunoglobulin heavy chain locus ($1hV_H$ HO).
Figure 11B:
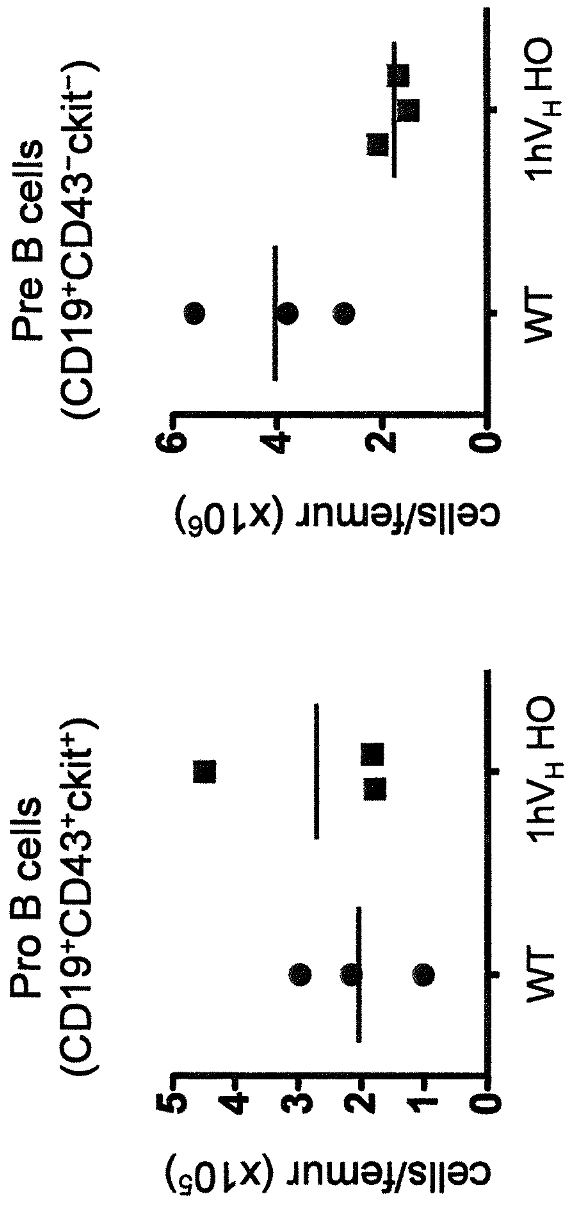
FIG. 11B shows the absolute number of cells per femur in populations of pro B ($CD19^+CD43^+ckit^+$) and pre B ($CD19^+CD43^-ckit^-$) cells in bone marrow harvested from wild type mice (WT) and mice homozygous for a single human $V_H$ gene segment, twenty-seven human $D_H$ and six human $J_H$ gene segments at the endogenous immunoglobulin heavy chain locus ($1hV_H$ HO).

A precise, in situ replacement of six megabases of the variable regions of the mouse heavy chain immunoglobulin loci ($V_H$-$D_H$-$J_H$) with a restricted human immunoglobulin heavy chain locus was performed, while leaving the flanking mouse sequences intact and functional within the hybrid loci, including all mouse constant chain genes and locus transcriptional control regions (FIG. 1 and FIG. 2). Specifically, a single human $V_H$, 27 $D_H$, and six $J_H$ gene segments were introduced through chimeric BAC targeting vectors into mouse ES cells using VELOCIGENE® genetic engineering technology (see, e.g., U.S. Pat. No. 6,586,251 and Valenzuela et al., 2003, High-throughput engineering of the mouse genome coupled with high-resolution expression analysis, *Nat Biotechnol* 21:652-659).

Non-Human Animals with Restricted Immunoglobulin $V_H$ Gene Segments

Non-human animals comprising immunoglobulin loci that comprise a restricted number of $V_H$ genes, and one or more D genes and one or more J genes, are provided, as are methods of making and using them. When immunized with an antigen of interest, the non-human animals generate B cell populations with antibody variable regions derived only from the restricted, pre-selected $V_H$ gene or set of $V_H$ genes (e.g., a pre-selected $V_H$ gene and variants thereof). In various embodiments, non-human animals are provided that generate B cell populations that express human antibody variable domains that are human heavy chain variable domains, along with cognate human light chain variable domains. In various embodiments, the non-human animals rearrange human heavy chain variable gene segments and human light chain variable gene segments from modified endogenous mouse immunoglobulin loci that comprise a replacement or insertion of the non-human unrearranged variable region sequences with human unrearranged variable region sequences.

Early work on the organization, structure, and function of the immunoglobulin genes was done in part on mice with disabled endogenous loci and engineered to have transgenic loci (randomly placed) with partial human immunoglobulin genes, e.g., a partial repertoire of human heavy chain genes linked with a human constant gene, randomly inserted into the genome, in the presence or absence of a human light chain transgene. Although these mice were somewhat less than optimal for making useful high affinity antibodies, they facilitated certain functional analyses of immunoglobulin loci. Some of these mice had as few as two or three, or even just a single, heavy chain variable gene.

Mice that express fully human immunoglobulin heavy chains derived from a single human $V_H$5-51 gene and 10 human $D_H$ genes and six human $J_H$ genes, with human μ and γ1 constant genes, on a randomly inserted transgene (and disabled endogenous immunoglobulin loci) have been reported (Xu and Davis, 2000, Diversity in the CDR3 Region of $V_H$ Is Sufficient for Most Antibody Specificities, *Immunity* 13:37-45). The fully human immunoglobulin heavy chains of these mice are mostly expressed with one of just two fully mouse λ light chains derived from the endogenous mouse λ light chain locus (Vλ1-Jλ1 or Vλ2-Jλ2 only), and can express no κ light chain (the mice are $Ig\kappa^{-/-}$). These mice exhibit severely abnormal dysfunction in B cell development and antibody expression. B cell numbers are reportedly 5-10% of wild-type, IgM levels 5-10% of wild-type, and IgG1 levels are only 0.1-1% of wild-type. The observed IgM repertoire revealed highly restricted junctional diversity. The fully human heavy chains display largely identical CDR3 length across antigens, the same $J_H$ ($J_H$2) usage across antigens, and an initial junctional Q residue, thus reflecting a certain lack of CDR3 diversity. The fully mouse λ light chains nearly all had a W96L substitution in Jλ1 as initial junctional residue. The mice are reportedly unable to generate any antibodies against bacterial polysaccharide. Because the human variable domains couple with mouse light chains, the utility of the human variable regions is highly limited.

Other mice that have just a single human $V_H$3-23 gene, human $D_H$ and $J_H$ genes, and mouse light chain genes have been reported, but they exhibit a limited diversity (and thus a limited usefulness) due in part to mispairing potential between human $V_H$ and mouse $V_L$ domains (see, e.g., Mageed et al., 2001, Rearrangement of the human heavy chain variable region gene V3-23 in transgenic mice generates antibodies reactive with a range of antigens on the basis of $V_H$CDR3 and residues intrinsic to the heavy chain variable region, *Clin. Exp. Immunol.* 123:1-5). Similarly, mice that bear two $V_H$ genes (3-23 and 6-1) along with human $D_H$ and $J_H$ genes in a transgene containing the human μ constant gene (Bruggemann et al., 1991, Human antibody production in transgenic mice: expression from 100 kb of the human IgH locus, *Eur. J. Immmunol.* 21:1323-1326) and express them in human IgM chains with mouse light chains may exhibit a repertoire limited by mispairing (Mackworth-Young et al., 2003, The role of antigen in the selection of the human V3-23 immunoglobulin heavy chain variable region gene, *Clin. Exp. Immunol.* 134:420-425).

Other transgenic mice that express $V_H$-restricted fully human heavy chains from a human transgene randomly inserted in the genome, with a limited human λ repertoire expressed from a fully human randomly inserted transgene, have also been reported (see, e.g., Taylor et al., 1992, A transgenic mouse that expresses a diversity of human sequence heavy and light chain immunoglobulins, *Nucleic Acids Res.* 20(23):6287-6295; Wagner et al., 1994, Antibodies generated form human immunoglobulin miniloci in transgenic mice, *Nucleic Acids Res.* 22(8):1389-1393). However, transgenic mice that express fully human antibodies from transgenes randomly integrated into the mouse genome, and that comprise damaged endogenous loci, are known to exhibit substantial differences in immune response as compared with wild-type mice that affect the diversity of the antibody variable domains obtainable from such mice.

Useful non-human animals that generate a diverse population of B cells that express human antibody variable domains from a restricted $V_H$ gene repertoire and one or more D genes and one or more J genes will be capable of generating, preferably in some embodiments, repertoires of rearranged variable region genes that will be sufficiently diverse. In various embodiments, diversity includes junctional diversity, somatic hypermutation, and polymorphic diversity in $V_H$ gene sequence (for embodiments where $V_H$ genes are present in polymorphic forms). Combinatorial diversity occurs in the pairing of the $V_H$ gene with one of a plurality of cognate human light chain variable domains (which, in various embodiments, comprise junctional diversity and/or somatic hypermutations).

Non-human animals comprising a restricted human $V_H$ gene repertoire and a complete or substantially complete human $V_L$ gene repertoire will in various embodiments generate populations of B cells that reflect the various sources of diversity, such as junctional diversity (e.g., VDJ, VJ joining, P additions, N additions), combinatorial diversity (e.g., cognate $V_H$-restricted human heavy, human light), and somatic hypermutations. In embodiments comprising a restriction of the $V_H$ repertoire to one human $V_H$ gene, the one human $V_H$ gene can be present in two or more variants. In various embodiments, the presence of two or more polymorphic forms of a $V_H$ gene will enrich the diversity of the variable domains of the B cell population.

Variations in the germline sequences of gene segments (e.g., V genes) contribute to the diversity of the antibody response in humans. The relative contribution to diversity due to V gene sequence differences varies among V genes. The degree of polymorphism varies across gene families, and is reflected in a plurality of haplotypes (stretches of sequence with coinherited polymorphisms) capable of generating further diversity as observed in $V_H$ haplotype differences between related and unrelated individuals in the human population (see, e.g., Souroujon et al., 1989, Polymorphisms in Human H Chain V Region Genes from the $V_H$III Gene Family, *J. Immunol.* 143(2):706-711). Some have suggested, based on data from particularly polymorphic human $V_H$ gene families, that haplotype diversity in the germline is a major contributor to $V_H$ gene heterogeneity in the human population, which is reflected in the large diversity of different germline $V_H$ genes across the human population (see, Sasso et al., 1990, Prevalence and Polymorphism of Human $V_H$3 Genes, *J. Immunol.* 145(8):2751-2757).

Although the human population displays a large diversity of haplotypes with respect to the $V_H$ gene repertoire due to widespread polymorphism, certain polymorphisms are reflected in prevalent (i.e., conserved) alleles observed in the human population (Sasso et al., 1990). $V_H$ polymorphism can be described in two principle forms. The first is variation arising from allelic variation associated with differences among the nucleotide sequence between alleles of the same gene segment. The second arises from the numerous duplications, insertions, and/or deletions that have occurred at the immunoglobulin heavy chain locus. This has resulted in the unique situation in which $V_H$ genes derived by duplication from identical genes differ from their respective alleles by one or more nucleotide substitutions. This also directly influences the copy number of $V_H$ genes at the heavy chain locus.

Polymorphic alleles of the human immunoglobulin heavy chain variable gene segments ($V_H$ genes) have largely been the result of insertion/deletion of gene segments and single nucleotide differences within coding regions, both of which have the potential to have functional consequences on the immunoglobulin molecule. Table 1 sets forth the functional $V_H$ genes listed by human $V_H$ gene family and the number of identified alleles for each $V_H$ gene in the human immunoglobulin heavy chain locus. There are some findings to suggest that polymorphic $V_H$ genes have been implicated in susceptibility to certain diseases such as, for example, rheumatoid arthritis, whereas in other cases a linkage between $V_H$ and disease has been less clear. This ambiguity has been attributed to the copy number and presence of various alleles in different human populations. In fact, several human $V_H$ genes demonstrate copy number variation (e.g., $V_H$1-2, $V_H$1-69, $V_H$2-26, $V_H$2-70, and $V_H$3-23). In various embodiments, humanized mice as described herein with restricted $V_H$ repertoires comprise multiple polymorphic variants of an individual $V_H$ family member (e.g., two or more polymorphic variants of $V_H$1-2, $V_H$1-69, $V_H$2-26, $V_H$2-70, or $V_H$3-23, replacing all or substantially all functional mouse $V_H$ segments at an endogenous mouse locus). In a specific embodiment, the two or more polymorphic variants of mice described herein are in number up to and including the number indicated for the corresponding $V_H$ family member in Table 1 (e.g., for $V_H$1-69, 13 variants; for $V_H$1-2, five variants; etc.).

Commonly observed variants of particular human $V_H$ genes are known in the art. For example, one of the most complex polymorphisms in the $V_H$ locus belongs to the $V_H$1-69 gene. The human $V_H$1-69 gene has 13 reported alleles (Sasso et al., 1993, A fetally expressed immunoglobulin $V_H$1 gene belongs to a complex set of alleles, *Journal of Clinical Investigation* 91:2358-2367; Sasso et al., 1996, Expression of the immunoglobulin $V_H$ gene 51p1 is proportional to its germline gene copy number, *Journal of Clinical Investigation* 97(9):2074-2080) and exists in at least three haplotypes that carry duplications of the $V_H$1-69 gene, which results in multiple copies of the $V_H$ gene at a given locus. These polymorphic alleles include differences in the complementarity determining regions (CDRs), which may dramatically influence antigen specificity. Table 2 sets for the reported alleles for human $V_H$1-69 and the SEQ ID NOs for the DNA and protein sequences of the mature heavy chain variable regions. Table 3 sets forth the reported alleles for human $V_H$1-2 genes and the SEQ ID NOs for the DNA and protein sequences of the mature heavy chain variable regions.

Representative genomic DNA and full-length protein sequences of a $V_H$1-69 gene are set forth in SEQ ID NO: 1 and SEQ ID NO: 2, respectively. FIG. 13 and FIG. 14 set forth DNA and protein alignments of thirteen reported $V_H$1-69 alleles, respectively. Representative DNA and protein sequences of a $V_H$1-2 gene are set forth in SEQ ID NO: 60 and SEQ ID NO: 61, respectively. FIG. 16 and FIG. 17 set forth DNA and protein alignments of five reported $V_H$1-2 alleles, respectively. FIG. 15 and FIG. 18 set forth a percent identity/similarity matrix for aligned protein sequences corresponding to thirteen reported human $V_H$1-69 alleles and five reported human $V_H$1-2 alleles, respectively. In various embodiments, the modified locus of the invention comprises a $V_H$ gene selected from Table 1, present in two or more copy number, wherein the copy number includes up to and including the number of alleles shown in Table 1. In one embodiment, the modified locus of the invention comprises a $V_H$1-69 gene selected from Table 2, present in two or more copy number, wherein the copy number includes up to and including the number of alleles shown in Table 1. In one embodiment, the modified locus of the invention comprises a $V_H$1-2 gene selected from Table 3, present in two or more copy number, wherein the copy number includes up to and including the number of alleles shown in Table 1.

Although embodiments employing a restricted human $V_H$ repertoire in a mouse are extensively discussed, other non-human animals that express a restricted human $V_H$ repertoire are also provided. Such non-human animals include any of those which can be genetically modified to express a restricted human $V_H$ repertoire as disclosed herein, including, e.g., mouse, rat, rabbit, pig, bovine (e.g., cow, bull, buffalo), deer, sheep, goat, chicken, cat, dog, ferret, primate (e.g., marmoset, rhesus monkey), etc. For example, for those non-human animals for which suitable genetically modifiable ES cells are not readily available, other methods are employed to make a non-human animal comprising the genetic modification. Such methods include, e.g., modifying a non-ES cell genome (e.g., a fibroblast or an induced pluripotent cell) and employing nuclear transfer to transfer the modified genome to a suitable cell, e.g., an oocyte, and gestating the modified cell (e.g., the modified oocyte) in a non-human animal under suitable conditions to form an embryo. Methods for modifying a non-human animal genome (e.g., a pig, cow, rodent, chicken, etc. genome) include, e.g., employing a zinc finger nuclease (ZFN) or a transcription activator-like effector nuclease (TALEN) to modify a genome to include a restricted human $V_H$ repertoire. Thus, in one embodiment a method is provided for editing a non-human animal genome to include a restricted human $V_H$ repertoire, comprising a step of editing the genome employing a ZFN or a TALEN to include no more than one, or no more than two, human $V_H$ gene segments (or polymorphic variants thereof), wherein the no more than one or no more than two human $V_H$ gene segments are operably linked to an immunoglobulin constant gene sequence. In one embodiment, the constant gene sequence is selected from a human heavy chain constant sequence and a non-human heavy chain constant sequence. In one embodiment, the constant sequence is non-human and the no more than one or no more than two human $V_H$ gene segments are operably linked to non-human constant gene sequence at an endogenous non-human immunoglobulin locus.

In one aspect, the non-human animal is a small mammal, e.g., of the superfamily Dipodoidea or Muroidea. In one embodiment, the genetically modified animal is a rodent. In one embodiment, the rodent is selected from a mouse, a rat, and a hamster. In one embodiment, the rodent is selected from the superfamily Muroidea. In one embodiment, the genetically modified animal is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, with-tailed rats, Malagasy rats and mice), Platacanthomyidae (e.g., spiny dormice), and Spalacidae (e.g., mole rates, bamboo rats, and zokors). In a specific embodiment, the genetically modified rodent is selected from a true mouse or rat (family Muridae), a gerbil, a spiny mouse, and a crested rat. In one embodiment, the genetically modified mouse is from a member of the family Muridae, In one embodiment, the non-human animal is a rodent that is a mouse of a C57BL strain. In one embodiment, the C57BL strain is selected from C57BL/A, C57BL/An, C57BL/GrFa, C57BL/KaLwN, C57BL/6, C57BL/6J, C57BL/6ByJ, C57BL/6N, C57BL/6NJ, C57BL/10, C57BL/10ScSn, C57BL/10Cr, and C57BL/Ola. In another embodiment, the mouse is a 129 strain. In one embodiment, the 129 strain is selected from the group consisting of 129P1, 129P2, 129P3, 129X1, 129S1 (e.g., 129S1/SV, 129S1/SvIm), 129S2, 129S4, 129S5, 129S9/SvEvH, 129S6 (129/SvEvTac), 129S7, 129S8, 129T1, 129T2 (see, e.g., Festing et al. (1999) Revised nomenclature for strain 129 mice, Mammalian Genome 10:836, see also, Auerbach et al. (2000) Establishment and Chimera Analysis of 129/SvEv- and C57BL/6-Derived Mouse Embryonic Stem Cell Lines). In one embodiment, the genetically modified mouse is a mix of an aforementioned 129 strain and an aforementioned C57BL strain (e.g., a C57BL/6 strain). In another embodiment, the mouse is a mix of aforementioned 129 strains, or a mix of aforementioned C57BL/6 strains. In one embodiment, the 129 strain of the mix is a 129S6 (129/SvEvTac) strain. In another embodiment, the mouse is a mix of a 129/SvEv- and a C57BL/6-derived strain. In a specific embodiment, the mouse is a mix of a 129/SvEv- and a C57BL/6-derived strain as described in Auerbach et al. 2000 *BioTechniques* 29:1024-1032. In another embodiment, the mouse is a BALB strain, e.g., BALB/c strain. In another embodiment, the mouse is a mix of a BALB strain (e.g., BALB/c strain) and another aforementioned strain.

In one embodiment, the non-human animal is a rat. In one embodiment, the rat is selected from a Wistar rat, an LEA strain, a Sprague Dawley strain, a Fischer strain, F344, F6, and Dark Agouti. In one embodiment, the rat strain is a mix of two or more of a strain selected from the group consisting of Wistar, LEA, Sprague Dawley, Fischer, F344, F6, and Dark Agouti.

TABLE 1

| $V_H$ Family | $V_H$ Gene | Alleles |
|---|---|---|
| $V_H1$ | 1-2 | 5 |
| | 1-3 | 2 |
| | 1-8 | 2 |
| | 1-18 | 3 |
| | 1-24 | 1 |
| | 1-45 | 3 |
| | 1-46 | 3 |
| | 1-58 | 2 |
| | 1-69 | 13 |
| $V_H2$ | 2-5 | 10 |
| | 2-26 | 1 |
| | 2-70 | 13 |
| $V_H3$ | 3-7 | 3 |
| | 3-9 | 2 |
| | 3-11 | 4 |
| | 3-13 | 4 |
| | 3-15 | 8 |
| | 3-16 | 2 |
| | 3-20 | 1 |
| | 3-21 | 4 |
| | 3-23 | 5 |
| | 3-30 | 19 |
| | 3-30-3 | 2 |
| | 3-30-5 | 1 |
| | 3-33 | 6 |
| | 3-35 | 1 |
| | 3-38 | 2 |
| | 3-43 | 2 |
| | 3-48 | 4 |
| | 3-49 | 5 |
| | 3-53 | 4 |
| | 3-64 | 5 |
| | 3-66 | 4 |
| | 3-72 | 2 |
| | 3-73 | 2 |
| | 3-74 | 3 |
| $V_H4$ | 4-4 | 7 |
| | 4-28 | 6 |
| | 4-30-1 | 1 |
| | 4-30-2 | 5 |
| | 4-30-4 | 6 |
| | 4-31 | 10 |
| | 4-34 | 13 |

TABLE 1-continued

| $V_H$ Family | $V_H$ Gene | Alleles |
|---|---|---|
| | 4-39 | 7 |
| | 4-59 | 10 |
| | 4-61 | 8 |
| $V_H5$ | 5-51 | 5 |
| $V_H6$ | 6-1 | 2 |
| $V_H7$ | 7-4-1 | 5 |
| | 7-81 | 1 |

TABLE 2

| IgHV1-69 Allele | Accession Number | SEQ ID NO: (DNA/Protein) |
|---|---|---|
| IgHV1-69*01 | L22582 | 34/35 |
| IgHV1-69*02 | Z27506 | 36/37 |
| IgHV1-69*03 | X92340 | 38/39 |
| IgHV1-69*04 | M83132 | 40/41 |
| IgHV1-69*05 | X67905 | 42/43 |
| IgHV1-69*06 | L22583 | 44/45 |
| IgHV1-69*07 | Z29978 | 46/47 |
| IgHV1-69*08 | Z14309 | 48/49 |
| IgHV1-69*09 | Z14307 | 50/51 |
| IgHV1-69*10 | Z14300 | 52/53 |
| IgHV1-69*11 | Z14296 | 54/55 |
| IgHV1-69*12 | Z14301 | 56/57 |
| IgHV1-69*13 | Z14214 | 58/59 |

TABLE 3

| IgHV1-2 Allele | Accession Number | SEQ ID NO: (DNA/Protein) |
|---|---|---|
| IgHV1-2*01 | X07448 | 60/61 |
| IgHV1-2*02 | X62106 | 62/63 |
| IgHV1-2*03 | X92208 | 64/65 |
| IgHV1-2*04 | Z12310 | 66/67 |
| IgHV1-2*05 | HM855674 | 68/69 |

Antigen-Dependent $V_H$ Gene Usage

Antigen-dependent preferential usage of $V_H$ genes can be exploited in the development of human therapeutics targeting clinically significant antigens. The ability to generate a repertoire of antibody variable domains using a particular $V_H$ gene can provide a significant advantage in the search for high-affinity antibody variable domains to use in human therapeutics. Studies on naive mouse and human $V_H$ gene usage in antibody variable domains reveal that most heavy chain variable domains are not derived from any particular single or dominantly used $V_H$ gene. On the other hand, studies of antibody response to certain antigens reveal that in some cases a particular antibody response displays a biased usage of a particular $V_H$ gene in the B cell repertoire following immunization.

Although the human $V_H$ repertoire is quite diverse, by some estimates the expected frequency of usage of any given $V_H$ gene, assuming random selection of $V_H$ genes, is about 2% (Brezinschek et al., 1995, Analysis of the Heavy Chain Repertoire of Human Peripheral B Cells Using Single-Cell Polymerase Chain Reaction, *J. Immunol.* 155:190-202). But $V_H$ usage in peripheral B cells in humans is skewed. In one study, functional V gene abundance followed the pattern $V_H3>V_H4>V_H1>V_H2>V_H5>V_H6$ (Davidkova et al., 1997, Selective Usage of $V_H$ Genes in Adult Human Lymphocyte Repertoires, *Scand. J. Immunol.* 45:62-73). One early study estimated that $V_H3$ family usage frequency was about 0.65, whereas $V_H1$ family usage frequency was about 0.15; these and other observations suggest that the germline complexity of the human $V_H$ repertoire is not precisely reflected in the peripheral B cell compartment in humans that have a normal germline $V_H$ repertoire, a situation that is similar to that observed in the mouse—i.e., $V_H$ gene expression is non-stochastic (Zouali and These, 1991, Probing $V_H$ Gene-Family Utilization in Human Peripheral B Cells by In Situ Hybridization, *J. Immunol.* 146(8):2855-2864). According to one report, $V_H$ gene usage in humans, from greatest to least, is $V_H3>V_H4>V_H1>V_H5>V_H2>V_H6$; rearrangements in peripheral B cells reveal that $V_H3$ family usage is higher than to be expected based on the relative number of germline $V_H3$ genes (Brezinschek et al., 1995). According to another report $V_H$ usage in humans follows the pattern $V_H3>V_H5>V_H2>V_H1>V_H4>V_H6$, based on analysis of pokeweed mitogen-activated peripheral small immunocompetent B cells (Davidkova et al., 1997, Selective Usage of $V_H$ Genes in Adult Human B Lymphocyte Repertoires, *Scand. J. Immunol.* 45:62-73). One report asserts that among the most frequently used $V_H3$ family members are 3-23, 3-30 and 3-54 (Brezinschek et al., 1995). In the $V_H4$ family, member 4-59 and 4-4-b were found relatively more frequently (Id.), as well as 4-39 and 4-34 (Brezinscheck et al., 1997, Analysis of the Human $V_H$ Gene Repertoire, *J. Clin. Invest.* 99(10):2488-2501). Others postulate that the activated heavy chain repertoire is skewed in favor of high $V_H5$ expression and lower $V_H3$ expression (Van Dijk-Hard and Lundkvist, 2002, Long-term kinetics of adult human antibody repertoires, *Immunology* 107:136-144). Other studies assert that the most commonly used $V_H$ gene in the adult human repertoire is $V_H4$-59, followed by $V_H3$-23 and $V_H3$-48 (Arnaout of al., 2001, High-Resolution Description of Antibody Heavy-Chain Repertoires in Humans, *PLoS ONE* 6(8):108). Although usage studies are based on relatively small sample numbers and thus exhibit high variance, taken together the studies suggest that V gene expression is not purely stochastic. Indeed, studies with particular antigens have established that—in certain cases—the deck is firmly stacked against certain usages and in favor of others.

Over time, it became apparent that the observed repertoire of human heavy chain variable domains generated in response to certain antigens is highly restricted. Some antigens are associated almost exclusively with neutralizing antibodies having only certain particular $V_H$ genes, in the sense that effective neutralizing antibodies are derived from essentially only one $V_H$ gene. Such is the case for a number of clinically important human pathogens.

$V_H1$-69-derived heavy chains have been observed in a variety of antigen-specific antibody repertoires of therapeutic significance. For instance, $V_H1$-69 was frequently observed in heavy chain transcripts of an IgE repertoire of peripheral blood lymphocytes in young children with atopic disease (Bando et al., 2004, Characterization of $V_H\varepsilon$ gene expressed in PBL from children with atopic diseases: detection of homologous $V_H1$-69 derived transcripts from three unrelated patients, *Immunology Letters* 94:99-106). $V_H1$-69-derived heavy chains with a high degree of somatic hypermutation also occur in B cell lymphomas (Perez of al., 2009, Primary cutaneous B-cell lymphoma is associated with somatically hypermutated immunoglobulin variable genes and frequent use of $V_H1$-69 and $V_H4$-59 segments, *British Journal of Dermatology* 162:611-618), whereas some $V_H1$-69-derived heavy chains with essentially germline sequences (i.e., little to no somatic hypermutation) have been observed among autoantibodies in patients with blood disorders (Pos et al., 2008, $V_H1$-69 germline encoded antibodies directed towards ADAMTS13 in patients with acquired thrombotic thrombocytopenic purpura, *Journal of Thrombosis and Haemostasis* 7:421-428).

Further, neutralizing antibodies against viral antigens such as HIV, influenza and hepatitis C(HCV) have been found to utilize germline and/or somatically mutated $V_H1$-69-derived sequences (Miklos of al., 2000, Salivary gland mucosa-associated lymphoid tissue lymphoma immunoglobulin $V_H$ genes show frequent use of V1-69 with distinctive CDR3 features, Blood 95(12):3878-3884; Kunert et al., 2004, Characterization of molecular features, antigen-binding, and in vitro properties of IgG and IgM variants of 4E10, an anti-HIV type I neutralizing monoclonal antibody, *Aids Research and Human Retroviruses* 20(7):755-762; Chan et al., 2001, $V_H1$-69 gene is preferentially used by hepatitis C virus-associated B cell lymphomas and by normal B cells responding to the E2 viral antigen, *Blood* 97(4):1023-1026; Carbonari et al., 2005, Hepatitis C virus drives the unconstrained monoclonal expansion of $V_H1$-69-expressing memory B cells in type II cryoglobulinemia: A model of infection-driven lymphomagenesis, *Journal of Immunology* 174:6532-6539; Wang and Palese, 2009, Universal epitopes of influenza virus hemagglutinins?, *Nature Structural & Molecular Biology* 16(3):233-234; Sui et al., 2009, Structural and functional bases for broad-spectrum neutralization of avian and human influenza A viruses, *Nature Structural & Molecular Biology* 16(3):265-273; Marasca et al., 2001, Immunoglobulin Gene Mutations and Frequent Use of $V_H1$-69 and $V_H4$-34 Segments in Hepatitis C Virus-Positive and Hepatitis C Virus-Negative Nodal Marginal Zone B-Cell Lymphoma, *Am. J. Pathol.* 159(1):253-261).

$V_H$ usage bias is also observed in the humoral immune response to *Haemophilus influenzae* type b (Hib PS) in humans. Studies suggest that the $V_H$III family (the $V_H$IIIb subfamily in particular, $V_H9.1$) exclusively characterizes the human humoral response to Hib PS, with diverse D and J genes (Adderson et al., 1991, Restricted Ig H Chain V Gene Usage in the Human Antibody Response to *Haemophilus influenzae* Type b Capsular Polysaccharide, *J. Immunol.* 147(5):1667-1674; Adderson et al., 1993, Restricted Immunoglobulin $V_H$ Usage and VDJ Combinations in the Human Response to *Haemophilus influenzae* Type b Capsular Polysaccharide, *J. Clin. Invest.* 91:2734-2743). Human $J_H$ genes also display biased usage; $J_H4$ and $J_H6$ are observed at about 38-41% in peripheral B cells in humans (Brezinschek et al., 1995).

$V_H$ usage in HIV-1-infected humans is reportedly biased against $V_H3$ usage and in favor of $V_H1$ and $V_H4$ gene families (Wisnewski et al., 1996, Human Antibody Variable Region Gene Usage in HIV-1 Infection, *J. Acquired Immune Deficiency Syndromes & Human Retroviology* 11(1):31-38). However, cDNA analysis of bone marrow from affected patients' revealed significant $V_H3$ usage not expressed in the functional B cell repertoire, where Fabs reflecting the $V_H3$ usage exhibited effective in vitro neutralization of HIV-1 (Id.). It might be postulated that the humoral immune response to HIV-1 infection is possibly attenuated due to the $V_H$ restriction; modified non-human animals as described herein (not infectable by HIV-1) might thus be useful for generating neutralizing antibody domains derived from particular $V_H$ genes present in the genetically modified animals described herein, but derived from different $V_H$ genes than those observed in the restricted repertoire of affected humans.

Thus, the ability to generate high affinity human antibody variable domains in $V_H$-restricted mice, e.g., (restricted, e.g., to a $V_H3$ family member and polymorph(s) thereof) immunized with HIV-1 might provide a rich resource for designing effective HIV-1-neutralizing human therapeutics by thoroughly mining the restricted (e.g., restricted to a $V_H3$ family member or variant(s) thereof) repertoire of such an immunized mouse.

Restriction of the human antibody response to certain pathogens may reduce the likelihood of obtaining antibody variable regions from affected humans that can serve as springboards for designing high affinity neutralizing antibodies against the pathogen. For example, the human immune response to HIV-1 infection is clonally restricted throughout HIV-1 infection and into AIDS progression (Muller et al., 1993, B-cell abnormalities in AIDS: stable and clonally restricted antibody response in HIV-1 infection, *Scand. J. Immunol.* 38:327-334; Wisnewski et al., 1996). Further, $V_H$ genes are in general not present in all polymorphic forms in any particular individual; certain individuals in certain populations possess one variant, whereas individuals in other populations possess a different variant. Thus, the availability of a biological system that is restricted to a single $V_H$ gene and its variants will in various embodiments provide a hitherto unexploited source of diversity for generating antibody variable regions (e.g., human heavy and light cognate domains) based on a restricted $V_H$ gene. Thus, in one aspect, a genetically modified non-human animal is provided that comprises a plurality of polymorphic variants of no more than one, or no more than two, human $V_H$ gene segment family member. In one embodiment, the no more than one, or no more than two, human $V_H$ gene segments are operably linked to one or more human $D_H$ gene segments, one or more human $J_H$ gene segments, and a human or non-human constant region gene segment. In one embodiment the constant region is at an endogenous non-human immunoglobulin constant gene locus. In one embodiment, the non-human animal further comprises a nucleic acid sequence derived from a human $V_L$ sequence, e.g., a rearranged or unrearranged human $V_L$ gene segment or a rearranged human $V_L/J_L$ sequence. In one embodiment, the nucleic acid sequence derived from the human $V_L$ sequence is at an endogenous non-human $V_L$ gene locus; in one embodiment, the nucleic acid sequence derived form the human $V_L$ sequence is on a transgene. In a specific embodiment, the non-human animal is incapable of expressing an immunoglobulin light chain variable domain that itself comprises an endogenous $V_L$ or $J_L$ gene segment, and comprises no more than one, or no more than two, light chain genes that encode rearranged human $V_L$ domains (i.e., from no more than one, or no more than two, rearranged human $V_L/J_L$ sequences).

Genetically modified mice that express human heavy chain variable regions with restricted $V_H$ gene segment usage are useful to generate a relatively large repertoire of junctionally diverse, combinatorially diverse, and somatically mutated high affinity human immunoglobulin heavy chain variable regions from an otherwise restricted repertoire. A restricted repertoire, in one embodiment, refers to a predetermined limitation in the number and/or identity of germline genes that results in the mouse being unable to form a rearranged heavy chain gene that is derived from any V gene other than a preselected V gene. In embodiments that employ a preselected V gene but not a preselected D and/or J gene, the repertoire is restricted with respect to the identity of the V gene but not the D and/or J gene (e.g., the repertoire consists essentially of no more than one, or no more than two, $V_H$ gene segments (and/or polymorphs thereof); and a plurality of D gene segments and a plurality of J gene segments)). The identity of the preselected V gene (and any preselected D and/or J genes) is not limited to any particular V gene.

Designing a mouse so that it rearranges a single $V_H$ gene (present as a single segment or a set of variants) with a variety of human D and J gene segments (e.g., $D_H$ and $J_H$ segments) provides an in vivo junctional diversity/combinatorial diversity/somatic hypermutation permutation machine that can be used to iterate mutations in resulting rearranged heavy chain variable region sequences (e.g., V/D/J or V/J, as the case may be). In such a mouse, the clonal selection process operates to select suitable variable regions that bind an antigen of interest that are based on a single preselected $V_H$ gene (or variants thereof). Because the mouse's clonal selection components are dedicated to selection based on the single preselected $V_H$ gene segment, background noise (e.g., a wide variety of non antigen-binding $V_H$ domains derived from many germline gene segments) is largely eradicated. With judicious selection of the $V_H$ gene segment, a relatively larger number of clonally selected, antigen-specific antibodies can be screened in a shorter period of time than with a mouse with a large diversity of V segments.

Preselecting limited repertoire and restricting a mouse to a single V segment provides a system for permuting V/D/J junctions at a rate that is in various embodiments higher than that observed in mice that otherwise have up to 40 or more V segments to recombine with D and J regions. Removal of other V segments frees the locus to form more V/D/J combinations for the preselected V segment than otherwise observed. The increased number of transcripts that result from the recombination of the preselected V with one of a plurality of D and one of a plurality of J segments will feed those transcripts into the clonal selection system in the form of pre-B cells, and the clonal selection system is thus dedicated to cycling B cells that express the preselected V region. In this way, more unique V region rearrangements derived from the preselected V segment can be screened by the organism than would otherwise be possible in a given amount of time.

In various aspects, mice are described that enhance the junctional diversity of V/D/J recombinations for the preselected V region, because all or substantially all recombinations of the immunoglobulin heavy chain variable locus will be of the preselected V segment and the D and J segments that are placed in such mice. Therefore, the mice provide a method for generating a diversity of CDR3 segments using a base, or restricted $V_H$ gene repertoire.

In one aspect, a non-human animal is provided, wherein the B cell population of the non-human animal expresses immunoglobulin heavy chains that are derived from no more than one, or no more than two human $V_H$ gene segments. In one embodiment, each of the no more than one, or no more than two, human $V_H$ gene segments are present in two or more polymorphic forms. In one embodiment, the human $V_H$ gene segment is present in three, four, five, six, seven, eight, nine, 10, 11, 12, 13, 14, 15, 16, 17, 18, 19 or 20 polymorphic forms. In one embodiment, the non-human animal expresses a human light chain variable domain derived from a human $V_L$ gene segment.

In one aspect, a method is provided for generating a B cell population in a non-human animal, wherein the B cell population expresses human heavy chains derived from a single germline human $V_H$ gene segment and two or more human D gene segments and two or more human J gene segments; the method comprising a step of immunizing a non-human animal as described herein with an antigen of interest, and allowing the non-human animal to mount an immune response to the antigen of interest, wherein the immune response comprises expressing the human heavy chains on the surface of B cells in the B cell population In one embodiment, the non-human animal is a rodent (e.g., a mouse or rat). In one embodiment, the human $V_H$ gene segment, human $D_H$ segment, and human $J_H$ segment are operably linked to a non-human constant region gene. In one embodiment, the non-human animal further comprises a nucleic acid sequence encoding a human $V_L$ domain. In one embodiment, the nucleic acid sequence encoding the human $V_L$ domain is linked to a non-human light chain constant region gene sequence.

In one aspect, a method for making a non-human animal that expresses an immunoglobulin population characterized by the immunoglobulins having heavy chains that are derived from a plurality of rearrangements of a single human $V_H$ gene segment (or sing human $V_H$ gene family member) and one of a plurality of $D_H$ gene segments and one of a plurality of $J_H$ gene segments, is provided. In one embodiment, the human $V_H$ gene segment is a human $V_H$1-69 gene segment. In one embodiment, the human $V_H$ gene segment is a human $V_H$1-2 gene segment.

In one aspect, a method is provided for generating a population of human immunoglobulin heavy chain variable domains whose CDR1 and CDR2 are derived from the same germline $V_H$ gene segment, and whose CDR3 are derived from the germline gene segment and two or more human D segments, and two or more human J segments; the method comprising immunizing a non-human animal as described herein with an antigen of interest, and allowing the non-human animal to mount an immune response to the antigen of interest, wherein the immune response comprises expressing the human heavy chain variable domains in the context of a light chain variable domain. In one embodiment, the non-human animal is a rodent (e.g., a mouse or rat). In one embodiment, the human $V_H$ gene segment, human D segment, and human J segment are operably linked to a non-human constant region gene. In one embodiment, the non-human animal further comprises a nucleic acid sequence encoding a human $V_L$ domain. In one embodiment, the nucleic acid sequence encoding the human $V_L$ domain is linked to a non-human light chain constant region gene sequence.

In one aspect, a genetically modified non-human animal is provided, wherein the non-human animal is incapable of expressing a non-human $V_H$ domain, and wherein each immunoglobulin heavy chain of the heavy chain population expressed in the animal comprises a human $V_H$ domain comprising a CDR1 and a CDR2 that are identical but for one or more somatic hypermutations, and wherein the heavy chain population comprises a plurality of CDR3 sequences derived from a plurality of rearrangements with a plurality of D and J gene segments.

In one aspect, a biological system for generating variation in CDR3 identity and length is provided, comprising a genetically modified non-human animal as described herein, wherein the non-human animal comprises no more than or no more than two human $V_H$ gene segments, and two or more D gene segments and one or more J gene segments, wherein the non-human animal further comprises a humanized immunoglobulin light chain locus. In various embodiments, the non-human animal in response to immunization with an antigen of interest generates an immune response that comprises expressing an immunoglobulin heavy chain population characterized by each heavy chain having CDR1s and CDR2s that differ only by somatic hypermutation, and CDR3s that differ by rearrangement and somatic hypermutation. In one embodiment, the biological system is a mouse that is genetically modified as described herein. In one embodiment, the human $V_H$ gene segment and the human $V_L$ gene segment are at endogenous mouse heavy and light immunoglobulin loci, respectively. In one embodiment, one or more of the human $V_H$ gene segment and the human $V_L$ gene segment are on transgenes (i.e., at a locus other than an endogenous immunoglobulin locus).

EXAMPLES

The following examples are provided so as to describe to those of ordinary skill in the art how to make and use methods and compositions of the invention, and are not intended to limit the scope of what the inventors regard as their invention. Unless indicated otherwise, temperature is indicated in Celsius, and pressure is at or near atmospheric. In the foregoing Examples, when the use of kits and/reagents from various suppliers is indicated, all procedures were carried out according to manufacturer's specifications.

Example 1 Construction of Restricted Heavy Chain Loci

A uniquely engineered human heavy chain locus containing a single human $V_H$ gene segment located upstream of all the human $D_H$ and $J_H$ gene segments was created by a series of homologous recombination reactions in bacterial cells (BHR) using Bacterial Artificial Chromosome (BAC) DNA. Several targeting constructs for creation of a single $V_H$ containing heavy chain locus were constructed using VELOCIGENE® genetic engineering technology (see, e.g., U.S. Pat. No. 6,586,251 and Valenzuela, D. M. et al. (2003) High-throughput engineering of the mouse genome coupled with high-resolution expression analysis. *Nature Biotechnology* 21(6): 652-659).

Construction of a Human $V_H$1-69 Restricted Heavy Chain Locus.

Briefly, four modifications were performed using human BAC DNA to create a targeting construct containing a human $V_H$1-69 gene segment with all the human $D_H$ and $J_H$ segments (FIG. 1). In the first modification, a modified human BAC containing multiple distal (5') human $V_H$ gene segments, including $V_H$1-69, an upstream hygromycin selection cassette and a 5' mouse homology arm was targeted with a second spectinomycin cassette, which also contained a modified recombination signal sequence (RSS; BHR 1, FIG. 1, top left). This modified recombination signal sequence (RSS) introduced two point mutations (T to A and G to A) in the 3' RSS region of the human $V_H$1-69 gene changing the RSS nonamer to the optimal consensus sequence. Thus, the first modification (BHR 1) created a human genomic fragment containing the human $V_H$1-69 gene segment with a modified 3' RSS, a unique AsiSI restriction site about 180 bp downstream of the RSS and a spectinomycin cassette (FIG. 1, middle left).

The second modification (BHR 2) included the use of a neomycin (Neo) cassette flanked by Frt sites to delete the hygromycin cassette and 5' human $V_H$ gene segments upstream of the $V_H$1-69 gene segment. This modification was targeted 5' to the human $V_H$1-69 gene segment to leave intact about 8.2 kb of the promoter region of human $V_H$1-69 and the 5' mouse homology arm (FIG. 1, bottom left).

The third modification (BHR 3) included another spectinomycin cassette flanked by uniquely engineered 5' PI-SceI and 3' AsiSI sites targeted to a human genomic fragment containing the first three functional human $V_H$ gene segments and all the human $D_H$ and $J_H$ gene segments (FIG. 1, middle right). The human genomic fragment was previously targeted with a neomycin cassette and contained 5' and 3' homology arms containing the mouse genomic sequence 5' and 3' of the endogenous heavy chain locus including the 3' intronic enhancer and the IgM gene. This modification deleted the 5' mouse genomic sequence and human $V_H$ gene segments, leaving about 3.3 kb of the $V_H$-$D_H$ intergenic region upstream of the human $D_H$1-1 gene segment, all of the human $D_H$ and $J_H$ segments, and the 3' mouse genomic fragment containing the 3' intronic enhancer and the IgM gene (FIG. 1, bottom right).

The fourth modification was achieved by employing the unique PI-SceI and AsiSI sites (described above) to ligate the two modified BACs from BHR 2 and BHR 3 (FIG. 1, bottom center), which yielded the final targeting construct. The final targeting construct for the creation of a modified heavy chain locus containing a single human $V_H$ gene segment and all the human $D_H$ and $J_H$ gene segments in ES cells contained, from 5' to 3', a 5' homology arm containing about 20 kb of mouse genomic sequence upstream of the endogenous heavy chain locus, a 5' Frt site, a neomycin cassette, a 3' Frt site, about 8.2 kb of the human $V_H$1-69 promoter, the human $V_H$1-69 gene segment with a modified 3' RSS, 27 human $D_H$ gene segments, six human $J_H$ segments, and a 3' homology arm containing about 8 kb of mouse genomic sequence downstream of the mouse $J_H$ gene segments including the 3' intronic enhancer and IgM gene (FIG. 1, bottom). The Human $V_H$1-69 Targeting Vector (SEQ ID NO: 3) was linearized and electroporated into mouse ES cells heterozygous for a deletion of the endogenous heavy chain locus.

Construction of a Human $V_H$1-2 Restricted Heavy Chain Locus.

Using the steps described above, other polymorphic $V_H$ gene segments in the context of mouse heavy chain constant regions are employed to construct a series of mice having a restricted number immunoglobulin heavy chain V segments (e.g., 1, 2, 3, 4, or 5), wherein the V segments are polymorphic variants of a V gene family member. Exemplary polymorphic $V_H$ gene segments are derived from human $V_H$ gene segments including, e.g., $V_H$1-2, $V_H$2-26, $V_H$2-70 and $V_H$3-23. Such human $V_H$ gene segments are obtained, e.g., by de novo synthesis (e.g., Blue Heron Biotechnology, Bothell, Wash.) using sequences available on published databases. Thus, DNA fragments encoding each $V_H$ gene are, in some embodiments, generated independently for incorporation into targeting vectors, as described herein. In this way, multiple modified immunoglobulin heavy chain loci comprising a restricted number of $V_H$ gene segments are engineered in the context of mouse heavy chain constant regions. An exemplary targeting strategy for creating a restricted humanized heavy chain locus containing a human $V_H$1-2 gene segment, 27 human $D_H$ gene segments, and six human $J_H$ gene segments is shown in FIG. 2.

Briefly, a modified human BAC clone containing three human $V_H$ gene segments ($V_H$6-1, $V_H$1-2, $V_H$1-3), 27 human $D_H$ gene segments, and six human $J_H$ gene segments (see U.S. Ser. No. 13/404,075; filed 24 Feb. 2012, herein incorporated by reference) is used to create a restricted humanized heavy chain locus containing a human $V_H$1-2 gene segment. This modified BAC clone functionally links the aforementioned human heavy chain gene segments with the mouse intronic enhancer and the IgM constant region. The restricted human $V_H$1-2 based heavy chain locus is achieved by two homologous recombinations using the modified human BAC clone described above.

For the first homologous recombination, 205 bp of the human $V_H$6-1 gene segment (from about 10 bp upstream (5') of the $V_H$6-1 start codon in exon 1 to about 63 bp downstream (3') of the beginning of exon 2) in the modified human BAC clone is deleted by bacterial homologous recombination using a spectinomycin (aadA) cassette flanked by unique PI-SceI restriction sites (FIG. 2, BHR 1). This allows for subsequent removal of the aadA cassette without disrupting other human gene segments within the restricted heavy chain locus.

For the second homologous recombination, the 5' end of the modified human BAC clone including the entire human $V_H$1-3 gene segment and about 60 bp downstream (3') of the gene segment is deleted by homologous recombination using a hygromycin cassette containing flanking 5' AsiSI and 3' AscI restriction sites (FIG. 2, BHR 2). As described above, the spectinomycin cassette is optionally removed after confirmation of the final targeting vector including deletion of the two human $V_H$ gene segments flanking the human $V_H$1-2 gene segment (FIG. 2, bottom). An exemplary human $V_H$1-2 targeting vector is set forth in SEQ ID NO: 70.

Employing polymorphic $V_H$ gene segments in a restricted immunoglobulin heavy chain locus represents a novel approach for generating antibodies, populations of antibodies, and populations of B cells that express antibodies having heavy chains with diverse CDRs derived from a single human $V_H$ gene segment. Exploiting the somatic hypermutation machinery of the host animal along with combinatorial association with rearranged human immunoglobulin light chain variable domains results in the engineering of unique heavy chains and unique $V_H$/$V_L$ pairs that expand the immune repertoire of genetically modified animals and enhance their usefulness as a next generation platform for making human therapeutics, especially useful as a platform for making neutralizing antibodies specific for human pathogens.

Thus, using the strategy outlined above for incorporation of additional and/or other polymorphic $V_H$ gene segments into the mouse immunoglobulin heavy chain locus allows for the generation of novel antibody repertoires for use in neutralizing human pathogens that might otherwise effectively evade the host immune system.

Targeted ES cells described above were used as donor ES cells and introduced into an 8-cell stage mouse embryo by the VELOCIMOUSE® method (supra). Mice bearing a humanized heavy chain locus containing a single human $V_H$ gene segment, all the human $D_H$ and $J_H$ gene segments operably linked to the mouse immunoglobulin constant region genes were identified by genotyping using a modification of allele assay (Valenzuela et al., supra) that detected the presence of the neomycin cassette, the human $V_H$ gene segment and a region within the human $D_H$ and $J_H$ gene segments as well as endogenous heavy chain sequences. Table 4 sets forth the primers and probes used in this assay to confirm mice harboring a restricted heavy chain locus containing a single human $V_H$1-69 gene segment, 27 human $D_H$ gene segments and six human $J_H$ gene segments.

Mice bearing an engineered heavy chain locus that contains a single human $V_H$ gene segment can be bred to a FLPe deletor mouse strain (see, e.g., Rodriguez, C. I. et al. (2000) High-efficiency deleter mice show that FLPe is an alternative to Cre-loxP. *Nature Genetics* 25: 139-140) in order to remove any Frt'ed neomycin cassette introduced by the targeting vector that is not removed, e.g., at the ES cell stage or in the embryo. Optionally, the neomycin cassette is retained in the mice.

Pups are genotyped and a pup heterozygous for a humanized heavy chain locus containing a single human $V_H$ gene segment, all the human $D_H$ and $J_H$ segments operably linked to the endogenous mouse immunoglobulin constant genes is selected for characterizing the immunoglobulin heavy chain repertoire.

TABLE 4

| Name (Region Detected) | Sequence 5'-3') | SEQ ID NO: |
|---|---|---|
| hyg (hygromycin cassette) | Forward: TGCGGCCGAT CTTAGCC<br>Reverse: TTGACCGATT CCTTGCGG<br>Probe: ACGAGCGGGT TCGGCCCATT C | 4<br>5<br>6 |
| neo (neomycin cassette) | Forward: GGTGGAGAGG CTATTCGGC<br>Reverse: GAACACGGCG GCATCAG<br>Probe: TGGGCACAAC AGACAATCGG CTG | 7<br>8<br>9 |
| hIgH9T (human $D_H$-$J_R$ genomic sequence) | Forward: TCCTCCAACG ACAGGTCCC<br>Reverse: GATGAACTGA CGGGCACAGG<br>Probe: TCCCTGGAAC TCTGCCCCGA CACA | 10<br>11<br>12 |
| 77h3 (human $V_H$1-69 gene segment) | Forward: CTCTGTGGAA AATGGTATGG AGATT<br>Reverse: GGTAAGCATA GAAGGTGGGT ATCTTT<br>Probe: ATAGAACTGT CATTTGGTCC AGCAATCCCA | 13<br>14<br>15 |
| mIgHA7 (mouse $D_H$-$J_H$ genomic sequence) | Forward: TGGTCACCTC CAGGAGCCTC<br>Reverse: GCTGCAGGGT GTATCAGGTG C<br>Probe: AGTCTCTGCT TCCCCCTTGT GGCTATGAGC | 16<br>17<br>18 |
| 88710T (mouse 3' $V_H$ genomic sequence) | Forward: GATGGGAAGA GACTGGTAAC ATTTGTAC<br>Reverse: TTCCTCTATT TCACTCTTTG AGGCTC<br>Probe: CCTCCACTGT GTTAATGGCT GCCACAA | 19<br>20<br>21 |
| mIgHd10 (mouse 5' $V_H$ genomic sequence) | Forward: GGTGTGCGAT GTACCCTCTG AAC<br>Reverse: TGTGGCAGTT TAATCCAGCT TTATC<br>Probe: CTAAAAATGC TACACCTGGG GCAAAACACC TG | 22<br>23<br>24 |
| mIgHp2 (mouse $J_H$ genomic sequence) | Forward: GCCATGCAAG GCCAAGC<br>Reverse: AGTTCTTGAG CCTTAGGGTG CTAG<br>Probe: CCAGGAAAAT GCTGCCAGAG CCTG | 25<br>26<br>27 |

Example 2 Characterization of Mice Expressing Heavy Chains Derived from a Single Human $V_H$ Gene Segment Mice homozygous for a single human $V_H$ gene segment at the endogenous heavy chain locus as described in Example 1 were evaluated for expression and B cell development using flow cytometry.

Briefly, spleens and bone marrow was harvested from wild type (n=3 per group; six weeks old, male and female) and mice homozygous for a single human $V_H$ gene segment, all human $D_H$ and $J_H$ gene segments operably linked to mouse heavy chain constant regions. Red blood cells from spleens were lysed with ACK lysis buffer (Lonza Walkersville), followed by washing with complete RPMI medium.

Flow Cytometry.

Cells ($1 \times 10^6$) were incubated with anti-mouse CD16/CD32 (2.4G2, BD PHARMINGEN™) on ice for 10 minutes, followed by labeling with the following antibody panels for 30 minutes on ice. Bone marrow panel: anti-mouse FITC-CD43 (1B11, BioLegend), PE-ckit (2B8, BIOLEGEND®), PeCy7-IgM (II/41, EBIOSCIENCE®), PerCP-Cy5.5-IgD (11-26c.2a, BIOLEGEND®), APC-eFluor 780-B220 (RA3-6B2, EBIOSCIENCE®), APC-CD19 (MB19-1, EBIOSCIENCE®). Bone marrow and spleen panel: anti-mouse FITC-Igκ (187.1, BD Biosciences), PE-Igλ (RML-42, BIOLEGEND®), PeCy7-IgM (II/41, EBIOSCIENCE®), PerCP-Cy5.5-IgD (11-26c.2a, BIOLEGEND®), Pacific Blue-CD3 (17A2, BIOLEGEND®), APC-B220 (RA3-6B2, EBIOSCIENCE®), APC-H7-CD19 (ID3, BD Biosciences). Bone marrow: immature B cells ($B220^{int}IgM^+$), mature B cells ($B220^{hi}IgM^+$), pro B cells ($CD19^+ckit^+CD43^+$), pre B cells ($CD19^+ckit^-CD43^-$), immature $Igλ^+$ B cells ($B220^{int}$ $IgM^+Igκ^+Igλ^-$), immature $Igλ^+$ B cells ($B220^{int}IgM^+Igκ^-Igλ^+$), mature $Igκ^+$ B cells ($B220^{hi}IgM^+Igκ^+Igλ^-$), mature $Igλ^+$ B cells ($B220^{hi}IgM^+Igκ^-Igλ^+$). Spleen: B cells ($CD19^+$), mature B cells ($CD19^+IgD^{hi}IgM^{int}$), transitional/immature B cells ($CD19^+IgD^{int}IgM^{hi}$). Bone marrow and spleen: $Igκ^+$ B cells ($CD19^+Igκ^+Igλ^-$), $Igλ^+$ B cells ($CD19^+Igκ^-Igλ^+$).

Following staining, cells were washed and fixed in 2% formaldehyde. Data acquisition was performed on a LSRII flow cytometer and analyzed with FLOWJO™ software (Tree Star, Inc.). Results for the splenic compartment are shown in FIGS. 3, 4A and 5-7. Results for the bone marrow compartment are shown in FIGS. 4B and 8-11B.

Human $V_H$ Expression.

Expression of the human $V_H$1-69 gene segment was determined for mice heterozygous and homozygous for a human $V_H$1-69 gene segment, all human $D_H$ and $J_H$ gene segments operably linked to mouse heavy chain constant regions by a quantitative PCR assay using TAQMAN® probes.

Figure 12:
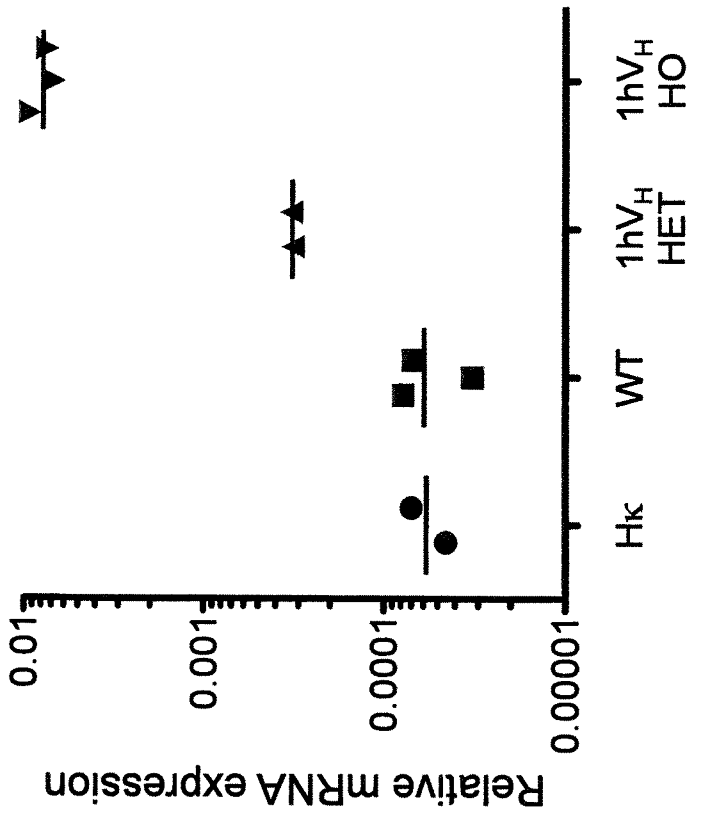
FIG. 12 shows the relative mRNA expression (y-axis) in purified splenic B cells of $V_H$1-69-derived heavy chains in a quantitative PCR assay using a probe specific for the human $V_H$1-69 gene segment in mice homozygous for a replacement of the endogenous heavy chain $V_H$, $D_H$, $J_H$, and a replacement of the endogenous light chain Vκ and Jκ gene segments with human $V_H$, $D_H$, $J_H$, Vκ and Jκ gene segments (Hκ), wild type mice (WT), mice heterozygous for a single human $V_H$ gene segment, twenty-seven human $D_H$ and six human $J_H$ gene segments at the endogenous immunoglobulin heavy chain locus ($1hV_H$ HET) and mice homozygous for a single human $V_H$ gene segment, twenty-seven human $D_H$ and six human $J_H$ gene segments at the endogenous immunoglobulin heavy chain locus ($1hV_H$ HO). Signals are normalized to expression of mouse Cκ.

Briefly, CD19+ B cells were purified from the spleens of groups of mice (n=3 per group) using mouse CD19 microbeads (Miltenyi Biotec) according to manufacturer's specifications. Total RNA was purified using the RNEASY™ Mini kit (Qiagen) and genomic RNA was removed using an RNase-free DNase on-column treatment (Qiagen). About 200 ng mRNA was reverse-transcribed into cDNA using the First Stand cDNA Synthesis kit (Invitrogen), followed by amplification with the TAQMAN® Universal PCR Master Mix (Applied Biosystems) using the ABI 7900 Sequence Detection System (Applied Biosystems). Unique primer/probe combinations were employed to specifically determine expression of human $V_H$1-69-derived heavy chains (Table 5). Relative expression was normalized to the mouse κ constant region (mCκ). The results are shown in FIG. 12.

TABLE 5

| Name | Sequence (5'-3') | SEQ ID NO: |
|---|---|---|
| hIgHV1-69 | Sense: AACTACGCAC AGAAGTTCCA GG | 28 |
| | Anti-sense: GCTCGTGGAT TTGTCCGC | 29 |
| | Probe: CAGAGTCACG ATTACC | 30 |
| mCκ | Sense: TGAGCAGCAC CCTCACGTT | 31 |
| | Antisense: GTGGCCTCAC AGGTATAGCT GTT | 32 |
| | Probe: ACCAAGGACG AGTATGAA | 33 |

Example 3 Humoral Immune Response in Mice Expressing Heavy Chains Derived from a Single Human $V_H$ Gene Segment The humoral immune response was determined for mice homozygous for human heavy and κ light chain variable gene loci (Hκ) and mice homozygous for a single human $V_H$ gene segment, all human $D_H$ and $J_H$ gene segments operably linked to mouse heavy chain constant regions (1h$V_H$HO) by comparative immunization using a human cell surface receptor (Antigen A).

Immunization. Serum was collected from groups of mice prior to immunization with the above antigen. Antigen (2.35 μg each) was administered in an initial priming immunization mixed with 10 μg of CpG oligonucleotide (Invivogen) and 25 μg of Adju-phos (Brenntag) as adjuvants. The immunogen was administered via footpad (f.p.) in a volume of 25 μl per mouse. Subsequently, mice were boosted via f.p. with 2.3 μg of antigen along with 10 μg CpG and 25 μg Adju-Phos as adjuvants on days 3, 6, 11, 13, 17, and 20 for a total of six boosts. Mice were bled on days 15 and 22 after the fourth and sixth boosts, respectively, and antisera were assayed for antibody titers to Antigen A.

Antibody titers were determined in sera of immunized mice using an ELISA assay. Ninety six-well microtiter plates (Thermo Scientific) were coated with Antigen A (1 μg/ml) in phosphate-buffered saline (PBS, Irvine Scientific) overnight at 4° C. The following day, plates were washed with phosphate-buffered saline containing 0.05% Tween 20 (PBS-T, Sigma-Aldrich) four times using a plate washer (Molecular Devices). Plates were then blocked with 250 μl of 1% bovine serum albumin (BSA, Sigma-Aldrich) in PBS and incubated for one hour at room temperature. The plates were then washed four times with PBS-T. Sera from immunized mice and pre-immune sera were serially diluted tenfold in 0.1% BSA PBS-T starting at 1:100 and added to the blocked plates in duplicate and incubated for one hour at room temperature. The last two wells were left blank to be used as secondary antibody control. The plates were again washed four times with PBS-T in a plate washer. A 1:5000 dilution of goat anti-mouse IgG-Fc-Horse Radish Peroxidase (HRP, Jackson Immunoresearch) conjugated secondary antibody was added to the plates and incubated for one hour at room temperature. Plates were again washed eight times with PBS-T and developed using $TMB/H_2O_2$ as substrate. The substrate was incubated for twenty minutes and the reaction stopped with 1 N $H_2SO_4$ (VWR). Plates were read on a spectrophotometer (Victor, Perkin Elmer) at 450 nm. Antibody titers were calculated using GRAPHPAD PRISM™ (GraphPad Software, Inc).

Figure 19:
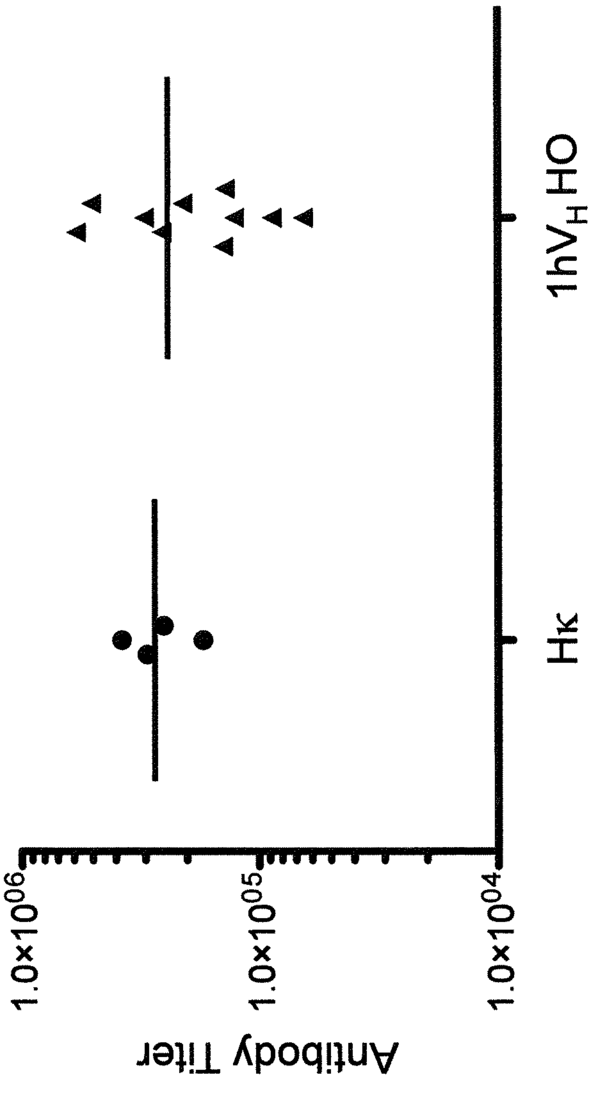
FIG. 19 shows the antibody titer from mice homozygous for human heavy and human κ light chain variable gene loci (HK; n=4) and mice homozygous for a single human $V_H$1-69 gene segment, twenty-seven human $D_H$ and six human $J_H$ gene segments at the endogenous immunoglobulin heavy chain locus (1h$V_H$HO; n=10) that were immunized with a human cell surface receptor (Antigen A).

Serum titer was calculated as serum dilution within experimental titration range at the signal of antigen binding equivalent to two times above background. Antibody titer for the humoral immune response against a human cell surface receptor (Antigen A) is set forth in FIG. 19.

In a similar experiment, humoral immune responses were determined for mice homozygous for human heavy and κ light chain variable gene loci (Hκ) and mice homozygous for a single human $V_H$ gene segment, all human $D_H$ and $J_H$ gene segments operably linked to mouse heavy chain constant regions (1h$V_H$ HO) by comparative immunization using influenza viral vaccines FLUVIRIN® (Novartis Vaccines) and FLUMIST® (MedImmune LLC).

Briefly, serum was collected from groups of mice prior to immunization with the above antigen (as described above). Mice (n=5) homozygous for a single human $V_H$ gene segment ($V_H$1-69), all human $D_H$ and $J_H$ gene segments operably linked to mouse heavy chain constant regions (1h$V_H$ HO) were immunized intra-nasally (i.n.) with FLUMIST® (live attenuated influenza vaccine) at ⅓ the normal dose/mouse. One normal dose of FLUMIST® contains $10^{6.5-7.5}$ FFU (fluorescent focus units) of live attenuated influenza vaccine. Therefore, each mouse was primed with 70 μl FLUMIST® on day 1 followed by i.n. boost on days 3, 6, 11, 13, 17, 20 for a total of 6 boosts. No adjuvants were employed in this immunization. The mice were bled on days 15 and 22 after 4th and 6th boosts respectively and antiserum assayed for antibody titers to FLUMIST® (as described above).

In a similar manner, in immunizations with FLUVIRIN®, pre-immune serum was collected from mice prior to initiation of immunization. Mice (n=5) homozygous for a single human $V_H$ gene segment ($V_H$1-69), all human $D_H$ and $J_H$ gene segments operably linked to mouse heavy chain constant regions (1h$V_H$ HO) were immunized with FLUVIRIN® (trivalent inactivated influenza vaccine) via footpad (f.p.) with 0.75 μg each of hemagglutinin/mouse/boost. Mice were primed on day 1 followed by f.p. boost on days 3, 6, 11, 13, 17, 20 for a total of 6 boosts. No adjuvants were employed in this immunization. The mice were bled on days 15 and 22 after 4th and 6th boosts respectively and antiserum assayed for antibody titers to FLUVIRIN® (as described above).

Figure 20:
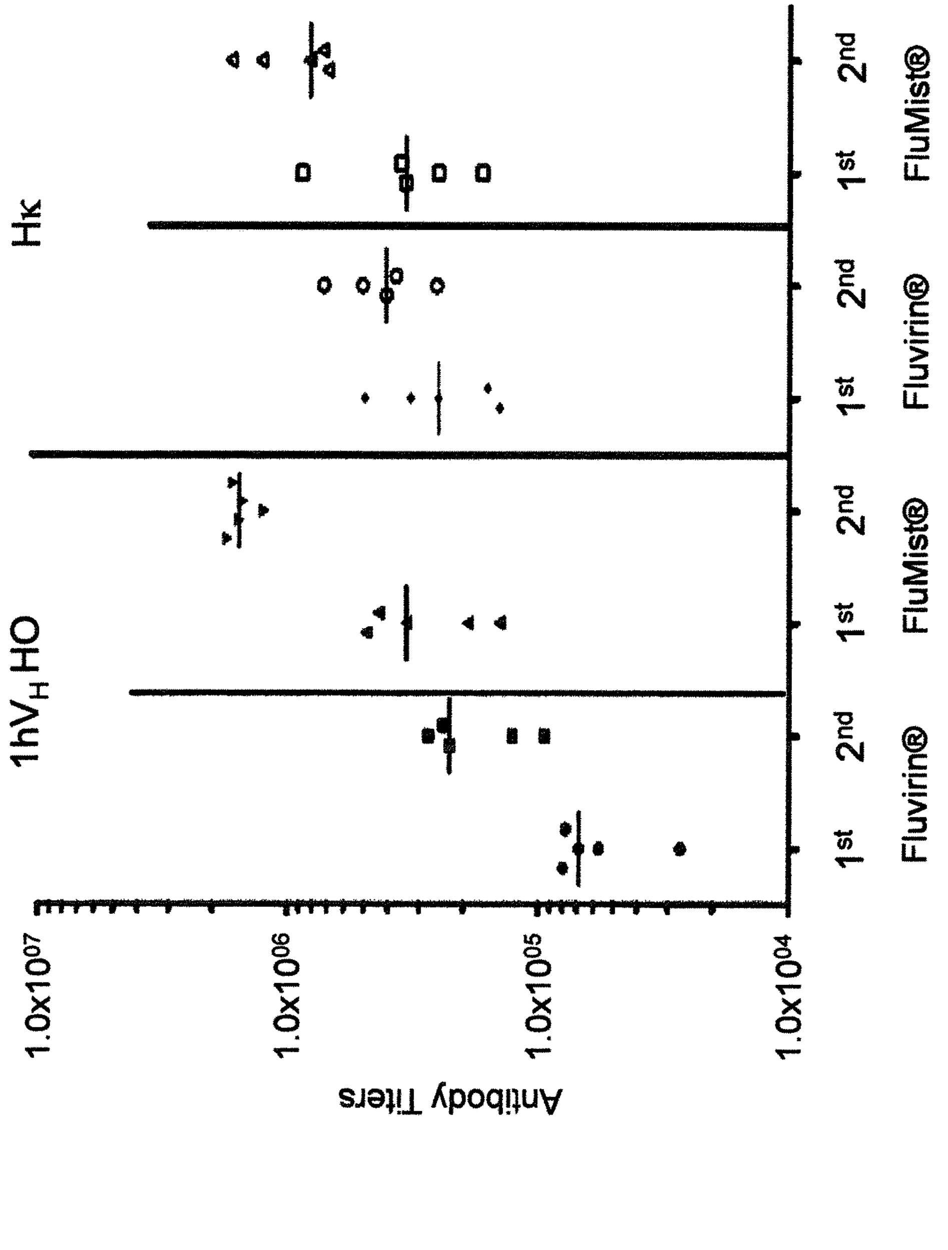
FIG. 20 shows the antibody titer from mice homozygous for human heavy and human κ light chain variable gene loci (Hκ; n=5) and mice homozygous for a single human $V_H$1-69 gene segment, twenty-seven human $D_H$ and six human $J_H$ gene segments at the endogenous immunoglobulin heavy chain locus (1h$V_H$HO; n=5) that were immunized with two different influenza vaccines.

Serum titer was calculated as serum dilution within experimental titration range at the signal of antigen binding equivalent to two times above background. Antibody titer for the humoral immune response against FLUMIST® and FLUVIRIN® is set forth in FIG. 20.

As shown in this Example, antibody titers generated in 1h$V_H$ HO mice were comparable to those generated in mice having a plurality of human $V_H$ gene segments (Hκ) for both a human cell surface receptor and a viral antigen (e.g., influenza). Thus, mice having immunoglobulin heavy chain loci restricted to a single $V_H$ gene segment are capable of mounting a robust immune response to antigen in a manner comparable to mice having immunoglobulin heavy chain loci containing a plurality of human $V_H$ gene segments (e.g., 80 $V_H$).

Example 4 Analysis of Antibody Gene Usage and CDR3 Length in Mice Having a Restricted Immunoglobulin Heavy Chain Locus Splenocytes harvested from mice homozygous for a single human $V_H$ gene segment at the endogenous heavy chain locus and homozygous for a replacement of the endogenous κ light chain variable loci with human κ light chain variable loci immunized with a human cell surface receptor (Antigen A) were analyzed for heavy and light chain gene segment usage by reverse-transcriptase polymerase chain reaction (RT-PCR) on mRNA from splenic B cells.

Briefly, spleens were harvested and homogenized in 1×PBS (Gibco) using glass slides. Cells were pelleted in a centrifuge (500×g for 5 minutes), and red blood cells were lysed in ACK Lysis buffer (Gibco) for 3 minutes. Cells were washed with 1×PBS and filtered using a 0.7 μm cell strainer. B-cells were isolated from spleen cells using MACS magnetic positive selection for CD19 (Miltenyi Biotec). Total RNA was isolated from pelleted B-cells using the RNeasy Plus Kit (Qiagen). Poly$A^+$ mRNA was isolated from total RNA using the Oligotex® Direct mRNA mini kit (Qiagen).

Double-stranded cDNA was prepared from splenic B cell mRNA by 5' RACE using the SMARTer™ Pico cDNA Synthesis Kit (Clontech) with substitution of the supplied reverse transcriptase and dNTPs with Superscript® II and dNTPs (Invitrogen). $V_H$ and Vκ antibody repertoires were amplified from the cDNA using primers specific for IgM, IgG, or Igκ constant regions and the SMARTer™ 5' RACE primer (Table 6). PCR products were purified using a QIAquick® PCR Purification Kit (Qiagen). A second round of PCR was done using the same 5' RACE primer and a nested 3' primer specific for the IgM, IgG, or Igκ constant regions (Table 7). Second round PCR products were purified using a SizeSelect™ E-Gel® system (Invitrogen). A third PCR was performed with primers that added 454 adapters and barcodes. Third round PCR products were purified using Agencourt® AMPure® XP Beads (Beckman Coulter). Purified PCR products were quantified by SYBR® qPCR using a KAPA Library Quantification Kit (KAPA Biosystems). Pooled libraries were subjected to emulsion PCR (emPCR) using a 454 GS Junior Titanium Series Lib-A emPCR Kit (Roche Diagnostics) and bidirectional sequencing using Roche 454 GS Junior instrument according to manufacturer's specifications.

Bioinformatic Analysis.

The 454 sequences were sorted based on the sample barcode perfect match and trimmed for quality. Sequences were annotated based on alignment of rearranged immunoglobulin sequences to human germline V(D)J segment database using local installation of Igblast (NCBI, v2.2.25+). A sequence was marked as ambiguous and removed from analysis when multiple best hits with identical score were detected. A set of perl scripts was developed to analyze results and store data in mysql database. CDR3 region was defined between conserved C codon and FGXG motif for light and WGXG motif for heavy chains. CDR3 length was determined using only productive antibodies. From the nucleic acid sequences and predicted amino acid sequences of the antibodies, gene usage was identified for IgM-primed (15,650), IgG-primed (18,967), and Igκ-primed (26,804) sequences. Results are shown in Table 8, Table 9, FIG. 21 and FIG. 22.

Table 8 sets forth the percentage of observed human $D_H$ and $J_H$ gene segments used among IgM-primed (15,650 sequences) and IgG-primed (18,967 sequences) $V_H$1-69 derived heavy chain variable region sequences. Human $D_H$4-4/$D_H$4-11 and human $D_H$5-5/$D_H$5-18 gene segments are presented in Table 8 together due to identical sequence identity between the respective pairs of $D_H$ gene segments. Table 9 sets forth the percentage of human Vκ and Jκ gene segments observed among light chains (26,804 sequences) cognate with $V_H$1-69 derived heavy chain variable regions. Percentages in Tables 8 and 9 represent rounded values and in some cases may not equal 100% when added together.

Figure 21:
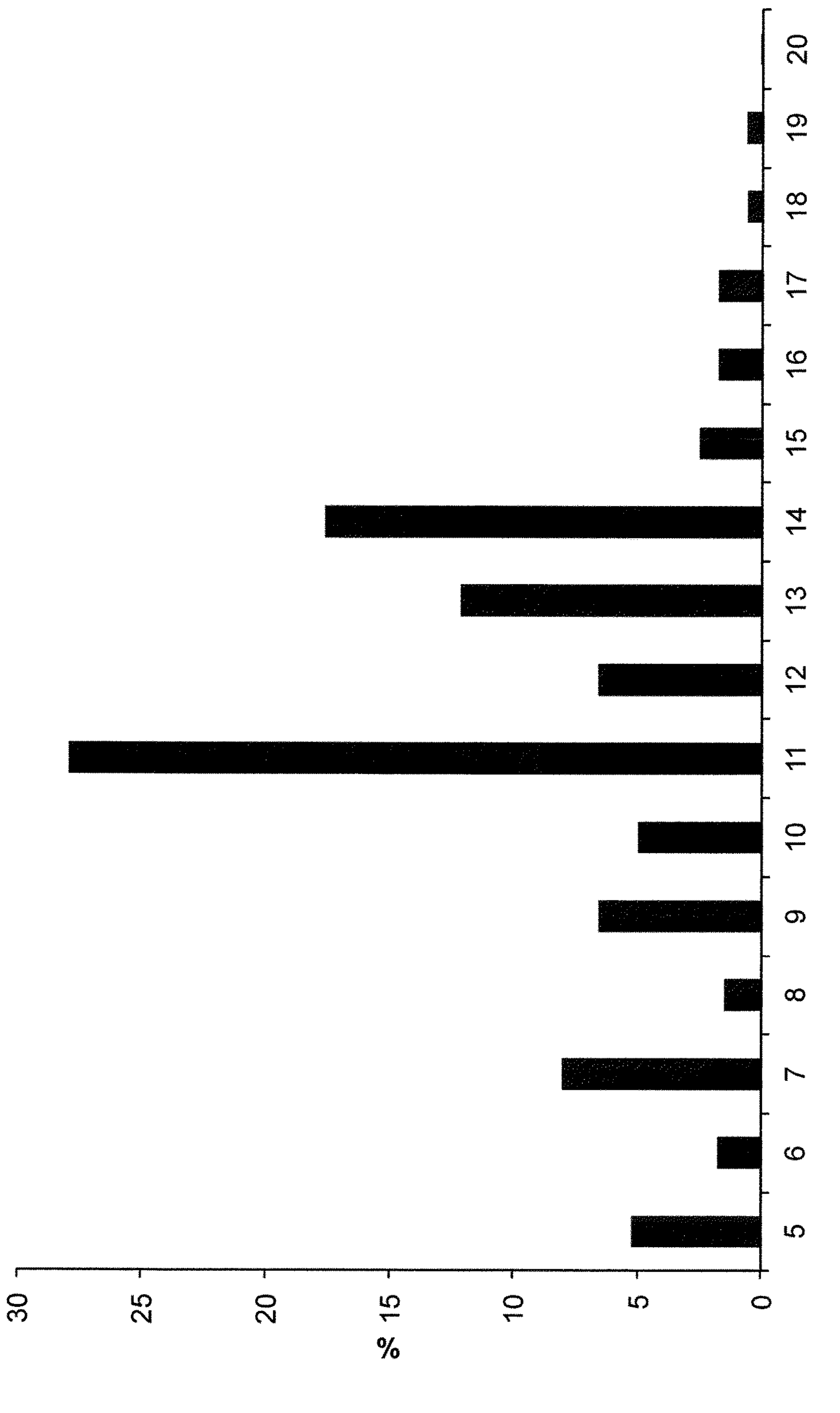
FIG. 21 shows the percentage (y-axis) of IgM-primed heavy chains having a specified amino acid length for the $V_H$ CDR3 region (x-axis) from mice homozygous for a single human $V_H$1-69 gene segment, twenty-seven human $D_H$ and six human $J_H$ gene segments at the endogenous immunoglobulin heavy chain locus and homozygous for a replacement of the endogenous κ light chain variable loci with human κ light chain variable loci that were immunized with a human cell surface receptor (Antigen A).
Figure 22:
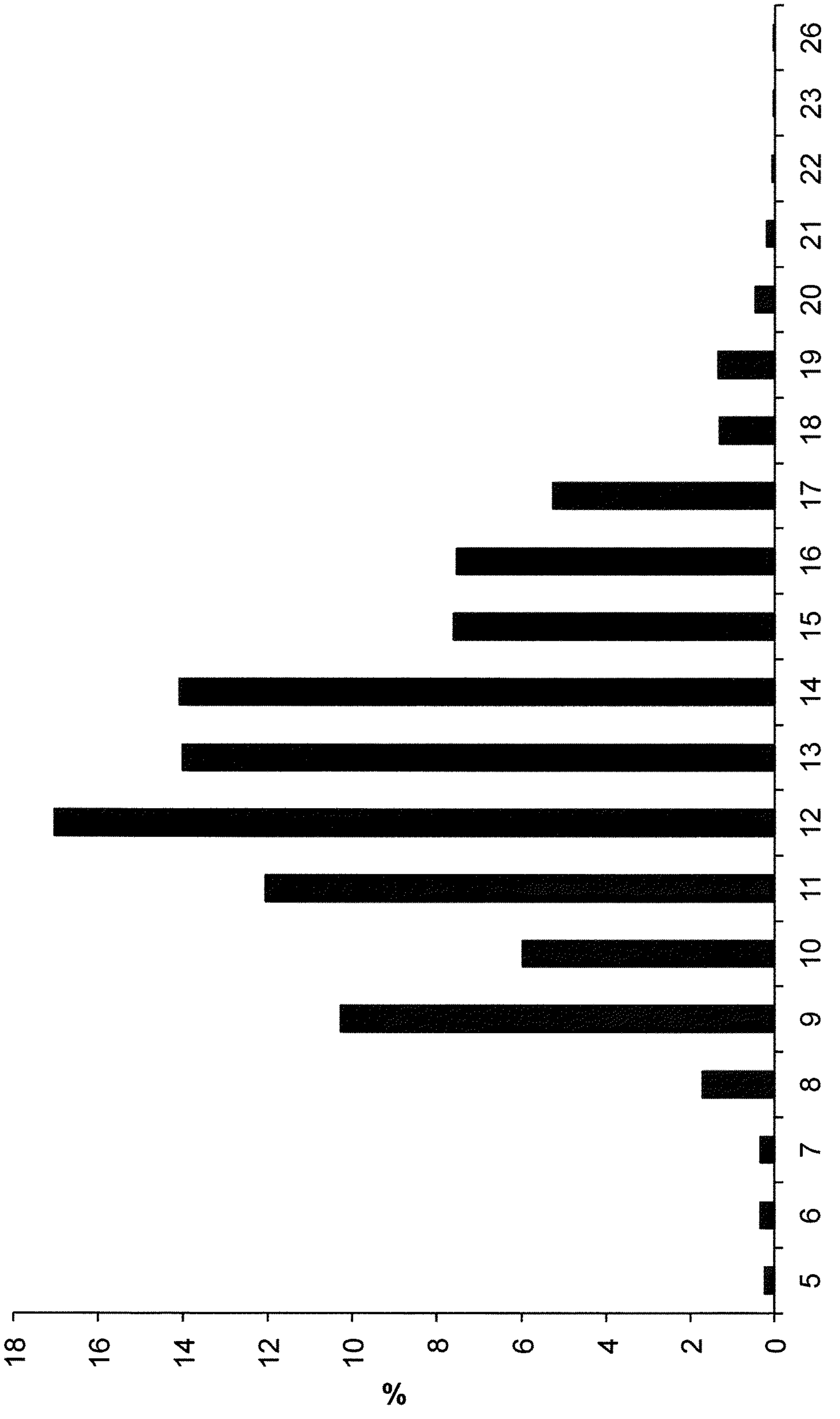
FIG. 22 shows the percentage (y-axis) of IgG-primed heavy chains having a specified amino acid length for the $V_H$ CDR3 region (x-axis) from mice homozygous for a single human $V_H$1-69 gene segment, twenty-seven human $D_H$ and six human $J_H$ gene segments at the endogenous immunoglobulin heavy chain locus and homozygous for a replacement of the endogenous κ light chain variable loci with human κ light chain variable loci that were immunized with a human cell surface receptor (Antigen A).

Amino acid length of the CDR3 region of IgM-primed $V_H$1-69-derived heavy chains is shown in FIG. 21. Amino acid length of the CDR3 region of IgG-primed $V_H$1-69-derived heavy chains is shown in FIG. 22.

As shown in Tables 8 and 9, mice according to the invention generate antigen-specific antibodies containing $V_H$1-69-derived heavy chains, which demonstrate a variety of rearrangements of a human $V_H$1-69 gene segment with a variety of human $D_H$ segments and human $J_H$ segments. Further, the antigen-specific antibodies contain cognate human light chains containing human Vκ domains resulting from a variety of rearrangements of human Vκ and Jκ gene segments.

TABLE 6

| Primer | Sequence (5'-3') |
|---|---|
| 3' Cg1 outer | GGAAGGTGTG CACACCGCTG GAC (SEQ ID NO: 71) |
| 3' Cg2ac outer | GGAAGGTGTG CACACCACTG GAC (SEQ ID NO: 72) |
| 3' Cg2b outer | GGAAGGTGTG CACACTGCTG GAC (SEQ ID NO: 73) |
| 3' Cg3 outer | AGACTGTGCG CACACCGCTG GAC (SEQ ID NO: 74) |
| 3' mIgM CH1 outer | TCTTATCAGA CAGGGGGCTC TC (SEQ ID NO: 75) |
| 3' mIgκC outer | AAGAAGCACA CGACTGAGGC AC (SEQ ID NO: 76) |

TABLE 7

| Primer | Sequence (5'-3') |
|---|---|
| 3' mIgG1/2b CH1 inner | AGTGGATAGA CWGATGGGGG TG (SEQ ID NO: 77) |
| 3' mIgG2a/2c CH1 inner | AGTGGATAGA CCGATGGGGC TG (SEQ ID NO: 78) |
| 3' mIgG3 CH1 inner | AAGGGATAGA CAGATGGGGC TG (SEQ ID NO: 79) |
| 3' mIgM CH1 inner | GGAAGACATT TGGGAAGGAC TG (SEQ ID NO: 80) |
| 3' mIgκC-2 inner | GGAAGATGGA TACAGTTGGT GC (SEQ ID NO: 81) |

TABLE 8

| | IgM | IgG |
|---|---|---|
| Human $D_H$ | | |
| 1-1 | 1.2 | 6.0 |
| 1-7 | 39.9 | 9.0 |
| 1-14 | 0.5 | 2.3 |
| 1-20 | 2.3 | 1.4 |
| 1-26 | 3.5 | 5.7 |
| 2-2 | 1.1 | 3.2 |
| 2-8 | 0.7 | 0.6 |
| 2-15 | 0.3 | 1.2 |
| 2-21 | 0.7 | 0.3 |
| 3-3 | 6.3 | 5.2 |
| 3-9 | 0.6 | 0.6 |
| 3-10 | 0.9 | 10.3 |
| 3-16 | 0.9 | 2.0 |
| 3-22 | 5.1 | 2.7 |
| 4-4/4-11 | 1.5 | 4.0 |
| 4-17 | 1.5 | 4.7 |
| 4-23 | 11.5 | 2.4 |
| 5-12 | 1.1 | 1.8 |
| 5-5/5-18 | 1.3 | 3.2 |
| 5-24 | 0.3 | 3.3 |
| 6-6 | 1.8 | 4.5 |
| 6-13 | 6.1 | 7.4 |
| 6-19 | 3.0 | 5.1 |
| 6-25 | 0.1 | 0.6 |
| 7-27 | 3.3 | 7.3 |
| Human $J_H$ | | |
| 1 | 7.5 | 1.5 |
| 2 | 3.3 | 4.2 |
| 3 | 22.2 | 12.8 |
| 4 | 51.5 | 36.4 |
| 5 | 10.5 | 9.5 |
| 6 | 4.9 | 29.4 |

TABLE 9

| | % Observed |
|---|---|
| Human $V_K$ | |
| 1-5 | 3.4 |
| 1-6 | 1.3 |
| 1-8 | 0 |
| 1-9 | 1.3 |
| 1-12 | 1.0 |
| 1-13 | 0 |
| 1-16 | 2.5 |
| 1-17 | 3.6 |
| 1-22 | 0 |
| 1-27 | 0.5 |
| 1-32 | 0 |
| 1-33 | 14.3 |
| 1-35 | 0 |
| 1-37 | 0 |
| 1-39 | 1.6 |
| 2-4 | 0 |
| 2-10 | 0 |
| 2-14 | 0 |
| 2-18 | 0 |
| 2-19 | 0 |
| 2-23 | 0 |
| 2-24 | 0.7 |
| 2-26 | 0 |
| 2-28 | 0 |
| 2-29 | 0 |
| 2-30 | 1.9 |
| 2-36 | 0 |
| 2-38 | 0 |
| 2-40 | 1.5 |
| 3-7 | 0 |
| 3-11 | 2.7 |
| 3-15 | 3.9 |
| 3-20 | 41.2 |
| 3-25 | 0 |
| 3-31 | 0 |
| 3-34 | 0 |
| 4-1 | 13.2 |
| 5-2 | 0.1 |
| 6-21 | 0 |
| 7-3 | 0 |
| Human $J_K$ | |
| 1 | 28.1 |
| 2 | 25.3 |
| 3 | 12.1 |
| 4 | 22.5 |
| 5 | 11.1 |

We claim:

1. A rat or a mouse whose germline genome comprises:

a restricted immunoglobulin heavy chain locus characterized by the presence of a single human unrearranged $V_H$1-69 gene segment, one or more human unrearranged $D_H$ gene segments, and one or more human unrearranged $J_H$ gene segments operably linked to a non-human immunoglobulin heavy chain constant region nucleic acid sequence comprising at least a non-human IgM gene at an endogenous heavy chain locus of the rat or mouse, wherein the restricted immunoglobulin heavy chain locus is capable of rearranging and forming a plurality of distinct rearrangements, wherein each rearrangement is derived from the single human $V_H$1-69 gene segment, one of the human $D_H$ segments, and one of the human $J_H$ segments, and wherein each rearrangement encodes a different heavy chain variable domain, and wherein the rat or mouse further comprises a population of mature $IgM^{int}IgD^{hi}$ B cells in its spleen, each B cell comprising a distinct rearranged human heavy chain variable region gene sequence derived from the restricted immunoglobulin heavy chain locus.

2. The rat or mouse of claim 1, wherein the rat or mouse comprises a deletion of all or substantially all endogenous $V_H$, $D_H$, and $J_H$ gene segments.

3. The rat or mouse of claim 1, wherein the non-human immunoglobulin constant region nucleic acid sequence is a mouse or rat immunoglobulin heavy chain constant region nucleic acid sequence.

4. The rat or mouse of claim 1, wherein the genome of the rat or mouse further comprises one or more human immunoglobulin $V_L$ gene segments operably linked to one or more human $J_L$ gene segments.

5. The rat or mouse of claim 4, wherein the one or more human $V_L$ gene segments and the one or more human $J_L$ gene segments are human Vκ and human Jκ gene segments.

6. The rat or mouse of claim 4, wherein the one or more human immunoglobulin $V_L$ gene segments and one or more human $J_L$ gene segments are operably linked to a non-human light chain constant gene.

7. The rat or mouse of claim 6, wherein the non-human light chain constant gene is selected from a mouse κ or λ constant region gene.

8. A cell or tissue derived from the rat or mouse of claim 1.

9. The rat or mouse of claim 4, wherein the one or more human $V_L$ gene segments and the one or more human $J_L$ gene segments are human Vλ and human Jλ, gene segments.

10. The rat or mouse of claim 1, wherein the single human unrearranged $V_H$ gene segment comprises a plurality of polymorphs of the $V_H$1-69 segment.

11. The rat or mouse of claim 1, wherein the single human unrearranged $V_H$ gene segment consists of a single allele of the $V_H$1-69 segment.

12. The rat or mouse of claim 1, wherein the rat or mouse comprises a higher ratio of mature $IgM^{int}IgD^{hi}$ B cells to immature $IgD^{int}IgM^{hi}$ B cells in the spleen as compared to a control ratio of mature $IgM^{int}IgD^{hi}$ B cells to immature $IgD^{int}IgM^{hi}$ B cells in the spleen of a control rat or mouse comprising a plurality of human $V_H$ gene segments.

13. The rat or mouse of claim 1, wherein the rat or mouse comprises at least $1\times10^7$ $IgM^{int}IgD^{hi}$ B cells in its spleen.

14. The rat or mouse of claim 1, wherein the number of $CD19^+$cells in the population of mature $IgM^{int}IgD^{hi}$ B cells in the spleen is within an order of magnitude of the number of $CD19^+$cells in a population of mature $IgM^{int}IgD^{hi}$ B cells in a spleen of a control rat or mouse comprising a plurality of human VH gene segments.

15. A mouse whose germline genome comprises:

a replacement at an endogenous immunoglobulin heavy chain locus of all or substantially all endogenous $V_H$, $D_H$, and $J_H$ gene segments with a single human unrearranged $V_H$1-69 gene segment, one or more human unrearranged $D_H$ gene segments, and one or more human unrearranged $J_H$ gene segments operably linked to an endogenous immunoglobulin heavy chain constant region nucleic acid sequence comprising at least an endogenous IgM gene at an endogenous heavy chain locus of the mouse, wherein the restricted immunoglobulin heavy chain locus is capable of rearranging and forming a plurality of distinct rearrangements, wherein each rearrangement is derived from the single human $V_H$1-69 gene segment, one of the human $D_H$ segments, and one of the human $J_H$ segments, and wherein each rearrangement encodes a different heavy chain variable domain, and wherein the mouse further comprises a population of mature $IgM^{int}IgD^{hi}$ B cells in the spleen, each B cell comprising a distinct rearranged human heavy chain variable region gene sequence derived from the single human unrearranged $V_H$ gene segment, the one or more human unrearranged $D_H$, and the one or more human unrearranged $J_H$ gene segments.

16. The mouse of claim 15, wherein the genome of the mouse further comprises:

a replacement at an endogenous immunoglobulin light chain locus of all or substantially all endogenous $V_L$ and $J_L$ gene segments with one or more human $V_L$ and one or more human $J_L$ gene segments, wherein the human $V_L$ and $J_L$ gene segments are operably linked with a non-human light chain constant region nucleic acid sequence.

17. The mouse of claim 16, wherein the human $V_L$ and $J_L$ gene segments are human $V_κ$and $J_κ$gene segments which replace endogenous $V_κ$and $J_κ$gene segments, and wherein the human $V_κ$and $J_κ$gene segments are operably linked to a mouse $C_κ$region nucleic acid sequence.

18. The mouse of claim 16, wherein the human $V_L$ and $J_L$ gene segments are human $V_λ$and $J_λ$gene segments which replace endogenous $V_λ$and $J_λ$gene segments, and wherein the human $V_λ$and $J_λ$gene segments are operably linked to a mouse $C_λ$region nucleic acid sequence.

19. The mouse of claim 15, wherein the rat or mouse comprises a higher ratio of mature $IgM^{int}IgD^{hi}$ B cells to immature $IgD^{int}IgM^{hi}$ B cells in the spleen as compared to a control ratio of mature $IgM^{int}IgD^{hi}$ B cells to immature $IgD^{int}IgM^{hi}$ B cells in the spleen of a control mouse comprising a plurality of human $V_H$ gene segments.

20. The mouse of claim 15, wherein the single human unrearranged $V_H$ gene segment comprises a plurality of polymorphs of the $V_H$1-69 segment.

21. The mouse of claim 15, wherein the single human unrearranged $V_H$ gene segment consists of a single allele of the $V_H$1-69 segment.

22. The mouse of claim 15, wherein the number of $CD19^+$cells in the population of mature $IgM^{int}IgD^{hi}$ B cells in the spleen is within an order of magnitude of the number of $CD19^+$cells in a population of mature $IgM^{int}IgD^{hi}$ B cells in a spleen of a control mouse comprising a plurality of human $V_H$ gene segments.

23. The mouse of claim 15, wherein the rat or mouse comprises a higher ratio of mature $IgM^{int}IgD^{hi}$ B cells to immature $IgD^{int}IgM^{hi}$ B cells in the spleen as compared to a control ratio of mature $IgM^{int}IgD^{hi}$ B cells to immature $IgD^{int}IgM^{hi}$ B cells in the spleen of a control mouse comprising a plurality of human $V_H$ gene segments.

24. The mouse of claim 15, wherein the mouse comprises at least $1 \times 10^7$ $IgM^{int}IgD^{hi}$ B cells in its spleen.

* * * * *

UNITED STATES PATENT AND TRADEMARK OFFICE

CERTIFICATE OF CORRECTION

PATENT NO. : 10,246,509 B2
APPLICATION NO. : 13/653456
DATED : April 2, 2019
INVENTOR(S) : Lynn Macdonald, John McWhirter and Andrew J. Murphy It is certified that error appears in the above-identified patent and that said Letters Patent is hereby corrected as shown below:

On the Title Page

(71) Inventors:
"Lynn Macdonald, Harrison, NY (US); John McWhirter, Hasings-on-Hudson, NY (US); Cagan Gurer, Chappaqua, NY (US); Karolina A. Hosiawa, Yorktown Heights, NY (US); Andrew J. Murphy, Croton-on-Hudson, NY (US)"
Should read:
--Lynn Macdonald, Harrison, NY (US); John McWhirter, Hastings-on-Hudson, NY (US); Andrew J. Murphy, Croton-on-Hudson, NY (US)--

(56) References Cited, OTHER PUBLICATIONS:

Page 3, Column 1:
"Chain, C. H., et al., "$V_H$I-69 gene is perferentially used by neptitis"
Should read:
--Chan, C. H., et al., $V_H$1-69 gene is preferentially used by the hepatitis--

Page 4, Column 1:
"Slick and Pasternak"
Should read:
--Glick and Pasternak--

In the Specification

Column 4, Line 52:
"JH"
Should read:
--$J_H$--

Signed and Sealed this
Twenty-fourth Day of September, 2019

Andrei Iancu
*Director of the United States Patent and Trademark Office*

Column 10, Line 2:
"Jλ0.3"
Should read:
--Jλ3--

Column 21, Line 2:
"a light"
Should read:
--a κ light--

Column 21, Line 15:
"x"
Should read:
--κ--

Column 23, Line 2:
"a an SVD"
Should read:
--a SVD--

Column 30, Line 16:
"$V_H$1-68*10"
Should read:
--$V_H$1-69*10--

Column 31, Line 6:
"HK"
Should read:
--Hκ--

Column 39, Line 22:
"4-4-b"
Should read:
--4-4b--

Column 39, Line 32:
"Arnaout of al"
Should read:
--Arnaout et al--

Column 39, Line 58:
"Perez of al"
Should read:
--Perez et al--

Column 40, Line 6:
“Miklos of al”
Should read:
--Miklos et al--

Column 41, Line 42:
“form”
Should read:
--from--

Column 48, Line 48:
“$Ig\lambda^+$ B cells”
Should read:
--$Ig\kappa^+$ B cells--

In the Claims

Column 303, Line 49:
“human Jλ,”
Should read:
--human Jλ--

Column 304, Line 2:
“VH”
Should read:
--$V_H$--

Column 304, Line 38:
“Vκand Jκgene”
Should read:
--Vκ and Jκ gene--

Column 304, Line 39:
“Vκand Jκgene”
Should read:
--Vκ and Jκ gene--

Column 304, Line 40:
“Vκand Jκgene”
Should read:
--Vκ and Jκ gene--

Column 304, Line 41:
"Cκregion"
Should read:
--Cκ region--

Column 304, Line 43:
"$V_λ$and $J_λ$gene"
Should read:
--$V_λ$ and $J_λ$ gene--

Column 304, Line 44:
"$V_λ$and $J_λ$gene"
Should read:
--$V_λ$ and $J_λ$ gene--

Column 304, Line 45:
"$V_λ$and $J_λ$gene"
Should read:
--$V_λ$ and $J_λ$ gene--

Column 304, Line 46:
"$C_λ$region"
Should read:
--$C_λ$ region--

Column 304, Line 65 - Column 305, Line 3:
"The mouse of claim 15, wherein the rat or mouse comprises a higher ratio of mature $IgM^{int}IgD^{hi}$ B cells to immature $IgD^{int}IgM^{hi}$ B cells in the spleen as compared to a control ratio of mature $IgM^{int}IgD^{hi}$ B cells to immature $IgD^{int}IgM^{hi}$ B cells in the spleen of a control mouse comprising a plurality of human $V_H$ gene segments."
Should read:
--A cell or tissue derived from the mouse of claim 15.--